(12) United States Patent
Cho et al.

(10) Patent No.: US 7,638,299 B2
(45) Date of Patent: Dec. 29, 2009

(54) BIOSYNTHETIC POLYPEPTIDES UTILIZING NON-NATURALLY ENCODED AMINO ACIDS

(75) Inventors: Ho Sung Cho, San Diego, CA (US); Thomas O. Daniel, La Jolla, CA (US); Anna-Maria Hays, La Jolla, CA (US); Troy E. Wilson, San Marino, CA (US); David C. Litzinger, Poway, CA (US); Roberto Mariani, San Diego, CA (US); Bruce E. Kimmel, San Diego, CA (US); William M. Keefe, San Diego, CA (US)

(73) Assignee: Ambrx, Inc., La Jolla, CA (US)

( * ) Notice: Subject to any disclaimer, the term of this patent is extended or adjusted under 35 U.S.C. 154(b) by 262 days.

(21) Appl. No.: 11/187,687

(22) Filed: Jul. 21, 2005

(65) Prior Publication Data

US 2006/0019347 A1 Jan. 26, 2006

Related U.S. Application Data

(60) Provisional application No. 60/590,035, filed on Jul. 21, 2004, provisional application No. 60/659,709, filed on Mar. 7, 2005.

(51) Int. Cl.
*C12P 21/06* (2006.01)
*C07H 21/04* (2006.01)
*C07K 14/00* (2006.01)

(52) U.S. Cl. ............... 435/69.1; 435/320; 435/325; 435/350; 435/23.5

(58) Field of Classification Search .................. None
See application file for complete search history.

(56) References Cited

U.S. PATENT DOCUMENTS

| | | | |
|---|---|---|---|
| 3,773,919 A | 11/1973 | Boswell et al. |
| 4,289,872 A | 9/1981 | Denkewalter et al. |
| 4,412,989 A | 11/1983 | Iwashita et al. |
| 4,414,148 A | 11/1983 | Jansen et al. |
| 4,485,045 A | 11/1984 | Regen |
| 4,511,502 A | 4/1985 | Builder et al. |
| 4,511,503 A | 4/1985 | Olson et al. |
| 4,512,922 A | 4/1985 | Jones et al. |
| 4,544,545 A | 10/1985 | Ryan et al. |
| 4,551,433 A | 11/1985 | DeBoer |
| 4,569,789 A | 2/1986 | Blattler et al. |
| 4,619,794 A | 10/1986 | Hauser |
| 4,659,839 A | 4/1987 | Nicolotti et al. |
| 4,670,417 A | 6/1987 | Iwasaki et al. |
| 4,671,958 A | 6/1987 | Rodwell et al. |
| 4,680,338 A | 7/1987 | Sundoro |
| 4,689,406 A | 8/1987 | Banks et al. |
| 4,699,784 A | 10/1987 | Shih et al. |
| 4,738,921 A | 4/1988 | Belagaje et al. |
| 4,755,465 A | 7/1988 | Gray et al. |
| 4,837,148 A | 6/1989 | Cregg |
| 4,859,600 A | 8/1989 | Gray et al. |
| 4,876,197 A | 10/1989 | Burke et al. |
| 4,880,734 A | 11/1989 | Burke et al. |
| 4,902,502 A | 2/1990 | Nitecki et al. |
| 4,904,584 A | 2/1990 | Shaw |
| 4,929,555 A | 5/1990 | Cregg et al. |
| 5,021,234 A | 6/1991 | Ehrenfeld |
| 5,089,398 A | 2/1992 | Rosenberg et al. |
| 5,122,614 A | 6/1992 | Zalipsky |
| 5,162,601 A | 11/1992 | Slightom |
| 5,219,564 A | 6/1993 | Zalipsky et al. |
| 5,229,490 A | 7/1993 | Tam |
| 5,231,178 A | 7/1993 | Holtz et al. |
| 5,252,714 A | 10/1993 | Harris et al. |
| 5,281,698 A | 1/1994 | Nitecki |
| 5,290,686 A | 3/1994 | Kendal et al. |
| 5,324,639 A | 6/1994 | Brierley et al. |
| 5,324,844 A | 6/1994 | Zalipsky |
| 5,382,657 A | 1/1995 | Karasiewicz et al. |
| 5,446,090 A | 8/1995 | Harris |
| 5,468,478 A | 11/1995 | Saifer et al. |
| 5,473,034 A | 12/1995 | Yasui et al. |
| 5,476,653 A | 12/1995 | Pitt et al. |
| 5,516,657 A | 5/1996 | Murphy et al. |
| 5,516,673 A | 5/1996 | Margel et al. |
| 5,532,142 A | 7/1996 | Johnston et al. |
| 5,545,618 A | 8/1996 | Buckley et al. |
| 5,559,213 A | 9/1996 | Hakimi et al. |
| 5,571,709 A | 11/1996 | Devauchelle et al. |
| 5,580,723 A | 12/1996 | Wells et al. |
| 5,583,023 A | 12/1996 | Cerutti et al. |
| 5,602,034 A | 2/1997 | Tekamp-Olson |
| 5,605,827 A | 2/1997 | Jackwood et al. |
| 5,612,460 A | 3/1997 | Zalipsky |
| 5,629,203 A | 5/1997 | Shuster |
| 5,629,384 A | 5/1997 | Veronese et al. |
| 5,643,575 A | 7/1997 | Martinez et al. |
| 5,650,234 A | 7/1997 | Dolence et al. |
| 5,672,662 A | 9/1997 | Harris et al. |
| 5,674,706 A | 10/1997 | Shuster |
| RE35,749 E | 3/1998 | Rosenberg et al. |
| 5,736,625 A | 4/1998 | Callstrom et al. |

(Continued)

FOREIGN PATENT DOCUMENTS

DE  3218121  11/1983

(Continued)

OTHER PUBLICATIONS

Caliceti, P et FM Veronese. "Pharmacokinetic and biodistribution properties of poly(ethylene glycol)-protein conjugates," Adv Drug Deliv Rev. Sep. 26, 2003;55(10):1261-77.

(Continued)

*Primary Examiner*—Andrew Wang
*Assistant Examiner*—Kagnew H Gebreyesus
(74) *Attorney, Agent, or Firm*—John W. Wallen, III; Kristin S. Eaton

(57) ABSTRACT

Modified biosynthetic polypeptide molecules, methods for manufacturing, and uses thereof are provided.

11 Claims, 13 Drawing Sheets

U.S. PATENT DOCUMENTS

| | | | |
|---|---|---|---|
| 5,739,208 A | 4/1998 | Harris |
| 5,747,646 A | 5/1998 | Hakimi et al. |
| 5,750,373 A | 5/1998 | Garrard et al. |
| 5,753,220 A | 5/1998 | Suzuki et al. |
| 5,762,939 A | 6/1998 | Smith et al. |
| 5,766,885 A | 6/1998 | Carrington et al. |
| 5,808,096 A | 9/1998 | Zalipsky |
| 5,824,778 A | 10/1998 | Ishikawa et al. |
| 5,824,784 A | 10/1998 | Kinstler et al. |
| 5,834,250 A | 11/1998 | Wells et al. |
| 5,834,594 A | 11/1998 | Hakimi et al. |
| 5,843,733 A | 12/1998 | Estes |
| 5,849,860 A | 12/1998 | Hakimi et al. |
| 5,858,368 A | 1/1999 | Smith et al. |
| 5,861,279 A | 1/1999 | Zhang et al. |
| 5,871,986 A | 2/1999 | Boyce |
| 5,891,676 A | 4/1999 | Estes |
| 5,900,461 A | 5/1999 | Harris |
| 5,932,462 A | 8/1999 | Harris et al. |
| 5,939,285 A | 8/1999 | Devauchelle et al. |
| 5,965,393 A | 10/1999 | Hasnain et al. |
| 5,980,948 A | 11/1999 | Goedemoed et al. |
| 5,989,868 A | 11/1999 | Harrison et al. |
| 5,990,237 A | 11/1999 | Bentley et al. |
| 6,004,573 A | 12/1999 | Rathi et al. |
| 6,013,433 A | 1/2000 | Pellett et al. |
| 6,013,478 A | 1/2000 | Wells et al. |
| 6,017,731 A | 1/2000 | Tekamp-Olson et al. |
| 6,083,723 A | 7/2000 | Tekamp-Olson |
| 6,096,304 A | 8/2000 | McCutchen |
| 6,126,944 A | 10/2000 | Pellett et al. |
| 6,129,912 A | 10/2000 | Hortin et al. |
| 6,168,932 B1 | 1/2001 | Uckun et al. |
| 6,183,985 B1 | 2/2001 | Shuster |
| 6,183,987 B1 | 2/2001 | van de Wiel et al. |
| 6,201,072 B1 | 3/2001 | Rathi et al. |
| 6,214,966 B1 | 4/2001 | Harris |
| 6,225,060 B1 | 5/2001 | Clark et al. |
| 6,245,528 B1 | 6/2001 | Chao |
| 6,261,805 B1 | 7/2001 | Wood |
| RE37,343 E | 8/2001 | Tekamp-Olson |
| 6,281,211 B1 | 8/2001 | Cai et al. |
| 6,306,821 B1 | 10/2001 | Mikos et al. |
| 6,312,923 B1 | 11/2001 | Tekamp-Olson |
| 6,337,191 B1 | 1/2002 | Swartz et al. |
| 6,338,846 B1 | 1/2002 | Kang et al. |
| 6,342,216 B1 | 1/2002 | Fidler et al. |
| 6,361,969 B1 | 3/2002 | Galeotti |
| 6,368,825 B1 | 4/2002 | Chao |
| 6,420,339 B1 | 7/2002 | Gegg et al. |
| 6,423,685 B1 | 7/2002 | Drummond et al. |
| 6,428,954 B1 | 8/2002 | Wells et al. |
| 6,436,386 B1 | 8/2002 | Roberts et al. |
| 6,451,346 B1 | 9/2002 | Shah et al. |
| 6,451,561 B1 | 9/2002 | Wells et al. |
| 6,461,603 B2 | 10/2002 | Bentley et al. |
| 6,515,100 B2 | 2/2003 | Harris |
| 6,521,427 B1 | 2/2003 | Evans |
| 6,552,167 B1 | 4/2003 | Rose |
| 6,586,207 B2 | 7/2003 | Tirrell et al. |
| 6,602,498 B2 | 8/2003 | Shen |
| 6,608,183 B1 | 8/2003 | Cox |
| 6,610,281 B2 | 8/2003 | Harris |
| 6,646,110 B2 | 11/2003 | Nissen et al. |
| 6,927,042 B2 * | 8/2005 | Schultz et al. ............. 435/69.1 |
| 7,045,337 B2 | 5/2006 | Schultz et al. |
| 7,083,970 B2 | 8/2006 | Schultz et al. |
| 2001/0021763 A1 | 9/2001 | Harris |
| 2001/0044526 A1 | 11/2001 | Shen |
| 2001/0056171 A1 | 12/2001 | Kozlowski |
| 2002/0002250 A1 | 1/2002 | Bentley et al. |
| 2002/0037949 A1 | 3/2002 | Harris et al. |
| 2002/0040076 A1 | 4/2002 | Harris et al. |
| 2002/0042097 A1 | 4/2002 | Tirrell et al. |
| 2002/0052009 A1 | 5/2002 | Hornauer et al. |
| 2002/0052430 A1 | 5/2002 | Harris et al. |
| 2002/0055169 A1 | 5/2002 | Tekamp-Olson |
| 2002/0072573 A1 | 6/2002 | Bentley et al. |
| 2002/0081660 A1 | 6/2002 | Swartz et al. |
| 2002/0082345 A1 | 6/2002 | Kozlowski et al. |
| 2002/0086939 A1 | 7/2002 | Kozlowski |
| 2002/0099133 A1 | 7/2002 | Kozlowski |
| 2002/0156047 A1 | 10/2002 | Zhao |
| 2003/0023023 A1 | 1/2003 | Harris et al. |
| 2003/0082575 A1 * | 5/2003 | Schultz et al. ................. 435/6 |
| 2003/0105224 A1 | 6/2003 | Roberts et al. |
| 2003/0105275 A1 | 6/2003 | Bentley et al. |
| 2003/0108885 A1 | 6/2003 | Schultz et al. |
| 2003/0114647 A1 | 6/2003 | Harris et al. |
| 2003/0124669 A1 * | 7/2003 | Pan et al. .................... 435/69.1 |
| 2003/0143596 A1 | 7/2003 | Bentley et al. |
| 2003/0158333 A1 | 8/2003 | Roberts et al. |
| 2003/0162949 A1 | 8/2003 | Cox |
| 2003/0220447 A1 | 11/2003 | Harris |
| 2003/0228274 A1 | 12/2003 | Rose |
| 2004/0001838 A1 | 1/2004 | Zhao et al. |
| 2004/0013637 A1 | 1/2004 | Bentley et al. |
| 2004/0198637 A1 | 10/2004 | Schultz et al. |
| 2005/0009049 A1 | 1/2005 | Chin et al. |
| 2005/0085619 A1 | 4/2005 | Wilson et al. |
| 2005/0170404 A1 | 8/2005 | Cho et al. |
| 2005/0220762 A1 | 10/2005 | Cho et al. |

FOREIGN PATENT DOCUMENTS

| | | |
|---|---|---|
| EP | 036 676 | 9/1981 |
| EP | 036 776 | 9/1981 |
| EP | 052 322 | 5/1982 |
| EP | 058 481 | 8/1982 |
| EP | 073 657 | 3/1983 |
| EP | 102 324 | 3/1984 |
| EP | 121 775 | 10/1984 |
| EP | 127 839 | 12/1984 |
| EP | 133 988 | 3/1985 |
| EP | 143 949 | 6/1985 |
| EP | 154 316 | 9/1985 |
| EP | 155 476 | 9/1985 |
| EP | 164 556 | 12/1985 |
| EP | 183 503 | 6/1986 |
| EP | 188 256 | 7/1986 |
| EP | 229 108 | 7/1987 |
| EP | 244 234 | 11/1987 |
| EP | 267 851 | 5/1988 |
| EP | 284 044 | 9/1988 |
| EP | 324 274 | 7/1989 |
| EP | 329 203 | 8/1989 |
| EP | 340 986 | 11/1989 |
| EP | 400 472 | 12/1990 |
| EP | 402 378 | 12/1990 |
| EP | 439 508 | 8/1991 |
| EP | 480 480 | 4/1992 |
| EP | 510 356 | 10/1992 |
| EP | 605 963 | 7/1994 |
| EP | 732 403 | 9/1996 |
| EP | 809 996 | 12/1997 |
| EP | 921 131 | 6/1999 |
| EP | 946 736 | 10/1999 |
| JP | 83-118008 | 1/1985 |
| WO | WO 88/07082 | 9/1988 |
| WO | WO 89/01037 | 2/1989 |
| WO | WO 89/01038 | 2/1989 |
| WO | WO 90/01556 | 2/1990 |
| WO | WO 90/02186 | 3/1990 |
| WO | WO 90/02566 | 3/1990 |

| | | |
|---|---|---|
| WO | WO 90/05785 | 5/1990 |
| WO | WO 90/10078 | 9/1990 |
| WO | WO 90/10277 | 9/1990 |
| WO | WO 90/13540 | 11/1990 |
| WO | WO 90/14428 | 11/1990 |
| WO | WO 91/00357 | 1/1991 |
| WO | WO 91/11457 A1 | 8/1991 |
| WO | WO 92/01801 | 2/1992 |
| WO | WO 92/02628 | 2/1992 |
| WO | WO 92/16555 | 10/1992 |
| WO | WO 92/16619 | 10/1992 |
| WO | WO 93/03173 | 2/1993 |
| WO | WO 93/15189 | 8/1993 |
| WO | WO 93/21259 | 10/1993 |
| WO | WO 94/04193 | 3/1994 |
| WO | WO 94/09027 | 4/1994 |
| WO | WO 94/14758 | 7/1994 |
| WO | WO 94/15625 | 7/1994 |
| WO | WO 94/17039 | 8/1994 |
| WO | WO 94/18247 | 8/1994 |
| WO | WO 94/28024 | 12/1994 |
| WO | WO 95/00162 | 1/1995 |
| WO | WO 95/06058 | 3/1995 |
| WO | WO 95/11924 | 5/1995 |
| WO | WO 95/13090 | 5/1995 |
| WO | WO 95/13312 | 5/1995 |
| WO | WO 95/20672 | 8/1995 |
| WO | WO 95/33490 | 12/1995 |
| WO | WO 96/00080 | 1/1996 |
| WO | WO 96/06161 | 2/1996 |
| WO | WO 96/07670 | 3/1996 |
| WO | WO 96/21469 | 7/1996 |
| WO | WO 96/25496 | 8/1996 |
| WO | WO 96/29400 | 9/1996 |
| WO | WO 96/40791 | 12/1996 |
| WO | WO 96/41813 | 12/1996 |
| WO | WO 97/03106 | 1/1997 |
| WO | WO 97/18832 | 5/1997 |
| WO | WO 97/26332 | 7/1997 |
| WO | WO 97/32607 | 9/1997 |
| WO | WO 98/05363 | 2/1998 |
| WO | WO 98/26080 | 6/1998 |
| WO | WO 98/32466 | 7/1998 |
| WO | WO 98/37208 | 8/1998 |
| WO | WO 98/41562 | 9/1998 |
| WO | WO 98/48837 | 11/1998 |
| WO | WO 99/03887 | 1/1999 |
| WO | WO 99/05297 | 2/1999 |
| WO | WO 99/07862 | 2/1999 |
| WO | WO 99/09193 | 2/1999 |
| WO | WO 99/10515 | 3/1999 |
| WO | WO 99/31257 | 6/1999 |
| WO | WO 99/32134 | 7/1999 |
| WO | WO 99/32139 | 7/1999 |
| WO | WO 99/32140 | 7/1999 |
| WO | WO 99/45130 | 9/1999 |
| WO | WO 99/51721 | 10/1999 |
| WO | WO 99/67291 | 12/1999 |
| WO | WO 00/20032 | 4/2000 |
| WO | WO 00/26354 | 5/2000 |
| WO | WO 00/55345 | 9/2000 |
| WO | WO 00/55353 | 9/2000 |
| WO | WO 01/05956 | 1/2001 |
| WO | WO 01/27301 | 4/2001 |
| WO | WO 01/90390 | 11/2001 |
| WO | WO 02/06305 | 1/2002 |
| WO | WO 02/085923 | 10/2002 |
| WO | WO 02/086075 | 10/2002 |
| WO | WO 03/101972 | 12/2003 |
| WO | WO 2004/035605 | 4/2004 |
| WO | WO 2004/035743 | 4/2004 |
| WO | WO 2004/058946 | 7/2004 |
| WO | WO 2004/094593 | 11/2004 |
| WO | WO 2005/007624 | 1/2005 |
| WO | WO 2005/007870 | 1/2005 |
| WO | WO 2005/019415 | 3/2005 |
| WO | WO 2005/035727 | 4/2005 |
| WO | WO 2005/074524 | 8/2005 |
| WO | WO 2005/074546 | 8/2005 |
| WO | WO 2005/074650 | 8/2005 |

OTHER PUBLICATIONS

Clark, EDB, "Refolding of recombinant proteins," Curr Opin Biotechnol Apr. 1, 1998;9(2):157-63.
Clark, EDB, "Protein refolding for industrial processes," Curr Opin Biotechnol Apr. 2001;12(2):202-7.
Davis, GD et al., "New fusion protein systems designed to give soluble expression in *Escherichia coli*," Biotechnol Bioeng Nov. 20, 1999;65(4):382-8.
Duncan, R. "The dawning era of polymer therapeutics," Nat Rev Drug Discov May 2003;2(5):347-60.
Gaertner, HF et RE Offord. "Site-specific attachment of functionalized poly(ethylene glycol) to the amino terminus of proteins," Bioconjug Chem Jan.-Feb. 1996;7(1):38-44.
Gu, Z et al. "Chromatographic methods for the isolation of, and refolding of proteins from, *Escherichia coli* inclusion bodies," Protein Expr Purif. Jun. 2002;25(1):174-9.
Hohsaka, T et M Sisido. "Incorporation of non-natural amino acids into proteins," Curr Opin Chem Biol. Dec. 2002;6(6):809-15.
Lilie, H et al. "Advances in refolding of proteins produced in *E. coli*," Curr Opin Biotechnol. Oct. 1998;9(5):497-501.
Tsumoto, K et al. "Practical considerations in refolding proteins from inclusion bodies," Protein Expr Purif. Mar. 2003;28(1):1-8.
Wang, W. "Instability, stabilization, and formulation of liquid protein pharmaceuticals," Int J Pharm. Aug. 20, 1999;185(2):129-88.
Abuchowski, A. et al. "Cancer therapy with chemically modified enzymes. I. Antitumor properties of polyethylene glycol-asparaginase conjugates," Cancer Biochem Biophys. Jun. 1984;7(2):175-86.
Altschul, SF et al. "Gapped BLAST and PSI-BLAST: a new generation of protein database search programs," Nucleic Acids Res. Sep. 1, 1997;25(17):3389-402.
Altschul, SF et al. "Basic local alignment search tool," J Mol Biol. Oct. 5, 1990;215(3):403-10.
Amann, E et al., "Vectors bearing a hybrid trp-lac promoter useful for regulated expression of cloned genes in *Escherichia coli*," Gene. Nov. 1983;25(2-3):167-78.
Anderson, JC et al., "Exploring the limits of codon and anticodon size," Chem Biol. Feb. 2002;9(2):237-44.
Andresz, H et al. Abstract of "Chemische Synthese verzweigter Polysaccharide, 5; Kopplung von Oligosacchariden und Amylose an verschiedene Träger durch Hydrazonbindung," Makromol. Chem. 1978;179:301 Abstract.
Arnold, FH. "Protein engineering for unusual environments," Curr Opin Biotechnol. Aug. 1993;4(4):450-5.
Azoulay, M., et al. "Glutamine analogues as Potential Antimalarials," Eur. J. Med. Chem. (1991); 26(2):201-5.
Bain, JD, et al. "Biosynthetic site-specific incorporation of a non-natural amino acid into a polypeptide," J. Am Chem Soc 1989;111(20):8013-8014.
Ballance, DJ et al., "Transformation of *Aspergillus nidulans* by the orotidine-5'-phosphate decarboxylase gene of *Neurospora crassa*," Biochem Biophys Res Commun. Apr. 15, 1983;112(1):284-9.
Barany, F. et al., "Genetic disease detection and DNA amplification using cloned thermostable ligase," Proc Natl Acad Sci U S A. Jan. 1, 1991;88(1):189-93.
Barton, DHR et al., "Synthesis of Novel alpha-Amino-Acids and Derivatives Using Radical Chemistry: Synthesis of L- and D-alpha-Amino-Adipic Acids, L-alpha-aminopimelic Acid and Appropriate Unsaturated Derivatives," Tetrahedron (1987) 43:4297-4308.
Bass, S et al., "Mutant Trp repressors with new DNA-binding specificities," Science (1988) 242:240-245.
Batzer, MA et al., "Enhanced evolutionary PCR using oligonucleotides with inosine at the 3'-terminus," Nucleic Acids Res. Sep. 25, 1991;19(18):5081.

Beach, D et al., "Functionally homologous cell cycle control genes in budding and fission yeast," Nature Dec. 1982; 300:706-709.

Beauchamp, CO et al., "A new procedure for the synthesis of polyethylene glycol-protein adducts; effects on function, receptor recognition, and clearance of superoxide dismutase, lactoferrin, and alpha 2-macroglobulin," Anal Biochem. May 1983;131(1):25-33.

Bernstein, FC, et al. "The protein data bank: a computer-based archival file for macromolecular structures," J. Mol. Biol. 1977; 112:535-542.

Boissel, JP et al., "Erythropoietin structure-function relationships. Mutant proteins that test a model of tertiary structure," J Biol Chem. Jul. 25, 1993;268(21):15983-93.

Boles, JO et al. "Bio-incorporation of telluromethionine into buried residues of dihydrofolate reductase," Nat Struct Biol. May 1994;1(5):283-4.

Botstein, D et D Shortle, "Strategies and applications of in vitro mutagenesis," Science. Sep. 20, 1985;229(4719):1193-201.

Brunner, J. "New photolabeling and crosslinking methods," Annu Rev Biochem. 1993;62:483-514.

Buchner, J. et al., "A method for increasing the yield of properly folded recombinant fusion proteins: Single-chain immunotoxins from renaturation of bacterial inclusion bodies," Anal. Biochem. 1992; 205(2): 263-270.

Bückmann et al. Functionalization of Poly(ethylene glycol) and Monomethoxy-Poly(ethylene glycol), Makromol. Chem. 1981;182:1379-84.

Budisa, N et al. "High-level biosynthetic substitution of methionine in proteins by its analogs 2-aminohexanoic acid, selenomethionine, telluromethionine and ethionine in *Escherichia coli*," Eur J Biochem. Jun. 1, 1995;230(2):788-96.

Budisa, N et al., "Bioincorporation of telluromethionine into proteins: a promising new approach for X-ray structure analysis of proteins," J Mol Biol. Jul. 25, 1997;270(4):616-23.

Budisa, N et al., "Toward the experimental codon reassignment in vivo: protein building with an expanded amino acid repertoire," FASEB J. Jan. 1999;13(1):41-51.

Cai, X-Y et al., "Expression, Purification, and Characterization of an Activated Cytokine-Suppressive Anti-inflammatory Drug-Binding Protein 2 (CSBP2) Kinase from Baculovirus-Infected Insect Cells," Protein Expression and Purification 1997; 10(2):263-74.

Carbonell, LF et al., "Baculovirus-mediated expression of bacterial genes in dipteran and mammalian cells," J Virol. Oct. 1985;56(1):153-60.

Carrasco, M. and R. Brown, "A Versatile Set of Aminooxy Amino Acids for the Synthesis of Neoglycopeptides," J. Org. Chem. (2003); 68(23): 8853-8858.

Carter, P. "Site-directed mutagenesis," Biochem J. Jul. 1, 1986; 237(1):1-7.

Carter, P et al., "Improved oligonucleotide site-directed mutagenesis using M13 vectors" Nucleic Acids Res. Jun. 25, 1985;13(12):4431-43.

Carter, P. "Improved oligonucleotide-directed mutagenesis using M13 vectors" Methods Enzymol. 1987;154:382-403.

Chaiken, IM. "Semisynthetic peptides and proteins," CRC Crit Rev Biochem. 1981;11(3):255-301.

Chin, JW et al., "Addition of p-azido-L-phenylalanine to the genetic code of *E. coli*," J Am Chem Soc. Aug. 7, 2002;124(31):9026-7.

Chin, JW et al., "Addition of a photocrosslinking amino acid to the genetic code of *Escherichia coli*," Proc Natl Acad Sci U S A. Aug. 20, 2002;99(17):11020-4. Epub Aug. 1, 2002.

Chin, JW et al., "An expanded eukaryotic genetic code," Science. Aug. 15, 2003;301(5635):964-7.

Chin, JW & P. G. Schultz, "In vivo photocrosslinking with unnatural amino acid mutagenesis," Chembiochem. Nov. 4, 2002; 3(11): 1135-7.

Christie, B.D. & Rapoport, H. "Synthesis of Optically Pure Pipecolates from L-Asparagine. Application to the Total Synthesis of (+)-Apovincamine through Amino Acid Decarbonylation and Iminium Ion Cyclization," J. Org. Chem. 1985;50(8):1239-1246.

Clark, R et al., "Long-acting growth hormones produced by conjugation with polyethylene glycol," J Biol Chem. Sep. 6, 1996;271(36):21969-77.

Corey, D.R., Schultz, P.G. "Generation of a hybrid sequence-specific single-stranded deoxyribonuclease," Science 1987; 238(4832):1401-1403.

Cornish, VW, et al., "Site-Specific Protein Modification Using a Ketone Handle," J. Am. Chem. Soc. 1996; 118(34):8150-8151.

Cornish, VW et al., "Probing Protein Structure and Function with an Expanded Genetic Code,"Angew Chem Int Ed Engl,1995;34(6):621-33.

Craig, J.C. et al. "Absolute Configuration of the Enantiomers of 7-Chloro-4 [[4-(diethylamino)-1-methylbutyl]amino]quinoline (Chloroquine)," J. Org. Chem. 1988; 53(6):1167-1170.

Cregg, JM et al., "*Pichia pastoris* as a host system for transformations," Mol Cell Biol. Dec. 1985;5(12):3376-85.

Crick, FHC, et al. "General nature of the genetic code for proteins," Nature. Dec. 30, 1961;192:1227-32.

Dale et al., Oligonucleotide-directed random mutagenesis using the phosphorothioate method, Methods Mol. Biol.1996;57:369-374.

Das, S et al., "Transformation of *Kluyveromyces fragilis*," J Bacteriol. Jun. 1984;158(3):1165-7.

Dawson, P. E. and S. B. H. Kent, "Synthesis of native proteins by chemical ligation," Annu. Rev. Biochem. 2000; 69:923-60.

De Boer, HA et al., "The tac promoter: a functional hybrid derived from the trp and lac promoters," Proc Natl Acad Sci U S A. Jan. 1983;80(1):21-5.

De Louvencourt, L et al., "Transformation of *Kluyveromyces lactis* by killer plasmid DNA," J Bacteriol. May 1983;154(2):737-42.

Debinski, W et al. "A wide range of human cancers express interleukin 4 (IL4) receptors that can be targeted with chimeric toxin composed of IL4 and *Pseudomonas exotoxin*," J Biol Chem. Jul. 5, 1993;268(19):14065-70.

Deiters, A., et al., "Adding Amino Acids with Novel Reactivity to the Genetic Code of *Saccharomyces cerevisiae*," J. Am. Chem. Soc. 2003; 125(39):11782-11783.

Delgado, C et al., "The uses and properties of PEG-linked proteins," Crit Rev Ther Drug Carrier Syst. 1992;9(3-4):249-304.

Dennis, MS et al., "Albumin binding as a general strategy for improving the pharmacokinetics of proteins," J Biol Chem. Sep. 20, 2002;277(38):35035-43. Epub Jul. 15, 2002.

Dolphin, CT et al., "Missense mutation in flavin-containing monooxygenase 3 gene, FMO3, underlies fish-odour syndrome," Nat Genet. Dec. 1997;17(4):491-4.

Doring, V et al., "Enlarging the amino acid set of *Escherichia coli* by infiltration of the valine coding pathway," Science. Apr. 20, 2001;292(5516):501-4.

Dougherty, DA. "Unnatural amino acids as probes of protein structure and function," Curr Opin Chem Biol. Dec. 2000;4(6):645-52.

Duewel, H et al., "Incorporation of trifluoromethionine into a phage lysozyme: implications and a new marker for use in protein 19F NMR," Biochemistry. Mar. 18, 1997;36(11):3404-16.

Eghtedarzadeh MK & S Henikoff "Use of oligonucleotides to generate large deletions" Nucleic Acids Res. Jun. 25, 1986;14(12):5115.

Elling L et MR Kula., "Immunoaffinity partitioning: synthesis and use of polyethylene glycol-oxirane for coupling to bovine serum albumin and monoclonal antibodies," Biotechnol Appl Biochem. Jun. 1991;13(3):354-62.

Elliott, S et al., "Yeast-derived recombinant human insulin-like growth factor I: production, purification, and structural characterization," J Protein Chem. Feb. 1990;9(1):95-104.

Ellman, J.A., Mendel, D., Anthony-Cahill, S., Noren, C.J., Schultz, P.G. "Biosynthetic method for introducing unnatural amino acids site-specifically into proteins," Methods in Enz., 1992; 202:301-336.

Ellman, JA, et al. "Site-specific incorporation of novel backbone structures into proteins," Science. Jan. 10, 1992;255(5041):197-200.

England, P. M., et al., "Backbone mutations in transmembrane domains of a ligand-gated ion channel: implications for the mechanism of gating," Cell. Jan. 8, 1999;96(1):89-98.

Eppstein et al., "Biological Activity of Liposome-Encapsulated Murine Interferon is Mediated by a Cell Membrane Receptor," Proc. Natl. Acad. Sci. U.S.A. (1985); 82: 3688-3692.

Fieschko, JC et al., "Controlled expression and purification of human immune interferon from high-cell-density fermentations of *Saccharomyces cerevisiae*," Biotech. Bioeng. (1987) 29(9):1113-21.

Forster, AC et al., "Programming peptidomimetic syntheses by translating genetic codes designed de novo," Proc Natl Acad Sci U S A. May 27, 2003;100(11):6353-7. Epub May 16, 2003.

Frankel, A et al., "Encodamers: unnatural peptide oligomers encoded in RNA," Chem Biol. Nov. 2003;10(11):1043-50.

Fraser, MJ et al., "Expression of eucaryotic genes in insect cell cultures," In Vitro Cell. Dev. Biol. 1989; 25:225-235.

Friedman, O.M. & R. Chatterrji. "Synthesis of Derivatives of Glutamine as Model Substrates for Anti-Tumor Agents," J. Am. Chem. Soc. 1959; 81(14):3750-3752.

Fritz HJ et al., "Oligonucleotide-directed construction of mutations: a gapped duplex DNA procedure without enzymatic reactions in vitro," Nucleic Acids Res. Jul. 25, 1988;16(14B):6987-99.

Fromm, M. et al., "Expression of Genes Transferred into Monocot and Dicot Plant Cells by Electroporation," Proc. Natl. Acad. Sci. USA (1985) 82:5824-8.

Furter, R. "Expansion of the genetic code: site-directed p-fluorophenylalanine incorporation in *Escherichia coli*," Protein Sci. Feb. 1998;7(2):419-26.

Gaertner, HF et al., "Construction of protein analogues by site-specific condensation of unprotected fragments," Bioconjug Chem. May-Jun. 1992;3(3):262-8.

Gaertner, HF et al., "Chemo-enzymic backbone engineering of proteins. Site-specific incorporation of synthetic peptides that mimic the 64-74 disulfide loop of granulocyte colony-stimulating factor," J Biol Chem. Mar. 11, 1994;269(10):7224-30.

Gallivan, JP et al., "Site-specific incorporation of biotinylated amino acids to identify surface-exposed residues in integral membrane proteins," Chem Biol. Oct. 1997;4(10):739-49.

Gellissen, G et al., "Heterologous protein production in yeast," Antonie Van Leeuwenhoek. Aug. 1992;62(1-2):79-93.

Geoghegan, KF and JG Stroh, "Site-directed conjugation of nonpeptide groups to peptides and proteins via periodate oxidation of a 2-amino alcohol. Application to modification at N-terminal serine," Bioconjug Chem. Mar.-Apr. 1992;3(2):138-46.

Gillam, S. & M Smith, "Site-specific mutagenesis using synthetic oligodeoxyribonucleotide primers: I. Optimum conditions and minimum oligodeoxyribonucleotide length," Gene 1979; 8(1):81-97.

Gleeson, MA et al., "Transformation of the methylotrophic yeast hansenula polymorphica," J. Gen. Microbiol. (1986) 132:3459-3465.

Goeddel, DV, "Systems for heterologous gene expression," Methods Enzymol. 1990;185:3-7.

Goeddel, DV et al., "Synthesis of human fibroblast interferon by *E. coli*," Nucleic Acids Res. Sep. 25, 1980;8(18):4057-74.

Goodson RJ et NV Katre. "Site-directed pegylation of recombinant interleukin-2 at its glycosylation site," Biotechnology (N Y). Apr. 1990;8(4):343-6.

Graves, SW et al., "Expression, purification, and initial kinetic characterization of the large subunit of the human mitochondrial DNA polymerase," Biochemistry. Apr. 28, 1998;37(17):6050-8.

Griffin, BA et al., "Specific Covalent Labeling of Recombinant Protein Molecules Inside Live Cells," Science (1998) 281:269-272.

Grundström T et al., "Oligonucleotide-directed mutagenesis by microscale 'shot-gun' gene synthesis," Nucleic Acids Res. May 10, 1985;13(9):3305-16.

Guckian, KM and ET Kool, "Highly Precise Shape Mimicry by a Difluorotoluene Deoxynucleoside, a Replication-Competent Substitute for Thymidine," Angew. Chem. Int. Ed. Engl (1998) 36(24):2825-8.

Hamano-Takaku, F et al., "A mutant *Escherichia coli* tyrosyl-tRNA synthetase utilizes the unnatural amino acid azatyrosine more efficiently than tyrosine," J Biol Chem. Dec. 22, 2000;275(51):40324-8.

Hang, HC and CR Bertozzi, "Chemoselective approaches to glycoprotein assembly," Acc Chem Res. Sep. 2001;34(9):727-36.

Harris, JM et al. "Synthesis and Characterization of Poly(ethylene Glycol) Derivatives," J. Polym. Sci. Chem. Ed. 1984; 22:341-352.

Harris, JM. "Laboratory Synthesis of Polyethylene Glycol Derivatives," JMS-Rev. Macromol. Chem. Phys. 1985;C25(3): 325-373.

Hendrickson, WA et al., "Selenomethionyl proteins produced for analysis by multiwavelength anomalous diffraction (MAD): a vehicle for direct determination of three-dimensional structure," EMBO J. May 1990;9(5):1665-72.

Henikoff, S and JG Henikoff "Amino Acid Substitution Matrices from Protein Blocks," Proc. Natl. Acad. Sci. USA 1992; 89:10915-9.

Hess, B. et al., "Cooperation of glycolytic enzymes," J. Adv. Enzyme Reg. (1969) 7:149-67.

Hinnen, A et al., "Transformation of yeast," Proc Natl Acad Sci U S A. Apr. 1978;75(4):1929-33.

Hirao, I et al., "An unnatural base pair for incorporating amino acid analogues into proteins," Nat Biotechnol. Feb. 2002;20(2):177-82.

Hitzeman, RA et al., "Isolation and characterization of the yeast 3-phosphoglycerokinase gene (PGK) by an immunological screening technique," J. Biol Chem. Dec. 25, 1980;255(24):12073-80.

Hofmann, K., et H. Bohn. "Studies on polypeptides. XXXVI. The effect of pyrazole-imidazole replacements on the S-protein activating potency of an S-peptide fragment," J. Am Chem, (1966); 88(24):5914-5919.

Hohsaka, T et al., "Efficient Incorporation of Nonnatural Amino Acids with Large Aromatic Groups into *Streptavidin* in In Vitro Protein Synthesizing Systems," J. Am. Chem. Soc. 1999; 121(1); 34-40.

Hohsaka, T et al., "Incorporation of Two Different Nonnatural Amino Acids Independently into a Single Protein through Extension of the Genetic Code," J. Am. Chem. Soc. 1999; 121(51):12194-12195.

Holland, MJ et JP Holland., "Isolation and identification of yeast messenger ribonucleic acids coding for enolase, glyceraldehyde-3-phosphate dehydrogenase, and phosphoglycerate kinase," Biochemistry. Nov. 14, 1978;17(23):4900-7.

Holland, MJ et al., "The primary structures of two yeast enolase genes. Homology between the 5' noncoding flanking regions of yeast enolase and glyceraldehyde-3-phosphate dehydrogenase genes," J Biol Chem. Feb. 10, 1981;256(3):1385-95.

Hsiao, CL et J Carbon, "High-frequency transformation of yeast by plasmids containing the cloned yeast ARG4 gene," Proc Natl Acad Sci U S A. Aug. 1979;76(8):3829-33.

Huisgen, R. in 1,3-Dipolar Cycloaddition Chemistry, vol. 1, 1984; Ed. Padwa A.; John Wiley and Sons, New York, p. 1-176.

Hwang, KJ et al., "Hepatic uptake and degradation of unilamellar sphingomyelin/cholesterol liposomes: a kinetic study," Proc Natl Acad Sci U S A. Jul. 1980;77(7):4030-4.

Ibba, M et al., "Substrate specificity is determined by amino acid binding pocket size in *Escherichia coli* phenylalanyl-tRNA synthetase," Biochemistry. Jun. 14, 1994;33(23):7107-12.

Ibba, M and H Hennecke, "Relaxing the substrate specificity of an aminoacyl-tRNA synthetase allows in vitro and in vivo synthesis of proteins containing unnatural amino acids," FEBS Lett. May 15, 1995;364(3):272-5.

Ito, H. et al., "Transformation of intact yeast cells treated with alkali cations," J. Bacteriol. 1983; 153(1):163-8.

Jackson, DY et al. "A designed peptide ligase for total synthesis of ribonuclease A with unnatural catalytic residues," Science. Oct. 14, 1994;266(5183):243-7.

Jakobsson, PJ et al., "Identification and characterization of a novel human microsomal glutathione S-transferase with leukotriene C4 synthase activity and significant sequence identity to 5-lipoxygenase-activating protein and leukotriene C4 synthase," J Biol Chem. Sep. 6, 1996;271(36):22203-10.

Jencks, W.P., "Studies on the Mechanism of Oxime and Semicarbazone Formation," J. Am. Chem. Soc.; 1959; 81(2):475-481.

Joppich, M. et al. "Peptides Flanked by Two Polymer Chains, 1; Synthesis of Glycyl-L-tryptophylglycine Substituted by Poly(ethylene oxide) at both the Carboxy and the Amino End Groups," Makromol. Chem. 1979;180:1381-4.

Kaiser, ET. "Synthetic approaches to biologically active peptides and proteins including enzymes," Acc Chem Res, (1989); 22(2):47-54.

Kaiser, ET et al. "The chemical modification of enzymatic specificity," Annu Rev Biochem. 1985;54:565-95.

Kaiser, ET and DS Lawrence. "Chemical mutation of enzyme active sites," Science. Nov. 2, 1984;226(4674):505-11.

Karlin, S and SF Altschul "Applications and statistics for multiple high-scoring segments in molecular sequences," Proc Natl Acad Sci U S A. Jun. 15, 1993;90(12):5873-7.

Kayser, B., et al., "Alkyne bridged alpha- amino acids by palladium mediated coupling of alkynes with N-t-Boc-4-iodo-phenylalanine methyl ester," Tetrahedron (1997); 53(7): 2475-2484.

Kelly, JM and MJ Hynes, "Transformation of *Aspergillus niger* by the amdS gene of *Aspergillus nidulans*," EMBO J. 1985; 4(2):475-479.

Kiick, K. L. and D. A. Tirrell, "Protein Engineering by In Vivo Incorporation of Non-Natural Amino Acids: Control of Incorporation of Methionine Analogues by Methionyl-tRNA Synthetase," Tetrahedron (2000), 56:9487-9493.

Kiick, KL et al., "Incorporation of azides into recombinant proteins for chemoselective modification by the Staudinger ligation," Proc Natl Acad Sci U S A. Jan. 8, 2002;99(1):19-24. Epub Dec. 18, 2001.

Kim, DM and JR Swartz, "Regeneration of adenosine triphosphate from glycolytic intermediates for cell-free protein synthesis," Biotechnol Bioeng. Aug. 20, 2001;74(4):309-16.

Kim, DM and JR Swartz, "Oxalate improves protein synthesis by enhancing ATP supply in a cell-free system derived from *Escherichia coli*," Biotechnology Letters, 2000; 22:1537-1542.

Kim, DM, and JR Swartz, "Prolonging cell-free protein synthesis by selective reagent additions," Biotechnol Prog. May-Jun. 2000;16(3):385-90.

Kim, DM, and JR Swartz, "Prolonging cell-free protein synthesis with a novel ATP regeneration system," Biotechnol Bioeng. 1999;66(3):180-8.

King, F.E. & Kidd, D.A.A. "A New Synthesis of Glutamine and of γ-Dipeptides of Glutamic Acid from Phthylated Intermediates," J. Chem. Soc. 1949; 3315-3319.

Kingsman, AJ et al., "Replication in *Saccharomyces cerevisiae* of plasmid pBR313 carrying DNA from the yeast trpl region," Gene. Oct. 1979;7(2):141-52.

Kitts, PA et al. "Linearization of baculovirus DNA enhances the recovery of recombinant virus expression vectors," Nucleic Acids Res. Oct. 11, 1990;18(19):5667-72.

Klein, TM et al., "High-velocity microprojectiles for delivering nucleic acids into living cells," Nature 1987; 327(6117):70-73.

Kobayashi, T. et al., "Structural basis for orthogonal tRNA specificities of tyrosyl-tRNA synthetases for genetic code expansion," Nature Structural Biology (2003); 10(6):425-432.

Kogan, TP. "The synthesis of substituted methoxy-poly(ethyleneglycol) derivatives suitable for selective protein modification," Synthetic Comm. 1992; 22(16):2417-24.

Kool, ET. "Synthetically modified DNAs as substrates for polymerases," Curr Opin Chem Biol. Dec. 2000;4(6):602-8.

Koskinen, A.M.P. & Rapoport, H. "Synthesis of 4-Substituted Prolines as Conformationally Constrained Amino Acid Analogues," J. Org. Chem. (1989) 54(8):1859-1866.

Kost, TA et al., "Production of a urokinase plasminogen activator-IgG fusion protein (uPA-IgG) in the baculovirus expression system," Gene. Apr. 29, 1997;190(1):139-44.

Kramer, W et al., "The gapped duplex DNA approach to oligonucleotide-directed mutation construction," Nucleic Acids Res. Dec. 21, 1984;12(24):9441-56.

Kramer, W & Fritz HJ. "Oligonucleotide-directed construction of mutations via gapped duplex DNA" Methods Enzymol. 1987;154:350-67.

Kramer, W. et al., "Improved enzymatic in vitro reactions in the gapped duplex DNA approach to oligonucleotide-directed construction of mutations," Nucleic Acids Res. Jul. 25, 1988;16(14B):7207.

Kramer, B. et al., "Different base/base mismatches are corrected with different efficiencies by the methyl-directed DNA mismatch-repair system of *E. coli*," Cell. Oct. 1984;38(3):879-87.

Kreitman, RJ and I. Pastan "Purification and characterization of IL6-PE4E, a recombinant fusion of interleukin 6 with *Pseudomonas exotoxin*," Bioconjug Chem. Nov.-Dec. 1993;4(6):581-5.

Krieg, UC, et al. "Photocrosslinking of the signal sequence of nascent preprolactin to the 54-kilodalton polypeptide of the signal recognition particle," Proc Natl Acad Sci U S A. Nov. 1986;83(22):8604-8.

Kunitani, M. et al., "Reversed-phase chromatography of interleukin-2 muteins," J Chromatogr. May 30, 1986;359:391-402.

Kunkel, "The efficiency of oligonucleotide directed mutagenesis," in Nucleic Acids & Molecular Biology 1987; Eckstein, F. and Lilley, D.M.J. eds.; Springer Verlag, Berlin; 124-135.

Kunkel, TA "Rapid and efficient site-specific mutagenesis without phenotypic selection," Proc Natl Acad Sci U S A. Jan. 1985;82(2):488-92.

Kunkel, TA et al., "Rapid and efficient site-specific mutagenesis without phenotypic selection," Methods Enzymol. 1987;154:367-82.

Kunze, G et al., "Transformation of the industrially important yeasts *Candida maltosa* and *Pichia guilliermondii*," J. Basic Microbiol. 1985; 25:141-4.

Kurtz et al., "Integrative transformation of *Candida albicans*, using a cloned *Candida* ADE2 gene," Mol Cell Biol. Jan. 1986;6(1):142-9.

Kurtzhals, P et al., "Albumin binding of insulins acylated with fatty acids: characterization of the ligand-protein interaction and correlation between binding affinity and timing of the insulin effect in vivo," Biochem J. Dec. 15, 1995;312 ( Pt 3):725-31.

Langer, R et al., "Biocompatibility of polymeric delivery systems for macromolecules," J Biomed Mater Res. Mar. 1981;15(2):267-77.

Langer, R. "Controlled release of macromolecules," Chem. Tech. 1982; 12: 98-105.

Liebman, JM et al., "When less is more: enhanced baculovirus production of recombinant proteins at very low multiplicities of infection," Biotechniques. Jan. 1999;26(1):36-8, 40, 42.

Ling, MM et BH Robinson, "Approaches to DNA mutagenesis: an overview" Anal Biochem. Dec. 15, 1997;254(2):157-78.

Liu, H. et al. "A Method for the Generation of Glycoprotein Mimetics," J. Am. Chem. Soc. 2003 125(7): 1702-1703.

Liu, D.R. & Schultz, P.G. "Progress toward the evolution of an organism with an expanded genetic code," Proc Natl Acad Sci U S A. Apr. 27, 1999;96(9):4780-5.

Lorimer, I. A. et I. Pastan, "Random recombination of antibody single chain Fv sequences after fragmentation with DNaseI in the presence of Mn2+," Nucleic Acids Res. Aug. 11, 1995;23(15):3067-8.

Lu, T. et al. "Probing ion permeation and gating in a K +channel with backbone mutations in the selectivity filter," Nature Neurosci. Mar. 2001;4(3):239-246.

Luckow, VA and MD Summers, "High level expression of nonfused foreign genes with *Autographa californica* nuclear polyhedrosis virus expression vectors," Virology. May 1989;170(1):31-9.

Ma, C et al., "In vitro protein engineering using synthetic tRNA(Ala) with different anticodons," Biochemistry. Aug. 10, 1993;32(31):7939-45.

Magliery, TJ et al. "Expanding the Genetic Code: Selection of Efficient Suppressors of Four-base Codons and Identification of "Shifty" Four-base Codons with a Library Approach in *Escherichia coli*," J Mol Biol. Mar. 30, 2001;307(3):755-69.

Mahal, L. K., et al., "Engineering chemical reactivity on cell surfaces through oligosaccharide biosynthesis," Science. May 16, 1997;276(5315):1125-8.

Makrides, SC et al., "Extended in vivo half-life of human soluble complement receptor type 1 fused to a serum albumin-binding receptor," J Pharmacol Exp Ther. Apr. 1996;277(1):534-42.

Mamot, C, et al., "Epidermal growth factor receptor (EGFR)-targeted immunoliposomes mediate specific and efficient drug delivery to EGFR- and EGFRvIII-overexpressing tumor cells," Cancer Res. Jun. 15, 2003;63(12):3154-61.

Mandecki, W. Oligonucleotide-directed double-strand break repair in plasmids of *Escherichia coli*: a method for site-specific mutagenesis, Proc Natl Acad Sci U S A. Oct. 1986;83(19):7177-81.

Mann, SG and LA King, "Efficient transfection of insect cells with baculovirus DNA using electroporation," J Gen Virol. Dec. 1989;70 (Pt 12):3501-5.

Matsoukas, JM et al., "Differences in backbone structure between angiotensin II agonists and type I antagonists," J Med Chem. Nov. 10, 1995;38(23):4660-9.

McMinn, DL et al., "Efforts toward Expansion of the Genetic Alphabet: DNA Polymerase Recognition of a Highly Stable, Self-Pairing Hydrophobic Base," J. Am. Chem. Soc. 1999; 121(49):11585-6.

Meggers, E et al., "A Novel Copper-Mediated DNA Base Pair," J. Am. Chem. Soc. 2000; 122(43):10714-10715.

Mehvar, R., "Modulation of the pharmacokinetics and pharmacodynamics of proteins by polyethylene glycol conjugation" J Pharm Pharm Sci. Jan.-Apr. 2000;3(1):125-36.

Mendel, D, et al. "Site-directed mutagenesis with an expanded genetic code," Annu Rev Biophys Biomol Struct. 1995;24:435-62.

Miller, LK, "Baculoviruses as gene expression vectors," Ann. Rev. Microbiol. 1988; 42:177-99.

Miller, LK. "Insect baculoviruses: powerful gene expression vectors," Bioessays. Oct. 1989;11(4):91-5.

Miller, JC et al. "Flash decaging of tyrosine sidechains in an ion channel," Neuron. Apr. 1998;20(4):619-24.

Minks, C. et al., Noninvasive tracing of recombinant proteins with "fluorophenylalanine-fingers," Anal Biochem. Aug. 15, 2000;284(1):29-34.

Miyanohara, A et al., "Expression of hepatitis B surface antigen gene in yeast," Proc Natl Acad Sci U S A. Jan. 1983;80(1):1-5.

Moore, B. et al., "Quadruplet codons: implications for code expansion and the specification of translation step size," J. Mol. Biol. 2000; 298(2):195-209.

Mosbach, K. et al., "Formation of proinsulin by immobilized *Bacillus subtilis*," Nature Apr. 1983; 302:543-545.

Nakamaye, KL & Eckstein F, "Inhibition of restriction endonuclease Nci I cleavage by phosphorothioate groups and its application to oligonucleotide-directed mutagenesis" Nucleic Acids Res. Dec. 22, 1986;14(24):9679-98.

Nakatsuka, T., et al. "Peptide segment coupling catalyzed by the semisynthetic enzyme thiosubtilisin," J Am Chem Soc, 1987; 109(12): 3808-3810.

Nambiar, KP et al., "Total synthesis and cloning of a gene coding for the ribonuclease S protein," Science (1984) 223: 1299-1301.

Needleman, SB and Wunsch CD, "A general method applicable to the search for similarities in the amino acid sequence of two proteins," J Mol Biol. Mar. 1970;48(3):443-53.

Neet, KE et al. "Properties of thiol-subtilisin. The consequences of converting the active serine residue to cysteine in a serine protease," J Biol Chem. Dec. 25, 1968;243(24):6392-401.

Nielsen, UB, et al., "Therapeutic efficacy of anti-ErbB2 immunoliposomes targeted by a phage antibody selected for cellular endocytosis," Biochim Biophys Acta. Aug. 19, 2002;1591(1-3):109-118.

Nomura, T. et al., "Purification, cDNA Cloning, and Expression of UDP-Gal: Glucosylceramide -1,4-Galactosyltransferase from Rat Brain," J. Biol. Chem. 1998; 273(22):13570-7.

Noren, CJ et al. "A general method for site-specific incorporation of unnatural amino acids into proteins," Science. Apr. 14, 1989;244(4901):182-8.

Nowak, MW et al., "Nicotinic receptor binding site probed with unnatural amino acid incorporation in intact cells," Science. Apr. 21, 1995;268(5209):439-42.

Ogawa, AK et al., "Efforts toward the Expansion of the Genetic Alphabet: Information Storage and Replication with Unnatural Hydrophobic Base Pairs," J. Am. Chem. Soc. 2000; 122(14):3274-3287.

Ogawa, AK et al., "Rational Design of an Unnatural Base Pair with Increased Kinetic Selectivity," J. Am. Chem. Soc. 2000; 122(36); 8803-8804.

Ohtsuka, E et al., "An alternative approach to deoxyoligonucleotides as hybridization probes by insertion of deoxyinosine at ambiguous codon positions," J Biol Chem. Mar. 10, 1985;260(5):2605-8.

Olson et al. "Preparation and Characterization of Poly(ethylene glycol)yated Human Growth Hormone Antagonist," in Poly(ethylene glycol) Chemistry & Biological Applications, 1997; Eds. JM Harris & S. Zalipsky; ACS, Washington, D.C., 170-181.

Padwa, A. "Intermolecular 1,3-Dipolar Cycloadditions," in Comprehensive Organic Synthesis, vol. 4, (1991) Ed. Trost, B. M.; Pergamon, Oxford, 1069-1109.

Palva, I et al., "Secretion of interferon by *Bacillus subtilis*," Gene. May-Jun. 1983;22(2-3):229-35.

Park, JW, et al., "Development of anti-p185HER2 immunoliposomes for cancer therapy," Proc Natl Acad Sci U S A. Feb. 28, 1995;92(5):1327-31.

Park, JW, et al., "Anti-HER2 immunoliposomes: enhanced efficacy attributable to targeted delivery," Clin Cancer Res. Apr. 2002;8(4):1172-81.

Patnaik, R. and JR Swartz, "*E. coli*-based in vitro transcription/translation: in vivo-specific synthesis rates and high yields in a batch system," Biotechniques. May 1998;24(5):862-8.

Pearson, WR and DJ Lipman, "Improved tools for biological sequence comparison," Proc Natl Acad Sci U S A. Apr. 1988;85(8):2444-8.

Pepinsky, RB., et al., "Improved pharmacokinetic properties of a polyethylene glycol-modified form of interferon-beta-1a with preserved in vitro bioactivity," J Pharmacol Exp Ther. Jun. 2001;297(3):1059-66.

Piccirilli, JA et al., "Enzymatic incorporation of a new base pair into DNA and RNA extends the genetic alphabet," Nature 1990; 343:33-37.

Pintar, A et al. "CX, an algorithm that identifies protruding atoms in proteins," Bioinformatics. Jul. 2002;18(7):980-4.

Pitha, J et al. "Detergents linked to polysaccharides: preparation and effects on membranes and cells," Eur J Biochem. Feb. 15, 1979;94(1):11-8.

Polgar, L. and ML Bender. "A new enzyme containing a synthetically formed active site. Thiol-subtilisin." J. Am Chem Soc., 1966; 88(13): 3153-3154.

Pollack, SJ et al. "Introduction of nucleophiles and spectroscopic probes into antibody combining sites," Science. Nov. 18, 1988;242(4881):1038-40.

Preneta, AZ. "Separation on the basis of size: gel permeation chromatography," in Protein Purification Methods, a practical approach, 1989; Eds. Harris & Angal; IRL Press, Oxford; 293-306.

Raibaud, O et M Schwartz. "Positive control of transcription initiation in bacteria," Annu Rev Genet. 1984;18:173-206.

Reverey, H. et al., "Differential Fatty Acid Selection during Biosynthetic S-Acylation of a Transmembrane Protein (HEF) and Other Proteins in Insect Cells (Sf9) and in Mammalian Cells (CV1)," J. Biol. Chem. 1996; 271(39):23607-10.

Rivier, J et R McClintock, "Reversed-phase high-performance liquid chromatography of insulins from different species," J Chromatogr. Sep. 23, 1983;268(1):112-9.

Roberts, et al., "Generation of an antibody with enhanced affinity and specificity for its antigen by protein engineering," Nature 1987;328:731-734.

Roberts, RW and JW Szostak, "RNA-peptide fusions for the in vitro selection of peptides and proteins," Proc Natl Acad Sci U S A. Nov. 11, 1997;94(23):12297-302.

Roggenkamp, R. et al., "Transformation of the methylotrophic yeast *Hansenula polymorpha* by autonomous replication and integration vectors," Mol. Genetics and Genomics 1986;202(2):302-8.

Romani et al. "Synthesis of unsymmetrical cystine peptides: directed disulfide pairing with the sulfenohydrazide method," in Chemistry of Peptides and Proteins 1984; eds. Voelter, W. et al.; Walter de Gruyter et al., Berlin; vol. 2:29-33.

Romanos, MA et al., "Foreign gene expression in yeast: a review," Yeast. Jun. 1992;8(6):423-88.

Rosenthal, GA. "L-canaline: a potent antimetabolite and anticancer agent from leguminous plants," Life Sci.1997;60(19):1635-41.

Rossolini, GM et al., "Use of deoxyinosine-containing primers vs degenerate primers for polymerase chain reaction based on ambiguous sequence information," Mol. Cell. Probes 1994; 8:91-98.

Rostovtsev, VV et al., "A stepwise huisgen cycloaddition process: copper(I)-catalyzed regioselective "ligation" of azides and terminal alkynes," Angew Chem Int Ed Engl Jul. 15, 2002;41(14):2596-9.

Rowles, J et al., "Cloning and characterization of PDK4 on 7q21.3 encoding a fourth pyruvate dehydrogenase kinase isoenzyme in human," J Biol Chem. Sep. 13, 1996;271(37):22376-82.

Sakmar, TP and Khorana HG, "Total synthesis and expression of a gene for the alpha-subunit of bovine rod outer segment guanine nucleotide-binding protein (transducin)" Nucleic Acids Res. Jul. 25, 1988;16(14A):6361-72.

Sandler and Karo, "Polyoxyalkylation of hydroxyl compounds," in Polymer Synthesis, vol. 3, 1980; Academic Press, New York, 138-161.

Sartore, L et al., "Enzyme modification by MPEG with an amino acid or peptide as spacer arms," Appl Biochem Biotechnol. Jan. 1991;27(1):45-54.

Sawhney, AS et al., "Bioerodible Hydrogels Based on Photopolymerized Poly(ethylene glycol)-co-poly(alpha-hydroxy acid) Diacrylate Macromers," Macromolecules 1993; 26(4):581-7.

Saxon, E and C. Bertozzi, "Cell Surface Engineering by a Modified Staudinger Reaction," Science (2000); 287(5460):2007-2010.

Sayers, JR et al., "Strand specific cleavage of phosphorothioate-containing DNA by reaction with restriction endonucleases in the presence of ethidium bromide" Nucleic Acids Res. Feb. 11, 1988;16(3):803-14.

Sayers, JR, et al. "5'-3' exonucleases in phosphorothioate-based oligonucleotide-directed mutagenesis," Nucleic Acids Res. Feb. 11, 1988;16(3):791-802.

Schanbacher, FL et al. "Galactosyltransferase Acceptor Specificity of the Lactose Synthetase A Protein," J. Biol. Chem. 1970; 245(19):5057-5061.

Schmidt, M et al., "Baculovirus-mediated large-scale expression and purification of a polyhistidine-tagged rubella virus capsid protein," Protein Expr Purif. Apr. 1998;12(3):323-30.

Schneider, E., et al., "Functional Purification of a Bacterial ATP-Binding Cassette Transporter Protein (MalK) from the Cytoplasmic Fraction of an Overproducing Strain," Protein Expr. Purif. 1995; 6(1):10-14.

Schnolzer, M. and SBH Kent. "Constructing proteins by dovetailing unprotected synthetic peptides: backbone-engineered HIV protease," Science. Apr. 10, 1992;256(5054):221-5.

Scouten, WH. "A survey of enzyme coupling techniques," Methods Enzymol. 1987;135:30-65.

Shao, J and JP Tam, "Unprotected Peptides as Building Blocks for the Synthesis of Peptide Dendrimers with Oxime, Hydrazone, and Thiazolidine Linkages," J. Am. Chem. Soc. 1995; 117(14):3893-3899.

Sharma, N et al., "Efficient introduction of aryl bromide functionality into proteins in vivo," FEBS Lett. Feb. 4, 2000;467(1):37-40.

Shimatake, H et M Rosenberg, "Purified λ regulatory protein cII positively activates promoters for lysogenic development," Nature Jul. 1981; 292:128-132.

Shine, J and L Dalgarno, "Determinant of cistron specificity in bacterial ribosomes," Nature. Mar. 6, 1975;254(5495):34-8.

Sidman, KR et al., "Controlled release of macromolecules and pharmaceuticals from synthetic polypeptides based on glutamic acid," Biopolymers. Jan. 1983;22(1):547-56.

Sieber, V. et al., "Libraries of hybrid proteins from distantly related sequences," Nature Biotechnology, May 2001;19:456-460.

Siffert, W et al., "Association of a human G-protein beta3 subunit variant with hypertension," Nat Genet. Jan. 1998;18(1):45-8.

Sikorski, RS et al., "A System of Shuttle Vectors and Yeast Host Strains Designed for Efficient Manipulation of DNA in Saccharomyces cerevisiae," Genetics (1989) 122:19-27.

Sisk, WP et al., "High-level expression and purification of secreted forms of herpes simplex virus type 1 glycoprotein gD synthesized by baculovirus-infected insect cells," J Virol. Feb. 1994;68(2):766-75.

Sjolander, A et al., "The serum albumin-binding region of streptococcal protein G: a bacterial fusion partner with carrier-related properties," J Immunol Methods. Feb. 14, 1997;201(1):115-23.

Smith, M. "In vitro mutagenesis" Ann. Rev. Genet. 1985; 19:423-462.

Smith, GE et al., "Production of human beta interferon in insect cells infected with a baculovirus expression vector," Mol Cell Biol. Dec. 1983;3(12):2156-65.

Stanley, SL et al., "The serine-rich *Entamoeba histolytica* protein is a phosphorylated membrane protein containing O-linked terminal N-acetylglucosamine residues," J Biol Chem. Feb. 24, 1995;270(8):4121-6.

Steitz, JA et al. "Genetic signals and nucleotide sequences in messenger RNA," in Biological Regulation and Development: Gene Expression 1979; ed. R. F. Goldberger; Plenum Press, New York; 349-399.

Stemmer, WPC, "Rapid evolution of a protein in vitro by DNA shuffling," Nature 1994;370(4):389-391.

Stemmer, WP "DNA shuffling by random fragmentation and reassembly: In vitro recombination for molecular evolution," Proc Natl Acad Sci U S A. Oct. 25, 1994;91(22):10747-51.

Studier, FW et BA Moffatt, "Use of bacteriophage T7 RNA polymerase to direct selective high-level expression of cloned genes," J. Mol Biol. May 5, 1986;189(1):113-30.

Subasinghe, N. et al., "Quisqualic acid analogues: synthesis of beta-heterocyclic 2-aminopropanoic acid derivatives and their activity at a novel quisqualate-sensitized site," J Med Chem. Nov. 27, 1992;35(24):4602-7.

Switzer, C et al., "Enzymatic incorporation of a new base pair into DNA and RNA," J. Am. Chem. Soc. 1989; 111(21):8322-8323.

Tabor, S et CC Richardson, "A bacteriophage T7 RNA polymerase/promoter system for controlled exclusive expression of specific genes," Proc Natl Acad Sci U S A. Feb. 1985;82(4):1074-8.

Tae, EL et al., "Efforts toward Expansion of the Genetic Alphabet: Replication of DNA with Three Base Pairs," J. Am. Chem. Soc. 2001; 123(30):7439-7440.

Tang, Y et al., "Fluorinated Coiled-Coil Proteins Prepared In Vivo Display Enhanced Thermal and Chemical Stability," Angew Chem Int Ed Engl. Apr. 17, 2001;40(8):1494-1496.

Taylor, JW et al., "The use of phosphorothioate-modified DNA in restriction enzyme reactions to prepare nicked DNA," Nucleic Acids Res. Dec. 20, 1985;13(24):8749-64.

Taylor, JW et al., "The rapid generation of oligonucleotide-directed mutations at high frequency using phosphorothioate-modified DNA," Nucleic Acids Res. Dec. 20, 1985;13(24):8765-85.

Tijssen, P. "Overview of principles of hybridization and the strategy of nucleic acid assays," in Laboratory Techniques in Biochemistry and Molecular Biology—Hybridization with Nucleic Probes, Part I, 1993; Elsevier Science Publishers, Amsterdam, 19-78.

Tilburn, J. et al., "Transformation by integration in *Aspergillus nidulans*," Gene. Dec. 1983;26(2-3):205-21.

Tondelli, L. et al. "Poly(ethylene Glycol) Imidazolyl Formates as Oligomeric Drug-Binding Matrices," J. Controlled Release 1985;1(4):251-7.

Tornoe, CW et al., "Peptidotriazoles on solid phase: [1,2,3]—triazoles by regiospecific copper(i)-catalyzed 1,3-dipolar cycloadditions of terminal alkynes to azides," J Org Chem. May 3, 2002;67(9):3057-64.

Trotter, KM and HA Wood, "Transfection techniques for producing recombinant baculoviruses," in Methods in Molecular Biology—Baculovirus Expression Protocols, vol. 39 (1995); Ed. C.D. Richardson, 97-107.

Tschumper, G. et al., "Sequence of a yeast DNA fragment containing a chromosomal replicator and the TRP1 gene," Gene 1980; 10(2):157-66.

Turcatti, G et al. "Probing the structure and function of the tachykinin neurokinin-2 receptor through biosynthetic incorporation of fluorescent amino acids at specific sites," J Biol Chem. Aug. 16, 1996;271(33):19991-8.

Van Den Berg, JA et al., "Kluyveromyces as a host for heterologous gene expression: expression and secretion of prochymosin," Biotechnology (N Y). Feb. 1990;8(2):135-9.

Van Hest, JC and DA Tirrell, "Efficient introduction of alkene functionality into proteins in vivo," FEBS Lett. May 22, 1998;428(1-2):68-70.

Van Hest, J. C. et al., "Efficient Incorporation of Unsaturated Methionine Analogues into Proteins in Vivo," J. Am. Chem. Soc.2000 ;122 (7); 1282-1288.

Van Solingen, P. et JB van der Plaat. "Fusion of yeast spheroplasts," J Bacteriol. May 1977;130(2):946-7.

Veronese, FM et al., "Surface modification of proteins. Activation of monomethoxy-polyethylene glycols by phenylchloroformates and modification of ribonuclease and superoxide dismutase," Appl Biochem Biotechnol. Apr. 1985;11(2):141-52.

Vlak, JM et al., "Functional studies on the p10 gene of *Autographa californica* nuclear polyhedrosis virus using a recombinant expressing a p10-beta-galactosidase fusion gene," J Gen Virol. Apr. 1988;69 ( Pt 4):765-76 .

Wang, Q., et al., "Bioconjugation by Copper(I)-Catalyzed Azide-Alkyne [3+2] Cycloaddition," J. Am. Chem. Soc. 2003; 125(11):3192-3193.

Wang, L. et al., "Addition of the keto functional group to the genetic code of *Escherichia coli*," Proc. Natl. Acad. Sci. (2003); 100(1):56-61.

Wang, L et al., "Expanding the genetic code of *Escherichia coli*," Science. Apr. 20, 2001;292(5516):498-500.

Wang, L & PG Schultz, "Expanding the genetic code," Chem Commun (Camb). Jan. 7, 2002;1:1-11.

Weissmann, C. "The cloning of interferon and other mistakes." in Interferon 3 1981; ed. I. Gresser; Academic Press, London, 101-134.

Wells, JA et al., "Importance of hydrogen-bond formation in stabilizing the transition state of subtilisin," Phil. Trans. R. Soc. Lond. A 1986; 317: 415-423.

Wells, JA et al., "Cassette mutagenesis: an efficient method for generation of multiple mutations at defined sites," Gene. 1985;34(2-3):315-23.

Woghiren, C et al. "Protected thiol-polyethylene glycol: a new activated polymer for reversible protein modification," Bioconjug Chem. Sep.-Oct. 1993;4(5):314-8.

Wong, SS et LJ Wong, "Chemical crosslinking and the stabilization of proteins and enzymes," Enzyme Microb Technol. Nov. 1992;14(11):866-74.

Wright, K. "Biotechnology: Insect virus as super-vector?," Nature (1986) 321(6072):718.

Yelton, MM et al., "Transformation of *Aspergillus nidulans* by using a trpC plasmid," Proc Natl Acad Sci U S A. Mar. 1984;81(5):1470-4.

Yelverton, E et al., "Bacterial synthesis of a novel human leukocyte interferon," Nucleic Acids Res. Feb. 11, 1981;9(3):731-41.

Zalipsky, S et al. "Attachment of drugs to polyethylene glycols," Eur. Polymer Journal. 1983 19(12):1177-83.

Zalipsky, S. "Functionalized poly(ethylene glycol) for preparation of biologically relevant conjugates," Bioconjug Chem. Mar.-Apr. 1995;6(2):150-65.

Zhang, Z., et al. "A new strategy for the site-specific modification of proteins in vivo," Biochemistry. Jun. 10, 2003;42(22):6735-46.

Zoller, MJ & M Smith, "Oligonucleotide-directed mutagenesis using M13-derived vectors: an efficient and general procedure for the production of point mutations in any fragment of DNA" Nucleic Acids Res. Oct. 25, 1982;10(20):6487-500.

Zoller, MJ & M. Smith, "Oligonucleotide-directed mutagenesis of DNA fragments cloned into M13 vectors" Methods Enzymol. 1983;100:468-500.

Zoller, MJ & Smith M, "Oligonucleotide-directed mutagenesis: a simple method using two oligonucleotide primers and a single-stranded DNA template," Methods Enzymol. 1987;154:329-50.

Liu K. et al., "Antagonists of Luteinizing Hormone Releasing Hormone with Novel Unnatural Amino Acids at Position Six", International Journal of Peptide and Protein Research, (1990) 35(2):157-160.

* cited by examiner

Helical Comparison between GLP-1 and Exendin-4

| Residue | 7 | 17 | 36 |
|---|---|---|---|
| GLP-1 | HAEGTFTSDV | SSYLEGQAAK | EFIAWLVKGR |
| Exendin-4 | HGEGTFTSDL | SKQMEEEAVR | LFIEWLKNGG PSSGAPPPS |

\* = conserved insert Met for CNBr cleavage trp LE polypeptide leader :

KAIFVLKGSLDRDLDSRIELELRTDHKELSEHLLLVDLARNDLARIATPGSRYVADL
TKVDRYSYVLHLVSRVVGELRHDLDALHAYRAALNLGTLSGAPKVRAKLW

Figure 10

```
         638                                               673
T20     YTSLIHSLIEESQNQQEKNEQELLELDKWASLWNWF
        ***    *    *
M       YTSLIHSLIEESQNQQEKNEQELLELDKWASLWNWF 630                                                       673
TEX     EWDREINNYTSLIHSLIEESQNQQEKNEQELLELDKWASLWNWF
        * *  *** ****    *      *
M       EWDREINNYTSLIHSLIEESQNQQEKNEQELLELDKWASLWNWF
```

\* non-natural amino acid
M=mutant

```
                                  *
T20-Mut651        YTSLIHSLIEESQNQQEKNEQELLELDKWASLWNWF
                        *
TEX-Mut636   EWDREINNYTSLIHSLIEESQNQQEKNEQELLELDKWASLWNWF
```

BIOSYNTHETIC POLYPEPTIDES UTILIZING NON-NATURALLY ENCODED AMINO ACIDS

CROSS-REFERENCE TO RELATED APPLICATIONS

This application claims priority to U.S. provisional patent application Ser. No. 60/590,035, filed Jul. 21, 2004, and U.S. provisional patent application 60/659,709 filed Mar. 7, 2005, the specifications of which are incorporated herein in their entirety.

FIELD OF THE INVENTION

This invention relates to biosynthetic polypeptides, and fusion proteins that comprise or are made utilizing at least one non-naturally-encoded amino acid.

BACKGROUND OF THE INVENTION

Peptides are widely used in research and medical practice, and it can be expected that their importance will increase as challenges to manufacturing and performance of the peptide products are addressed. Therapeutic peptides such as those described herein are referred to as biosynthetic polypeptides (BSPs). Many endogenous peptides have been described as key components of biological processes. Some of these peptides have been identified as key therapeutic agents for the management of various disorders. In general, endogenous peptides are more desirable as therapeutic agents than synthetic peptides with non-native sequences, because they do not produce an immune response due to their endogenous character. In addition, endogenous peptides are highly specific for their target receptors and are easy to synthesize and manufacture. However, a major difficulty with the delivery of such therapeutic peptides is their short plasma half-life, mainly due to rapid serum clearance and proteolytic degradation via the action of peptidases.

When native peptides or analogues thereof are used in therapy, it is generally found that they have a high rate of degradation and/or clearance. A high rate of clearance of a therapeutic agent is inconvenient in cases where it is desired to maintain a high blood level thereof over a prolonged period of time since repeated administrations will then be necessary. Examples of peptides which have a high rate of degradation and/or clearance include: ACTH, corticotropin-releasing factor, angiotensin, calcitonin, insulin, glucagon, glucagon-like peptide-1, glucagon-like peptide-2, insulin-like growth factor-1, insulin-like growth factor-2, gastric inhibitory peptide, growth hormone-releasing factor, pituitary adenylate cyclase activating peptide, secretin, enterogastrin, somatostatin, somatotropin, somatomedin, parathyroid hormone, thrombopoietin, erythropoietin, hypothalamic releasing factors, prolactin, thyroid stimulating hormones, endorphins, enkephalins, vasopressin, oxytocin, opioids and analogues thereof, superoxide dismutase, interferon, asparaginase, arginase, arginine deaminase, adenosine deaminase and ribonuclease. In some cases it is possible to influence the release profile of peptides by applying suitable pharmaceutical compositions, but this approach has various shortcomings and is not generally applicable.

Peptidases break a peptide bond in peptides by inserting a water molecule across the bond. Generally, most peptides are broken down by peptidases in the body in a manner of a few minutes or less. In addition, some peptidases are specific for certain types of peptides, making their degradation even more rapid. Thus, if a peptide is used as a therapeutic agent, its activity is generally reduced as the peptide quickly degrades in the body due to the action of peptidases.

One way to overcome this disadvantage is to administer large dosages of the therapeutic peptide of interest to the patient so that even if some of the peptide is degraded, enough remains to be therapeutically effective. However, this method is quite uncomfortable for the patient. Since most therapeutic peptides cannot be administered orally, the therapeutic peptide would have to be either constantly infused, frequently administered by intravenous injections, or administered frequently by the inconvenient route of subcutaneous injections. The need for frequent administration also results in an unacceptably high projected cost per treatment course for many potential peptide therapeutics. The presence of large amounts of degraded peptide may also generate undesired side effects.

Discomfort in administration and high costs are two reasons why most therapeutic peptides with attractive bioactivity profiles are not developed as drug candidates. Instead, these therapeutic peptides are used as templates for the development of peptidomimetic compounds to substitute for the therapeutic peptide. Biotechnology and large pharmaceutical firms frequently undertake lengthy and expensive optimization programs to attempt to develop non-peptide, organic compounds which mimic the activity seen with therapeutic peptides without incurring an unacceptable side effect profile. For example, cyclic peptides, peptidomimetics and small molecules coming from expensive SAR (Structure Activity Relationship) and molecular modeling studies have led to the development of an incredible amount of peptide mimics. However, these peptide mimics in no way reflect the exact original biological nature of the therapeutic peptide, and thus are inferior to the endogenous therapeutic peptide as therapeutic agents.

An alternative to creating peptide mimics is to block the action of peptidases to prevent degradation of the therapeutic peptide or to modify the therapeutic peptides in such a way that their degradation is slowed down while still maintaining biological activity. Such methods include conjugation with polymeric materials such as dextrans, polyvinyl pyrrolidones, glycopeptides, polyethylene glycol and polyamino acids, conjugation with adroitin sulfates, as well as conjugation with polysaccharides, low molecular weight compounds such as aminolethicin, fatty acids, vitamin B12, and glycosides. Several methods include ex vivo conjugation with carrier proteins. Improvements to therapeutic peptides are needed such that the production of randomized conjugates and/or the decreases in therapeutic activity resulting from the addition of polymeric material are prevented. There is thus a need for improved therapeutic peptides that are protected from peptidase activity and have longer duration of action in vivo, while maintaining low toxicity yet retaining the therapeutic advantages of the modified peptides.

Covalent attachment of the hydrophilic polymer poly(ethylene glycol), abbreviated PEG, is a method of increasing water solubility, bioavailability, increasing serum half-life, increasing therapeutic half-life, modulating immunogenicity, modulating biological activity, or extending the circulation time of many biologically active molecules, including proteins, peptides, and particularly hydrophobic molecules. PEG has been used extensively in pharmaceuticals, on artificial implants, and in other applications where biocompatibility, lack of toxicity, and lack of immunogenicity are of importance. In order to maximize the desired properties of PEG, the total molecular weight and hydration state of the PEG polymer or polymers attached to the biologically active molecule must be sufficiently high to impart the advantageous characteristics typically associated with PEG polymer attachment, such as increased water solubility and circulating half life, while not adversely impacting the bioactivity of the parent molecule.

PEG derivatives are frequently linked to biologically active molecules through reactive chemical functionalities, such as lysine, cysteine and histidine residues, the N-terminus and carbohydrate moieties. Proteins and other molecules often have a limited number of reactive sites available for polymer attachment. Often, the sites most suitable for modification via polymer attachment play a significant role in receptor binding, and are necessary for retention of the biological activity of the molecule. As a result, indiscriminate attachment of polymer chains to such reactive sites on a biologically active molecule often leads to a significant reduction or even total loss of biological activity of the polymer-modified molecule. R. Clark et al., (1996), *J. Biol. Chem.*, 271:21969-21977. To form conjugates having sufficient polymer molecular weight for imparting the desired advantages to a target molecule, prior art approaches have typically involved random attachment of numerous polymer arms to the molecule, thereby increasing the risk of a reduction or even total loss in bioactivity of the parent molecule.

Reactive sites that form the loci for attachment of PEG derivatives to proteins are dictated by the protein's structure. Proteins, including enzymes, are composed of various sequences of alpha-amino acids, which have the general structure $H_2N-CHR-COOH$. The alpha amino moiety ($H_2N-$) of one amino acid joins to the carboxyl moiety ($-COOH$) of an adjacent amino acid to form amide linkages, which can be represented as $-(NH-CHR-CO)_n-$, where the subscript "n" can equal hundreds or thousands. The fragment represented by R can contain reactive sites for protein biological activity and for attachment of PEG derivatives.

For example, in the case of the amino acid lysine, there exists an $-NH_2$ moiety in the epsilon position as well as in the alpha position. The epsilon $-NH_2$ is free for reaction under conditions of basic pH. Much of the art in the field of protein derivatization with PEG has been directed to developing PEG derivatives for attachment to the epsilon $-NH_2$ moiety of lysine residues present in proteins. "Polyethylene Glycol and Derivatives for Advanced PEGylation", Nektar Molecular Engineering Catalog, 2003, pp. 1-17. These PEG derivatives all have the common limitation, however, that they cannot be installed selectively among the often numerous lysine residues present on the surfaces of proteins. This can be a significant limitation in instances where a lysine residue is important to protein activity, existing in an enzyme active site for example, or in cases where a lysine residue plays a role in mediating the interaction of the protein with other biological molecules, as in the case of receptor binding sites.

A second and equally important complication of existing methods for protein PEGylation is that the PEG derivatives can undergo undesired side reactions with residues other than those desired. Histidine contains a reactive imino moiety, represented structurally as $-N(H)-$, but many chemically reactive species that react with epsilon $-NH_2$ can also react with $-N(H)-$. Similarly, the side chain of the amino acid cysteine bears a free sulfhydryl group, represented structurally as $-SH$. In some instances, the PEG derivatives directed at the epsilon $-NH_2$ group of lysine also react with cysteine, histidine or other residues. This can create complex, heterogeneous mixtures of PEG-derivatized bioactive molecules and risks destroying the activity of the bioactive molecule being targeted. It would be desirable to develop PEG derivatives that permit a chemical functional group to be introduced at a single site within the protein that would then enable the selective coupling of one or more PEG polymers to the bioactive molecule at specific sites on the protein surface that are both well-defined and predictable.

In addition to lysine residues, considerable effort in the art has been directed toward the development of activated PEG reagents that target other amino acid side chains, including cysteine, histidine and the N-terminus. See, e.g., U.S. Pat. No. 6,610,281 which is incorporated by reference herein, and "Polyethylene Glycol and Derivatives for Advanced PEGylation", Nektar Molecular Engineering Catalog, 2003, pp. 1-17. A cysteine residue can be introduced site-selectively into the structure of proteins using site-directed mutagenesis and other techniques known in the art, and the resulting free sulfhydryl moiety can be reacted with PEG derivatives that bear thiol-reactive functional groups. This approach is complicated, however, in that the introduction of a free sulfhydryl group can complicate the expression, folding and stability of the resulting protein. Thus, it would be desirable to have a means to introduce a chemical functional group into bioactive molecules that enables the selective coupling of one or more PEG polymers to the protein while simultaneously being compatible with (i.e., not engaging in undesired side reactions with) sulfhydryls and other chemical functional groups typically found in proteins.

As can be seen from a sampling of the art, many of these derivatives that have been developed for attachment to the side chains of proteins, in particular, the $-NH_2$ moiety on the lysine amino acid side chain and the $-SH$ moiety on the cysteine side chain, have proven problematic in their synthesis and use. Some form unstable linkages with the protein that are subject to hydrolysis and therefore decompose, degrade, or are otherwise unstable in aqueous environments, such as in the bloodstream. Some form more stable linkages but are subject to hydrolysis before the linkage is formed, which means that the reactive group on the PEG derivative may be inactivated before the protein can be attached. Some are somewhat toxic and are therefore less suitable for use in vivo. Some are too slow to react to be practically useful. Some result in a loss of protein activity by attaching to sites responsible for the protein's activity. Some are not specific in the sites to which they will attach, which can also result in a loss of desirable activity and in a lack of reproducibility of results. In order to overcome the challenges associated with modifying proteins with poly(ethylene glycol) moieties, PEG derivatives have been developed that are more stable (e.g., U.S. Pat. No. 6,602,498, which is incorporated by reference herein) or that react selectively with thiol moieties on molecules and surfaces (e.g., U.S. Pat. No. 6,610,281, which is incorporated by reference herein). There is clearly a need in the art for PEG derivatives that are chemically inert in physiological environments until called upon to react selectively to form stable chemical bonds.

Recently, an entirely new technology in the protein sciences has been reported, which promises to overcome many of the limitations associated with site-specific modifications of proteins. Specifically, new components have been added to the protein biosynthetic machinery of the prokaryote *Escherichia coli* (*E. coli*) (e.g., L. Wang, et al., (2001), *Science* 292:498-500) and the eukaryote *Sacchromyces cerevisiae* (*S. cerevisiae*) (e.g., J. Chin et al., *Science* 301:964-7 (2003)), which has enabled the incorporation of non-genetically encoded amino acids to proteins in vivo. A number of new amino acids with novel chemical, physical or biological properties, including photoaffinity labels and photoisomerizable amino acids, keto amino acids, and glycosylated amino acids have been incorporated efficiently and with high fidelity into proteins in *E. coli* and in yeast in response to the amber codon, TAG, using this methodology. See, e.g., J. W. Chin et al., (2002), *Journal of the American Chemical Society* 124:9026-9027; J. W. Chin, & P. G. Schultz, (2002), *Chem Bio Chem* 3(11):1135-1137; J. W. Chin, et al., (2002), *PNAS United States of America* 99:11020-11024; and, L. Wang, & P. G. Schultz, (2002), *Chem. Comm.*, 1:1-11. These studies have demonstrated that it is possible to selectively and routinely introduce chemical functional groups, such as ketone groups, alkyne groups and azide moieties, that are not found in proteins, that are chemically inert to all of the functional groups found in the 20 common, genetically-encoded amino acids and that may be used to react efficiently and selectively to form stable covalent linkages.

The ability to incorporate non-genetically encoded amino acids into proteins permits the introduction of chemical functional groups that could provide valuable alternatives to the naturally-occurring functional groups, such as the epsilon —$NH_2$ of lysine, the sulfhydryl —SH of cysteine, the imino group of histidine, etc. Certain chemical functional groups are known to be inert to the functional groups found in the 20 common, genetically-encoded amino acids but react cleanly and efficiently to form stable linkages. Azide and acetylene groups, for example, are known in the art to undergo a Huisgen [3+2] cycloaddition reaction in aqueous conditions in the presence of a catalytic amount of copper. See, e.g., Tomoe, et al., (2002) *J. Org. Chem.* 67:3057-3064; and, Rostovtsev, et al., (2002) *Angew. Chem. Int. Ed.* 41:2596-2599. By introducing an azide moiety into a protein structure, for example, one is able to incorporate a functional group that is chemically inert to amines, sulfhydryls, carboxylic acids, hydroxyl groups found in proteins, but that also reacts smoothly and efficiently with an acetylene moiety to form a cycloaddition product. Importantly, in the absence of the acetylene moiety, the azide remains chemically inert and unreactive in the presence of other protein side chains and under physiological conditions.

The present invention addresses, among other things, problems associated with the activity and production of biosynthetic polypeptides (BSPs), and also addresses the production of a BSP with improved biological or pharmacological properties, such as improved therapeutic half-life.

BRIEF SUMMARY OF THE INVENTION

This invention provides biosynthetic peptides (BSPs) including, but not limited to, glucagon gene-derived polypeptides such as GLP-1, T-20 polypeptides, membrane fusion inhibitory peptides, and peptide YY peptides, comprising one or more non-naturally encoded amino acids. Any BSP, fragment, analog, or variant thereof with therapeutic activity may be used in this invention. Numerous examples of BSPs that may be used in this invention have been provided. However, the lists provided are not exhaustive and in no way limit the number or type of BSPs that may be used in this invention. Thus, any BSP and/or fragments, analogs, and variants produced from any BSP including novel BSPs may be modified according to the present invention, and used therapeutically.

In some embodiments, the BSP comprises one or more post-translational modifications. In some embodiments, the BSP is linked to a linker, polymer, or biologically active molecule. In some embodiments, the BSP is linked to a bifunctional polymer, bifunctional linker, or at least one additional BSP.

In some embodiments, the non-naturally encoded amino acid is linked to a water soluble polymer. In some embodiments, the water soluble polymer comprises a poly(ethylene glycol) moiety. In some embodiments, the poly(ethylene glycol) molecule is a bifunctional polymer. In some embodiments, the bifunctional polymer is linked to a second polypeptide. In some embodiments, the second polypeptide is a BSP.

In some embodiments, the non-naturally encoded amino acid is linked to a water soluble polymer. In some embodiments, the non-naturally encoded amino acid is linked to the water soluble polymer with a linker. In some embodiments, the non-naturally encoded amino acid is linked to the water soluble polymer with a linker that is biodegradable. In some embodiments, the biodegradable linker can be used to form a prodrug comprising the BSP. In one example of this prodrug approach, the water soluble polymer blocks GLP-1 activity, and degradation of the linker releases active GLP-1. In some embodiments, the non-naturally encoded amino acid is linked to an acyl moiety or acyl chain. In some embodiments, the non-naturally encoded amino acid is linked to an acyl moiety or acyl chain by a linker. In some embodiments, the non-naturally encoded amino acid is linked to an acyl moiety or acyl chain by a poly(ethylene glycol) linker or a prodrug. In some embodiments, the non-naturally encoded amino acid is linked to serum albumin. In some embodiments, the non-naturally encoded amino acid is linked to serum albumin by a linker. In some embodiments, the linker is a poly(ethylene glycol) or a prodrug. In some embodiments, the linker is a dual cleavage prodrug in which step 1 is controlled release of a molecule such as albumin and step 2 is a second cleavage releasing the linker or a portion thereof.

In some embodiments, the BSP comprises an intramolecular bridge between two amino acids present in the BSP. In some embodiments, the BSP comprises one or more non-naturally encoded amino acids. One of the two bridged residues may be a non-naturally encoded amino acid or a naturally encoded amino acid. The non-natural amino acids may be joined by a linker, polymer, or a biologically active molecule.

In some embodiments, the BSP comprises at least two amino acids linked to a water soluble polymer comprising a poly(ethylene glycol) moiety. In some embodiments, at least one amino acid is a non-naturally encoded amino acid.

In some embodiments, one or more non-naturally encoded amino acids are incorporated at any position in the BSP, such as GLP-1, before the first amino acid (at the amino terminus), an addition at the carboxy terminus, or any combination thereof. In some embodiments, one or more non-naturally encoded amino acids are incorporated at any position in GLP-1, including but not limited to, the residues as follows: before the first amino acid at position 7 (i.e. at the N terminus), 7H, 8A, 9E, V16, 17S, 18S, 19Y, 20L, 21E, 22G, 23Q, 24A, 25A, 26K, 27E, 28F, 29I, 30A, 31W, 32L, 33V, 34K, 35G, 36R, 37G, an addition at position 38 (i.e. at the carboxyl terminus), or any combination thereof.

In some embodiments, the non-naturally occurring amino acid at one or more of these positions is linked to a water soluble polymer, including but not limited to, GLP-1 positions: before the first amino acid at position 7 (i.e. at the N terminus), 7H, 8A, 9E, V16, 17S, 18S, 19Y, 20L, 21E, 22G, 23Q, 24A, 25A, 26K, 27E, 28F, 29I, 30A, 31W, 32L, 33V, 34K, 35G, 36R, 37G, an addition at position 38 (i.e. at the carboxyl terminus) or any combination thereof.

In some embodiments, the GLP-1 polypeptides of the invention comprise one or more non-naturally occurring amino acids at one or more of the following positions providing an antagonist: 7, 8, 9, 22, 18, 29, 25, 32, 21, 28, 17, 24, 31, 20, or any combination thereof.

In some embodiments, one or more non-naturally encoded amino acids are incorporated at any position in a T-20 polypeptide (including TEX), before the first amino acid (at the amino terminus), an addition at the carboxy terminus, or any combination thereof. In some embodiments, one or more non-naturally encoded amino acids are incorporated at any position in T-20 (including TEX), including but not limited to, the residues as follows: W631, D632, I635, N636, N637, Y638, T639, S640, L641, L645, N651, or any combination thereof.

In some embodiments, one or more non-naturally encoded amino acids are incorporated at any position in Peptide YY, before the first amino acid (at the amino terminus), an addition at the carboxy terminus, or any combination thereof.

In some embodiments, the BSP comprises a substitution, addition or deletion that modulates affinity of the BSP for a BSP receptor or a binding partner, including, but not limited to, a protein, polypeptide, small molecule, or nucleic acid. In some embodiments, the BSP comprises a substitution, addition, or deletion that increases the stability of the BSP when compared with the stability of the corresponding BSP without the substitution, addition, or deletion. In some embodiments, the BSP comprises a substitution, addition, or deletion that modulates the immunogenicity of the BSP when compared with the immunogenicity of the corresponding BSP without the substitution, addition, or deletion. In some embodiments, the BSP comprises a substitution, addition, or deletion that modulates serum half-life or circulation time of the BSP when compared with the serum half-life or circulation time of the corresponding BSP without the substitution, addition, or deletion.

In some embodiments, the BSP comprises a substitution, addition, or deletion that increases the aqueous solubility of BSP when compared with the aqueous solubility of the corresponding BSP without the substitution, addition, or deletion. In some embodiments, the BSP comprises a substitution, addition, or deletion that increases the solubility of the BSP produced in a host cell when compared with the solubility of the corresponding BSP without the substitution, addition, or deletion. In some embodiments, the BSP comprises a substitution, addition, or deletion that increases the expression of the BSP in a host cell or increases synthesis in vitro when compared with the expression or synthesis of the corresponding BSP without the substitution, addition, or deletion. In some embodiments, the BSP comprises a substitution, addition, or deletion that decreases peptidase or protease susceptibility of the BSP when compared with the peptidase or protease susceptibility of the corresponding BSP without the substitution, addition, or deletion. In some embodiments, the BSP comprises a substitution, addition, or deletion that modulates signal transduction activity of the BSP receptor or binding partner when compared with the activity of the corresponding BSP without the substitution, addition, or deletion. In some embodiments, the BSP comprises a substitution, addition, or deletion that modulates its binding to another molecule such as a receptor when compared with the binding of the corresponding BSP without the substitution, addition, or deletion. In some embodiments, the BSP comprises a substitution, addition, or deletion that modulates the conformation or one or more biological activities of its binding partner when compared with the binding partner's conformation or biological activity after binding of corresponding BSP without the substitution, addition, or deletion.

In some embodiments the amino acid substitutions in the BSP may be with naturally occurring or non-naturally occurring amino acids, provided that at least one substitution is with a non-naturally encoded amino acid.

In some embodiments, the non-naturally encoded amino acid comprises a carbonyl group, an aminooxy group, a hydrazine group, a hydrazide group, a semicarbazide group, an azide group, or an alkyne group.

In some embodiments, the non-naturally encoded amino acid comprises a carbonyl group. In some embodiments, the non-naturally encoded amino acid has the structure:

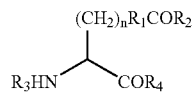

wherein n is 0-10; $R_1$ is an alkyl, aryl, substituted alkyl, or substituted aryl; $R_2$ is H, an alkyl aryl, substituted alkyl, and substituted aryl; and $R_3$ is H, an amino acid, a polypeptide, or an amino terminus modification group, and $R_4$ is H, an amino acid, a polypeptide, or a carboxy terminus modification group.

In some embodiments, the non-naturally encoded amino acid comprises an aminooxy group. In some embodiments, the non-naturally encoded amino acid comprises a hydrazide group. In some embodiments, the non-naturally encoded amino acid comprises a hydrazine group. In some embodiments, the non-naturally encoded amino acid residue comprises a semicarbazide group.

In some embodiments, the non-naturally encoded amino acid residue comprises an azide group. In some embodiments, the non-naturally encoded amino acid has the structure:

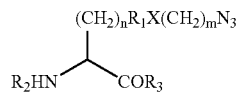

wherein n is 0-10; $R_1$ is an alkyl, aryl, substituted alkyl, substituted aryl or not present; X is O, N, S or not present; m is 0-10; $R_2$ is H, an amino acid, a polypeptide, or an amino terminus modification group, and $R_3$ is H, an amino acid, a polypeptide, or a carboxy terminus modification group.

In some embodiments, the non-naturally encoded amino acid comprises an alkyne group. In some embodiments, the non-naturally encoded amino acid has the structure:

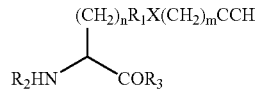

wherein n is 0-10; $R_1$ is an alkyl, aryl, substituted alkyl, or substituted aryl; X is O, N, S or not present; m is 0-10, $R_2$ is H, an amino acid, a polypeptide, or an amino terminus modification group, and $R_3$ is H, an amino acid, a polypeptide, or a carboxy terminus modification group.

In some embodiments, the polypeptide is a BSP agonist, partial agonist, antagonist, partial antagonist, or inverse agonist. In some embodiments, the BSP agonist, partial agonist, antagonist, partial antagonist, or inverse agonist comprises a non-naturally encoded amino acid linked to a water soluble polymer. In some embodiments, the water soluble polymer comprises a poly(ethylene glycol) moiety. In some embodiments, the BSP agonist, partial agonist, antagonist, partial antagonist, or inverse agonist comprises a non-naturally encoded amino acid and one or more post-translational modification, linker, polymer, or biologically active molecule. In some embodiments, the non-naturally encoded amino acid linked to a water soluble polymer is present within the receptor binding region of the BSP or interferes with the receptor binding of the BSP. In some embodiments, the non-naturally encoded amino acid linked to a water soluble polymer is present within the region of the BSP that binds to a binding partner or interferes with the binding of a binding partner to the BSP.

The present invention also provides isolated nucleic acids comprising a polynucleotide that hybridizes under stringent conditions to a nucleotide sequence encoding a polypeptide having the amino acid sequence in SEQ ID NO: 1, 2, 3, 21, 22, 23, or 24 wherein the polynucleotide comprises at least one selector codon. In some embodiments, the selector codon is selected from the group consisting of an amber codon, ochre codon, opal codon, a unique codon, a rare codon, and a four-base codon.

The present invention also provides methods of making a BSP linked to a water soluble polymer. In some embodiments, the method comprises contacting an isolated BSP comprising a non-naturally encoded amino acid with a water soluble polymer comprising a moiety that reacts with the non-naturally encoded amino acid. In some embodiments, the non-naturally encoded amino acid incorporated into the BSP is reactive toward a water soluble polymer that is otherwise unreactive toward any of the 20 common amino acids. In some embodiments, the non-naturally encoded amino acid incorporated into the BSP is reactive toward a linker, polymer, or biologically active molecule that is otherwise unreactive toward any of the 20 common amino acids.

In some embodiments, the BSP linked to the water soluble polymer is made by reacting a BSP comprising a carbonyl-containing amino acid with a poly(ethylene glycol) molecule comprising an aminooxy, hydrazine, hydrazide or semicarbazide group. In some embodiments, the aminooxy, hydrazine, hydrazide or semicarbazide group is linked to the poly(ethylene glycol) molecule through an amide linkage.

In some embodiments, the BSP linked to the water soluble polymer is made by reacting a poly(ethylene glycol) molecule comprising a carbonyl group with a BSP comprising a non-naturally encoded amino acid that comprises an aminooxy, hydrazine, hydrazide or semicarbazide group.

In some embodiments, the BSP linked to the water soluble polymer is made by reacting a BSP comprising an alkyne-containing amino acid with a poly(ethylene glycol) molecule comprising an azide moiety. In some embodiments, the azide or alkyne group is linked to the poly(ethylene glycol) molecule through an amide linkage.

In some embodiments, the BSP linked to the water soluble polymer is made by reacting a BSP comprising an azide-containing amino acid with a poly(ethylene glycol) molecule comprising an alkyne moiety. In some embodiments, the azide or alkyne group is linked to the poly(ethylene glycol) molecule through an amide linkage.

In some embodiments, the poly(ethylene glycol) molecule has a molecular weight of between about 0.1 kDa and about 100 kDa. In some embodiments, the poly(ethylene glycol) molecule has a molecular weight of between 0.1 kDa and 50 kDa.

In some embodiments, the poly(ethylene glycol) molecule is a branched polymer. In some embodiments, each branch of the poly(ethylene glycol) branched polymer has a molecular weight of between 1 kDa and 100 kDa, or between 1 kDa and 50 kDa.

In some embodiments, the water soluble polymer linked to BSP comprises a polyalkylene glycol moiety. In some embodiments, the non-naturally encoded amino acid residue incorporated into BSP comprises a carbonyl group, an aminooxy group, a hydrazide group, a hydrazine, a semicarbazide group, an azide group, or an alkyne group. In some embodiments, the non-naturally encoded amino acid residue incorporated into BSP comprises a carbonyl moiety and the water soluble polymer comprises an aminooxy, hydrazide, hydrazine, or semicarbazide moiety. In some embodiments, the non-naturally encoded amino acid residue incorporated into BSP comprises an alkyne moiety and the water soluble polymer comprises an azide moiety. In some embodiments, the non-naturally encoded amino acid residue incorporated into BSP comprises an azide moiety and the water soluble polymer comprises an alkyne moiety.

The present invention also provides compositions comprising a BSP comprising a non-naturally encoded amino acid and a pharmaceutically acceptable carrier. In some embodiments, the non-naturally encoded amino acid is linked to a water soluble polymer.

The present invention also provides cells comprising a polynucleotide encoding the BSP comprising a selector codon. In some embodiments, the cells comprise an orthogonal RNA synthetase and/or an orthogonal tRNA for substituting a non-naturally encoded amino acid into the BSP.

The present invention also provides methods of making a BSP comprising a non-naturally encoded amino acid. In some embodiments, the methods comprise culturing cells comprising a polynucleotide or polynucleotides encoding a BSP, an orthogonal RNA synthetase and/or an orthogonal tRNA under conditions to permit expression of the BSP; and purifying the BSP from the cells and/or culture medium.

The present invention also provides methods of increasing therapeutic half-life, serum half-life or circulation time of BSP. The present invention also provides methods of modulating immunogenicity of BSP. In some embodiments, the methods comprise substituting a non-naturally encoded amino acid for any one or more amino acids in naturally occurring BSP and/or linking the BSP to a linker, a polymer, a water soluble polymer, or a biologically active molecule.

The present invention also provides methods of treating a patient in need of such treatment with an effective amount of a BSP of the present invention. In some embodiments, the methods comprise administering to the patient a therapeutically-effective amount of a pharmaceutical composition comprising a BSP comprising a non-naturally-encoded amino acid and a pharmaceutically acceptable carrier. In some embodiments, the non-naturally encoded amino acid is linked to a water soluble polymer.

The present invention also provides BSP comprising a sequence shown in SEQ ID NO: 1, 2, 3, 21, or any other GLP-1 polypeptide sequence, SEQ ID NO: 22, 24, or any other T-20 polypeptide sequence, or SEQ ID NO: 23 or any other peptide YY sequence, except that at least one amino acid is substituted by a non-naturally encoded amino acid. In some embodiments, the non-naturally encoded amino acid is linked to a water soluble polymer. In some embodiments, the water soluble polymer comprises a poly(ethylene glycol) moiety. In some embodiments, the non-naturally encoded amino acid comprises a carbonyl group, an aminooxy group, a hydrazide group, a hydrazine group, a semicarbazide group, an azide group, or an alkyne group.

The present invention also provides pharmaceutical compositions comprising a pharmaceutically acceptable carrier and a BSP comprising the sequence shown in SEQ ID NO: 1, 2, 3, 21, or any other GLP-1 polypeptide sequence, SEQ ID NO: 22, 24, or any other T-20 polypeptide sequence, or SEQ ID NO: 23 or any other peptide YY sequence, wherein at least one amino acid is substituted by a non-naturally encoded amino acid. In some embodiments, the non-naturally encoded amino acid comprises a saccharide moiety. In some embodiments, the water soluble polymer is linked to the polypeptide via a saccharide moiety. In some embodiments, a linker, polymer, or biologically active molecule is linked to the BSP via a saccharide moiety.

The present invention also provides a BSP comprising a water soluble polymer linked by a covalent bond to the BSP at a single amino acid. In some embodiments, the water soluble polymer comprises a poly(ethylene glycol) moiety. In some embodiments, the amino acid covalently linked to the water soluble polymer is a non-naturally encoded amino acid present in the polypeptide.

The present invention provides a BSP comprising at least one linker, polymer, or biologically active molecule, wherein said linker, polymer, or biologically active molecule is attached to the polypeptide through a functional group of a non-naturally encoded amino acid ribosomally incorporated into the polypeptide. In some embodiments, the BSP is monoPEGylated. The present invention also provides a BSP comprising a linker, polymer, or biologically active molecule that is attached to one or more non-naturally encoded amino acid wherein said non-naturally encoded amino acid is ribosomally incorporated into the polypeptide at pre-selected sites.

In another embodiment, conjugation of the BSP comprising one or more non-naturally occurring amino acids to another molecule, including but not limited to PEG, provides substantially purified BSP due to the unique chemical reaction utilized for conjugation to the non-natural amino acid. Conjugation of BSP comprising one or more non-naturally encoded amino acids to another molecule, such as PEG, may be performed with other purification techniques performed prior to or following the conjugation step to provide substantially pure BSP.

The present invention also provides a polypeptide comprising the formula (LT)-P-T', wherein (LT) is selected from the group consisting of: a localization peptide (L), a tag or linker (T), a localization peptide (L) and tag or linker (T) in any order, methionine, and absent; P comprises a BSP sequence; and T' comprises a tag or linker, or is absent, wherein L, T, P, or T' comprises one or more non-naturally encoded amino acids. The present invention also provides a polypeptide comprising the formula F-(LT)-P-T'-F', wherein F comprises a polypeptide sequence, or is absent; (LT) is selected from the group consisting of: a localization peptide (L), a tag or linker (T), a localization peptide (L) and tag or linker (T) in any order, methionine, and absent; P comprises a desired polypeptide sequence having up to 100 amino acids and is different from F or F'; T' comprises a tag or linker, or is absent, F' comprises a polypeptide sequence, or is absent, wherein F, L, T, P, T', or F' comprises one or more non-naturally encoded amino acids. P may further comprise a BSP comprising one or more non-naturally encoded amino acids.

The present invention also provides a nucleic acid molecule comprising a promoter sequence operably linked to a polypeptide coding sequence, wherein said polypeptide coding sequence has the formula (WX)-Z, wherein (WX) is selected from the group consisting of: a nucleotide sequence encoding a localization peptide (W), a nucleotide sequence encoding a tag or linker (X), a nucleotide sequence encoding a localization peptide (W) and a nucleotide sequence encoding a tag or linker (X) in any order, and absent; and Z comprises a nucleotide sequence encoding a desired BSP, wherein the nucleotide sequence encoding W, X, or Z comprises a selector codon. The nucleic acid molecule may further comprise—Y' operably linked to Z, wherein Y' comprises a nucleotide sequence encoding a tag, wherein said nucleotide sequence encoding said tag optionally comprises a selector codon. The present invention also provides a method comprising: a) producing in a recombinant host cell a polypeptide comprising the formula (LT)-P-T', wherein (LT) is selected from the group consisting of: a localization peptide (L), a tag or linker (T), a localization peptide (L) and tag or linker (T) in any order, methionine, and absent; P comprises a BSP sequence; and T' comprises a tag or linker, or is absent, wherein L, T, P, or T' comprises one or more non-naturally encoded amino acids having a functional group determined to cleave one or more peptide bonds under selected conditions; b) reacting the polypeptide under the selected conditions for a period of time sufficient to at least partially cleave one or more peptide bonds; and c) recovering peptides comprising P from the reaction products.

The present invention also encompasses a method for normalizing blood glucose levels in a mammal in need thereof comprising the administration of a therapeutically effective amount of a GLP-1 polypeptide. The present invention also encompasses a method for modulating viral levels in a mammal in need thereof comprising the administration of a therapeutically effective amount of a T-20 polypeptide. The present invention also encompasses a method comprising the administration of a therapeutically effective amount of a PYY polypeptide to a mammal in need thereof.

BRIEF DESCRIPTION OF THE DRAWINGS

FIG. 10—A comparison of wild-type T-20 (SEQ ID NO: 22) and TEX sequence (SEQ ID NO: 24) is shown in FIG. 10, and residues encoded by codons that were substituted with an amber codon are marked with an asterisk.

FIG. 9, Panel B shows T-20 polypeptides before and after CNBr cleavage.

FIG. 10—A comparison of wild-type T-20 and TEX sequences is shown in FIG. 10, and residues encoded by codons that were substituted with an amber codon are marked with an asterisk.

FIG. 12, Panel E shows the residues substituted with p-acetyl-phenylalanine with asterisks in T-20 (T-20-Mut651) comprising the sequence SEQ ID NO: 22 and in TEX (TEX-Mut636) comprising the sequence SEQ ID NO: 24.

DEFINITIONS

Figure 1:
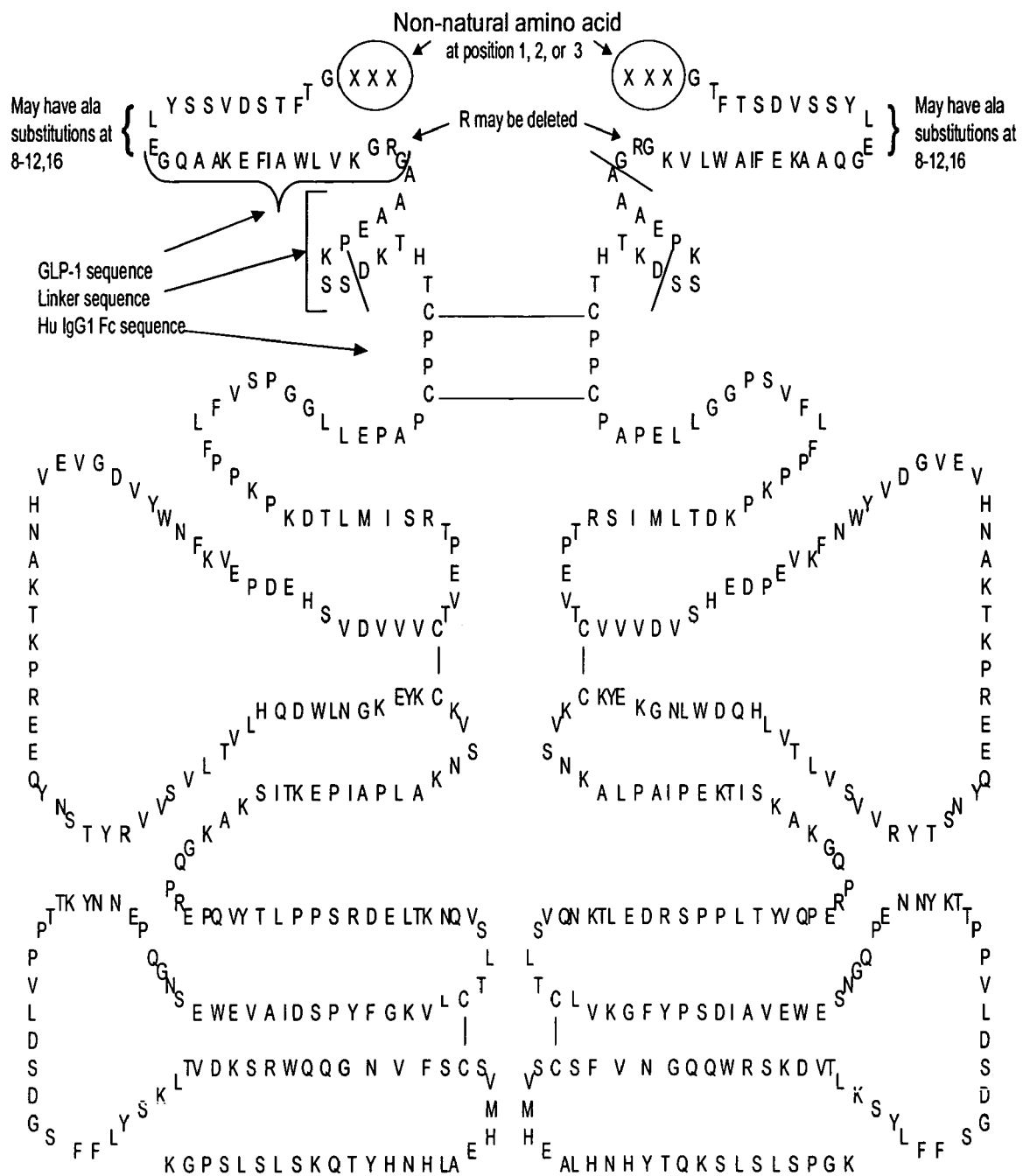
FIG. 1—A diagram of a GLP-1 dimeric polypeptide comprising a GLP-1-Fc fusion protein is shown.

It is to be understood that this invention is not limited to the particular methodology, protocols, cell lines, constructs, and reagents described herein and as such may vary. It is also to be understood that the terminology used herein is for the purpose of describing particular embodiments only, and is not intended to limit the scope of the present invention, which will be limited only by the appended claims.

As used herein and in the appended claims, the singular forms "a," "an," and "the" include plural reference unless the context clearly indicates otherwise. Thus, for example, reference to a "BSP" or a "GLP-1," "T-20," or "PYY" is a reference to one or more such polypeptides and includes equivalents thereof known to those skilled in the art, and so forth.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, the preferred methods, devices and materials are now described.

All publications and patents mentioned herein are incorporated herein by reference for the purpose of describing and disclosing, for example, the constructs and methodologies that are described in the publications, which might be used in connection with the presently described invention. The publications discussed herein are provided solely for their disclosure prior to the filing date of the present application. Nothing herein is to be construed as an admission that the inventors are not entitled to antedate such disclosure by virtue of prior invention or for any other reason.

A "biosynthetic polypeptide" or "BSP" refers to a polymer of about 100 or fewer amino acid residues covalently linked by peptide bonds that is produced from an mRNA with a selector codon. BSPs include, but are not limited to, "GLP-1," "T-20," and "PYY" as well as "GLP-1 polypeptides," "T-20 polypeptides," and "PYY polypeptides." A BSP may be a fragment of a polymer that is greater than about 100 amino acids in length and may or may not include additional amino acids such as, but not limited to, a leader sequence or secretion signal sequence.

A description directed to a "polypeptide" applies equally to a description of a "peptide" and vice versa. The terms "polypeptide", "peptide", and "protein" apply to naturally occurring amino acid polymers as well as amino acid polymers in which one or more amino acid residues is a non-naturally encoded amino acid. One of skill of the art would understand techniques and modifications to proteins are applicable to polypeptides and peptides, and thus BSPs.

The term "substantially purified" refers to BSP that may be substantially or essentially free of components that normally accompany or interact with the protein as found in its naturally occurring environment, i.e. a native cell, or host cell in the case of recombinantly produced BSP. BSP that may be substantially free of cellular material includes preparations of protein having less than about 30%, less than about 25%, less than about 20%, less than about 15%, less than about 10%, less than about 5%, less than about 4%, less than about 3%, less than about 2%, or less than about 1% (by dry weight) of contaminating protein. When the BSP or variant thereof is recombinantly produced by the host cells, the protein may be present at about 30%, about 25%, about 20%, about 15%, about 10%, about 5%, about 4%, about 3%, about 2%, or about 1% or less of the dry weight of the cells. When the BSP or variant thereof is recombinantly produced by the host cells, the protein may be present in the culture medium at about 5 g/L, about 4 g/L, about 3 g/L, about 2 g/L, about 1 g/L, about 750 mg/L, about 500 mg/L, about 250 mg/L, about 100 mg/L, about 50 mg/L, about 10 mg/L, or about 1 mg/L or less of the dry weight of the cells. Thus, "substantially purified" BSP as produced by the methods of the present invention may have a purity level of at least about 30%, at least about 35%, at least about 40%, at least about 45%, at least about 50%, at least about 55%, at least about 60%, at least about 65%, at least about 70%, specifically, a purity level of at least about 75%, 80%, 85%, and more specifically, a purity level of at least about 90%, a purity level of at least about 95%, a purity level of at least about 99% or greater as determined by appropriate methods such as SDS/PAGE analysis, RP-HPLC, SEC, and capillary electrophoresis.

A "recombinant host cell" or "host cell" refers to a cell that includes an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome.

As used herein, the term "medium" or "media" includes any culture medium, solution, solid, semi-solid, or rigid support that may support or contain any host cell, including bacterial host cells, yeast host cells, insect host cells, plant host cells, eukaryotic host cells, mammalian host cells, CHO cells or E. coli, and cell contents. Thus, the term may encompass medium in which the host cell has been grown, e.g., medium into which BSP has been secreted, including medium either before or after a proliferation step. The term also may encompass buffers or reagents that contain host cell lysates, such as in the case where BSP is produced intracellularly and the host cells are lysed or disrupted to release BSP.

"Reducing agent," as used herein with respect to protein refolding, is defined as any compound or material which maintains sulfhydryl groups in the reduced state and reduces intra- or intermolecular disulfide bonds. Suitable reducing agents include, but are not limited to, dithiothreitol (DTT), 2-mercaptoethanol, dithioerythritol, cysteine, cysteamine (2-aminoethanethiol), and reduced glutathione. It is readily apparent to those of ordinary skill in the art that a wide variety of reducing agents are suitable for use in the methods and compositions of the present invention.

"Oxidizing agent," as used hereinwith respect to protein refolding, is defined as any compound or material which is capable of removing an electron from a compound being oxidized. Suitable oxidizing agents include, but are not limited to, oxidized glutathione, cystine, cystamine, oxidized dithiothreitol, oxidized erythreitol, and oxygen. It is readily apparent to those of ordinary skill in the art that a wide variety of oxidizing agents are suitable for use in the methods of the present invention.

"Denaturing agent" or "denaturant," as used herein, is defined as any compound or material which will cause a reversible unfolding of a polypeptide. The strength of a denaturing agent or denaturant will be determined both by the properties and the concentration of the particular denaturing agent or denaturant. Suitable denaturing agents or denaturants may be chaotropes, detergents, organic solvents, water miscible solvents, phospholipids, or a combination of two or more such agents. Suitable chaotropes include, but are not limited to, urea, guanidine, and sodium thiocyanate. Useful detergents may include, but are not limited to, strong detergents such as sodium dodecyl sulfate, or polyoxyethylene ethers (e.g. Tween or Triton detergents), Sarkosyl, mild nonionic detergents (e.g., digitonin), mild cationic detergents such as N->2,3-(Dioleyoxy)-propyl-N,N,N-trimethylammonium, mild ionic detergents (e.g. sodium cholate or sodium deoxycholate) or zwitterionic detergents including, but not limited to, sulfobetaines (Zwittergent), 3-(3-chlolamidopropyl)dimethylammonio-1-propane sulfate (CHAPS), and 3-(3-chlolamidopropyl)dimethylammonio-2-hydroxy-1-propane sulfonate (CHAPSO). Organic, water miscible solvents such as acetonitrile, lower alkanols (especially $C_2$-$C_4$ alkanols such as ethanol or isopropanol), or lower alkandiols (especially $C_2$-$C_4$ alkandiols such as ethylene-glycol) may be used as denaturants. Phospholipids useful in the present invention may be naturally occurring phospholipids such as phosphatidylethanolamine, phosphatidylcholine, phosphatidylserine, and phosphatidylinositol or synthetic phospholipid derivatives or variants such as dihexanoylphosphatidylcholine or diheptanoylphosphatidylcholine.

"Refolding," as used herein describes any process, reaction or method which transforms disulfide bond containing polypeptides from an improperly folded or unfolded state to a native or properly folded conformation with respect to disulfide bonds.

"Cofolding," as used herein, refers specifically to refolding processes, reactions, or methods which employ at least two polypeptides which interact with each other and result in the transformation of unfolded or improperly folded polypeptides to native, properly folded polypeptides.

As used herein, "glucagon-like peptide-1" or "GLP-1" shall include those polypeptides and proteins that have at least one biological activity of human GLP-1, including but not limited to those described in U.S. Patent Publication No. 20040127412, EP 0699686-A2 and EP0733,644, U.S. Pat. Nos. 5,545,618; 5,118,666; 5,512,549; WO 91/11457; WO 90/11296; WO 87/06941 which are incorporated by reference herein, as well as GLP-1 analogs, GLP-1 isoforms, GLP-1 mimetics, GLP-1 fragments, hybrid GLP-1 proteins, fusion proteins, oligomers and multimers, homologues, glycosylation pattern variants, and muteins, thereof, regardless of the biological activity of same, and further regardless of the method of synthesis or manufacture thereof including, but not limited to, recombinant (whether produced from cDNA, genomic DNA, synthetic DNA or other form of nucleic acid), synthetic, transgenic, and gene activated methods. Numerous GLP-1 analogs and derivatives are known and are referred to herein as "GLP-1 compounds." These GLP-1 analogs include the Exendins which are peptides found in the venom of the GILA-monster. Specific examples of GLP-1 include, but are not limited to, GLP-1(3-36), GLP-1(3-37), GLP-1(1-45), and Exendins 1 through 4. Further, it is possible to obtain GLP-1 through the use of recombinant DNA technology, as disclosed by Maniatis, T., et al., Molecular Biology: A Laboratory Manual, Cold Spring Harbor, N.Y. (1982), and produce GLP-1 in host cells by methods known to one of ordinary skill in the art.

The term "human GLP-1 (GLP-1)" or "GLP-1 polypeptide" refers to GLP-1 as described herein, as well as a polypeptide that retains at least one biological activity of a naturally-occurring GLP-1. GLP-1 polypeptides also include the pharmaceutically acceptable salts and prodrugs, and prodrugs of the salts, polymorphs, hydrates, solvates, biologically-active fragments, biologically active variants and stereoisomers of the naturally-occurring human GLP-1 as well as agonist, mimetic, and antagonist variants of the naturally-occurring human GLP-1, the family of exendins including exendins 1 through 4, and polypeptide fusions thereof. Examples of GLP-1 polypeptides include, but are not limited to, those described in U.S. Pat. No. 5,118,666; which is incorporated by reference herein. Fusions comprising additional amino acids at the amino terminus, carboxyl terminus, or both, are encompassed by the term "GLP-1 polypeptide." Exemplary fusions include, but are not limited to, e.g., methionyl GLP-1 in which a methionine is linked to the N-terminus of GLP-1 resulting from the recombinant expression of GLP-1, fusions for the purpose of purification (including, but not limited to, to poly-histidine or affinity epitopes), fusions with serum albumin binding peptides; fusions with serum proteins such as serum albumin; fusions with constant regions of immunoglobulin molecules such as Fc; and fusions with fatty acids. The naturally-occurring GLP-1 nucleic acid and amino acid sequences for various forms are known, as are variants such as single amino acid variants or splice variants.

The term "GLP-1 polypeptide" encompasses GLP-1 polypeptides comprising one or more amino acid substitutions, additions or deletions. Exemplary substitutions in a wide variety of amino acid positions in naturally-occurring GLP-1 have been described, including but not limited to, substitutions that modulate one or more of the biological activities of GLP-1, such as but not limited to, increase agonist activity, increase solubility of the polypeptide, convert the polypeptide into an antagonist, decrease peptidase or protease susceptibility, etc. and are encompassed by the term "GLP-1 polypeptide."

Human GLP-1 antagonists include, but are not limited to, those with a substitutions at: 7, 8, 9, 22, 18, 29, 25, 32, 21, 28, 17, 24, 31, and 20 (SEQ ID NO:1, 2, 3, 21, or any other GLP-1 sequence). In some embodiments, the GLP-1 antagonist comprises a non-naturally encoded amino acid linked to a water soluble polymer that is present in a receptor binding region of the GLP-1 molecule. In some embodiments the water soluble polymer is coupled to the GLP-1 polypeptide at one or more of the amino acid positions: 7, 8, 9, 22, 18, 29, 25, 32, 21, 28, 17, 24, 31, and 20 (SEQ ID NO:1, 2, 3, 21, or any other GLP-1 polypeptide).

For the GLP-1 amino acid sequence as well as the exendin-4 and exendin-3 amino acid sequence, see SEQ ID NO: 1 (GLP-1(7-36)), SEQ ID NO: 2 (GLP-1(7-37)), SEQ ID NO: 3 (exendin-4), and SEQ ID NO: 21 (exendin-3), respectively, herein. In some embodiments, GLP-1 polypeptides of the invention are substantially identical to SEQ ID NO: 1, or SEQ ID NO: 2, or SEQ ID NO: 3, or SEQ ID NO: 21, or any other sequence of a GLP-1 polypeptide. Nucleic acid molecules encoding GLP-1 mutants and mutant GLP-1 polypeptides are well known. Examples of GLP-1 mutants include those disclosed in U.S. Patent Publication No. 20040127412A1; which is incorporated by reference herein.

A number of GLP-1 products are in preclinical and clinical development, including GLP-1 peptide analogs, conjugates, fusion proteins, and drug delivery or combination therapies. Some of the products in development are Exenatide (AC2993, Amylin/Eli Lilly), AVE-0010 (ZP10, Zealand Pharm/Aventis), BIM-51077 (Ipsen/Roche), Liraglutide (NN2211, Novo Nordisk), CJC-1131 (Conjuchem), Albugon (Human Genome Sciences/Glaxo Smith Kline), GLP-1 transferrin (Biorexis), AC2993 LAR (Amylin/Alkermes), GLP-1 nasal (Suntory) and GLP-1-INT (Transition Therapeutics).

The biological activities of GLP-1 have been disclosed and are known in the art, and can be found, for example, in U.S. Patent Publication No: 20040082507A1 and 20040232754A1 which are incorporated by reference herein.

Variants of GLP-1(7-37) and analogs thereof, also have been disclosed. These variants and analogs include, for example, $Gln^9$-GLP-1(7-37), D-$Gln^9$-GLP-1(7-37), acetyl- Lys⁹-GLP-1(7-37), Thr¹⁶-Lys¹⁸-GLP-1(7-37), Lys¹⁸-GLP-1 (7-37) and the like, and derivatives thereof including, for example, acid addition salts, carboxylate salts, lower alkyl esters, and amides [see, e.g., WO 91/11457; EP0733,644 (1996); and U.S. Pat. No. 5,512,549 (1996), which are incorporated by reference]. Generally, the various disclosed forms of GLP-1 are known to stimulate insulin secretion (insulinotropic action) and cAMP formation [see, e.g., Mojsov, S., Int. J. Peptide Protein Research, 40:333-343 (1992)].

As used herein, "T-20" or "DP-178" shall include those polypeptides and proteins that have at least one biological activity of human DP-178, as well as DP-178 analogs, DP-178 isoforms, DP-178 mimetics, DP-178 fragments, hybrid DP-178 proteins, fusion proteins, oligomers and multimers, homologues, glycosylation pattern variants, and muteins, thereof, regardless of the biological activity of same, and further regardless of the method of synthesis or manufacture thereof including, but not limited to, recombinant (whether produced from cDNA, genomic DNA, synthetic DNA or other form of nucleic acid), synthetic, transgenic, and gene activated methods. Hyphenated and non-hyphenated forms (T20, DP178) of the terms are equivalent.

The term "human DP-178" or "DP-178 polypeptide" refers to DP-178 or T-20 as described herein, as well as a polypeptide that retains at least one biological activity of a naturally-occurring DP-178. "DP-178" includes portions, analogs, and homologs of DP-178, all of which exhibit antiviral activity. Antiviral activity includes, but is not limited to., the inhibition of HIV transmission to uninfected CD-4+ cells. Further, the invention relates to the use of DP-178 and DP-178 fragments and/or analogs or homologs as inhibitors of retroviral transmission, in particular HIV, to uninfected cells, in both humans and non-humans. Non retroviral viruses whose transmission may be inhibited by the peptides of the invention include, but are not limited to enveloped viruses, human respiratory syncytial virus, canine distemper virus, Newcastle disease virus, human parainfluenza virus, and influenza viruses.

DP-178 polypeptides also include the pharmaceutically acceptable salts and prodrugs, and prodrugs of the salts, polymorphs, hydrates, solvates, biologically-active fragments, biologically active variants and stereoisomers of the naturally-occurring human DP-178 as well as agonist, mimetic, and antagonist variants of the naturally-occurring human DP-178, and polypeptide fusions thereof. Fusions comprising additional amino acids at the amino terminus, carboxyl terminus, or both, are encompassed by the term "DP-178 polypeptide." Exemplary fusions include, but are not limited to, e.g., methionyl DP-178 in which a methionine is linked to the N-terminus of DP-178 resulting from the recombinant expression of DP-178, fusions for the purpose of purification (including, but not limited to, to poly-histidine or affinity epitopes), T-20 extended at the N-terminus, fusions with serum albumin binding peptides; fusions with serum proteins such as serum albumin; fusions with constant regions of immunoglobulin molecules such as Fc; and fusions with fatty acids. The naturally-occurring DP-178 nucleic acid and amino acid sequences are known, as are variants such as single amino acid variants or splice variants.

The term "DP-178 polypeptide" encompasses DP-178 polypeptides comprising one or more amino acid substitutions, additions or deletions. Exemplary substitutions in a wide variety of amino acid positions in naturally-occurring DP-178 have been described, including but not limited to, substitutions that modulate one or more of the biological activities of DP-178, such as but not limited to, increase agonist activity, increase solubility of the polypeptide, convert the polypeptide into an antagonist, decrease peptidase or protease susceptibility, etc. and are encompassed by the term "DP-178 polypeptide."

For the DP-178 amino acid sequence, see SEQ ID NO: 22, respectively, herein. In some embodiments, DP-178 polypeptides of the invention are substantially identical to SEQ ID NO: 22, 24, or any other sequence of a DP-178 polypeptide. Nucleic acid molecules encoding DP-178 mutants and mutant DP-178 polypeptides are well known.

A commercially available form of DP-178 is Fuzeon® (enfuvirtide. Roche Laboratories Inc. and Trimeris, Inc.). Fuzeon® has an acetylated N terminus and a carboxamide as the C-terminus. It is used in combination with other antivirals in HIV-1 patients that show HIV-1 replication despite ongoing antiretroviral therapy.

As used herein, "PYY" and "peptide YY" shall include those polypeptides and proteins that have at least one biological activity of human PYY, as well as PYY analogs, PYY isoforms, PYY mimetics, PYY fragments, hybrid PYY proteins, fusion proteins, oligomers and multimers, homologues, glycosylation pattern variants, and muteins, thereof, regardless of the biological activity of same, and further regardless of the method of synthesis or manufacture thereof including, but not limited to, recombinant (whether produced from cDNA, genomic DNA, synthetic DNA or other form of nucleic acid), synthetic, transgenic, and gene activated methods.

The term "PYY" or "PYY polypeptide" refers to PYY as described herein, as well as a polypeptide that retains at least one biological activity of a naturally-occurring PYY. "PYY" includes portions, analogs, and homologs of PYY including, but not limited to, PYY(3-36), full-length PYY, PYY(22-36), and DPPIV resistant variants of PYY. The term "PYY" includes both the human full length, 36 amino acid peptide as set forth in SEQ ID NO: 2 of International Publication No. WO 02/47712 (which is the PCT counterpart to U.S. patent Publication No. 2002/0141985, which is hereby incorporated by reference) and Tatemoto, Proc Natl Acad Sci U.S.A. 79:2514-8, 1982, which are incorporated by reference herein.

PYY agonists are also included in the term "PYY". PYY agonists include any compound which elicits an effect of PYY to reduce nutrient availability, for example a compound (1) having activity in the food intake, gastric emptying, pancreatic secretion, or weight loss assays described in Examples 1, 2, 5, or 6 of WO 02/47712 and U.S. patent Publication No. 2002/0141985, and (2) which binds specifically in a Y receptor assay (Example 10 of WO 02/47712 and U.S. patent Publication No. 2002/0141985) or in a competitive binding assay with labeled PYY or PYY [3-36] from certain tissues having an abundance of Y receptors, including e.g., area postrema (Example 9 of WO 02/47712 and U.S. patent Publication No. 2002/0141985), wherein the PYY agonist is not pancreatic polypeptide. Preferably, PYY agonists would bind in such assays with an affinity of greater than about 1 μM, and more preferably with an affinity of greater than about 1 to about 5 nM.

Such agonists can comprise a polypeptide having a functional PYY domain, an active fragment of PYY, or a chemical or small molecule. PYY agonists may be peptide or nonpeptide compounds, and include "PYY agonist analogs," which refer to any compound structurally similar to a PYY that have PYY activity typically by virtue of binding to or otherwise directly or indirectly interacting with a PYY receptor or other receptor or receptors with which PYY itself may interact to elicit a biological response. Such compounds include derivatives of PYY, fragments of PYY, extended PYY molecules having more than 36 amino acids, truncated PYY molecules having less than 36 amino acids, and substituted PYY molecules having one or more different amino acids, or any combination of the above. Such compounds may also be modified by processes such as pegylation, amidation, glycosylation, acylation, sulfation, phosphorylation, acetylation and cyclization.

One such PYY agonist analog is PYY [3-36], identified as SEQ ID NO: 3 of WO 02/47712 and U.S. patent Publication No. 2002/0141985; Eberlein, Eysselein et al., Peptides 10:797-803 (1989); and Grandy, Schimiczek et al., Regul Pept 51:151-9 (1994). Additional PYY fragments, analogs, and derivatives are described in U.S. Patent Publication 20050002927. All of the above referenced patent publications are incorporated by reference herein.

PYY polypeptides also include the pharmaceutically acceptable salts and prodrugs, and prodrugs of the salts, polymorphs, hydrates, solvates, biologically-active fragments, biologically active variants and stereoisomers of the naturally-occurring human PYY as well as agonist, mimetic, and antagonist variants of the naturally-occurring human PYY, and polypeptide fusions thereof. Fusions comprising additional amino acids at the amino terminus, carboxyl terminus, or both, are encompassed by the term "PYY polypeptide." Exemplary fusions include, but are not limited to, e.g., methionyl PYY in which a methionine is linked to the N-terminus of PYY resulting from the recombinant expression of PYY lacking the secretion signal peptide or portion thereof, fusions for the purpose of purification (including, but not limited to, to poly-histidine or affinity epitopes), fusions with serum albumin binding peptides; fusions with serum proteins such as serum albumin; fusions with constant regions of immunoglobulin molecules such as Fc; and fusions with fatty acids. The naturally-occurring PYY nucleic acid and amino acid sequences are known, as are variants such as single amino acid variants or splice variants.

The term "PYY polypeptide" encompasses PYY polypeptides comprising one or more amino acid substitutions, additions or deletions. Exemplary substitutions in a wide variety of amino acid positions in naturally-occurring PYY have been described, including but not limited to, substitutions that modulate one or more of the biological activities of PYY, such as but not limited to, increase agonist activity, increase solubility of the polypeptide, convert the polypeptide into an antagonist, decrease peptidase or protease susceptibility, etc. and are encompassed by the term "PYY polypeptide."

For the PYY(3-36) amino acid sequence, see SEQ ID NO: 23, respectively, herein. In some embodiments, PYY polypeptides of the invention are substantially identical to SEQ ID NO: 23 or any other sequence of a PYY polypeptide. Nucleic acid molecules encoding PYY mutants and mutant PYY polypeptides are well known.

Various references disclose modification of polypeptides by polymer conjugation or glycosylation. The term BSP includes polypeptides conjugated to a polymer such as PEG and may be comprised of one or more additional derivitizations of cysteine, lysine, or other residues. In addition, BSPs may comprise a linker or polymer, wherein the amino acid to which the linker or polymer is conjugated may be a non-natural amino acid according to the present invention, or may be conjugated to a naturally encoded amino acid utilizing techniques known in the art such as coupling to lysine or cysteine.

Polymer modification of polypeptides has been reported. U.S. Pat. No. 4,904,584 discloses PEGylated lysine depleted polypeptides, wherein at least one lysine residue has been deleted or replaced with any other amino acid residue. WO 99/67291 discloses a process for conjugating a protein with PEG, wherein at least one amino acid residue on the protein is deleted and the protein is contacted with PEG under conditions sufficient to achieve conjugation to the protein. WO 99/03887 discloses PEGylated variants of polypeptides belonging to the growth hormone superfamily, wherein a cysteine residue has been susbstituted with a non-essential amino acid residue located in a specified region of the polypeptide. WO 00/26354 discloses a method of producing a glycosylated polypeptide variant with reduced allergenicity, which as compared to a corresponding parent polypeptide comprises at least one additional glycosylation site. U.S. Pat. No. 5,218,092 discloses modification of granulocyte colony stimulating factor (G-CSF) and other polypeptides so as to introduce at least one additional carbohydrate chain as compared to the native polypeptide. Examples of PEGylated peptides include GW395058, a PEGylated peptide thrombopoietin receptor (TPOr) agonist (de Serres M., et al., Stem Cells. 1999; 17(4):203-9), and a PEGylated analogue of growth hormone releasing factor (PEG-GRP; D'Antonio M, et al. Growth Horm IGF Res. 2004 June; 14(3):226-34).

The term BSP also includes glycosylated BSP's, such as but not limited to, BSPs glycosylated at any amino acid position, N-linked or O-linked glycosylated forms of the polypeptide. Variants containing single nucleotide changes are also considered as biologically active variants of BSP. In addition, splice variants are also included. The term BSP also includes BSP heterodimers, homodimers, heteromultimers, or homomultimers of any one or more BSP or any other polypeptide, protein, carbohydrate, polymer, small molecule, linker, ligand, or other biologically active molecule of any type, linked by chemical means or expressed as a fusion protein, as well as polypeptide analogues containing, for example, specific deletions or other modifications yet maintain biological activity.

Various references disclose additional variants of GLP-1 and acylation of GLP-1, including, but not limited to, the GLP-1 parent analogs and acylation sites described in J. of Med. Chem. (2000) 43:1664-1669, which is incorporated by reference.

All references to amino acid positions in GLP-1 described herein are based on the position in SEQ ID NO:1, 2, 3, or 21, unless otherwise specified. Those of skill in the art will appreciate that amino acid positions corresponding to positions in SEQ ID NO: 1, 2, 3, 21, or any other GLP-1 sequence can be readily identified in any other GLP-1 molecule such as GLP-1 fusions, variants, fragments, etc. For example, sequence alignment by visual means or computer programs such as BLAST can be used to align and identify a particular position in a protein that corresponds with a position in SEQ ID NO: 1, 2, 3, 21 or other GLP-1 sequence. Similar analyses may be performed for SEQ ID NO: 22, 24, and any other DP-178 sequence or SEQ ID NO: 23 (PYY(3-36)) and any other PYY sequence. Substitutions, deletions or additions of amino acids described herein in reference to SEQ ID NO: 1, 2, 3, 21 or other GLP-1 sequence, SEQ ID NO: 22, 24, or other DP-178 sequence, or SEQ ID NO: 23 and any other PYY sequence are intended to also refer to substitutions, deletions or additions in corresponding positions in GLP-1, DP-178, or PYY fusions, variants, fragments, etc. described herein or known in the art and are expressly encompassed by the present invention.

The term BSP encompasses BSP polypeptides comprising one or more amino acid substitutions, additions or deletions. BSPs of the present invention may be comprised of modifications with one or more natural amino acids in conjunction with one or more non-natural amino acid modification. Exemplary substitutions in a wide variety of amino acid positions in naturally-occurring BSPs have been described, including but not limited to substitutions that modulate one or more of the biological activities of the BSP, such as but not limited to, increase agonist activity, increase solubility of the polypeptide, convert the polypeptide into an antagonist, decrease peptidase or protease susceptibility, etc. and are encompassed by the term BSP.

Human GLP-1 antagonists include, but are not limited to, those with a substitutions at: 19, 23, 26, 27, 28, 29, 30, and 33 of (SEQ ID NO:1, 2, 3, 21 or any other GLP-1 sequence). In some embodiments, the GLP-1 antagonist comprises a non-naturally encoded amino acid linked to a water soluble polymer that is present in a receptor binding region of the GLP-1 molecule. In some embodiments the water soluble polymer is coupled to the GLP-1 polypeptide at one or more of the amino acid positions: 19, 23, 26, 27, 30, and 33 (SEQ ID NO:1, 2, 3, 21 or any other GLP-1 polypeptide).

In some embodiments, the BSPs further comprise an addition, substitution or deletion that modulates biological activity of BSP. For example, the additions, substitution or deletions may modulate one or more properties or activities of BSP. For example, the additions, substitutions or deletions may modulate affinity for the BSP receptor or binding partner, modulate (including but not limited to, increases or decreases) receptor dimerization, stabilize receptor dimers, modulate the conformation or one or more biological activities of a binding partner, modulate circulating half-life, modulate therapeutic half-life, modulate stability of the polypeptide, modulate cleavage by peptidases or proteases, modulate dose, modulate release or bio-availability, facilitate purification, or improve or alter a particular route of administration. Similarly, BSPs may comprise protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification or other traits of the polypeptide.

The term BSP also encompasses homodimers, heterodimers, homomultimers, and heteromultimers that are linked, including but not limited to those linked directly via non-naturally encoded amino acid side chains, either to the same or different non-naturally encoded amino acid side chains, to naturally-encoded amino acid side chains, or indirectly via a linker. Exemplary linkers including but are not limited to, small organic compounds, water soluble polymers of a variety of lengths such as poly(ethylene glycol) or polydextran, or polypeptides of various lengths.

A "non-naturally encoded amino acid" refers to an amino acid that is not one of the 20 common amino acids or pyrolysine or seienocysteine. Other terms that may be used synonymously with the term "non-naturally encoded amino acid" are "non-natural amino acid," "unnatural amino acid," "non-naturally-occurring amino acid," and variously hyphenated and non-hyphenated versions thereof. The term "non-naturally encoded amino acid" also includes, but is not limited to, amino acids that occur by modification (e.g. post-translational modifications) of a naturally encoded amino acid (including but not limited to, the 20 common amino acids or pyrolysine and selenocysteine) but are not themselves naturally incorporated into a growing polypeptide chain by the translation complex. Examples of such non-naturally-occurring amino acids include, but are not limited to, N-acetylglucosaminyl-L-serine, N-acetylglucosaminyl-L-threonine, and O-phosphotyrosine.

An "amino terminus modification group" refers to any molecule that can be attached to the amino terminus of a polypeptide. Similarly, a "carboxy terminus modification group" refers to any molecule that can be attached to the carboxy terminus of a polypeptide. Terminus modification groups include, but are not limited to, various water soluble polymers, peptides or proteins such as serum albumin, immunoglobulin constant region portions such as Fc, or other moieties that increase serum half-life of peptides.

The terms "functional group", "active moiety", "activating group", "leaving group", "reactive site", "chemically reactive group" and "chemically reactive moiety" are used in the art and herein to refer to distinct, definable portions or units of a molecule. The terms are somewhat synonymous in the chemical arts and are used herein to indicate the portions of molecules that perform some function or activity and are reactive with other molecules.

The term "linkage" or "linker" is used herein to refer to groups or bonds that normally are formed as the result of a chemical reaction and typically are covalent linkages. Hydrolytically stable linkages means that the linkages are substantially stable in water and do not react with water at useful pH values, including but not limited to, under physiological conditions for an extended period of time, perhaps even indefinitely. Hydrolytically unstable or degradable linkages mean that the linkages are degradable in water or in aqueous solutions, including for example, blood. Enzymatically unstable or degradable linkages mean that the linkage can be degraded by one or more enzymes. As understood in the art, PEG and related polymers may include degradable linkages in the polymer backbone or in the linker group between the polymer backbone and one or more of the terminal functional groups of the polymer molecule. For example, ester linkages formed by the reaction of PEG carboxylic acids or activated PEG carboxylic acids with alcohol groups on a biologically active agent generally hydrolyze under physiological conditions to release the agent. Other hydrolytically degradable linkages include, but are not limited to, carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide.

The term "biologically active molecule", "biologically active moiety" or "biologically active agent" when used herein means any substance which can affect any physical or biochemical properties of a biological system, pathway, molecule, or interaction relating to an organism, including but not limited to, viruses, bacteria, bacteriophage, transposon, prion, insects, fungi, plants, animals, and humans. In particular, as used herein, biologically active molecules include, but are not limited to, any substance intended for diagnosis, cure, mitigation, treatment, or prevention of disease in humans or other animals, or to otherwise enhance physical or mental well-being of humans or animals. Examples of biologically active molecules include, but are not limited to, peptides, proteins, enzymes, small molecule drugs, hard drugs, soft drugs, carbohydrates, inorganic atoms or molecules, dyes, lipids, nucleosides, radionuclides, oligonucleotides, toxins, cells, viruses, liposomes, microparticles and micelles. Classes of biologically active agents that are suitable for use with the invention include, but are not limited to, drugs, prodrugs, radionuclides, imaging agents, polymers, antibiotics, fungicides, anti-viral agents, anti-inflammatory agents, anti-tumor agents, cardiovascular agents, anti-anxiety agents, hormones, growth factors, steroidal agents, microbially derived toxins, and the like.

A "bifunctional polymer" refers to a polymer comprising two discrete functional groups that are capable of reacting specifically with other moieties (including but not limited to, amino acid side groups) to form covalent or non-covalent linkages. A bifunctional linker having one functional group reactive with a group on a particular biologically active component, and another group reactive with a group on a second biological component, may be used to form a conjugate that includes the first biologically active component, the bifunctional linker and the second biologically active component. Many procedures and linker molecules for attachment of various compounds to peptides are known. See, e.g., European Patent Application No 188,256; U.S. Pat. Nos. 4,671,958, 4,659,839, 4,414,148, 4,699,784; 4,680,338; 4,569,789; and 4,589,071 which are incorporated by reference herein. A "multi-functional polymer" refers to a polymer comprising two or more discrete functional groups that are capable of reacting specifically with other moieties (including but not limited to, amino acid side groups) to form covalent or non-covalent linkages. A bi-functional polymer or multi-functional polymer may be any desired molecular length or molecular weight, and may be selected to provide a particular desired spacing or conformation between one or more molecules linked to the BSP and its binding partner or the BSP.

Where substituent groups are specified by their conventional chemical formulas, written from left to right, they equally encompass the chemically identical substituents that would result from writing the structure from right to left, for example, the structure —CH$_2$O— is equivalent to the structure —OCH$_2$—.

The term "substituents" includes but is not limited to "non-interfering substituents". "Non-interfering substituents" are those groups that yield stable compounds. Suitable non-interfering substituents or radicals include, but are not limited to, halo, $C_1$-$C_{10}$ alkyl, $C_2$-$C_{10}$ alkenyl, $C_2$-$C_{10}$ alkynyl, $C_1$-$C_{10}$ alkoxy, $C_1$-$C_{12}$ aralkyl, $C_1$-$C_{12}$ alkaryl, $C_3$-$C_{12}$ cycloalkyl, $C_3$-$C_{12}$ cycloalkenyl, phenyl, substituted phenyl, toluoyl, xylenyl, biphenyl, $C_2$-$C_{12}$ alkoxyalkyl, $C_2$-$C_{12}$ alkoxyaryl, $C_7$-$C_{12}$ aryloxyalkyl, $C_7$-$C_{12}$ oxyaryl, $C_1$-$C_6$ alkylsulfinyl, $C_1$-$C_{10}$ alkylsulfonyl, —(CH$_2$)$_m$—O—($C_1$-$C_{10}$ alkyl) wherein m is from 1 to 8, aryl, substituted aryl, substituted alkoxy, fluoroalkyl, heterocyclic radical, substituted heterocyclic radical, nitroalkyl, —NO$_2$, —CN, —NRC(O)— ($C_1$-$C_{10}$ alkyl), —C(O)—($C_1$-$C_{10}$ alkyl), $C_2$-$C_{10}$ alkyl thioalkyl, —C(O)O—($C_1$-$C_{10}$ alkyl), —OH, —SO$_2$, =S, —COOH, —NR$_2$, carbonyl, —C(O)—($C_1$-$C_{10}$ alkyl)-CF3, —C(O)CF3, —C(O)NR2, —($C_1$-$C_{10}$ aryl)-S—($C_6$-$C_{10}$ aryl), —C(O)—($C_1$-$C_{10}$ aryl), —(CH$_2$)$_m$—O—(—(CH$_2$)$_m$—O— ($C_1$-$C_{10}$ alkyl) wherein each m is from 1 to 8, —C(O)NR$_2$, —C(S)NR$_2$, —SO$_2$NR$_2$, —NRC(O)NR$_2$, —NRC(S)NR$_2$, salts thereof, and the like. Each R as used herein is H, alkyl or substituted alkyl, aryl or substituted aryl, aralkyl, or alkaryl.

The term "halogen" includes fluorine, chlorine, iodine, and bromine.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups which are limited to hydrocarbon groups are termed "homoalkyl".

The term "alkylene" by itself or as part of another substituent means a divalent radical derived from an alkane, as exemplified, but not limited, by the structures —CH$_2$CH$_2$— and —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by —CH$_2$—CH$_2$—S—CH$_2$—CH$_2$— and —CH$_2$—S—CH$_2$—CH$_2$—NH—CH$_2$—. For heteroalkylene groups, the same or different heteroatoms can also occupy either or both of the chain termini (including but not limited to, alkyleneoxy, alkylenedioxy, alkyleneamino, alkylenediamino, aminooxyalkylene, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Thus, a cycloalkyl or heterocycloalkyl include saturated and unsaturated ring linkages. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. Additionally, the term encompasses bicyclic and tricyclic ring structures. Similarly, the term "heterocycloalkylene" by itself or as part of another substituent means a divalent radical derived from heterocycloalkyl, and the term "cycloalkylene" by itself or as part of another substituent means a divalent radical derived from cycloalkyl.

As used herein, the term "water soluble polymer" refers to any polymer that is soluble in aqueous solvents. Linkage of water soluble polymers to BSP can result in changes including, but not limited to, increased or modulated serum half-life, or increased or modulated therapeutic half-life relative to the unmodified form, modulated immunogenicity, modulated physical association characteristics such as aggregation and multimer formation, altered receptor binding, altered binding to one or more binding partners, and altered receptor dimerization or multimerization. The water soluble polymer may or may not have its own biological activity, and may be utilized as a linker for attaching BSP to other substances, including but not limited to, one or more BSPs or one or more biologically active molecules. Suitable polymers include, but are not limited to, polyethylene glycol, polyethylene glycol propionaldehyde, mono C1-C10 alkoxy or aryloxy derivatives thereof (described in U.S. Pat. No. 5,252,714 which is incorporated by reference herein), monomethoxy-polyethylene glycol, polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polypropylene oxide/ethylene oxide copolymer, polyoxyethylated polyol, heparin, heparin fragments, polysaccharides, oligosaccharides, glycans, cellulose and cellulose derivatives, including but not limited to methylcellulose and carboxymethyl cellulose, starch and starch derivatives, polypeptides, polyalkylene glycol and derivatives thereof, copolymers of polyalkylene glycols and derivatives thereof, polyvinyl ethyl ethers, and alpha-beta-poly[(2-hydroxyethyl)-DL-aspartamide, and the like, or mixtures thereof. Examples of such water soluble polymers include, but are not limited to, polyethylene glycol and serum albumin.

As used herein, the term "polyalkylene glycol" or "poly(alkene glycol)" refers to polyethylene glycol (poly(ethylene glycol)), polypropylene glycol, polybutylene glycol, and derivatives thereof. The term "polyalkylene glycol" encompasses both linear and branched polymers and average molecular weights of between 0.1 kDa and 100 kDa. Other exemplary embodiments are listed, for example, in commercial supplier catalogs, such as Shearwater Corporation's catalog "Polyethylene Glycol and Derivatives for Biomedical Applications" (2001).

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (including but not limited to, aryloxy, arylthioxy, arylalkyl) includes both aryl and heteroaryl rings as defined above. Thus, the term "arylalkyl" is meant to include those radicals in which an aryl group is attached to an alkyl group (including but not limited to, benzyl, phenethyl, pyridylmethyl and the like) including those alkyl groups in which a carbon atom (including but not limited to, a methylene group) has been replaced by, for example, an oxygen atom (including but not limited to, phenoxymethyl, 2-pyridyloxymethyl, 3-(1-naphthyloxy)propyl, and the like).

Each of the above terms (including but not limited to, "alkyl," "heteroalkyl," "aryl" and "heteroaryl") are meant to include both substituted and unsubstituted forms of the indicated radical. Exemplary substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R" R''', —OC(O)R', —C(O)R', —CO$_2$R', —CONR'R", —OC(O)NR'R", —NR"C(O)R', —NR'—C(O) NR"R''', —NR"C(O)$_2$R', —NR—C(NR'R" R''')=NR'''', —NR—C(NR'R")=NR''', —S(O)R', —S(O)$_2$R', —S(O)$_2$ NR'R", —NRSO$_2$R', —CN and —NO$_2$ in a number ranging from zero to (2m'+1), where m' is the total number of carbon atoms in such a radical. R', R", R''' and R'''' each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, —CF$_3$ and —CH$_2$CF$_3$) and acyl (including but not limited to, —C(O) CH$_3$, —C(O)CF$_3$, —C(O)CH$_2$OCH$_3$, and the like).

Similar to the substituents described for the alkyl radical, substituents for the aryl and heteroaryl groups are varied and are selected from, but are not limited to: halogen, —OR', =O, =NR', =N—OR', —NR'R", —SR', -halogen, —SiR'R" R''', —OC(O)R', —C(O)R', —CO$_2$R', —CONR'R", —OC(O) NR'R", —NR"C(O)R', —NR'—C(O)NR"R''', —NR"C(O)$_2$ R', —NR—C(NR'R"R''')=NR'''', —NR—C(NR'R") =NR''', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$) alkoxy, and fluoro(C$_1$-C$_4$)alkyl, in a number ranging from zero to the total number of open valences on the aromatic ring system; and where R', R", R'" and R"" are independently selected from hydrogen, alkyl, heteroalkyl, aryl and heteroaryl. When a compound of the invention includes more than one R group, for example, each of the R groups is independently selected as are each R', R", R'" and R"" groups when more than one of these groups is present.

As used herein, the term "modulated serum half-life" means the positive or negative change in circulating half-life of a modified BSP relative to its non-modified form. Serum half-life is measured by taking blood samples at various time points after administration of the BSP, and determining the concentration of that molecule in each sample. Correlation of the serum concentration with time allows calculation of the serum half-life. Increased serum half-life desirably has at least about two-fold, but a smaller increase may be useful, for example where it enables a satisfactory dosing regimen or avoids a toxic effect. In some embodiments, the increase is at least about three-fold, at least about five-fold, or at least about ten-fold.

The term "modulated therapeutic half-life" as used herein means the positive or negative change in the half-life of the therapeutically effective amount of BSP, relative to its non-modified form. Therapeutic half-life is measured by measuring pharmacokinetic and/or pharmacodynamic properties and/or therapeutic effect of the molecule at various time points after administration. Increased therapeutic half-life desirably enables a particular beneficial dosing regimen, a particular beneficial total dose, or avoids an undesired effect. In some embodiments, the increased therapeutic half-life results from increased potency, increased or decreased binding of the modified molecule to its target, increased or decreased breakdown of the molecule by enzymes such as peptidases or proteases, or an increase or decrease in another parameter or mechanism of action of the non-modified molecule.

The term "isolated," when applied to a nucleic acid or protein, denotes that the nucleic acid or protein is substantially free of other cellular components with which it is associated in the natural state. It can be in a homogeneous state. Isolated substances can be in either a dry or semi-dry state, or in solution, including but not limited to, an aqueous solution. Purity and homogeneity are typically determined using analytical chemistry techniques such as polyacrylamide gel electrophoresis or high performance liquid chromatography. A protein which is the predominant species present in a preparation is substantially purified. In particular, an isolated gene is separated from open reading frames which flank the gene and encode a protein other than the gene of interest. The term "purified" denotes that a nucleic acid or protein gives rise to substantially one band in an electrophoretic gel. Particularly, it means that the nucleic acid or protein is at least 85% pure, at least 90% pure, at least 95% pure, at least 99% or greater pure.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers to oligonucleofide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Cassol et al. (1992); Rossolini et al., *Mol. Cell. Probes* 8:91-98 (1994)).

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refers to compounds that have the same basic chemical structure as a naturally occurring amino acid, i.e., an α carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

1) Alanine (A), Glycine (G);

2) Aspartic acid (D), Glutamic acid (E);

3) Asparagine (N), Glutamine (Q);

4) Arginine (R), Lysine (K);

5) Isoleucine (I), Leucine (L), Methionine (M), Valine (V);

6) Phenylalanine (F), Tyrosine (Y), Tryptophan (W);

7) Serine (S), Threonine (T); and

8) Cysteine (C), Methionine (M)

(see, e.g., Creighton, *Proteins: Structures and Molecular Properties* (W H Freeman & Co.; 2nd edition (December 1993))

The terms "identical" or percent "identity," in the context of two or more nucleic acids or polypeptide sequences, refer to two or more sequences or subsequences that are the same. Sequences are "substantially identical" if they have a percentage of amino acid residues or nucleotides that are the same (i.e., about 60% identity, optionally about 65%, about 70%, about 75%, about 80%, about 85%, about 90%, or about 95% identity over a specified region), when compared and aligned for maximum correspondence over a comparison window, or designated region as measured using one of the following sequence comparison algorithms or by manual alignment and visual inspection. This definition also refers to the complement of a test sequence. The identity can exist over a region that is at least about 50 amino acids or nucleotides in length, or over a region that is 75-100 amino acids or nucleotides in length, or, where not specified, across the entire sequence of a polynucleotide or polypeptide, or less than 50 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, including but not limited to, by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

One example of an algorithm that is suitable for determining percent sequence identity and sequence similarity are the BLAST and BLAST 2.0 algorithms, which are described in Altschul et al. (1997) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. The BLAST algorithm parameters W, T, and X determine the sensitivity and speed of the alignment. The BLASTN program (for nucleotide sequences) uses as defaults a wordlength (W) of 11, an expectation (E) or 10, $M=5$, $N=-4$ and a comparison of both strands. For amino acid sequences, the BLASTP program uses as defaults a wordlength of 3, and expectation (E) of 10, and the BLOSUM62 scoring matrix (see Henikoff and Henikoff (1992) *Proc. Natl. Acad. Sci. USA* 89:10915) alignments (B) of 50, expectation (E) of 10, $M=5$, $N=-4$, and a comparison of both strands. The BLAST algorithm is typically performed with the "low complexity" filter turned off.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The phrase "selectively (or specifically) hybridizes to" refers to the binding, duplexing, or hybridizing of a molecule only to a particular nucleotide sequence under stringent hybridization conditions when that sequence is present in a complex mixture (including but not limited to, total cellular or library DNA or RNA).

The phrase "stringent hybridization conditions" refers to conditions of low ionic strength and high temperature as is known in the art. Typically, under stringent conditions a probe will hybridize to its target subsequence in a complex mixture of nucleic acid (including but not limited to, total cellular or library DNA or RNA) but does not hybridize to other sequences in the complex mixture. Stringent conditions are sequence-dependent and will be different in different circumstances. Longer sequences hybridize specifically at higher temperatures. An extensive guide to the hybridization of nucleic acids is found in Tijssen, *Laboratory Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, typically about 0.01 to 1.0 M sodium ion concentration (or other salts) at pH 7.0 to 8.3 and the temperature is at least about 30° C. for short probes (including but not limited to, 10 to 50 nucleotides) and at least about 60° C. for long probes (including but not limited to, greater than 50 nucleotides). Stringent conditions may also be achieved with the addition of destabilizing agents such as formamide. For selective or specific hybridization, a positive signal may be at least two times background, optionally 10 times background hybridization. Exemplary stringent hybridization conditions can be as following: 50% formamide, 5×SSC, and 1% SDS, incubating at 42° C., or 5×SSC, 1% SDS, incubating at 65° C., with wash in 0.2×SSC, and 0.1% SDS at 65° C. Such washes can be performed for 5, 15, 30, 60, 120, or more minutes.

As used herein, the term "eukaryote" refers to organisms belonging to the phylogenetic domain Eucarya such as animals (including but not limited to, mammals, insects, reptiles, birds, etc.), ciliates, plants (including but not limited to, monocots, dicots, algae, etc.), fungi, yeasts, flagellates, microsporidia, protists, etc.

As used herein, the term "non-eukaryote" refers to non-eukaryotic organisms. For example, a non-eukaryotic organism can belong to the Eubacteria (including but not limited to, *Escherichia coli, Thermus thermophilus, Bacillus stearothermophilus, Pseudomonas fluorescens, Pseudomonas aentginosa, Pseudomonas putida*, etc.) phylogenetic domain, or the Archaea (including but not limited to, *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix*, etc.) phylogenetic domain.

The term "subject" as used herein, refers to an animal, preferably a mammal, most preferably a human, who is the object of treatment, observation or experiment.

The term "effective amount" as used herein refers to that amount of the (modified) non-natural amino acid polypeptide being administered which will relieve to some extent one or more of the symptoms of the disease, condition or disorder being treated. Compositions containing the (modified) non-natural amino acid polypeptide described herein can be administered for prophylactic, enhancing, and/or therapeutic treatments.

The terms "enhance" or "enhancing" means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system. When used in a patient, amounts effective for this use will depend on the severity and course of the disease, disorder or condition, previous therapy, the patient's health status and response to the drugs, and the judgment of the treating physician.

The term "modified," as used herein refers to any changes made to a given polypeptide, such as changes to the length of the polypeptide, the amino acid sequence, amino acid composition, chemical structure, co-translational modification, or post-translational modification of a polypeptide. The form "(modified)" term means that the polypeptides being discussed are optionally modified, that is, the polypeptides under discussion can be modified or unmodified.

The term "post-translationally modified" refers to any modification of a natural or non-natural amino acid that occurs to such an amino acid after it has been incorporated into a polypeptide chain. The term encompasses, by way of example only, co-translational in vivo modifications, co-translational in vitro modifications (such as in a cell-free translation system), post-translational in vivo modifications, and post-translational in vitro modifications.

In prophylactic applications, compositions containing the (modified) non-natural amino acid polypeptide are administered to a patient susceptible to or otherwise at risk of a particular disease, disorder or condition. Such an amount is defined to be a "prophylactically effective amount." In this use, the precise amounts also depend on the patient's state of health, weight, and the like. It is considered well within the skill of the art for one to determine such prophylactically effective amounts by routine experimentation (e.g., a dose escalation clinical trial).

The term "protected" refers to the presence of a "protecting group" or moiety that prevents reaction of the chemically reactive functional group under certain reaction conditions. The protecting group will vary depending on the type of chemically reactive group being protected. For example, if the chemically reactive group is an amine or a hydrazide, the protecting group can be selected from the group of tert-butyloxycarbonyl (t-Boc) and 9-fluorenylmethoxycarbonyl (Fmoc). If the chemically reactive group is a thiol, the protecting group can be orthopyridyldisulfide. If the chemically reactive group is a carboxylic acid, such as butanoic or propionic acid, or a hydroxyl group, the protecting group can be benzyl or an alkyl group such as methyl, ethyl, or tert-butyl. Other protecting groups known in the art may also be used in or with the methods and compositions described herein.

By way of example only, blocking/protecting groups may be selected from:

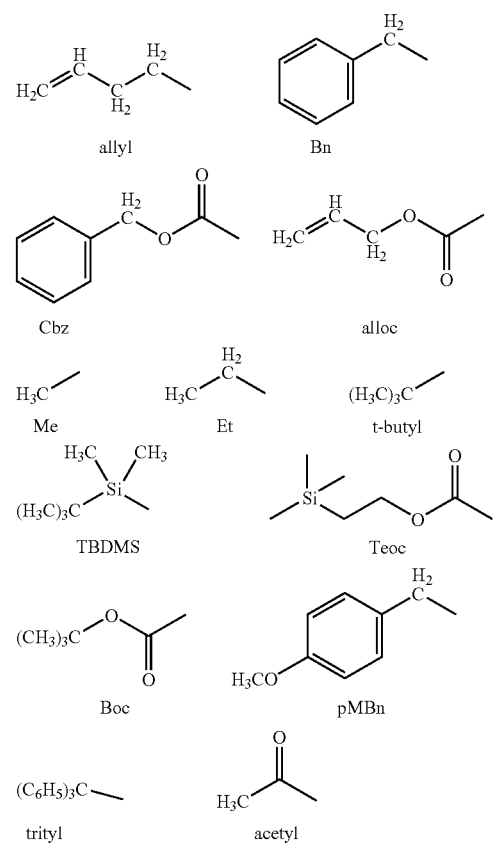

-continued

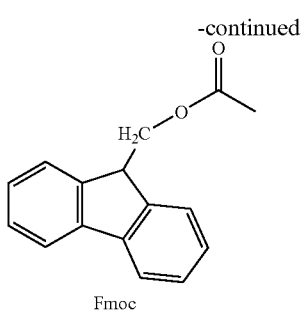

Fmoc

Other protecting groups are described in Greene and Wuts, Protective Groups in Organic Synthesis, 3rd Ed., John Wiley & Sons, New York, N.Y., 1999, which is incorporated herein by reference in its entirety.

In therapeutic applications, compositions containing the (modified) non-natural amino acid polypeptide are administered to a patient already suffering from a disease, condition or disorder, in an amount sufficient to cure or at least partially arrest the symptoms of the disease, disorder or condition. Such an amount is defined to be a "therapeutically effective amount," and will depend on the severity and course of the disease, disorder or condition, previous therapy, the patient's health status and response to the drugs, and the judgment of the treating physician. It is considered well within the skill of the art for one to determine such therapeutically effective amounts by routine experimentation (e.g., a dose escalation clinical trial).

The term "treating" is used to refer to either prophylactic and/or therapeutic treatments.

Unless otherwise indicated, conventional methods of mass spectroscopy, NMR, HPLC, protein chemistry, biochemistry, recombinant DNA techniques and pharmacology, within the skill of the art are employed.

DETAILED DESCRIPTION

I. Introduction

Non-limiting examples of BSPs or fragments thereof that may be useful in the present invention include the following. It is to be understood that other variants, analogs, fragments, and/or analog fragments that retain some or all of the activity of the particular BSP or any protein may also be useful in embodiments of the present invention.

Representative non-limiting classes of polypeptides useful in the present invention include those falling into the following therapeutic categories: adrenocorticotropic hormone peptides, adrenomedullin peptides, allatostatin peptides, amylin peptides, amyloid beta-protein fragment peptides, angiotensin peptides, antibiotic peptides, antigenic polypeptides, anti-microbial peptides, apoptosis related peptides, atrial natriuretic peptides, bag cell peptides, bombesin peptides, bone GLA peptides, bradykinin peptides, brain natriuretic peptides, C-peptides, C-type natriuretic peptides, calcitonin peptides, calcitonin gene related peptides, CART peptides, casomorphin peptides, chemotactic peptides, cholecystokinin peptides, colony-stimulating factor peptides, corticortropin releasing factor peptides, cortistatin peptides, cytokine peptides, dermorphin peptides, dynorphin peptides, endorphin peptides, endothelin peptides, ETa receptor antagonist peptides, ETh receptor antagonist peptides, enkephalin peptides, fibronectin peptides, galanin peptides, gastrin peptides, glucagon peptides, Gn-RH associated peptides, growth factor peptides, growth hormone peptides, GTP-binding protein fragment peptides, guanylin peptides, inhibin peptides, insulin peptides, interleukin peptides, laminin peptides, leptin peptides, leucokinin peptides, luteinizing hormone-releasing hormone peptides, mastoparan peptides, mast cell degranulating peptides, melanocyte stimulating hormone peptides, morphiceptin peptides, motilin peptides, neuro-peptides, neuropeptide Y peptides, neurotropic factor peptides, orexin peptides, opioid peptides, oxytocin peptides, PACAP peptides, pancreastatin peptides, pancreatic polypeptides, parathyroid hormone peptides, parathyroid hormone-related peptides, peptide T peptides, prolactin-releasing peptides, peptide YY peptides, renin substrate peptides, secretin peptides, somatostatin peptides, substance P peptides, tachykinin peptides, thyrotropin-releasing hormone peptides, toxin peptides, vasoactive intestinal peptides, vasopressin peptides, and virus related peptides. (see U.S. Pat. No. 6,858,580).

Examples of polypeptides include, but are not limited to, pituitary hormones such as vasopressin, oxytocin, melanocyte stimulating hormones, adrenocorticotropic hormones, growth hormones; hypothalamic hormones such as growth hormone releasing factor, corticotropin releasing factor, prolactin releasing peptides, gonadotropin releasing hormone and its associated peptides, luteinizing hormone release hormones, thyrotropin releasing hormone, orexins, and somatostatin; thyroid hormones such as calcitonins, calcitonin precursors, and calcitonin gene related peptides; parathyroid hormones and their related proteins; pancreatic hormones such as insulin and insulin-like peptides, glucagon, somatostatin, pancreatic polypeptides, amylin, peptide YY, and neuropeptide Y; digestive hormones such as gastrin, gastrin releasing peptides, gastrin inhibitory peptides, cholecystokinin, secretin, motilin, and vasoactive intestinal peptide; natriuretic peptides such as atrial natriuretic peptides, brain natriuretic peptides, and C-type natriuretic peptides; neurokinins such as neurokinin A, neurokinin B, and substance P; renin related peptides such as renin substrates and inhibitors and angiotensins; endothelins, including big endothelin, endothelin A receptor antagonists, and sarafotoxin peptides; and other peptides such as adrenomedullin peptides, allatostatin peptides, amyloid beta protein fragments, antibiotic and antimicrobial peptides, apoptosis related peptides, bag cell peptides, bombesin, bone Gla protein peptides, CART peptides, chemotactic peptides, cortistatin peptides, fibronectin fragments and fibrin related peptides. FMRF and analog peptides, galanin and related peptides, growth factors and related peptides, G therapeutic peptide-binding protein fragments, guanylin and uroguanylin, inhibin peptides, interleukin and interleukin receptor proteins, laminin fragments, leptin fragment peptides, leucokinins, mast cell degranulating peptides, pituitary adenylate cyclase activating polypeptides, pancreastatin, peptide T, polypeptides, virus related peptides, signal transduction reagents, toxins, and miscellaneous peptides such as adjuvant peptide analogs, alpha mating factor, anti-arrhythmic peptide, antifreeze polypeptide, anorexigenic peptide, bovine pineal antireproductive peptide, bursin, C3 peptide P16, tumor necrosis factor, cadherin peptide, chromogranin A fragment, contraceptive tetrapeptide, conantokin G, conantokin T, crustacean cardioactive peptide, C-telopeptide, cytochrome b588 peptide, decorsin, delicious peptide, delta-sleep-inducing peptide, diazempam-binding inhibitor fragment, nitric oxide synthase blocking peptide, OVA peptide, platelet calpain inhibitor (P1), plasminogen activator inhibitor 1, rigin, schizophrenia related peptide, serum thymic factor, sodium potassium A therapeutic peptidease inhibitor-1, speract, sperm activating peptide, systemin, thrombin receptor agonists, thymic humoral gamma2 factor, thymopentin, thymosin alpha 1, thymus factor, tuftsin, adipokinetic hormone, uremic pentapeptide, glucose-dependent insulinotropic polypeptide (GIP), glucagon-like peptide-1 (GLP-1), glucagon-like peptide-2 (GLP-1), exendin-3, exendin-4, and other therapeutic peptides or fragments thereof. Additional examples of peptides include ghrelin, opioid peptides (casomorphin peptides, demorphins, endorphins, enkephalins, deltorphins, dynorphins, and analogs and derivatives of these), thymic peptides (thymopoietin, thymulin, thymopentin, thymosin, Thymic Humoral Factor (THF)), cell adhesion peptides, complement inhibitors, thrombin inhibitors, trypsin inhibitors, alpha-1 antitrypsin, Sea Urchin Sperm Activating Peptide, SHU-9119 MC3-R & MC4-R Antagonist, glaspimod (immunostimulant, useful against bacterial infections, fungal infections, immune deficiency immune disorder, leukopenia), HP-228 (melanocortin, useful against chemotherapy induced emesis, toxicity, pain, diabetes mellitus, inflammation, rheumatoid arthritis, obesity), alpha 2-plasmin inhibitor (plasmin inhibitor), APC tumor suppressor (tumor suppressor, useful against neoplasm), early pregnancy factor (immunosuppressor), endozepine diazepam binding inhibitor (receptor peptide), gamma interferon (useful against leukemia), glandular kallikrein-1 (immunostimulant), placental ribonuclease inhibitor, sarcolecin binding protein, surfactant protein D, Wilms' tumor suppressor, GABAB 1b receptor peptide, prion related peptide (iPrP13), choline binding protein fragment (bacterial related peptide), telomerase inhibitor, cardiostatin peptide, endostatin derived peptide (angiogenesis inhibitor), prion inhibiting peptide, N-methyl D-aspartate receptor antagonist, C-peptide analog (useful against diabetic complications), RANTES, NTY receptors, NPY2-R (neuropeptide Y type 2-receptor) ligands, NC4R peptides, or fragments thereof. See U.S. Pat. No. 6,849,714 which is incorporated by reference herein.

The hormones regulating insulin secretion belong to the so-called enteroinsular axis, designating a group of hormones released from the gastrointestinal mucosa in response to the presence and absorption of nutrients in the gut, which promote an early and potentiated release of insulin. The enhancing effect on insulin secretion, the so-called incretin effect, is probably essential for a normal glucose tolerance. Many of the gastrointestinal hormones, including gastrin and secretin (cholecystokinin is not insulinotropic in man), are insulinotropic, but the only physiologically important ones, those that are responsible for the incretin effect, are the glucose-dependent insulinotropic polypeptide, GIP, and glucagon-like peptide-1 (GLP-1).

GIP is composed of 42 amino acids, processed from a 153 amino acid precursor (Takeda et al., PNAS USA (1987) 84:7005-7008). GIP is secreted by K cells present in the duodenum and in the small intestinal mucosa in response to carbohydrate and lipid containing meals (Mortensen et al. Ann. NY Acad. Sci. (2000) 921:469-472). Expression of the GIP receptor has been shown in pancreatic islets, the adrenal cortex, gut, heart, adipose tissue, several regions of the brain, and the pituitary gland (Usdin et al. (1993) Endocrinology 133:2861-2870).

Because of its insulinotropic effect, GIP, isolated in 1973 (Pederson R A. Gastric Inhibitory Polypeptide. In Walsh J H, Dockray G J (eds.) Gut peptides: Biochemistry and Physiology. Raven Press, New York 1994, pp. 217-259) immediately attracted considerable interest among diabetologists. However, numerous investigations carried out during the following years clearly indicated that a defective secretion of GIP was not involved in the pathogenesis of insulin dependent diabetes mellitus (IDDM) or non insulin-dependent diabetes mellitus (NIDDM) (Krarup T., Endocr Rev 1988; 9: 122-134). Furthermore, as an insulinotropic hormone, GIP was found to be almost ineffective in NIDDM (Krarup T., Endocr Rev 1988; 9: 122-134). The other incretin hormone, GLP-1 is the most potent insulinotropic substance known (O'rskov C., Diabetologia 1992; 35:701-711). Unlike GIP, it is surprisingly effective in stimulating insulin secretion in NIDDM patients. In addition, and in contrast to the other insulinotropic hormones (perhaps with the exception of secretin), it also potently inhibits glucagon secretion. Because of these actions, it has pronounced blood glucose lowering effects particularly in patients with NIDDM.

GLP-1, a product of the proglucagon gene (Bell G I, et al., Nature 1983; 304: 368-371), is one of the members of the secretin-VIP family of peptides, and is established as an important gut hormone with regulatory function in glucose metabolism and gastrointestinal secretion and metabolism (Hoist J J., 1994; Gastroenterology. 1994 December; 107(6): 1848-55). The glucagon gene is processed differently in the pancreas and in the intestine. In the pancreas (Hoist J J, et al., J Biol Chem, 1994; 269: 18827-18833), the processing leads to the formation and parallel secretion of 1) glucagon itself, occupying positions 33-61 of proglucagon (PG); 2) an N-terminal peptide of 30 amino acids (PG (1-30)) often called glicentin-related pancreatic peptide, GRPP (Moody A J, et al., Nature 1981; 289: 514-516; Thim L, et al., Biochim Biophys Acta 1982; 703:134-141); 3) a hexapeptide corresponding to PG (64-69); 4) and, finally, the so-called major proglucagon fragment (PG (72-158)), in which the two glucagon-like sequences are buried (Hoist J J, et al., J Biol Chem, 1994; 269: 18827-18833). Glucagon seems to be the only biologically active product. In contrast, in the intestinal mucosa, it is glucagon that is buried in a larger molecule, while the two glucagon-like peptides are formed separately (O'rskov C, et al., Endocrinology 1986; 119:1467-1475). The following products are formed and secreted in parallel: 1) glicentin, corresponding to PG (1-69), with the glucagon sequence occupying residues Nos. 33-61 (Thim L, et al., Regul Pept 1981; 2:139-151); 2) GLP-1(7-36)amide (PG (78-107))amide (O'rskov C, et al., J. Biol. Chem. 1989; 264: 12826-12829), not as originally believed PG (72-107)amide or 108, which is inactive). Small amounts of C-terminally glycine-extended but equally bioactive GLP-1(7-37), (PG (78-108)) are also formed (Orskov C, et al., Diabetes 1991; 43: 535-539); 3) intervening peptide-2 (PG (111-122)amide) (Buhl T, et al., J. Biol. Chem. 1988; 263:8621-8624); and 4) GLP-2 (PG (126-158)) (Buhl T, et al., J. Biol. Chem. 1988; 263:8621-8624; O'rskov C, et al., FEBS letters, 1989; 247: 193-106). A fraction of glicentin is cleaved further into GRPP (PG (1-30)) and oxyntomodulin (PG (33-69)) (Hoist J J. Biochem J. 1980; 187:337-343; Bataille D, et al., FEBS Lett 1982; 146:79-86). Of these peptides, GLP-1, has the most conspicuous biological activities.

Being secreted in parallel with glicentin/enteroglucagon, it follows that the many studies of enteroglucagon secretion (Hoist J J., Gastroenterology 1983; 84:1602-1613; Hoist J J, et al., Glucagon and other proglucagon-derived peptides. In Walsh J H, Dockray G J, eds. Gut peptides: Biochemistry and Physiology. Raven Press, New York, pp. 305-340, 1993) to some extent also apply to GLP-1 secretion, but GLP-1 is metabolized more quickly with a plasma half-life in humans of 2 minutes (O'rskov C, et al., Diabetes 1993; 42:658-661). Carbohydrate or fat-rich meals stimulate secretion (Elliott R M, et al., J Endocrinol 1993; 138: 159-166), presumably as a result of direct interaction of yet unabsorbed nutrients with the microvilli of the open-type L-cells of the gut mucosa. Endocrine or neural mechanisms promoting GLP-1 secretion may exist, but have not yet been demonstrated in humans.

The incretin function of GLP-1(29-31) has been clearly illustrated in experiments with the GLP-1 receptor antagonist, exendin 9-39, which dramatically reduces the incretin effect elicited by oral glucose in rats (Kolligs F, et al., Diabetes 1995 44: 16-19; Wang Z, et al., J. Clin. Invest. 1995 95: 417-421). The hormone interacts directly with the β cells via the GLP-1 receptor (Thorens B., Proc Natl Acad Sci 1992; 89:8641-4645, U.S. Pat. Nos. 5,670,360 and 6,051,689, which are incorporated by reference herein) which belongs to the glucagon/VIP/calcitonin family of G-protein-coupled 7-transmembrane spanning receptors. The importance of the GLP-1 receptor in regulating insulin secretion was illustrated in recent experiments in which a targeted disruption of the GLP-1 receptor gene was carried out in mice. Animals homozygous for the disruption had greatly deteriorated glucose tolerance and fasting hyperglycaemia, and even heterozygous animals were glucose intolerant (Scrocchi L, et al., Diabetes 1996; 45: 21A). The signal transduction mechanism (Fehmann H C, et al., Endocrine Reviews, 1995; 16: 390-410) primarily involves activation of adenylate cyclase, but elevations of intracellular $Ca^{2+}$ are also essential (Fehmann H C, et al., Endocrine Reviews, 1995; 16: 390-410; Gromada J, et al., Diabetes 1995; 44: 767-774). A model of GLP-1 receptor-ligand interaction is shown in Lopez de Maturana, R. et al. (2003) J. Biol. Chem. 278, 10195-10200. Lopez de Maturana et al. indicate that the N-terminal domain of the receptor binds to the conserved face of the central helix of exendin-4, GLP-1, and exendin (9-39). The N-terminal regions of exendin-4 and GLP-1 interact with the extracellular loops and/or the transmembrane regions of the GLP-1R. Also the N-terminal domain of the receptor interacts with the Trp-cage portion of the exendin-4 and exendin (9-39). Neidigh et al. Nature Structural Biology (2002) 9(6):425-430 describe the Trp-cage structure of Exendin-4 and mutants thereof.

The action of the hormone is best described as a potentiation of glucose stimulated insulin release (Fehmann H C, et al., Endocrine Reviews, 1995; 16: 390-410), but the mechanism that couples glucose and GLP-1 stimulation is not known. It may involve a calcium-induced calcium release (Gromada J, et al., Diabetes 1995; 44: 767-774; Holz G G. et al., J Biol Chem, 1996; 270: 17749-17759). As already mentioned, the insulinotropic action of GLP-1 is preserved in diabetic P-cells. The relation of the latter to its ability to convey "glucose competence" to isolated insulin-secreting cells (Gromada J, et al., Diabetes 1995, 44: 767-774; Holz G G, et al., Nature 1993, 361:362-365), which respond poorly to glucose or GLP-1 alone, but fully to a combination of the two, is also not known. Equally importantly, however, the hormone also potently inhibits glucagon secretion (O'rskov C, et al., Endocrinology 1988; 123:2009-2013). The mechanism is not known, but seems to be paracrine, via neighbouring insulin or somatostatin cells (Fehmann H C, et al., Endocrine Reviews, 1995; 16: 390-410). Also the glucagonostatic action is glucose-dependent, so that the inhibitory effect decreases as blood glucose decreases. Because of this dual effect, if the plasma GLP-1 concentrations increase either by increased secretion or by exogenous infusion, the molar ratio of insulin to glucagon in the blood that reaches the liver via the portal circulation is greatly increased, whereby hepatic glucose production decreases (Hvidberg A, et al., Metabolism 1994; 43:104-108). As a result blood glucose concentrations decrease. Because of the glucose dependency of the insulinotropic and glucagonostatic actions, the glucose lowering effect is self-limiting, and the hormone, therefore, does not cause hypoglycaemia regardless of dose (Qualmann C, et al., Acta Diabetologica, 1995; 32: 13-16). The effects are preserved in patients with diabetes mellitus (Nauck M A, et al., J Clin Invest 1993; 91:301-307), in whom infusions of slightly supraphysiological doses of GLP-1 may completely normalise blood glucose values in spite of poor metabolic control and secondary failure to sulphonylurea (Nauck M A, et al., Diabetologia 1993; 36:741-744). The importance of the glucagonostatic effect is illustrated by the finding that GLP-1 also lowers blood glucose in type-I diabetic patients without residual P-cell secretory capacity (Creutzfeldt W, et al., Diabetes Care 1996; 19: 580-586).

GLP-1 is involved in increasing beta-cell mass as well as regulating beta-cell differentiation, beta-cell proliferation and beta-cell survival (Stoffers D A, Horm Metab Res. 2004 November-December; 36(11-12):811-21), and has a role in increasing proinsulin gene transcription and biosynthesis.

In addition to its effects on the pancreatic islets, GLP-1 has powerful actions on the gastrointestinal tract. Infused in physiological amounts, GLP-1 potently inhibits pentagastrin-induced as well as meal-induced gastric acid secretion (Schjoldager B T G, et al., Dig. Dis. Sci. 1989; 35:703-708; Wettergren A, et al., Dig Dis Sci 1993; 38:665-673). It also inhibits gastric emntying rate and pancreatic enzyme secretion (Wettergren A., et al., Dig Dis Sci 1993; 38:665-673). Similar inhibitory effects on gastric and pancreatic secretion and motility may be elicited in humans upon perfusion of the ileum with carbohydrate- or lipid-containing solutions (Layer P, et al., Dig Dis Sci 1995; 40: 1074-1082; Layer P, et al., Digestion 1993; 54: 385-386). Concomitantly, GLP-1 secretion is greatly stimulated, and it has been speculated that GLP-1 may be at least partly responsible for this so-called "ileal-brake" effect (Layer P, et al., Digestion 1993; 54: 385-386). In fact, recent studies suggest that, physiologically, the ileal-brake effects of GLP-1 may be more important than its effects on the pancreatic islets. Thus, in dose response studies GLP-1 influences gastric emptying rate at infusion rates at least as low as those required to influence islet secretion (Nauck M, et al., Gut 1995; 37 (suppl. 2): A124).

GLP-1 seems to have an effect on food intake. Intraventricular administration of GLP-1 profoundly inhibits food intake in rats (Schick R R, vorm Walde T, Zimmermann J P, Schusdziarra V, Classen M. Glucagon-like peptide 1—a novel brain peptide involved in feeding regulation. in Ditschuneit H, Gries F A, Hauner H, Schusdziarra V, Wechsler J G (eds.) Obesity in Europe. John Libbey & Company Ltd., 1994; pp. 363-367; 42). This effect seems to be highly specific. Thus, N-terminally extended GLP-1 (PG 72-107)amide is inactive and appropriate doses of the GLP-1 antagonist, exendin 9-39, abolish the effects of GLP-1. Acute, peripheral administration of GLP-1 does not inhibit food intake acutely in rats (Turton M D, et al., Nature 1996; 379: 69-72). However, it remains possible that GLP-1 secreted from the intestinal L-cells may also act as a satiety signal.

Not only the insulinotropic effects but also the effects of GLP-1 on the gastrointestinal tract are preserved in diabetic patients (Willms B, et al., Diabetologia 1994; 37, suppl.1: A118), and may help curtailing meal-induced glucose excursions, but, more importantly, may also influence food intake. Administered intravenously, continuously for one week, GLP-1 at 4 ng/kg/min has been demonstrated to dramatically improve glycaemic control in NIDDM patients without significant side effects (Larsen J, et al., Diabetes 1996; 45, suppl. 2: 233A). The peptide is fully active after subcutaneous administration (Ritzel R, et al., Diabetologia 1995; 38: 720-725), but is rapidly degraded mainly due to degradation by dipeptidyl peptidase IV-like enzymes (Deacon C F, et al., J Clin Endocrinol Metab 1995; 80: 952-957; Deacon C F, et al., Diabetes 44: 1126-1131).

The amino acid sequence of GLP-1 is disclosed in Schmidt et al. (Diabetologia 28 704-707 (1985). Human GLP-1 is a 30-31 amino acid residue peptide originating from preproglucagon which is synthesized, i.a. in the L-cells in the distal ileum, in the pancreas and in the brain. Processing of preproglucagon to GLP-1(7-36)amide, GLP-1(7-37) and GLP-2 occurs mainly in the L-cells. Although the interesting pharmacological properties of GLP-1(7-37) and analogues thereof have attracted much attention in recent years only little is known about the structure of these molecules. The secondary structure of GLP-1 in micelles has been described by Thorton et al. (Biochemistry 33: 3532-3539 (1994)), but in normal solution, GLP-1 is considered a very flexible molecule. Derivatisation of this relatively small and very flexible molecule resulted in compounds whose plasma profile were highly protracted and still had retained activity.

GLP-1 and analogues of GLP-1 and fragments thereof are useful i.a. in the treatment of Type 1 and Type 2 diabetes and obesity.

WO 87/06941 discloses GLP-1 fragments, including GLP-1(7-37), and functional derivatives thereof and to their use as an insulinotropic agent. GLP-1(7-37), certain derivatives thereof and the use thereof to treat Diabetes mellitus in a mammal are disclosed in U.S. Pat. No. 5,120,712, which is incorporated by reference herein.

WO 90/11296 discloses GLP-1 fragments, including GLP-1(7-36), and functional derivatives thereof which have an insulinotropic activity which exceeds the insulinotropic activity of GLP-1(1-36) or GLP-1(1-37) and to their use as insulinotropic agents.

The amino acid sequence of GLP-1(7-36) and GLP-1(7-37) is (SEQ ID NO: 1 and SEQ ID NO: 2): His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-X, wherein X is $NH_2$ for GLP-1(7-36) and X is Gly for GLP-1 (7-37).

WO 91/11457 discloses analogues of the active GLP-1 peptides 7-34, 7-35, 7-36, and 7-37 which can also be useful as GLP-1 moieties.

EP 0708179-A2 (Eli Lilly & Co.) discloses GLP-1 analogues and derivatives that include an N-terminal imidazole group and optionally an unbranched $C_6$-$C_{10}$ acyl group in attached to the lysine residue in position 34.

EP 0699686-A2 (Eli Lilly & Co.) discloses certain N-terminal truncated fragments of GLP-1 that are reported to be biologically active.

Another example of a peptide is T-20 (DP-178) which is a peptide corresponding to amino acids 638 to 673 of the HIV-$1_{LAI}$ transmembrane protein (TM) gp41, the carboxyl-terminal helical segment of the extracellular portion of gp41. The extracellular portion of gp41 has another α-helical region which is the amino-terminal proposed zipper domain, DP-107, DP-107 exhibits potent antiviral activity by inhibiting viral fusion. It is a 38 amino acid peptide, corresponding to residues 558 to 595 of the HIV-$1_{LAI}$ transmembrane gp41 protein. Studies with DP-107 have proven both are non-toxic in in vitro studies and in animals. U.S. Pat. No. 5,656,480, which is incorporated by reference herein, describes DP-107 and its antiviral activity.

T-20 inhibits entry of HIV into cells by acting as a viral fusion inhibitor. The fusion process of HIV is well characterized. HIV binds to CD4 receptor via gp120, and upon binding to its receptor, gp120 goes through a series of conformational changes that allows it to bind to its coreceptors, CCR5 or CXCR4. After binding to both receptor and coreceptor, gp120 exposes gp41 to begin the fusion process. gp41 has two regions named heptad repeat 1 and 2 (HR1 and 2). The extracellular domain identified as HR1 is an β-helical region which is the amino-terminal of a proposed zipper domain. HR1 comes together with HR2 of gp41 to form a hairpin. The structure that it is formed is a α-helix bundle that places the HIV envelope in the proximity of the cellular membrane causing fusion between the two membranes. T-20 prevents the conformational changes necessary for viral fusion by binding the first heptad-repeat (HR1) of the gp41 transmembrane glycoprotein. Thus, the formation of the 6-helix bundle is blocked by T-20's binding to the HR1 region of gp41. The DP107 and DP178 domains (i.e., the HR1 and HR2 domains) of the HIV gp41 protein non-covalently complex with each other, and their interaction is required for the normal infectivity of the virus. Compounds that disrupt the interaction between DP107 and DP178, and/or between DP107-like and DP178-like peptides are antifusogenic, including antiviral.

DP-178 acts as a potent inhibitor of HIV-1 mediated CD-4$^+$ cell-cell fusion (i.e., syncytial formation) and infection of CD-4$^+$ cells by cell-free virus. Such anti-retroviral activity includes, but is not limited to, the inhibition of HIV transmission to uninfected CD-4$^+$ cells. DP-178 act at low concentrations, and it has been proven that it is non-toxic in in vitro studies and in animals. The amino acid conservation within the DP-178—corresponding regions of HIV-1 and HIV-2 has been described.

Potential uses for DP-178 peptides are described in U.S. Pat. Nos. 5,464,933 and 6,133,418, as well as U.S. Pat. Nos. 6,750,008 and 6,824,783, all of which are incorporated by reference herein, for use in inhibition of fusion events associated with HIV transmission.

Portions, homologs, and analogs of DP178 and DP-107 as well as modulators of DP178/DP107, DP178-like/DP107-like or HR1/HR2 interactions have been investigated that show antiviral activity, and/or show anti-membrane fusion capability, or an ability to modulate intracellular processes involving coiled-coil peptide structures in retroviruses other than HIV-1 and nonretroviral viruses. Viruses in such studies include, simian immunodeficiency virus (U.S. Pat. No. 6,017, 536), respiratory synctial virus (U.S. Pat. Nos. 6,228,983; 6,440,656; 6,479,055; 6,623,741), Epstein-Barr virus (U.S. Pat. Nos. 6,093,794; 6,518,013), parainfluenza virus (U.S. Pat. No. 6,333,395), influenza virus (U.S. Pat. Nos. 6,068, 973; 6,060,065), and measles virus (U.S. Pat. No. 6,013,263). All of which are incorporated by reference herein.

A commercially available form of DP-178 is Fuzeon® (enfuvirtide, Roche Laboratories Inc. and Trimeris, Inc.). Fuzeon® has an acetylated N terminus and a carboxamide as the C-terminus, and is described by the following primary amino acid sequence: $CH_3CO$-YTSLIHSLIEESQN-QQEKNEQELLELDKWASLWNWF—$NH_2$. It is used in combination with other antivirals in HIV-1 patients that show HIV-1 replication despite ongoing antiretroviral therapy.

U.S. Pat. Nos. 5,464,933 and 6,824,783, which are incorporated by reference herein, describes DP-178, DP-178 fragments, analogs, and homologs, including, but not limited to, molecules with amino and carboxy terminal truncations, substitutions, insertions, deletions, additions, or macromolecular carrier groups as well as DP-178 molecules with chemical groups such as hydrophobic groups present at their amino and/or carboxy termini. Additional variants, include but are not limited to, those described in U.S. Pat. No. 6,830,893 and the derivatives of DP-178 disclosed in U.S. Pat. No. 6,861, 059. A set of T-20 hybrid polypeptides are described in U.S. Pat. Nos. 6,656,906, 6,562,787, 6,348,568 and 6,258,782, and a DP-178-toxin fusion is described in U.S. Pat. No. 6,627, 197.

HAART (Highly Active Anti-Retroviral Therapy) is the standard of therapy for HIV which combines drugs from a few classes of antiretroviral agents to reduce viral loads. U.S. Pat. No. 6,861,059, which is incorporated by reference herein, discloses methods of treating HIV-1 infection or inhibiting HIV-1 replication employing DP-178 or DP-107 or derivatives thereof, in combination with at least one other antiviral therapeutic agent such as a reverse transcriptase inhibitor (e.g. AZT, ddI, ddC, ddA, d4T, 3TC, or other dideoxynucleotides or dideoxyfluoronucleosides) or an inhibitor of HIV-1 protease (e.g. indinavir; ritonavir). Other antivirals include cytokines (e.g., rIFNα, rIFNβ, rIFNγ), inhibitors of viral mRNA capping (e.g. ribavirin), inhibitors of HIV protease (e.g. ABT-538 and MK-639), amphotericin B as a lipid-binding molecule with anti-HIV activity, and castanospermine as an inhibitor of glycoprotein processing. Potential combination therapies of other anti-viral agents, including but not limited to, reverse transcriptase inhibitors, integrase inhibitors, protease inhibitors, cytokine antagonists, and chemokine receptor modulators with T-20 are described in a number of references including U.S. Pat. Nos. 6,855,724; 6,844,340; 6,841,558; 6,833,457; 6,825,210; 6,811,780; 6,809,109; 6,806,265; 6,768,007; 6,750,230; 6,706,706; 6,696,494; 6,673,821; 6,673,791; 6,667,314; 6,642,237; 6,599,911; 6,596,729; 6,593,346; 6,589,962; 6,586,430; 6,541,515; 6,538,002; 6,531,484; 6,511,994; 6,506,777; 6,500,844; 6,498,161; 6,472,410; 6,432,981; 6,410,726; 6,399,619; 6,395,743; 6,358,979; 6,265,434; 6,248,755; 6,245,806; and 6,172,110.

Potential delivery systems for DP-178 include, but are not limited to those described in U.S. Pat. Nos. 6,844,324 and 6,706,892. In addition, a process for producing T-20 in inclusion bodies was described in U.S. Pat. No. 6,858,410.

T20/DP178, T21/DP107, and fragments thereof have also been found to interact with N-formyl peptide receptor (FPR members). T-20 activates the N-formyl peptide receptor present in human phagocytes (Su et al. (1999) Blood 93(11): 3885-3892) and is a chemoattractant and activator of monocytes and neutrophils (see U.S. Pat. No. 6,830,893). The FPR class receptors are G-protein-coupled, STM receptors that bind the chemoattractant fMLP (N-formyl-methionyl-leucyl-phenylalanine) and are involved in monocyte chemotaxis and the induction of a host immune response to a pathogen. The prototype FPR class receptor, FPR, binds fMLP with high affinity and is activated by low concentrations of fMLP. The binding of FPR by fMLP induces a cascade of G protein-mediated signaling events leading to phagocytic cell adhesion, chemotaxis, release of oxygen intermediates, enhanced phagocytosis and bacterial killing, as well as MAP kinase activation and gene transcription. (Krump et al., J Biol Chem 272:937 (1997); Prossnitz et al., Pharmacol Ther 74:73 (1997); Murphy, Annu. Rev. Immuno. 12: 593 (1994); and Murphy, The N-formyl peptide chemotactic receptors, Chemoattractant ligands and their receptors. CRC Press, Boca Raton, p. 269 (1996)). Another FPR class receptor is the highly homologous variant of FPR, named FPRL1 (also referred to as FPRH2 and LXA4R). FPRL1 was originally cloned as an orphan receptor (Murphy et al., J. Biol. Chem., 267:7637-7643 (1992); Ye et al., Biochem. Biophys. Res. Commun., 184:582-589 (1992); Bao et al., Genomics, 13:437-440 (1992); Gao, J. L. and P. M. Murphy, J. Biol. Chem., 268:25395-25401 (1993); and Nomura et al., Int. Immunol., 5:1239-1249 (1993)) but was subsequently found to mediate $Ca^{2+}$ mobilization in response to high concentrations of fMLP. (Ye et al., Biochem. Biophys. Res. Commun., 184:582-589 (1992); and Gao, J. L. and P. M. Murphy, J. Biol. Chem. 268:25395-25401 (1993)).

The chemokine receptor CCR5 is another G-protein-coupled, STM receptor and is a major fusion-cofactor exploited by most primary isolates of the human immunodeficiency virus type 1 (HIV-1). (Al Khatib et al., Science 1996, 272:1955; Doranz et al., Cell 1996, 85:1149; Deng et al., Nature 1996, 381:661; Dragic et al., Nature 1996; 381:667; Horuk, Immunol Today, 20:89 (1999); Dimitrov and Broder, "HIV and Membrane Receptors," HIV and membrane fusion: Medical Intelligence Unit, Landes Bioscience, Austin, Tex., 1997:99; and Berger, AIDS 11, Suppl A:S3 (1997)). Individuals that fail to express CCR5 are largely resistant to HIV-1 infection. (Liu et al., Cell 1996, 86:367-77; Huang, Y, Nat Med 1996, 2:1240; Dean, et al., Science, 273:1856 (1996)). Due to its prominent role in HIV-1 fusion and entry, investigators have focused considerable research on developing molecules that interrupt the interaction between the HIV-1 envelope and CCR5. Chemokine ligands and antibodies specific for CCR5, for example, have been shown to inhibit HIV-1 entry and replication. (Cocchi et al., Science, 270:1811 (1995); Wu et al., J Exp Med, 186: 373 (1997); Proudfoot et al., J Biol Chem, 271:2599 (1996); Arenzana-Seisdedos et al., Nature, 383:400 (1996); Gong et al., J Biol Chem, 273:4289 (1998)). U.S. Pat. No. 6,808,877 discusses DP-178 and its role in phosphorylation and downregulation of CCR5 and/or the inhibition of HIV infection by acting as a ligand to the N-formyl peptide receptor.

Peptide YY (PYY) is a thirty six amino acid long peptide, first isolated from porcine intestinal tissue and mainly localized in intestinal endocrine cells. PYY is secreted postprandially by endocrine cells of the distal gastrointestinal tract and acts at the hypothalamus signaling satiety. See Batterham, R. L. et al., Nature 418:650-654 (2002), which is incorporated by reference herein. It has many biological activities, including a range of activities within the digestive system and potent inhibition of intestinal electrolyte and fluid secretion. Like its relatives, neuropeptide Y (NPY) and pancreatic polypeptide (PP), peptide YY (PYY) is bent into hairpin configuration that is important in bringing the free ends of the molecule together for binding to the receptors.

Recent studies have shown that fasting and postprandial PYY levels are low in obese subjects, which may account for their high appetite and food consumption. When administered intravenously, it suppresses appetite and food intake in both lean and obese subjects (Batterham, R. L. et al., N Engl J Med 349:941-948 (2003)). Other peptides from the pancreatic peptide (PP) family, like peptide YY fragments (e.g. PYY[3-36]), and PYY agonists (including those not in the PP family) also suppress appetite. Its oral activity, however, is negligible due to its low absorption and rapid degradation in the gastrointestinal tract. PYY [3-36] is identified as SEQ ID NO: 3 of WO 02/47712 and U.S. patent Publication No. 2002/0141985; Eberlein, Eysselein et al., Peptides 10:797-803 (1989); and Grandy, Schimiczek et al., Regul Pept 51:151-9 (1994), which are incorporated by reference herein.

PYY [3-36] has a sequence identical to PYY over amino acids 3 to 36. PYY[3-36] contains approximately 40% of total peptide YY-like immunoreactivity in human and canine intestinal extracts and about 36% of total plasma peptide YY immunoreactivity in a fasting state to slightly over 50% following a meal. It is apparently a dipeptidyl peptidase-IV (DPP4) cleavage product of peptide YY. Peptide YY[3-36] is reportedly a selective ligand at the Y2 and Y5 receptors, which appear pharmacologically unique in preferring N-terminally truncated (i.e. C terminal fragments of) neuropeptide Y analogs. A PYY agonist may bind to a PYY receptor with higher or lower affinity, demonstrate a longer or shorter half-life in vivo or in vitro, or be more or less effective than native PYY.

Current antiobesity drugs have limited efficacy and numerous side effects. Crowley, V. E., Yeo, G. S. & O'Rahilly, S., Nat. Rev. Drug Discov 1, 276-86 (2002). With obesity reaching epidemic proportions worldwide, there is a pressing need for the development of adequate therapeutics in this area. In recent years, hormones and neuropeptides involved in the regulation of appetite, body energy expenditure, and fat mass accumulation such as PYY have emerged as potential antiobesity drugs. See McMinn, J. E., Baskin, D. G. & Schwartz, M. W., Obes Rev 1:37-46 (2000), Drazen, D. L. & Woods, S. C., Curr Opin Clin Nutr Metab Care 6:621-629 (2003), which are incorporated by reference herein.

According to Batterham et al., Nature 418:650-654 (2002), which is hereby incorporated by reference, the peptide YY [3-36] system may provide a therapeutic target for the treatment of obesity. International Publication No. WO 02/47712 and U.S. Patent Application Publication No. 2002/0141985 disclose methods for treating obesity and diabetes with peptide YY and peptide YY agonists, such as peptide YY[3-36]. U.S. Patent Application Publication No. 20050002927 describes the use of at least one Y2 receptor-binding peptide, such as peptide YY, Neuropeptide Y (NPY) or Pancreatic Peptide (PP) for treating a variety of diseases and conditions in mammalian subjects such as obesity.

Intranasal PYY(3-36) (Merck, Nastech) is in clinical development as a treatment of obesity. Other PYY(3-36) compounds in development include oral PYY(3-36) (Emisphere) and AC162352 (Amylin).

In addition, treatment with DPP-IV inhibitors prevents degradation of Peptide YY which has been linked to gastrointestinal conditions such as ulcers, irritable bowel disease and inflammatory bowel disease. Peptide YY and its analogs or agonists have been used to manipulate endocrine regulation of cell proliferation, nutrient transport, and intestinal water and electrolyte secretion. (U.S. Pat. No. 5,604,203; WO9820885A1; EP692971A1; U.S. Pat. No. 5,912,227, which are incorporated by reference herein). A role for peptide YY in the regulation of intestinal motility, secretion, and blood flow has also been suggested, as well as its use in a treatment of malabsorptive disorders. Analogs of PYY have been reported that emulate and enhance the duration, effect, biological activity and selectivity of the natural peptide in the treatment of pancreatic tumors (See U.S. Ser. No. 5,574,010, incorporated herein by reference).

Other suitable PYY agonists include those described in International Publication No. WO 98/20885, which is hereby incorporated by reference.

In one aspect, the invention provides a method of treating obesity in an obese or overweight animal by administering a therapeutically effective amount of PYY, a PYY agonist, or a mixture thereof with at least one delivery agent compound. While "obesity" is generally defined as a body mass index over 30, for purposes of this disclosure, any subject, including those with a body mass index of less than 30, who needs or wishes to reduce body weight is included in the scope of "obese." Subjects who are insulin resistant, glucose intolerant, or have any form of diabetes mellitus (e.g., type 1, 2 or gestational diabetes) can benefit from this method.

In other aspects, the invention features methods of reducing food intake, treating diabetes mellitus, and improving lipid profile (including reducing LDL cholesterol and triglyceride levels and/or changing HDL cholesterol levels) comprising administering to a subject a therapeutically effective amount of PYY, a PYY agonist, or a mixture thereof with at least one delivery agent compound. In a preferred embodiment, the methods of the invention are used to treat conditions or disorders which can be alleviated by reducing nutrient availability in a subject in need thereof, comprising administering to said subject a therapeutically effective amount of PYY, a PYY agonist, or a mixture thereof with at least one delivery agent compound. Such conditions and disorders include, but are not limited to, hypertension, dyslipidemia, cardiovascular disease, eating disorders, insulin-resistance, obesity, and diabetes mellitus of any kind.

Preferred PYY agonists may have a potency in one of the assays described in WO 02/47712 and U.S. patent Publication No. 2002/0141985 (preferably food intake, gastric emptying, pancreatic secretion, or weight reduction assays) which is greater than the potency of NPY in that same assay. PYY's and PYY agonists with the delivery agent compound may be administered separately or together with one or more other compounds and compositions that exhibit a long term or short-term action to reduce nutrient availability, including, but not limited to other compounds and compositions that comprise an amylin or amylin agonist, a cholecystokinin (CCK) or CCK agonist, a leptin (OB protein) or leptin agonist, an exendin or exendin agonist, or a GLP-1 or GLP-1 agonist as described in U.S. Patent Publication 20050009748. Suitable amylin agonists include, for example, [25,28, 29Pro-]-human amylin (also known as "pramlintide", and described in U.S. Pat. Nos. 5,686,511 and 5,998,367), calcitonin (e.g., salmon calcitonin), including those described in U.S. Pat. No. 5,739,106, which is hereby incorporated by reference. The CCK used is preferably CCK octopeptide (CCK-8). Leptin is discussed in, for example, Pelleymounter, C. et al., Science 269: 540-543 (1995), Halaas, G. et al., Science 269: 543-6 (1995) and Campfield, S. et al., Science 269: 546-549 (1995). Suitable CCK agonist includes those described in U.S. Pat. No. 5,739,106, which is hereby incorporated by reference. Suitable exendins include exendin-3 and exendin-4, and exendin agonist compounds include, for example, those described in PCT Publications WO 99/07404, WO 99/25727, and WO 99/25728, all of which are hereby incorporated by reference. According to one embodiment, the composition of the present invention includes at least one delivery agent compound, PYY, a PYY agonist, or a mixture thereof, at least one amylin agonist, and a CCK agonist. Suitable combinations of amylin agonist and CCK agonist include, but are not limited to, those described in U.S. Pat. No. 5,739,106, which is hereby incorporated by reference.

Adrenocorticotropic hormone (ACTH) peptides including, but not limited to, ACTH, human; ACTH 1-10; ACTH 1-13, human; ACTH 1-16, human; ACTH 1-17; ACTH 1-24, human; ACTH 4-10; ACTH 4-11; ACTH 6-24; ACTH 7-38, human; ACTH 18-39, human; ACTH, rat; ACTH 12-39, rat; beta-cell tropin (ACTH 22-39); biotinyl-ACTH 1-24, human; biotinyl-ACTH 7-38, human; corticostatin, human; corticostatin, rabbit; [Met(02)$^4$, DLys$^8$, Phe$^9$] ACTH 4-9, human; [Met(0)$^4$,DLys$^8$, Phe$^9$] ACTH 4-9, human; N-acetyl, ACTH 1-17, human; and ebiratide.

Adrenomedullin peptides including, but not limited to, adrenomedullin, adrenomedullin 1-52, human; adrenomedullin 1-12, human; adrenomedullin 13-52, human; adrenomedullin 22-52, human; pro-adrenomedullin 45-92, human; pro-adrenomedullin 153-185, human; adrenomedullin 1-52, porcine; pro-adrenomedullin (N-20), porcine; adrenomedullin 1-50, rat; adrenomedullin 11-50, rat; and proAM-N20 (proadrenomedullin N-terminal 20 peptide), rat.

Allatostatin peptides including, but not limited to, allatostatin I; allatostatin II; allatostatin III; and allatostatin IV.

Amylin peptides including, but not limited to, acetyl-amylin 8-37, human; acetylated amylin 8-37, rat; AC187 amylin antagonist; AC253 amylin antagonist; AC625 amylin antagonist; amylin 8-37, human; amylin (IAPP), cat; amylin (insulinoma or islet amyloid polypeptide(IAPP)); amylin amide, human; amylin 1-13 (diabetes-associated peptide 1-13), human; amylin 20-29 (IAPP 20-29), human; AC625 amylin antagonist; amylin 8-37, human; amylin (IAPP), cat; amylin, rat; amylin 8-37, rat; biotinyl-amylin, rat; and biotinyl-amylin amide, human.

Amyloid beta-protein fragment peptides including, but not limited to, Alzheimer's disease beta-protein 12-28 (SP17); amyloid beta-protein 25-35; amyloid beta/A4-protein precursor 328-332; amyloid beta/A4 protein precursor (APP) 319-335; amyloid beta-protein 1-43; amyloid beta-protein 1-42; amyloid beta-protein 1-40; amyloid beta-protein 10-20; amyloid beta-protein 22-35; Alzheimer's disease beta-protein (SP28); beta-amyloid peptide 1-42, rat; beta-amyloid peptide 1-40, rat; beta-amyloid 1-11; beta-amyloid 31-35; beta-amyloid 32-35; beta-amyloid 35-25; beta-amyloid/A4 protein precursor 96-110; beta-amyloid precursor protein 657-676; beta-amyloid 1-38; [Gln$^{11}$]-Alzheimer's disease beta-protein; [Gln$^{11}$]-beta-amyloid 1-40; [Gln$^{22}$]-beta-amyloid 6-40; non-A beta component of Alzheimer's disease amyloid (NAC); P3, (A beta 17-40) Alzheimer's disease amyloid β-peptide; and SAP (serum amyloid P component) 194-204.

Angiotensin peptides including, but not limited to, A-779; Ala-Pro-Gly-angiotensin II; [Ile$^3$,Val$^5$]-angiotensin II; angiotensin III antipeptide; angiogenin fragment 108-122; angiogenin fragment 108-123; angiotensin I converting enzyme inhibitor; angiotensin I, human; angiotensin I converting enzyme substrate; angiotensin I 1-7, human; angiopeptin; angiotensin II, human; angiotensin II antipeptide; angiotensin II 1-4, human; angiotensin II 3-8, human; angiotensin II 4-8, human; angiotensin II 5-8, human; angiotensin III ([Des-Asp$^1$]-angiotensin II), human; angiotensin III inhibitor ([Ile$^7$]-angiotensin III); angiotensin-converting enzyme inhibitor (Neothunnus macropterus); [Asn$^1$, Val$^5$]-angiotensin I, goosefish; [Asn$^1$, Val$^5$, Asn$^9$]-angiotensin I, salmon; [Asn$^1$, Val$^5$, Gly$^9$]-angiotensin I, eel; [Asn$^1$, Val$^5$]-angiotensin I 1-7, eel, goosefish, salmon; [Asn$^1$, Val$^5$]-angiotensin II; biotinyl-angiotensin I, human; biotinyl-angiotensin II, human; biotinyl-Ala-Ala-Ala-angiotensin II; [Des-Asp$^1$]-angiotensin I, human; [p-aminophenylalanine$^6$]-angiotensin II; renin substrate (angiotensinogen 1-13), human; preangiotensinogen 1-14 (renin substrate tetradecapeptide), human; renin substrate tetradecapeptide (angiotensinogen 1-14), porcine; [Sar$^1$]-angiotensin II, [Sar$^1$]-angiotensin II 1-7 amide; [Sar$^1$, Ala$^8$]-angiotensin II; [Sar$^1$, Ile$^8$]-angiotensin II; [Sar$^1$, Thr$^8$]-angiotensin II; [Sar$^1$, Tyr(Me)$^4$]-angiotensin II (Sarmesin); [Sar$^1$, Val$^5$, Ala$^8$]-angiotensin II; [Sar$^1$, Ile$^7$]-angiotensin III; synthetic tetradecapeptide renin substrate (No. 2); [Val$^4$]-angiotensin III; [Val$^5$]-angiotensin II; [Val$^5$]-angiotensin I, human; [Val$^5$]-angiotensin I; [Val$^5$, Asn$^9$]-angiotensin I, bullfrog; and [Val$^5$, Ser$^9$]-angiotensin I, fowl.

Antibiotic peptides including, but not limited to, Ac-SQNY; bactenecin, bovine; CAP 37 (20-44); carbormethoxycarbonyl-DPro-DPhe-OBzl; CD36 peptide P 139-155; CD36 peptide P 93-110; cecropin A-melittin hybrid peptide [CA(1-7)M(2-9)NH2]; cecropin B, free acid; CYS (Bzl)84 CD fragment 81-92; defensin (human) HNP-2; dermaseptin; immunostimulating peptide, human; lactoferricin, bovine (BLFC); and magainin spacer.

Antigenic polypeptides, which can elicit an enhanced immune response, enhance an immune response and or cause an immunizingly effective response to diseases and/or disease causing agents including, but not limited to, adenoviruses; anthrax; Bordetella pertussus; botulism; bovine rhinotracheitis; Branhamella catarrhalis; canine hepatitis; canine distemper; Chlamydiae; cholera; coccidiomycosis; cowpox; cytomegalovirus; Dengue fever; dengue toxoplasmosis; diphtheria; encephalitis; enterotoxigenic E. coli; Epstein Barr virus; equine encephalitis; equine infectious anemia; equine influenza; equine pneumonia; equine rhinovirus; Escherichia coli; feline leukemia; flavivirus; globulin; haemophilus influenza type b; Haemophilus influenzae; Haemophilus pertussis; Helicobacter pylori; hemophilus; hepatitis; hepatitis A; hepatitis B; Hepatitis C; herpes viruses; HIV; HIV-1 viruses; HIV-2 viruses; HTLV; influenza; Japanese encephalitis; Klebsiellae species; Legionella pneumophila; leishmania; leprosy; lyme disease; malaria immunogen; measles; meningitis; meningococcal; Meningococcal polysaccharide group A; Meningococcal polysaccharide group C; mumps; mumps virus; mycobacteria; Mycobacterium tuberculosis; Neisseria; Neisseria gonorrhea; Neisseria meningitidis; ovine blue tongue; ovine encephalitis; papilloma; parainfluenza; paramyxoviruses; Pertussis; plague; pneumococcus; Pneumocystis carinii; pneumonia; poiiovirus; proteus species; Pseudomonas aeruginosa; rabies; respiratory syncytial virus; rotavirus; rubella; salmonellae; schistosomiasis; shigellae; simian immunodeficiency virus; smallpox; Staphylococcus aureus; Staphylococcus species; Streptococcus pneumoniae; Streptococcus pyogenes; Streptococcus species; swine influenza; tetanus; Treponema pallidum; typhoid; vaccinia; varicella-zoster virus; and vibrio cholerae.

Anti-microbial peptides including, but not limited to, buforin I; buforin II; cecropin A; cecropin B; cecropin P1, porcine; gaegurin 2 (Rana rugosa); gaegurin 5 (Rana rugosa); indolicidin; protegrin-(PG)-I; magainin 1; and magainin 2; and T-22 [Tyr$^{5,12}$, Lys$^7$]-poly-phemusin II peptide.

Apoptosis related peptides including, but not limited to, Alzheimer's disease beta-protein (SP28); calpain inhibitor peptide; capsase-1 inhibitor V; capsase-3, substrate IV; caspase-1 inhibitor I, cell-permeable; caspase-1 inhibitor VI; caspase-3 substrate III, fluorogenic; caspase-1 substrate V, fluorogenic; caspase-3 inhibitor I, cell-permeable; caspase-6 ICE inhibitor III; [Des-Ac, biotin]-ICE inhibitor III; IL-1B converting enzyme (ICE) inhibitor II; IL-1 B converting enzyme (ICE) substrate IV; MDL 28170; and MG-132.

Atrial natriuretic peptides including, but not limited to, alpha-ANP (alpha-chANP), chicken; anantin; ANP 1-11, rat; ANP 8-30, frog; ANP 11-30, frog; ANP-21 (fANP-21), frog; ANP-24 (fANP-24), frog; ANP-30, frog; ANP fragment 5-28, human, canine; ANP-7-23, human; ANP fragment 7-28, human, canine; alpha-atrial natriuretic polypeptide 1-28, human, canine; A71915, rat; atrial natriuretic factor 8-33, rat; atrial natriuretic polypeptide 3-28, human; atrial natriuretic polypeptide 4-28, human, canine; atrial natriuretic polypeptide 5-27; human; atrial natriuretic aeptide (ANP), eel; atriopeptin I, rat, rabbit, mouse; atriopeptin II, rat, rabbit, mouse; atriopeptin III, rat, rabbit, mouse; atrial natriuretic factor (rANF), rat, auriculin A (rat ANF 126-149); auriculin B (rat ANF 126-150); beta-ANP (1-28, dimer, antiparallel); beta-rANF 17-48; biotinyl-alpha-ANP 1-28, human, canine; biotinyl-atrial natriuretic factor (biotinyl-rANF), rat; cardiodilatin 1-16, human; C-ANF 4-23, rat; Des-[Cys$^{105}$, Cys$^{121}$]-atrial natriuretic factor 104-126, rat; [Met(O)$^{12}$]ANP 1-28, human; [Mpr$^7$,DAla$^9$]ANP 7-28, amide, rat; prepro-ANF 104-116, human; prepro-ANF 26-55 (proANF 1-30), human; prepro-ANF 56-92 (proANF 31-67), human; prepro-ANF 104-123, human; [Tyr$^0$]-atriopeptin I, rat, rabbit, mouse; [Tyr$^0$]-atriopeptin II, rat, rabbit, mouse; [Tyr$^0$-prepro ANF 104-123, human; urodilatin (CDD/ANP 95-126); ventricular natriuretic peptide (VNP), eel; and ventricular natriuretic peptide (VNP), rainbow trout.

Bag cell peptides including, but not limited to, alpha bag cell peptide; alpha-bag cell peptide 1-9; alpha-bag cell peptide 1-8; alpba-bag cell peptide 1-7; beta-bag cell factor, and gamma-bag cell factor.

Bombesin peptides including, but not limited to, alpha-s1 casein 101-123 (bovine milk); biotinyl-bombesin; bombesin 8-14; bombesin; [Leu$^{13}$-psi (CH2NH)Leu$^{14}$]-bombesin; [D-Phe$^6$, Des-Met$^{14}$]-bombesin 6-14 ethylamide; [DPhe$^{12}$] bombesin; [DPhe$^{12}$,Leu$^{14}$]-bombesin; [Tyr$^4$]-bombesin; and [Tyr$^4$,DPhe$^{12}$]-bombesin.

Bone GLA peptides (BGP) including, but not limited to, bone GLA protein; bone GLA protein 45-49; [Glu$^{17}$, Gla$^{21,24}$]-osteocalcin 1-49, human; myclopeptide-2 (MP-2); osteocalcin 1-49 human; osteocalcin 37-49, human; and [Tyr$^{38}$, Phe$^{42,46}$] bone GLA protein 38-49, human.

Bradykinin peptides including, but not limited to, [Ala$^{2,6}$, des-Pro$^3$]-bradykinin; bradykinin; bradykinin (Bowfin. Gar); bradykinin potentiating peptide; bradykinin 1-3; bradykinin 1-5; bradykinin 1-6; bradykinin 1-7; bradykinin 2-7; bradykinin 2-9; [DPhe$^7$] bradykinin; [Des-Arg$^9$]-bradykinin; [Des-Arg$^{10}$]-Lys-bradykinin ([Des-Arg$^{10}$]-kallidin); [D-N-Me-Phe$^7$]-bradykinin; [Des-Arg$^9$, Leu$^8$]-bradykinin; Lys-bradykinin (kallidin); Lys-(Des-Arg$^9$, Leu$^8$]-bradykinin ([Des-Arg$^{10}$,Leu$^9$]-kallidin); [Lys$^0$-Hyp$^3$]-bradykinin; ovokinin; [Lys$^0$, Ala$^3$]-bradykinin; Met-Lys-bradykinin; peptide K12 bradykinin potentiating peptide; [(pCl)Phe$^{5,8}$]-bradykinin; T-kinin (Ile-Ser-bradykinin); [Thi$^{5,8}$, D-Phe$^7$]-bradykinin; [Tyr$^0$]-bradykinin; [Tyr$^5$]-bradykinin; [Tyr$^8$]-bradykinin; and kallikrein.

Brain natriuretic peptides (BNP) including, but not limited to, BNP 32, canine; BNP-like Peptide, eel; BNP-32, human; BNP-45, mouse; BNP-26, porcine; BNP-32, porcine; biotinyl-BNP-32, porcine; BNP-32, rat; biotinyl-BNP-32, rat; BNP45 (BNP 51-95, 5K cardiac natriuretic peptide), rat; and [Tyr$^0$]-BNP 1-32, human.

C-peptides including, but not limited to, C-peptide; and [Tyr$^0$]-C-peptide, human.

C-type natriuretic peptides (CNP) including, but not limited to, C-type natriuretic peptide, chicken; C-type natriuretic peptide-22 (CNP-22), porcine, rat, human; C-type natriuretic peptide-53 (CNP-53), human; C-type natriuretic peptide-53 (CNP-53), porcine, rat; C-type natriuretic peptide-53 (porcine, rat) 1-29 (CNP-531-29); prepro-CNP 1-27, rat; prepro-CNP 30-50, porcine, rat; vasonatrin peptide (VNP); and [Tyr$^0$]-C-type natriuretic peptide-22 ([Tyr$^0$]-CNP-22).

Calcitonin peptides including, but not limited to, biotinyl-calcitonin, human; biotinyl-calcitonin, rat; biotinyl-calcitonin, salmon; calcitonin, chicken; calcitonin, eel; calcitonin, human; calcitonin, porcine; calcitonin, rat; calcitonin, salmon; calcitonin 1-7, human; calcitonin 8-32, salmon; katacalcin (PDN-21) (C-procalcitonin); and N-proCT (aminoterminal procalcitonin cleavage peptide), human.

Calcitonin gene related peptides (CGRP) including, but not limited to, acetyl-alpha-CGRP 19-37, human; alpha-CGRP 19-37, human; alpha-CGRP 23-37, human; biotinyl-CGRP, human; biotinyl-CGRP II, human; biotinyl-CGRP, rat; beta-CGRP, rat; biotinyl-beta-CGRP, rat; CGRP, rat; CGRP, human; calcitonin C-terminal adjacent peptide; CGRP 1-19, human; CGRP 20-37, human; CGRP 8-37, human; CGRP II, human; CGRP, rat; CGRP 8-37, rat; CGRP 29-37, rat; CGRP 30-37, rat; CGRP 31-37, rat; CGRP 32-37, rat; CGRP 33-37, rat; CGRP 31-37, rat; ([Cys(Acm)$^{2,7}$]-CGRP; elcatonin; [Tyr$^0$]-CGRP, human; [Tyr$^0$]-CGRP II, human; [Tyr$^0$]-CGRP 28-37, rat; [Tyr$^0$]-CGRP, rat; and [Tyr$^{22}$]-CGRP 22-37, rat.

CART peptides including, but not limited to, CART, human; CART 55-102, human; CART, rat; and CART 55-102, rat.

Casomorphin peptides including, but not limited to, beta-casomorphin, human; beta-casomorphin 1-3; beta-casomorphin 1-3, amide; beta-casomorphin, bovine; beta-casomorphin 1-4, bovine; beta-casomorphin 1-5, bovine; beta-casomorphin 1-5, amide, bovine; beta-casomorphin 1-6, bovine; [DAla$^2$]-beta-casomorphin 1-3, amide, bovine; [DAla$^2$,Hyp$^4$,Tyr$^5$]-beta-casomorphin 1-5 amide; [DAla$^2$, DPro$^4$,Tyr$^5$]-beta-casomorphin 1-5, amide; [DAla$^2$,Tyr$^5$]-beta-casomorphin 1-5, amide, bovine; [DAla$^{2,4}$,Tyr$^5$]-beta-casomorphin 1-5, amide, bovine; [DAla$^2$, (pCl)Phe$^3$]-beta-casomorphin, amide, bovine; [DAla$^2$]-beta-casomorphin 1-4, amide, bovine; [DAla$^2$]-beta-casomorphin 1-5, bovine; [DAla$^2$]-beta-casomorphin 1-5, amide, bovine; [DAla$^2$, Met$^5$]-beta-casomorphin 1-5, bovine; [DPro$^2$]-beta-casomorphin 1-5, amide, bovine; [DAla$^2$]-beta-casomorphin 1-6, bovine; [DPro$^2$]-beta-casomorphin 1-4, amide; [Des-Tyr$^1$]-beta-casomorphin, bovine; [DAla$^{2,4}$,Tyr$^5$]-beta-casomorphin 1-5, amide, bovine; [DAla$^2$, (pCl)Phe$^3$]-beta-casomorphin, amide, bovine; [DAla$^2$]-beta-casomorphin 1-4, amide, bovine; [DAla$^2$]-beta-casomorphin 1-5, bovine; [DAla$^2$]-beta-casomorphin 1-5, amide, bovine; [DAla$^2$,Met$^5$]-beta-casomorphin 1-5, bovine; [DPro$^2$]-beta-casomorphin 1-5, amide, bovine; [DAla$^2$]-beta-casomorphin 1-6, bovine; [DPro$^2$]-beta-casomorphin 14, amide; [Des-Tyr$^1$]-beta-casomorphin, bovine; and [Val$^3$]-beta-casomorphin 1-4, amide, bovine.

Chemotactic peptides including, but not limited to, defensin 1 (human) HNP-1 (human neutrophil peptide-1); and N-formyl-Met-Leu-Phe.

Cholecystokinin (CCK) peptides including, but not limited to, caerulein; cholecystokinin; cholecystokinin-pancreozymin; CCK-33, human; cholecystokinin octapeptide 14 (non-sulfated) (CCK 26-29, unsulfated); cholecystokinin octapeptide (CCK 26-33); cholecystokinin octapeptide (non-sulfated) (CCK 26-33, unsulfated); cholecystokinin heptapeptide (CCK 27-33); cholecystokinin tetrapeptide (CCK 30-33); CCK-33, porcine; CR 1409, cholecystokinin antagonist; CCK flanking peptide (unsulfated); N-acetyl cholecystokinin, CCK 26-30, sulfated; N-acetyl cholecystokinin, CCK 26-31, sulfated; N-acetyl cholecystokinin, CCK 26-31, non-sulfated; prepro CCK fragment V-9-M; and proglumide.

Colony-stimulating factor peptides including, but not limited to, colony-stimulating factor (CSF); GMCSF; MCSF; and G-CSF.

Corticortropin releasing factor (CRF) peptides including, but not limited to, astressin; alpha-helical CRF 12-41; biotinyl-CRF, ovine; biotinyl-CRF, human, rat; CRF, bovine; CRF, human, rat; CRF, ovine; CRF, porcine; [Cys$^{21}$]-CRF, human, rat; CRF antagonist (alpha-helical CRF 9-41); CRF 6-33, human, rat; [DPro$^5$]-CRF, human, rat; [D-Phe$^{12}$, Nle$^{21,38}$]-CRF 12-41, human, rat; eosinophilotactic peptide; [Met(0)$^{21}$]-CRF, ovine; [Nle$^{21}$,Tyr$^{32}$]-CRF, ovine; prepro CRF 125-151, human; sauvagine, frog; [Tyr$^0$]-CRF, human, rat; [Tyr$^0$]-CRF, ovine; [Tyr$^0$]-CRF 34-41, ovine; [Tyr$^0$]-urocortin; urocortin amide, human; urocortin, rat; urotensin I (Catostomus commersoni); urotensin II; and urotensin II (Rana ridibunda).

Cortistatin peptides including, but not limited to, cortistatin 29; cortistatin 29 (1-13); [Tyr$^0$]-cortistatin 29; pro-cortistatin 28-47; and pro-cortistatin 51-81.

Cytokine peptides including, but not limited to, tumor necrosis factor; and tumor necrosis factor-β (TNF-β).

Dermorphin peptides including, but not limited to, dermorphin and dermorphin analog 1-4.

Dynorphin peptides including, but not limited to, big dynorphin (prodynorphin 209-240), porcine; biotinyl-dynorphin A (biotinyl-prodynorphin 209-225); [DAla$^2$, DArg$^6$] dynorphin A 1-13, porcine; [D-Ala$^2$]-dynorphin A, porcine; [D-Ala$^2$]-dynorphin A amide, porcine; [D-Ala$^2$]-dynorphin A 1-13, amide, porcine; [D-Ala$^2$]-dynorphin A 1-9, porcine; [DArg$^6$]-dynorphin A 1-13, porcine; [DArg$^8$]-dynorphin A 1-13, porcine; [Des-Tyr$^1$]-dynorphin A 1-8; [D-Pro$^{10}$]-dynorphin A 1-11, porcine; dynorphin A amide, porcine; dynorphin A 1-6, porcine; dynorphin A 1-7, porcine; dynorphin A 1-8, porcine; dynorphin A 1-9, porcine; dynorphin A 1-10, porcine; dynorphin A 1-10 amide, porcine; dynorphin A 1-11, porcine; dynorphin A 1-12, porcine; dynorphin A 1-13, porcine; dynorphin A 1-13 amide, porcine; DAKLI (dynorphin A-analogue kappa ligand); DAKLI-biotin ([Arg$^{11,13}$]-dynorphin A (1-13)-Gly-NH(CH2)$_5$NH-biotin); dynorphin A 2-17, porcine; dynorphin 2-17, amide, porcine; dynorphin A 2-12, porcine; dynorphin A 3-17, amide, porcine; dynorphin A 3-8, porcine; dynorphin A 3-13, porcine; dynorphin A 3-17, porcine; dynorphin A 7-17, porcine; dynorphin A 8-17, porcine; dynorphin A 6-17, porcine; dynorphin A 13-17, porcine; dynorphin B (prodynorphin 209-225), porcine; dynorphin B 1-9; [MeTyr$^1$, MeArg$^7$, D-Leu$^8$]-dynorphin 1-8 ethyl amide; [(nMe)Tyr$^1$] dynorphin A 1-13, amide, porcine; [Phe$^7$]-dynorphin A 1-7, porcine; [Phe$^7$]-dynorphin A 1-7, amide, porcine; and prodynorphin 228-256 (dynorphin B 29) (leumorphin), porcine.

Endorphin peptides including, but not limited to, alpha-neo-endorphin, porcine; beta-neoendorphin; Ac-beta-endorphin, camel, bovine, ovine; Ac-beta-endorphin 1-27, camel, bovine, ovine; Ac-beta-endorphin, human; Ac-beta-endorphin 1-26, human; Ac-beta-endorphin 1-27, human; Ac-gamma-endorphin (Ac-beta-lipotropin 61-77); acetyl-alpha-endorphin; alpha-endorphin (beta-lipotropin 61-76); alpha-neo-endorphin analog; alpha-neo-endorphin 1-7; [Arg$^8$]-alpha-neoendorphin 1-8; beta-endorphin (beta-lipotropin 61-91), camel, bovine, ovine; beta-endorphin 1-27, camel, bovine, ovine; beta-endorphin, equine; beta-endorphin (beta-lipotropin 61-91), human; beta-endorphin (1-5)+(16-31), human; beta-endorphin 1-26, human; beta-endorphin 1-27, human; beta-endorphin 6-31, human; beta-endorphin 18-31, human; beta-endorphin, porcine; beta-endorphin, rat; beta-lipotropin 1-10, porcine; beta-lipotropin 60-65; beta-lipotropin 61-64; beta-lipotropin 61-69; beta-lipotropin 88-91; biotinyl-beta-endorphin (biotinyl-bets-lipotropin 61-91); biocytin-beta-endorphin, human; gamma-endorphin (beta-lipotropin 61-77); [DAla$^2$]-alpha-neoendorphin 1-2, amide; [DAla$^2$]-beta-lipotropin 61-69; [DAla$^2$]-gamma-endorphin; [Des-Tyr$^1$]-beta-endorphin, human; [Des-Tyr$^1$]-gamma-endorphin (beta-lipotropin 62-77); [Leu$^5$]-beta-endorphin, camel, bovine, ovine; [Met$^5$, Lys$^6$]-alpha-neo-endorphin 1-6; [Met$^5$, Lys$^{6,7}$]-alpha-neo-endorphin 1-7; and [Met$^5$, Lys$^6$, Arg$^7$]-alpha-neo-endorphin 1-7.

Endothelin peptides including, but not limited to, endothelin-1 (ET-1); endothelin-1[Biotin-Lys$^9$]; endothelin-1 (1-15), human; endothelin-1 (1-15), amide, human; Ac-endothelin-1 (16-21), human; Ac-[DTrp$^{16}$]-endothelin-1 (16-21), human; [Ala$^{3,11}$]-endothelin-1; [Dpr1, Asp$^{15}$]-endothelin-1; [Ala$^2$]-endothelin-3, human; [Ala$^{18}$]-endothelin-1, human; [Asn$^{18}$]-endothelin-1, human; [Res-701-1]-endothelin B receptor antagonist; Suc-[Glu$^9$, Ala$^{11,15}$]-endothelin-1 (8-21), IRL-1620; endothelin-C-terminal hexapeptide; [D-Val$^{22}$]-big endothelin-1 (16-38), human; endothelin-2 (ET-2), human, canine; endothelin-3 (ET-3), human, rat, porcine, rabbit; biotinyl-endothelin-3 (biotinyl-ET-3); prepro-endothelin-1 (94-109), porcine; BQ-518; BQ-610; BQ-788; endothelium-dependent relaxation antagonist; FR139317; IRL-1038; JKC-30 1; JKC-302; PD-145065; PD-142893; sarafotoxin S6a (atractaspis engaddensis); sarafotoxin S6b (atractaspis engaddensis); sarafotoxin S6c (atractaspis engaddensis); [Lys$^4$]-sarafotoxin S6c; sarafotoxin S6d; big endothelin-1, human; biotinyl-big endothelin-1, human; big endothelin-1 (1-39), porcine; big endothelin-3 (22-41), amide, human; big endothelin-1 (22-39), rat; big endothelin-1 (1-39), bovine; big endothelin-1 (22-39), bovine; big endothelin-1 (19-38), human; big endothelin-1 (22-38), human; big endothelin-2, human; big endothelin-2 (22-37), human; big endothelin-3, human; big endothelin-1, porcine; big endothelin-1 (22-39) (prepro-endothelin-1 (74-91)); big endothelin-1, rat; big endothelin-2 (1-38), human; big endothelin-2 (22-38), human; big endothelin-3, rat; biotinyl-big endothelin-1, human; and [Tyr$^{123}$]-prepro-endothelin (110-130), amide, human.

ETa receptor antagonist peptides including, but not limited to, [BQ-123]; [BE18257B]; [BE-18257A]/[W-7338A]; [BQ-485]; FR139317; PD-151242; and TTA-386.

ETb receptor antagonist peptides including, but not limited to, [BQ-3020]; [RES-701-3]; and [IRL-1720]

Enkephalin peptides including, but not limited to, adrenorphin, free acid; amidorphin (proenkephalin A (104-129)-NII2), bovine; BAM-12P (bovine adrenal medulla enkephalin; [D-Ala$^2$, D-Leu$^5$]-enkephalin; [D-Ala$^2$, D-Met$^5$]-enkephalin; [DAla$^2$]-Leu-enkephalin, amide; [DAla$^2$,Leu$^5$, Arg$^6$]-enkephalin; [Des-Tyr$^1$,DPen$^{2,5}$]-enkephalin; [Des-Tyr$^1$,DPen$^2$,Pen$^5$]-enkephalin; [Des-Tyr$^1$]-Leu-enkephalin; [D-Pen$^{2,5}$]-enkephalin; [DPen$^2$, Pen$^5$]-enkephalin; enkephalinase substrate; [D-Pen$^2$, pCI-Phe$^4$, D-Pen$^5$]-enkephalin; Leu-enkephalin; Leu-enkephalin, amide; biotinyl-Leu-enkephalin; [D-Ala$^2$]-Leu-enkephalin; [D-Ser$^2$]-Leu-enkephalin-Thr (delta-receptor peptide) (DSLET); [D-Thr$^2$]-Leu-enkephalin-Thr (DTLET); [Lys$^6$]-Leu-enkephalin; [Met$^5$, Arg$^6$]-enkephalin; [Met$^5$,Arg$^6$-enkephalin-Arg; [Met$^5$,Arg$^6$, Phe$^7$]-enkephalin, amide; Met-enkephalin; biotinyl-Met-enkephalin; [D-Ala$^2$]-Met-enkephalin; [D-Ala$^2$]-Met-enkephalin, amide; Met-enkephalin-Arg-Phe; Met-enkephalin, amide; [Ala$^2$]-Met-enkephalin, amide; [DMet$^2$, Pro$^5$]-enkephalin, amide; [DTrp$^2$]-Met-enkephalin, amide; metorphinamide (adrenorphin); peptide B, bovine; 3200-Dalton adrenal peptide E, bovine; peptide F, bovine; preproenkephalin B 186-204, human; spinorphin, bovine; and thiorphan (D,L,3-mercapto-2-benzylpropanoyl-glycine).

Fibronectin peptides including, but not limited to platelet factor-4 (58-70), human; echistatin (Echis carinatus); E, P, L selectin conserved region; fibronectin analog; fibronectin-binding protein; fibrinopeptide A, human; [Tyr$^0$]-fibrinopeptide A, human; fibrinopeptide B, human; [Glu$^1$]-fibrinopeptide B, human; [Tyr$^{15}$]-fibrinopeptide B, human; fibrinogen beta-chain fragment of 24-42; fibrinogen binding inhibitor peptide; fibronectin related peptide (collagen binding fragment); fibrinolysis inhibiting factor; FN—C/H-1 (fibronectin heparin-binding fragment); FN—C/H—V (fibronectin heparin-binding fragment); heparin-binding peptide; laminin penta peptide, amide; Leu-Asp-Val-NH2 (LDV-NH2), human, bovine, rat, chicken; necrofibrin, human; necrofibrin, rat; and platelet membrane glycoprotein IIB peptide 296-306.

Galanin peptides including, but not limited to, galanin, human; galanin 1-19, human; preprogalanin 1-30, human; preprogalanin 65-88, human; preprogalanin 89-123, human; galanin, porcine; galanin 1-16, porcine, rat; galanin, rat; biotinyl-galanin, rat; preprogalanin 28-67, rat; galanin 1-13-bradykinin 2-9, amide; M40, galanin 1-13-Pro-Pro-(Ala- Leu) 2-Ala-amide; C7, galanin 1-13-spantide-amide; GMAP 1-41, amide; GMAP 16-41, amide; GMAP 25-41, amide; galantide; and entero-kassinin.

Gastrin peptides including, but not limited to, gastrin, chicken; gastric inhibitory peptide (GIP), human; gastrin I, human; biotinyl-gastrin I, human; big gastrin-1, human; gastrin releasing peptide, human; gastrin releasing peptide 1-16, human; gastric inhibitory polypeptide (GIP), porcine; gastrin releasing peptide, porcine; biotinyl-gastrin releasing peptide, porcine; gastrin releasing peptide 14-27, porcine, human; little gastrin, rat; pentagastrin; gastric inhibitory peptide 1-30, porcine; gastric inhibitory peptide 1-30, amide, porcine; [$Tyr^0$]-gastric inhibitory peptide 23-42, human; and gastric inhibitory peptide, rat.

Glucagon peptides including, but not limited to, [Des-$His^1$-$Glu^9$]-glucagon, exendin-4, glucagon, human; biotinyl-glucagon, human; glucagon 19-29, human; glucagon 22-29, human; [Des-$His^1$-$Glu^9$]-glucagon, amide; glucagon-like peptide 1, amide; glucagon-like peptide 1, human; glucagon-like peptide 1 (7-36); glucagon-like peptide 2, rat; biotinyl-glucagon-like peptide-1 (7-36) (biofinyl-preproglucagon 78-107, amide); glucagon-like peptide 2, human; intervening peptide-2; oxyntomodulin/glucagon 37; and valosin (peptide VQY), porcine.

Gn-RH associated peptides (GAP) including, but not limited to, Gn-RH associated peptide 25-53, human; Gn-RH associated peptide 1-24, human; Gn-RH associated peptide 1-13, human; Gn-RH associated peptide 1-13, rat; gonadotropin releasing peptide, follicular, human; [$Tyr^0$]-GAP ([$Tyr^0$]-Gn-RH Precursor Peptide 14-69), human; and proo-piomelanocortin (POMC) precursor 27-52, porcine.

Growth factor peptides including, but not limited to, cell growth factors; epidermal growth factors; tumor growth factor; alpha-TGF; beta-TF; alpha-TGF 34-43, rat; EGF, human; acidic fibroblast growth factor; basic fibroblast growth factor; basic fibroblast growth factor 13-18; basic fibroblast growth factor 120-125; brain derived acidic fibroblast growth factor 1-11; brain derived basic fibroblast growth factor 1-24; brain derived acidic fibroblast growth factor 102-111; [Cys($Acm^{20,31}$)]-epidermal growth factor 20-31; epidermal growth factor receptor peptide 985-996; insulin-like growth factor (IGF)-I, chicken; IGF-I, rat; IGF-I, human; Des (1-3) IGF-I, human; R3 IGF-I, human; R3 IGF-I, human; long R3 IGF-I, human; adjuvant peptide analog; anorexigenic peptide; Des (1-6) IGF-II, human; R6 IGF-II, human; IGF-I analogue; IGF 1 (24-41); IGF 1 (57-70); IGF I (30-41); IGF II; IGF II (33-40); [$Tyr^0$]-IGF II (33-40); liver cell growth factor; midkine; midkine 60-121, human; N-acetyl, alpha-TGF 34-43, methyl ester, rat; nerve growth factor (NGF), mouse; platelet-derived growth factor; platelet-derived growth factor antagonist; transforming growth factor-alpha, human; and transforming growth factor-I, rat.

Growth hormone peptides including, but not limited to, growth hormone (hGH), human; growth hormone 1-43, human; growth hormone 6-13, human; growth hormone releasing factor, human; growth hormone releasing factor, bovine; growth hormone releasing factor, porcine; growth hormone releasing factor 1-29, amide, rat; growth hormone pro-releasing factor, human; biotinyl-growth hormone releasing factor, human; growth hormone releasing factor 1-29, amide, human; [$D-Ala^2$]-growth hormone releasing factor 1-29, amide, human; [$N-Ac-Tyr^1$, $D-Arg^2$]-GRF 1-29, amide; [$His^1$, $Nle^{27}$]-growth hormone releasing factor 1-32, amide; growth hormone releasing factor 1-37, human; growth hormone releasing factor 140, human; growth hormone releasing factor 1-40, amide, human; growth hormone releasing factor 30-44, amide, human; growth hormone releasing factor, mouse; growth hormone releasing factor, ovine; growth hormone releasing factor, rat; biotinyl-growth hormone releasing factor, rat; GHRP-6 ([$His^1$, $Lys^6$]-GHRP); hexarelin (growth hormone releasing hexapeptide); and [$D-Lys^3$]-GHRP-6.

GTP-binding protein fragment peptides including, but not limited to, [$Arg^8$]-GTP-binding protein fragment, Gs alpha; GTP-binding protein fragment, G beta; GTP-binding protein fragment, GAlpha; GTP-binding protein fragment, Go Alpha; GTP-binding protein fragment, Gs Alpha; and GTP-binding protein fragment, G Alpha i2.

Guanylin peptides including, but not limited to, guanylin, human; guanylin, rat; and uroguanylin.

Inhibin peptides including, but not limited to, inhibin, bovine; inhibin, alpha-subunit 1-32, human; [$Tyr^0$]-inhibin, alpha-subunit 1-32, human; seminal plasma inhibin-like peptide, human; [$Tyr^0$]-seminal plasma inhibin-like peptide, human; inhibin, alpha-subunit 1-32, porcine; and [$Tyr^0$]-inhibin, alpha-subunit 1-32, porcine.

Insulin peptides including, but not limited to, insulin, human; insulin, porcine; IGF-I, human; insulin-like growth factor II (69-84); pro-insulin-like growth factor 11 (68-102), human; pro-insulin-like growth factor II (105-128), human; [$Asp^{B28}$]-insulin, human; [$Lys^{B28}$]-insulin, human; [$Leu^{B28}$]-insulin, human; [$Val^{B28}$]-insulin, human; [$Ala^{B28}$]-insulin, human; [$Asp^{B28}$, $Pro^{B29}$]-insulin, human; [$Lys^{B28}$, $Pro^{B29}$]-insulin, human; [$Leu^{B28}$ $Pro^{B29}$]-insulin, human; [$Val^{B28}$, $Pro^{B29}$]-insulin, human; [$Ala^{B28}$, $Pro^{B29}$]-insulin, human; [$Gly^{A21}$]-insulin, human; [$Gly^{A21}$ $Gln^{B3}$]-insulin, human; [$Ala^{A21}$]-insulin, human; [$Ala^{A21}$ Gln.$sup.^{B3}$] insulin, human; [$Gln^{B3}$]-insulin, human; [$Gln^{B30}$]-insulin, human; [$Gly^{A21}$ $Glu^{B30}$]-insulin, human; [$Gly^{A21}$ $Gln^{B3}$ $Glu^{B30}$]-insulin, human; [$Gln^{B3}$ $Glu^{B30}$]-insulin, human; B22-B30 insulin, human; B23-B30 insulin, human; B25-B30 insulin, human; B26-B30 insulin, human; B27-B30 insulin, human; B29-B30 insulin, human; the A chain of human insulin, and the B chain of human insulin.

Interleukin peptides including, but not limited to, interleukin-1 beta 165-181, rat; and interleukin-8 (IL-8, CINC/gro), rat.

Lamimin peptides including, but not limited to, laminin; alpha1 (I)-CB3 435-438, rat; and laminin binding inhibitor.

Leptin peptides including, but not limited to, leptin 93-105, human; leptin 22-56, rat; Tyr-leptin 26-39, human; and leptin 116-130, amide, mouse.

Leucokinin peptides including, but not limited to, leucomyosuppressin (LMS); leucopyrokinin (LPK); leucokinin I; leucokinin II; leucokinin III; leucokinin IV; leucokinin VI; leucokinin VII; and leucokinin VIII.

Luteinizing hormone-releasing hormone peptides including, but not limited to, antide; Gn-RH II, chicken; luteinizing hormone-releasing hormone (LH-RH) (GnRH); biotinyl-LH-RH; cetrorelix (D-20761); [$D-Ala^6$]-LH-RH; [$Gln^8$]-LH-RH (Chicken LH-RH); [$DLeu^6$, $Val^7$] LH-RH 1-9, ethyl amide; [$D-Lys^6$]-LH-RH; [$D-Phe^2$, $Pro^3$, $D-Phe^6$]-LH-RH; [$DPhe^2$, $DAla^6$] LH-RH; [$Des-Gly^{10}$]-LH-RH, ethyl amide; [$D-Ala^6$, $Des-Gly^{10}$]-LH-RH, ethyl amide; [$DTrp^6$]-LH-RH, ethyl amide; [$D-Trp^6$, $Des-Gly^{10}$]-LH-RH, ethyl amide (Deslorelin); [$DSer(But)_6$, $Des-Gly^{10}$]-LH-RH, ethyl amide; ethyl amide; leuprolide; LH-RH 4-10; LH-RH 7-10; LH-RH, free acid; LH-RH, lanprey; LH-RH, salmon; [$Lys^8$]-LH-RH; [$Trp^7$,$Leu^8$] LH-RH, free acid; and [(t-Bu)$DSer^6$, (Aza)$Gly^{10}$]-LH-RH.

Mastoparan peptides including, but not limited to, mastoparan; mas7; mas8; mas17; and mastoparan X.

Mast cell degranulating peptides including, but not limited to, mast cell degranulating peptide HR-1; and mast cell degranulating peptide HR-2.

Melanocyte stimulating hormone (MSH) peptides including, but not limited to, [Ac-Cys$^4$,DPhe$^7$,Cys$^{10}$] alpha-MSH 4-13, amide; alpha-melanocyte stimulating hormone; alpha-MSH, free acid; beta-MSH, porcine; biotinyl-alpha-melanocyte stimulating hormone; biotinyl-[Nle$^4$, D-Phe$^7$] alpha-melanocyte stimulating hormone; [Des-Acetyl]-alpha-MSH; [DPhe$^7$]-alpha-MSH, amide; gamma-1-MSH, amide; [Lys$^0$]-gamma-1-MSH, amide; MSH release inhibiting factor, amide; [Nle$^4$]-alpha-MSH, amide; [Nle$^4$, D-Phe$^7$]-alpha-MSH; N-Acetyl, [Nle$^4$,DPhe$^7$] alpha-MSH 4-10, amide; beta-MSH, human; and gamma-MSH.

Morphiceptin peptides including, but not limited to, morphiceptin (beta-casomorphin 14 amide); [D-Pro$^4$]-morphiceptin; and [N-MePhe$^3$,D-Pro$^4$]-morphiceptin.

Motilin peptides including, but not limited to, motilin, canine; motilin, porcine; biotinyl-motilin, porcine; and [Leu$^{13}$]-motilin, porcine.

Neuro-peptides including, but not limited to, Ac-Asp-Glu; achatina cardio-excitatory peptide-1 (ACEP-1) (Achatina fulica); adipokinetic hormone (AKH) (Locust); adipokinetic hormone (*Heliothis zea* and *Manduca sexta*); alytesin; *Tabanus atratus* adipokinetic hormone (Taa-AKH); adipokinetic hormone II (*Locusta migratoria*); adipokinetic hormone II (*Schistocera gregaria*); adipokinetic hormone III (AKH-3); adipokinetic hormone G (AKH-G) (*Gryllus bimaculatus*); allatotropin (AT) (*Manduca sexta*); allatotropin 6-13 (*Manduca sexta*); APGW amide (*Lymnaea stagnalis*); buccalin; cerebellin; [Des-Ser$^1$]-cerebellin; corazonin (American Cockroach *Periplaneta americana*); crustacean cardioactive peptide (CCAP); crustacean erythrophore; DF2 (Procambarus clarkii); diazepam-binding inhibitor fragment, human; diazepam binding inhibitor fragment (ODN); eledoisin related peptide; FMRF amide (molluscan cardioexcitatory neuropeptide); Gly-Pro-Glu (GPE), human; granuliberin R; head activator neuropeptide; [His$^7$]-corazonin; stick insect hypertrehalosaemic factor II; *Tabanus atratus* hypotrehalosemic hormone (Taa-HoTH); isoguvacine hydrochloride; bicuculline methiodide; piperidine-4-sulphonic acid; joining peptide of proopiomelanocortin (POMC), bovine; joining peptide, rat; KSAYMRF amide (*P. redivivus*); kassinin; kinetensin; levitide; litorin; LUQ 81-91 (*Aplysia californica*); LUQ 83-91 (*Aplysia californica*); myoactive peptide I (Periplanetin CC-1) (Neuro-homone D); myoactive peptide II (Periplanetin CC-2); myomodulin; neuron specific peptide; neuron specific enolase 404-443, rat; neuropeptide FF; neuropeptide K, porcine; NEI (prepro-MCH 131-143) neuropeptide, rat; NGE (prepro-MCH 110-128) neuropeptide, rat; NFI (*Procambarus clarkii*); PBAN-1 (*Bombyx mori*); Hez-PBAN (*Heliothis zea*); SCPB (cardioactive peptide from aplysia); secretoneurin, rat; uperolein; urechistachykinin I; urechistachykinin II; xenopsin-related peptide I; xenopsin-related peptide II; pedal peptide (Pep), aplysia; peptide F1, lobster; phyllomedusin; polistes mastoparan; proctolin; ranatensin; Ro I (Lubber Grasshopper, Romalea microptera); Ro II (Lubber Grasshopper, Romalea microptera); SALMF amide 1 (S1); SALMF amide 2 (S2); and SCPA.

Neuropeptide Y (NPY) peptides including, but not limited to, [Leu$^{31}$, Pro$^{34}$]-neuropeptide Y, human; neuropeptide F (Moniezia expansa); B1BP3226 NPY antagonist; Bis (31/31') {[Cys$^{31}$, Trp$^{32}$, Nva$^{34}$] NPY 31-36}; neuropeptide Y, human, rat; neuropeptide Y 1-24 amide, human; biotinyl-neuropeptide Y; [D-Tyr$^{27,36}$, D-Thr$^{32}$]-NPY 27-36; Des 10-17 (cyclo 7-21) [Cys$^{7,21}$, Pro$^{34}$]-NPY; C2-NPY; [Leu$^{31}$, Pro$^{34}$] neuropeptide Y, human neuropeptide Y, free acid, human; neuropeptide Y, free acid, porcine; prepro NPY 68-97, human; N-acetyl-[Leu$^{28}$, Leu$^{31}$] NPY 24-36; neuropeptide Y, porcine; [D-Trp$^{32}$]-neuropeptide Y, porcine; [D-Trp$^{32}$] NPY 1-36, human; [Leu$^{17}$,DTrp$^{32}$] neuropeptide Y, human; [Leu$^{31}$, Pro$^{34}$]-NPY, porcine; NPY 2-36, porcine; NPY 3-36, human; NPY 3-36, porcine; NPY 13-36, human; NPY 13-36, porcine; NPY 16-36, porcine; NPY 18-36, porcine; NPY 20-36; NFY 22-36; NPY 26-36; [Pro$^{34}$]-NPY 1-36, human; [Pro$^{34}$]-neuropeptide Y, porcine; PYX-1; PYX-2; T4-[NPY(33-36)]4; and Tyr(OMe)$^{21}$]-neuropeptide Y, human.

Neurotropic factor peptides including, but not limited to, glial derived neurotropic factor (GDNF); brain derived neurotropic factor (BDNF); and ciliary neurotropic factor (CNTF).

Orexin peptides including, but not limited to, orexin A; orexin B, human; orexin B, rat, mouse.

Opioid peptides including, but not limited to, alpha-casein fragment 90-95; BAM-18P; casomokinin L; casoxin D; crystalline; DALDA; dermenkephalin (deltorphin) (Phylomedusa sauvagei); [D-Ala$^2$]-deltorphin I; [D-Ala2]-deltorphin II; endomorphin-1; endomorphin-2; kyotorphin; [DArg$^2$]-kyotorphin; morphine tolerance peptide; morphine modulating peptide, C-terminal fragment; morphine modulating neuropeptide (A-18-F—NH2); nociceptin [orphanin FQ] (ORL1 agonist); TIPP; Tyr-MIF-1; Tyr-W-MIF-1; valorphin; LW-hemorphin-6, human; Leu-valorphin-Arg; and Z-Pro-D-Leu.

Oxytocin peptides including, but not limited to, [Asu$^6$]-oxytocin; oxytocin; biotinyl-oxytocin; [Thr$^4$, Gly$^7$]-oxytocin; and tocinoic acid ([Ile$^3$]-pressinoic acid).

PACAP (pituitary adenylating cyclase activating peptide) peptides including, but not limited to, PACAP 1-27, human, ovine, rat; PACAP (1-27)-Gly-Lys-Arg-NH2, human; [Des-Gln$^{16}$]-PACAP 6-27, human, ovine, rat; PACAP38, frog; PACAP27-NH2, human, ovine, rat; biotinyl-PACAP27-NH2, human, ovine, rat; PACAP 6-27, human, ovine, rat; PACAP38, human, ovine, rat; biotinyl-PACAP38, human, ovine, rat; PACAP 6-38, human, ovine, rat; PACAP27-NH2, human, ovine, rat; biotinyl-PACAP27-NH2, human, ovine, rat; PACAP 6-27, human, ovine, rat; PACAP38, human, ovine, rat; biotinyl-PACAP38, human, ovine, rat; PACAP 6-38, human, ovine, rat; PACAP38 16-38, human, ovine, rat; PACAP38 31-38, human, ovine, rat; PACAP38 31-38, human, ovine, rat; PACAP-related peptide (PRP), human; and PACAP-related peptide (PRP), rat.

Pancreastatin peptides including, but not limited to, chromostatin, bovine; pancreastatin (hPST-52) (chromogranin A 250-301, amide); pancreastatin 24-52 (hPST-29), human; chromogranin A 286-301, amide, human; pancreastatin, porcine; biotinyl-pancreastatin, porcine; [Nle$^8$]-pancreastatin, porcine; [Tyr$^0$,Nle$^8$]-pancreastatin, porcine; [Tyr$^0$]-pancreastatin, porcine; parastatin 1-19 (chromogranin A 347-365), porcine; pancreastatin (chromogranin A 264-314-amide, rat; biotinyl-pancreastatin (biotinyl-chromogranin A 264-314-amide; [Tyr$^0$]-pancreastatin, rat; pancreastatin 26-51, rat; and pancreastatin 33-49, porcine.

Pancreatic polypeptides including, but not limited to, pancreatic polypeptide, avian; pancreatic polypeptide, human; C-fragment pancreatic polypeptide acid, human; C-fragment pancreatic polypeptide amide, human; pancreatic polypeptide (*Rana temporaria*); pancreatic polypeptide, rat; and pancreatic polypeptide, salmon.

Parathyroid hormone peptides including, but not limited to, [Asp$^{76}$-parathyroid hormone 39-84, human; [Asp$^{76}$]-parathyroid hormone 53-84, human; [Asn$^{76}$]-parathyroid hormone 1-84, hormone; [Asn$^{76}$]-parathyroid hormone 64-84, human; [Asn$^8$, Leu$^{18}$]-parathyroid hormone 1-34, human;

[Cys$^{5,28}$]-parathyroid hormone 1-34, human; hypercalcemia malignancy factor 1-40; [Leu$^{18}$]-parathyroid hormone 1-34, human; [Lys(biotinyl)$^{13}$, Nle$^{8,18}$, Tyr$^{34}$]-parathyroid hormone 1-34 amide; [Nle$^{8,18}$, Tyr$^{34}$]-parathyroid hormone 1-34 amide; [Nle$^{8,18}$, Tyr$^{34}$]-parathyroid hormone 3-34 amide, bovine; [Nle8,18, Tyr$^{34}$]-parathyroid hormone 1-34, human; [Nle$^{8,18}$, Tyr$^{34}$]-parathyroid hormone 1-34 amide human; [Nle$^{8,18}$, Tyr$^{34}$]-parathyroid hormone 3-34 amide, human; [Nle$^{8,18}$, Tyr$^{34}$]-parathyroid hormone 7-34 amide, bovine; [Nle$^{8,21}$, Tyr$^{34}$]-parathyroid hormone 1-34 amide, rat; parathyroid hormone 44-68, human; parathyroid hormone 1-34, bovine; parathyroid hormone 3-34, bovine; parathyroid hormone 1-31 amide, human; parathyroid hormone 1-34, human; parathyroid hormone 13-34, human; parathyroid hormone 1-34, rat; parathyroid hormone 1-38, human; parathyroid hormone 1-44, human; parathyroid hormone 28-48, human; parathyroid hormone 39-68, human; parathyroid hormone 39-84, human; parathyroid hormone 53-84, human; parathyroid hormone 69-84, human; parathyroid hormone 70-84, human; [Pro$^{34}$]-peptide YY (PYY), human; [Tyr$^{0}$]-hypercalcemia malignancy factor 1-40; [Tyr$^{0}$]-parathyroid hormone 1-44, human; [Tyr$^{0}$]-parathyroid hormone 1-34, human; [Tyr$^{1}$]-parathyroid hormone 1-34, human; [Tyr$^{27}$]-parathyroid hormone 27-48, human; [Tyr$^{34}$]-parathyroid hormone 7-34 amide, bovine; [Tyr$^{43}$]-parathyroid hormone 43-68, human; [Tyr$^{52}$, Asn$^{76}$]-parathyroid hormone 52-84, human; and [Tyr$^{63}$]-parathyroid hormone 63-84, human.

Parathyroid hormone (PTH)-related peptides including, but not limited to, PTHrP ([Tyr$^{36}$]-PTHrP 1-36 amide), chicken; hHCF-(1-34)—NH2 (humoral hypercalcemic factor), human; PTH-related protein 1-34, human; biotinyl-PTH-related protein 1-34, human; [Tyr$^{0}$]-PTH-related protein 1-34, human; [Tyr$^{34}$]-PTH-related protein 1-34 amide, human; PTH-related protein 1-37, human; PTH-related protein 7-34 amide, human; PTH-related protein 38-64 amide, human; PTH-related protein 67-86 amide, human; PTH-related protein 107-111, human, rat, mouse; PTH-related protein 107-111 free acid; PTH-related protein 107-138, human; and PTH-related protein 109-111, human.

Peptide T peptides including, but not limited to, peptide T; [D-Ala$^{1}$]-peptide T; and [D-Ala$^{1}$]-peptide T amide.

Prolactin-releasing peptides including, but not limited to, prolactin-releasing peptide 31, human; prolactin-releasing peptide 20, human; prolactin-releasing peptide 31, rat; prolactin-releasing peptide 20, rat; prolactin-releasing peptide 31, bovine; and prolactin-releasing peptide 20, bovine.

Peptide YY (PYY) peptides including, but not limited to, PYY, human; PYY 3-36, human; biotinyl-PYY, human; PYY, porcine, rat; and [Leu$^{31}$, Pro$^{34}$]-PYY, human.

Renin substrate peptides including, but not limited to, acetyl, angiotensinogen 1-14, human; angiotensinogen 1-14, porcine; renin substrate tetradecapeptide, rat; [Cys$^{8}$]-renin substrate tetradecapeptide, rat; [Leu$^{8}$]-renin substrate tetradecapeptide, rat; and [Val$^{8}$]-renin substrate tetradecapeptide, rat.

Secretin peptides including, but not limited to, secretin, canine; secretin, chicken; secretin, human; biotinyl-secretin, human; secretin, porcine; and secretin, rat.

Somatostatin (GIF) peptides including, but not limited to, BIM-23027; biotinyl-somatostatin; biotinylated cortistatin 17, human; cortistatin 14, rat; cortistatin 17, human; [Tyr$^{0}$]-cortistatin 17, human; cortistatin 29, rat; [D-Trp$^{8}$]-somatostatin; [DTrp$^{8}$,DCys$^{14}$]-somatostatin; [DTrp$^{8}$,Tyr$^{11}$]-somatostatin; [D-Trp$^{11}$]-somatostatin; NTB (Naltriben); [Nle$^{8}$]-somatostatin 1-28; octreotide (SMS 201-995); prosomatostatin 1-32, porcine; [Tyr$^{0}$]-somatostatin; [Tyr$^{0}$]-somatostatin; [Tyr$^{1}$]-somatostatin 28 (1-14); [Tyr$^{11}$]-somatostatin; [Tyr$^{0}$], D-Trp$^{8}$]-somatostatin; somatostatin; somatostatin antagonist; somatostatin-25; somatostatin-28; somatostatin 28 (1-12); biotinyl-somatostatin-28; [Tyr$^{0}$]-somatostatin-28; [Leu$^{8}$, D-Trp$^{22}$, Tyr$^{25}$]-somatostatin-28; biotinyl-[Leu$^{8}$, D-Trp 22, Tyr$^{25}$]-somatostatin-28; somatostatin-28 (1-14); and somatostatin analog, RC-160.

Substance P peptides including, but not limited to, G protein antagonist-2; Ac-[Arg$^{6}$, Sar$^{9}$, Met(02)$^{11}$]-substance P 6-11; [Arg$^{3}$]-substance P; Ac-Trp-3,5-bis(trifluoromethyl) benzyl ester; Ac-[Arg$^{6}$, Sar$^{9}$, Met(O2)$^{11}$]-substance P 6-11; [D-Ala$^{4}$]-substance P 4-11; [Tyr$^{6}$, D-Phe$^{7}$, D-His$^{9}$]-substance P 6-11 (sendide); biotinyl-substance P; biotinyl-NTE [Arg$^{3}$]-substance P; (Tyr$^{8}$]-substance P; [Sar$^{9}$, Met(O2)$^{11}$]-substance P; [D-Pro$^{2}$, DTrp$^{7,9}$]-substance P; [D-Pro$^{4}$, O-Trp$^{7,9}$]-substance P 4-11; substance P 4-11; [DTrp$^{2,7,9}$]-substance P; [(Dehydro)Pro$^{2,4}$, Pro$^{9}$]-substance P; [Dehydro-Pro$^{4}$]-substance P 4-11; [Glp$^{5}$,(Me)Phe$^{8}$,Sar$^{9}$]-substance P 5-11; [Glp$^{5}$,Sar$^{9}$]-substance P 5-11; [Glp$^{5}$]-substance P 5-11; hepta-substance P (substance P 5-11); hexa-substance P(substance P 6-11); [MePhe$^{8}$,Sar$^{9}$]-substance P; [Nle$^{11}$]-substance P; Octa-substance P(substance P 4-11); [pGlu$^{1}$]-hexa-substance P ([pGlu$^{6}$]-substance P 6-11); [pGlu$^{6}$, D-Pro$^{9}$]-substance P 6-11; [(pNO2)Phe$^{7}$ Nle$^{11}$]-substance P; penta-substance P (substance P 7-11); [Pro$^{9}$]-substance P; GR73632, substance P 7-11; [Sar$^{4}$]-substance P 4-11; [Sar$^{9}$]-substance P; septide ([pGlu$^{6}$, Pro$^{9}$]-substance P 6-11); spantide I; spantide II; substance P; substance P, cod; substance P, trout; substance P antagonist; substance P-Gly-Lys-Arg; substance P 1-4; substance P 1-6; substance P 1-7; substance P 1-9; deca-substance P (substance P 2-11); nona-substance P (substance P 3-11); substance P tetrapeptide (substance P 8-11); substance P tripeptide (substance P 9-11); substance P, free acid; substance P methyl ester, and [Tyr$^{8}$,Nle$^{11}$] substance P.

Tachykinin peptides including, but not limited to, [Ala$^{5}$, beta-Ala$^{8}$] neurokinin A 4-10; eledoisin; locustatachykinin I (Lom-TK-I) (*Locusta migratoria*); locustatachykinin II (Lom-TK-II) (*Locusta migratoria*); neurokinin A 4-10; neurokinin A (neuromedin L, substance K); neurokinin A, cod and trout; biotinyl-neurokinin A (biotinyl-neuromedin L, biotinyl-substance K); [Tyr$^{0}$]-neurokinin A; [Tyr$^{6}$]-substance K; FR64349; [Lys$^{3}$, Gly$^{8}$-(R)-gamma-lactam-Leu$^{9}$]-neurokinin A 3-10; GR83074; GR87389; GR94800; [Beta-Ala$^{8}$]-neurokinin A 4-10; [Nle$^{10}$]-neurokinin A 4-10; [Trp$^{7}$, beta-Ala$^{8}$]-neurokinin A 4-10; neurokinin B (neuromedin K); biotinyl-neurokinin B (biotinyl-neuromedin K); [MePhe$^{7}$]-neurokinin B; [Pro$^{7}$]-neurokinin B; [Tyr$^{0}$]-neurokinin B; neuromedin B, porcine; biotinyl-neuromedin B, porcine; neuromedin B-30, porcine; neuromedin B-32, porcine; neuromedin B receptor antagonist; neuromedin C, porcine; neuromedin N, porcine; neuromedin (U-8), porcine; neuromedin (U-25), porcine; neuromedin U, rat; neuropeptide-gamma (gamma-preprotachykinin 72-92); PG-KII; phyllolitorin; [Leu$^{8}$]-phyllolitorin (Phyllomedusa sauvagei); physalaemin; physalaemin 1-11; scyliorhinin II, amide, dogfish; senktide, selective neurokinin B receptor peptide; [Ser$^{2}$]-neuromedin C; beta-preprotachykinin 69-91, human; beta-preprotachykinin 111-129, human; tachyplesin I; xenopsin; and xenopsin 25 (xenin 25), human.

Thyrotropin-releasing hormone (TRH) peptides including, but not limited to, biotinyl-thyrotropin-releasing hormone; [Glu$^{1}$]-TRH; His-Pro-diketopiperazine; [3-Me-His$^{2}$]-TRH; pGlu-Gln-Pro-amide; pGlu-His; [Phe$^{2}$]-TRH; prepro TRH 53-74; prepro TRH 83-106; prepro-TRH 160-169 (Ps4, TRH-potentiating peptide); prepro-TRH 178-199, thyrotropin-releasing hormone (TRH); TRH, free acid; TRH—SH Pro; and TRH precursor peptide.

Toxin peptides including, but not limited to, omega-agatoxin TK; agelenin, (spider, *Agelena opulenta*); apamin (honeybee, *Apis mellifera*); calcicudine (CaC) (green mamba, *Dedroaspis angusticeps*); calciseptine (black mamba, *Dendroaspis polylepis polylepis*); charybdotoxin (ChTX) (scorpion, *Leiurus quinquestriatus* var. *hebraeus*); chlorotoxin; conotoxin GI (marine snail, *Conus geographus*); conotoxin GS (marine snail, *Conus geographus*); conotoxin MI (Marine *Conus magus*); alpha-conotoxin EI, *Conus ermineus*; alpha-conotoxin SIA; alpha-conotoxin ImI; alpha-conotoxin SI (cone snail, *Conus striatus*); micro-conotoxin GIIIB (marine snail, *Conus geographus*); omega-conotoxin GVIA (marine snail, *Conus geographus*); omega-conotoxin MVIIA (*Conus magus*); omega-conotoxin MVIIC (*Conus magus*); omega-conotoxin SVIB, (cone snail, *Conus striatus*); endotoxin inhibitor; geographutoxin I (GTX-I) (μ-Conotoxin GIIIA); iberiotoxin (IbTX) (scorpion, *Buthus tamulus*); kaliotoxin 1-37; kaliotoxin (scorpion, *Androctonus mauretanicus mauretanicus*); mast cell-degranulating peptide (MCD-peptide, peptide 401); margatoxin (MgTX) (scorpion, *Centruriodes Margaritatus*); neurotoxin NSTX-3 (Papua New Guinean spider, *Nephilia maculata*); PLTX-II (spider, *Plectreurys tristes*); scyllatoxin (leiurotoxin I); and stichodactyla toxin (ShK).

Vasoactive intestinal peptides (VIP/PHI) including, but not limited to, VIP, human, porcine, rat, ovine; VIP-Gly-Lys-Arg-NH2; biotinyl-PHI (biotinyl-PHI-27), porcine; [Glp$^{16}$] VIP 16-28, porcine; PHI (PHI-27), porcine; PHI (PHI-27), rat; PHM-27 (PHI), human; prepro VIP 81-122, human; preproVIP/PHM 111-122; prepro VIP/PHM 156-170; biotinyl-PHM-27 (biotinyl-PHI), human; vasoactive intestinal contractor (endothelin-beta); vasoactive intestinal octacosapeptide, chicken; vasoactive intestinal peptide, guinea pig; biotinyl-VIP, human, porcine, rat; vasoactive intestinal peptide 1-12, human, porcine, rat; vasoactive intestinal peptide 10-28, human, porcine, rat; vasoactive intestinal peptide 11-28, human, porcine, rat, ovine; vasoactive intestinal peptide (cod, *Gadus morhua*); vasoactive intestinal peptide 6-28; vasoactive intestinal peptide antagonist; vasoactive intestinal peptide antagonist ([Ac-Tyr$^1$, D-Phe$^2$]-GHRF 1-29 amide); vasoactive intestinal peptide receptor antagonist (4-Cl-D-Phe$^6$, Leu$^{17}$]-VIP); and vasoactive intestinal peptide receptor binding inhibitor, L-8-K.

Vasopressin (ADH) peptides including, but not limited to, vasopressin; [Asu$^{1,6}$,Arg$^8$]-vasopressin; vasotocin; [Asu$^{1,6}$, Arg$^8$]-vasotocin; [Lys$^8$]-vasopressin; pressinoic acid; [Arg$^8$]-desamino vasopressin desglycinamide; [Arg8]-vasopressin (AVP); [Arg$^8$]-vasopressin desglycinamide; biotinyl-[Arg$^8$]-vasopressin (biotinyl-AVP); [D-Arg$^8$]-vasopressin; desamino-[Arg$^8$]-vasopressin; desamino-[D-Arg$^8$]-vasopressin (DDAVP); [deamino-[D-3-(3'-pyridyl-Ala)]-[Arg$^8$]-vasopressin; [1-(beta-Mercapto-beta, beta-cyclopentamethylene propionic acid), 2-(O-methyl)tyrosine]-[Arg$^8$]-vasopressin; vasopressin metabolite neuropeptide [pGlu$^4$, Cys$^6$]; vasopressin metabolite neuropeptide [pGlu$^4$, Cys$^6$]; [Lys$^8$]-deamino vasopressin desglycinamide; [Lys8]-vasopressin; [Mpr$^1$,Val$^4$,DArg$^8$]-vasopressin; [Phe$^2$, Ile$^3$, Orn$^8$]-vasopressin ([Phe$^2$, Orn$^8$]-vasotocin); [Arg$^8$]-vasotocin; and [d(CH2)$_5$, Tyr(Me) 2, Orn$^8$]-vasotocin.

Virus related peptides including, but not limited to, viral membrane fusion proteins, fluorogenic human CMV protease substrate; HCV core protein 59-68; HCV NS4A protein 1840 (JT strain); HCV NS4A protein 21-34 (JT strain); hepatitis B virus receptor binding fragment; hepatitis B virus pre-S region 120-145; [Ala$^{127}$]-hepatitis B virus pre-S region 120-131; herpes virus inhibitor 2; HIV envelope protein fragment 254-274; HIV gag fragment 129-135; HIV substrate; P 18 peptide; peptide T; [3,5 diiodo-Tyr$^7$] peptide T; R15K HIV-1 inhibitory peptide; T20; T21; V3 decapeptide P 18-110; and virus replication inhibiting peptide.

The human hormone glucagon is a 29-amino acid peptide hormone produced in the A-cells of the pancreas. The hormone belongs to a multi-gene family of structurally related peptides that include secretin, gastric inhibitory peptide, vasoactive intestinal peptide and glicentin. These peptides variously regulate carbohydrate metabolism, gastrointestinal mobility and secretory processing. The principal recognized actions of pancreatic glucagon, however, are to promote hepatic glycogenolysis and glyconeogenesis, resulting in an elevation of blood sugar levels. In this regard, the actions of glucagon are counter regulatory to those of insulin and may contribute to the hyperglycemia that accompanies Diabetes mellitus [(Lund, P. K., et al., Proc. Natl. Acad. Sci. U.S.A., 79:345-349 (1982)].

Glucagon has been found to be capable of binding to specific receptors which lie on the surface of insulin producing cells. Glucagon, when bound to these receptors, stimulates the rapid synthesis of cAMP by these cells. cAMP, in turn, has been found to stimulate insulin expression [Korman, L. Y., et al., Diabetes, 34:717-722 (1985)]. Insulin acts to inhibit glucagon synthesis [Ganong, W. F., Review of Medical Physiology, Lange Publications, Los Altos, Calif., p. 273 (1979)]. Thus, the expression of glucagon is carefully regulated by insulin, and ultimately by the serum glucose level.

The glucagon gene is initially translated from a 360 base pair precursor to form the polypeptide, preproglucagon [Lund, et al., Proc. Natl. Acad. Sci. U.S.A. 79:345-349 (1982)]. This polypeptide is subsequently processed to form proglucagon. Patzelt, C., et al., Nature, 282:260-266 (1979) demonstrated that proglucagon was subsequently cleaved into glucagon and a second polypeptide. Subsequent work by Lund, P. K., et al. supra, Lopez L. C., et al., Proc. Natl. Acad. Sci. U.S.A., 80:5485-5489 (1983), and Bell, G. I., et al., Nature 302:716-718 (1983), demonstrated that the proglucagon molecule was cleaved immediately after lysine-arginine dipeptide residues. Studies of proglucagon produced by channel catfish (*Ictalurus punctata*) indicated that glucagon from this animal was also proteolytically cleaved after adjacent lysine-arginine dipeptide residues [Andrews P. C., et al., J. Biol. Chem., 260:3910-3914 (1985), Lopez, L. C., et al., Proc. Natl. Acad. Sci. U.S.A., 80:5485-5489 (1983)]. Bell, G. I., et al., supra, discovered that mammalian proglucagon was cleaved at lysine-arginine or arginine—arginine dipeptides, and demonstrated that the proglucagon molecule contained three discrete and highly homologous peptide molecules which were designated glucagon, glucagon-like peptide 1 (GLP-1) and glucagon-like peptide 2 (GLP-2). Lopez, et al., concluded that glucagon-like peptide 1 was 37 amino acid residues long and that glucagon-like peptide 2 was 34 amino acid residues long. Analogous studies on the structure of rat preproglucagon revealed a similar pattern of proteolytic cleavage between adjacent lysine-arginine or arginine-arginine dipeptide residues, resulting in the formation of glucagon, GLP-1 and GLP-2 [Heinrich, G., et al., Endocrinol., 115: 2176-2181 (1984)].

Glucagon-like peptide-2 (GLP-2) is a 33 amino acid peptide expressed in a tissue-specific manner from the pleiotropic glucagon gene. GLP-2 shows remarkable homology in terms of amino acid sequence to glucagon and Glucagon-like peptide-1 (GLP-1). Further, different mammalian forms of GLP-2 are highly conserved. The sequence of human GLP-2, is as follows: His-Ala-Asp-Gly-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr-Lys-Ile-Thr-Asp. Further, a large number of agonist GLP-2 peptides that are described in PCT Application PCT/CA97/00252, filed Apr. 11, 1997. Analogs are described in U.S. Pat. No. 6,051,557, and examples of GLP-2 variants are found in U.S. Pat. Nos. 5,990,077 and 6,184,201.

Recently it was demonstrated that GLP-2 is an intestinotrophic peptide hormone (Drucker et al., (1996) PNAS, 93:7911-7916). When given exogenously, GLP-2 can produce a marked increase in the proliferation of small intestinal epithelium of the test mice, apparently with no undesirable side effects. Subsequently it was shown that peptide analogs of native GLP-2 with certain modifications to the peptide sequence possess enhanced intestinotrophic activity (U.S. patent application Ser. No. 08/669,791). Moreover, GLP-2 has also been shown to increase D-Glucose maximal transport rate across the intestinal basolateral membrane (Cheeseman and Tseng (1996) American Journal of Physiology 271: G477-G482).

A number of peptide hormones (IGF-2, IGF-1, GH), structurally unrelated to GLP-2, have been demonstrated to have varying degrees of intestinotrophic activity. (U.S. Pat. No. 5,482,926, WO 91/12018, U.S. Pat. No. 5,288,703). However, none of the above peptide hormones possess the efficacy or specificity of GLP-2 in promoting proliferation of the intestine epithelium. GLP-2 acts synergistically with the peptide hormones IGF-1 and/or GH to promote the proliferation of cells in the large intestine. Furthermore, the intestinotrophic effects on the small and large intestines of this combination therapy are greater than that seen with any one of alone. Coadministration of GLP-2 with IGF-2 to promote growth of small and/or large intestine tissue is discussed in U.S. Pat. No. 5,952,301.

Nucleic acid encoding the GLP-2 receptor has been isolated and methods to identify GLP-2 receptor agonists are described (U.S. patent application Ser. No. 08/767,224 and U.S. Ser. No. 08/845,546). GLP-2's role in diseases involving the esophagus and the stomach, in assisting patients at risk of developing a malfunctioning of the upper gastrointestinal tract, and in increasing tissue growth in the upper gastrointestinal tract have been discussed (see U.S. Pat. No. 6,051,557). GLP-2 receptor agonists act to enhance functioning of the large intestine. (U.S. Pat. No. 6,297,214). GLP-2 and peptidic agonists of GLP-2 can cause proliferation of the tissue of large intestine. GLP-2 may also be useful to treat or prevent inflammatory conditions of the large intestine, including inflammatory bowel diseases (U.S. Pat. No. 6,586,399).

Human, rat, bovine, and hamster sequences of GLP-1 have been found to be identical [Ghiglione, M., et al., Diabetologia, 27:599-600 (1984)]. The conclusion reached by Lopez, et al., regarding the size of GLP-1 was confirmed by the work of Uttenthal, L. O., et al., J. Clin. Endocrinol. Metabol., 61:472-479 (1985). Uttenthal et al. examined the molecular forms of GLP-1 which were present in the human pancreas. Their research shows that GLP-1 and GLP-2 are present in the pancreas as 37 amino acid and 34 amino acid peptides, respectively.

The similarity between GLP-1 and glucagon suggested to early investigators that GLP-1 might have biological activity. Although some investigators found that GLP-1 could induce rat brain cells to synthesize cAMP [Hoosein, N. M., et al., FEBS Lett. 178:83-86 (1984)], other investigators failed to identify any physiological role for GLP-1 (Lopez, L. C., et al.). The failure to identify any physiological role for GLP-1 caused some investigators to question whether GLP-1 was in fact a hormone and whether the relatedness between glucagon and GLP-1 might be artifactual.

Variants of GLP-1(7-37) and analogs thereof, also have been disclosed. These variants and analogs include, for example, $Gln^9$-GLP-1(7-37), $D$-$Gln^9$-GLP-1(7-37), acetyl-$Lys^9$-GLP-1(7-37), $Thr^{16}$-$Lys^{18}$-GLP-1(7-37), $Lys^{18}$-GLP-1 (7-37) and the like, and derivatives thereof including, for example, acid addition salts, carboxylate salts, lower alkyl esters, and amides [see, e.g., WO 91/11457; EP0733,644 (1996); and U.S. Pat. No. 5,512,549 (1996), which are incorporated by reference]. Generally, the various disclosed forms of GLP-1 are known to stimulate insulin secretion (insulinotropic action) and cAMP formation [see, e.g., Mojsov, S., Int. J. Peptide Protein Research, 40:333-343 (1992)].

More importantly, multiple authors have demonstrated the nexus between laboratory experimentation and mammalian, particularly human, insulinotropic responses to exogenous administration of GLP-1, particularly GLP-1(7-36) $NH_2$ and GLP-1(7-37) [see, e.g., Nauck, M. A., et al., Diabetologia, 36:741-744 (1993); Gutniak, M., et al., New England J. of Medicine, 326(20):1316-1322 (1992); Nauck, M. A., et al., J. Clin. Invest., 91:301-307 (1993); and Thorens, B., et al., Diabetes, 42:1219-1225 (1993)].

More particularly, the fundamental defects identified as causing hyperglycemia in maturity onset diabetes are impaired secretion of endogenous insulin and resistance to the effects of insulin by muscle and liver [Galloway, J. S., Diabetes Care, 13:1209-1239, (1990)]. The latter defect results in excessive production of glucose from the liver. Thus, whereas a normal individual releases glucose at the rate of approximately 2 mg/kg/minute, in patients with maturity onset diabetes, this amount usually exceeds 2.5 mg/kg/minute resulting in a net excess of at least 70 grams of glucose per 24 hours. The fact that there exists exceedingly high correlations between hepatic glucose production, the fasting blood glucose and overall metabolic control as indicated by glycohemoglobin measurements [Galloway, J. A., supra; and Galloway, J. A., et al., Clin. Therap., 12:460-472 (1990)], it is readily apparent that control of the fasting blood glucose is a sine quo non for achieving overall normalization of metabolism sufficient to prevent the complication of hyperglycemia. In view of the fact that present forms of insulin rarely normalize hepatic glucose production without producing significant hyperinsulinemia and hypoglycemia (Galloway, J. A., and Galloway, J. A., et al., supra), alternative approaches are needed.

However, the long-term stability of GLP-1, particularly GLP-1 as a component of a pharmaceutical composition for administration to mammals, is questionable. In fact, when stored at the low temperature of 4° C., by-products of GLP-1(7-37) have been found as early as eleven months after sample preparation (Mojsov, S., supra). Thus, there exists a need for a more stable GLP-1 compound which can safely be administered to mammals in need of such treatment.

Furthermore, the biological half-life of GLP-1 molecules, particularly those molecules which are affected by the activity of dipeptidyl-peptidase IV (DPP IV), is quite short. For example, the biological half-life of GLP-1(7-37) is a mere 3 to 5 minutes (U.S. Pat. No. 5,118,666), and is further influenced by its rapid absorption following parenteral administration to a mammal. Thus, there also exists a need for a GLP-1 compound which delays absorption following such administration.

Glucagon-Like Peptide 1 (GLP-1) is a 37 amino acid peptide that is secreted by the L-cells of the intestine in response to food ingestion. It has been found to stimulate insulin secretion (insulinotropic action), thereby causing glucose uptake by cells and decreased serum glucose levels [see, e.g., Mojsov, S., (1992) Int. J. Peptide Protein Research, 40:333-

343]. However, GLP-1 is poorly active. A subsequent endogenous cleavage between the 6th and 7th position produces a more potent biologically active GLP-1(7-37)OH peptide. Numerous GLP-1 analogs and derivatives are known and are referred to herein as "GLP-1 compounds." These GLP-1 analogs include the Exendins which are peptides found in the venom of the GILA-monster. The Exendins have sequence homology to native GLP-1 and can bind the GLP-1 receptor and initiate the signal transduction cascade responsible for the numerous activities that have been attributed to GLP-1(7-37)OH.

U.S. Pat. No. 6,569,832 discusses administration of a GLP-1 agonist to modulate, inhibit or decrease or prevent beta cell degeneration, loss of beta cell function, beta cell dysfunction, and/or death of beta cells, such as necrosis or apoptosis of beta cells. Apoptosis is an active process of cellular self-destruction that is regulated by extrinsic and intrinsic signals occurring during normal development. It is well documented that apoptosis plays a key role in regulation of pancreatic endocrine beta cells. There is increasing evidence that in adult mammalians the beta-cell mass is submitted to dynamic changes to adapt insulin production for maintaining euglycemia in particular conditions, such as pregnancy and obesity (J. Dev. Physiol. 5: 373, 1983 and Endocrinology 130: 1459, 1992). The control of beta cell mass depends on a subtle balance between cell proliferation, growth and cell death (apoptosis). A disruption of this balance may lead to impairment of glucose homeostasis. For example, it is noteworthy that glucose intolerance develops with aging when beta cell replication rates are reduced (Diabetes 32: 14, 1983) and human autopsy studies repeatedly showed a 40-60% reduction of beta cell mass in patients with non-insulin-dependent-diabetes mellitus compared with non-diabetic subjects (Am. J. Med. 70: 105, 1981 and Diabetes Res. 9: 151, 1988). It is generally agreed that insulin resistance is an invariable accompaniment of obesity but that normoglycemia is maintained by compensatory hyperinsulinemia until the beta cells become unable to meet the increased demand for insulin, at which point Type 2 Diabetes begins. Other studies have been performed investigating GLP-1 and islet cell proliferation and islet cell differentiation.

GLP-1 compounds have a variety of physiologically significant activities. For example, GLP-1 has been shown to stimulate insulin release, lower glucagon secretion, inhibit gastric emptying, and enhance glucose utilization. [Nauck, M. A., et al. (1993) Diabetologia 36:741-744; Gutniak, M., et al. (1992) New England J. of Med. 326:1316-1322; Nauck, M. A., et al., (1993) J. Clin. Invest. 91:301-307].

GLP-1 shows promise as a treatment for non-insulin dependent diabetes mellitus (NIDDM). There are numerous oral drugs on the market to treat the insulin resistance associated with NIDDM. As the disease progresses, however, patients must move to treatments that stimulate the release of insulin and eventually to treatments that involve injections of insulin. Current drugs which stimulate the release of insulin, however, can also cause hypoglycemia as can the actual administration of insulin. GLP-1 activity, however, is controlled by blood glucose levels. When blood glucose levels drop to a certain threshold level, GLP-1 is not active. Thus, there is no risk of hypoglycemia associated with treatment involving GLP-1.

However, the usefulness of therapy involving GLP-1 peptides has been limited by their fast clearance and short half-lives. For example, GLP-1(7-37) has a serum half-life of only 3 to 5 minutes (U.S. Pat. No. 5,118,666). GLP-1(7-36) amide has a time action of about 50 minutes when administered subcutaneously. Even analogs and derivatives that are resistant to endogenous protease cleavage, do not have half-lives long enough to avoid repeated administrations over a 24 hour period. Fast clearance of a therapeutic agent is inconvenient in cases where it is desired to maintain a high blood level of the agent over a prolonged period of time since repeated administrations will then be necessary. Furthermore, a long-acting compound is particularly important for diabetic patients whose past treatment regimen has involved taking only oral medication. These patients often have an extremely difficult time transitioning to a regimen that involves multiple injections of medication.

The present invention overcomes the problems associated with delivering a BSP such as GLP-1 that has a short plasma half-life. The compounds of the present invention encompass BSPs fused to another protein with a long circulating half-life such as the Fc portion of an immunoglobulin or albumin.

The human immunodeficiency virus (HIV) is a pathogenic retrovirus and the causative agent of acquired immune deficiency syndrome (AIDS) and related disorders (Barre-Sinossi, F. et al., 1983, Science 220:868-870; Gallo, R. et al., 1984, Science 224:500-503). At least two distinct types of HIV have been described: HIV-1 (Barre-Sinossi, F. et al., 1983, Science 220:868-870; Gallo, R. et al., 1984, Science 224:500-503) and HIV-2 (Clavel, F. et al., 1986, Science 223:343-346; Guyader, M. et al., 1987, Nature 326:662-669). Further, a large amount of genetic heterogeneity exists within populations of each of these types. Infection of human CD4+ T-lymphocytes with an HIV virus leads to depletion of the cell type and eventually to opportunistic infections, neurological dysfunctions, neoplastic growth, and untimely death.

HIV is a member of the lentivirus family of retroviruses (Teich, N. et al., 1984; RNA Tumor Viruses, Weiss, R. et al., eds., CSH-press, pp. 949-956). Retroviruses are small enveloped viruses that contain a diploid, single-stranded RNA genome, and replicate via a DNA intermediate produced by a virally-encoded reverse transcriptase, an RNA-dependent DNA polymerase (Varmus, H., 1988, Science 240:1427-1439). Other retroviruses include, for example, oncogenic viruses such as human T-cell leukemia viruses (HTLV-1, -II, -III), and feline leukemia virus. The HIV viral particle consists of a viral core, made up of proteins designated p24 and p18. The viral core contains the viral RNA genome and those enzymes required for replicative events. Myristylated gag protein forms an outer viral shell around the viral core, which is, in turn, surrounded by a lipid membrane envelope derived from the infected cell membrane. The HIV envelope surface glycoproteins are synthesized as a single 160 kD precursor protein which is cleaved by a cellular protease during viral budding into two glycoproteins, gp41 and gp120. gp41 is a transmembrane protein and gp120 is an extracellular protein which remains noncovalently associated with gp41, possibly in a trimeric or multimeric form (Hammerwskjold, M. and Rekosh, D., 1989, Biochem. Biophys. Acta 989:269-280).

HIV is targeted to CD-4+ T lymphocytes because the CD-4 surface protein acts as the cellular receptor for the HIV-1 virus (Dalgleish, A. et al., 1984, Nature 312: 767-768, Maddon et al., 1986, Cell 47:333-348). Viral entry into cells is dependent upon gp120 binding the cellular CD-4+ receptor molecules, while gp41 anchors the envelope glycoprotein complex in the viral membrane (McDougal, J. S. et al., 1986, Science 231: 382-385; Maddon, P. J. et al., 1986, Cell 47:333-348) and thus explains HIV's tropism for CD-4+ cells.

Several stages of the viral life cycle have been considered targets for therapeutic intervention (Mitsuya, H. et al., 1991, FASEB J. 5:2369-2381). Intervention could potentially inhibit the binding of HIV to cell membranes, the reverse transcription of HIV RNA genome into DNA, or the exit of the virus from the host cell and infection of new cellular targets.

Attempts are being made to develop drugs which can inhibit viral entry into the cell, the earliest stage of HIV infection. Here, the focus has been on CD-4+, the cell surface receptor for HIV. For example, recombinant soluble CD-4 has been shown to block HIV infectivity by binding to viral particles before they encounter CD4 molecules embedded in cell membranes (Smith, D. H. et al., 1987, Science 238:1704-1707). Certain primary HIV-1 isolates are relatively less sensitive to inhibition by recombinant CD4 (Daar, E. et al., 1990, Ann. Int. Med. 112:247-253). In addition, recombinant soluble CD-4 clinical trials have produced inconclusive results (Schooley, R. et al., 1990, Ann. Int. Med. 112:247-253; Kahn, J. O. et al., 1990, Ann. Int. Med. 112:254-261; Yarchoan, R. et al., 1989, Proc. Vth Int. Conf. on AIDS, p564, MCP 137).

The virally encoded reverse-transcriptase-targeted drugs, including 2',3'-dideoxynucleoside analogs such as AZT, ddI, ddC, and d4T, have been developed which have also been shown to be active against HIV (Mitsuya, H. et al., 1991, Science 249:1533-1544). While beneficial, these nucleoside analogs are not curative, probably due to the rapid appearance of drug resistant HIV mutants (Lander, B. et al., 1989, Science 243:1731-1734). In addition, the drugs often exhibit toxic side effects such as bone marrow suppression, vomiting, and liver function abnormalities.

The late stages of HIV replication that involve crucial virus-specific secondary processing of certain viral proteins have also been suggested as possible anti-HIV drug targets. Late stage processing is dependent on the activity of a viral protease, and drugs are being developed which inhibit this protease (Erikson, J., 1990, Science 249:527-533).

Vaccines are in development for the treatment of HIV infection. The HIV-1 envelope proteins (gp160, gp120, gp41) have been shown to be the major antigens for anti-HIV antibodies present in AIDS patients (Barin et al., 1985, Science 228:1094-1096). Thus far, these proteins seem to be the most promising candidates to act as antigens for anti-HIV development. Several groups have begun to use various portions of gp160, gp120, and/or gp41 as immunogenic targets for the host immune systems. See for example, Ivanoff, L. et al., U.S. Pat. No. 5,141,867; Saith, G. et al., WO 92/22, 654; Schafferman, A., WO 91/09,872; Formoso, C. et al., WO 90/07, 119.

Recently, double stranded RNAs, which elicit a general immune response, have been used in combination with antivirals such as interferon, AZT and phosphonoformate to treat viral infections. See Carter, W., U.S. Pat. No. 4,950,652. In addition, a therapy combining a pyrimidine nucleoside analog and a uridine phosphorylase inhibitor has been developed for the treatment of HIV (Sommadossi, J. P. et al., U.S. Pat. No. 5,077,280). Although these specific therapies may prove to be beneficial, combination therapy in general has the potential for antagonism as demonstrated in vitro with azidothymidine (AZT) and ribavirin. See U.S. Pat. No. 4,950, 652. Moreover, combination therapy is potentially problematic given the high toxicity of most anti-HIV therapeutics and their low level of effectiveness.

T-20 acts as an inhibitor of HIV-1 fusion to $CD^{4+}$ cells, targeting HIV with a different mechanism than other antiviral therapeutics. U.S. Pat. No. 6,861,059 discloses methods of treating HIV-1 infection or inhibiting HIV-1 replication employing DP-178 or DP-107 or derivatives thereof, in combination with at least one other antiviral therapeutic agent such as a reverse transcriptase inhibitor (e.g. AZT, ddI, ddC, ddA, d4T, 3TC, or other dideoxynucleotides or dideoxyfluoronucleosides) or an inhibitor of HIV-1 protease (e.g. indinavir; ritonavir). Other antivirals include cytokines (e.g., rIFNα, rIFNβ, rIFNγ), inhibitors of viral mRNA capping (e.g. ribavirin), inhibitors of HIV protease (e.g. ABT-538 and MK-639), amphotericin B as a lipid-binding molecule with anti-HIV activity, and castanospermine as an inhibitor of glycoprotein processing.

Current antiobesity drugs have limited efficacy and numerous side effects. Crowley, V. E., Yeo, G. S. & O'Rahilly, S., Nat. Rev. Drug Discov 1, 276-86 (2002). With obesity reaching epidemic proportions worldwide, there is a pressing need for the development of adequate therapeutics in this area. In recent years, hormones and neuropeptides involved in the regulation of appetite, body energy expenditure, and fat mass accumulation such as PYY and PYY(3-36) in particular have emerged as potential antiobesity drugs. McMinn, J. E., Baskin, D. G. & Schwartz, M. W., Obes Rev 1:37-46 (2000), Drazen, D. L. & Woods, S.C., Curr Opin Clin Nutr Metab Care 6:621-629 (2003).

Generally, small therapeutic peptides are difficult to manipulate because even slight changes in their structure can affect stability and/or biological activity. This has been especially true for GLP-1 compounds which may undergo a conformational change from a primarily alpha helix structure to a primarily beta sheet structure. This beta sheet form results in aggregated material that is thought to be inactive. However, biologically active GLP-1 fusion proteins with increased half-lives have been developed. This was especially unexpected given the difficulty of working with GLP-1(7-37)OH alone and the large size of the fusion partner relative to the small GLP-1 peptide attached. Similarly, other BSP fusions may be made to increase serum half-life or to create a molecule with other desired properties.

Compounds of the present invention include heterologous fusion proteins comprising a first polypeptide with a N-terminus and a C-terminus fused to a second polypeptide with a N-terminus and a C-terminus wherein the first polypeptide is a BSP such as a GLP-1 compound and the second polypeptide is selected from the group consisting of: a) human albumin; b) human albumin analogs; and c) fragments of human albumin, and wherein the C-terminus of the first polypeptide is fused to the N-terminus of the second polypeptide.

Compounds of the present invention also include a heterologous fusion protein comprising a first polypeptide with a N-terminus and a C-terminus fused to a second polypeptide with a N-terminus and a C-terminus wherein the first polypeptide is a BSP such as a GLP-1 compound and the second polypeptide is selected from the group consisting of: a) human albumin; b) human albumin analogs; and c) fragments of human albumin, and wherein the C-terminus of the first polypeptide is fused to the N-terminus of the second polypeptide via a peptide linker, prodrug linker, or water soluble polymer. The peptide linker may be selected from the group consisting of: a) a glycine rich peptide; b) a peptide having the sequence $[Gly-Gly-Gly-Gly-Ser]_n$ where n is 1, 2, 3, 4, 5, 6, or more; and c) a peptide having the sequence $[Gly-Gly-Gly-Gly-Ser]_3$.

Additional compounds of the present invention include a heterologous fusion protein comprising a first polypeptide with a N-terminus and a C-terminus fused to a second polypeptide with a N-terminus and a C-terminus wherein the first polypeptide is a BSP such as a GLP-1 compound and the second polypeptide is selected from the group consisting of: a) the Fc portion of an immunoglobulin; b) an analog of the Fc portion of an immunoglobulin; and c) fragments of the Fc portion of an immunoglobulin, and wherein the C-terminus of the first polypeptide is fused to the N-terminus of the second polypeptide. The BSP such as the GLP-1 compound may be fused to the second polypeptide via a peptide linker prodrug linker, or water soluble polymer. The peptide linker may be selected from the group consisting of: a) a glycine rich peptide; b) a peptide having the sequence [Gly-Gly-Gly-Gly-Ser]$_n$, where n is 1, 2, 3, 4, 5, 6, or more; and c) a peptide having the sequence [Gly-Gly-Gly-Gly-Ser]$_3$.

The GLP-1 compound that is part of the heterologous fusion protein may have multiple amino acid substitutions, and may have more than 6, 5, 4, 3, 2, or 1 amino acids that differ from GLP-1(7-36), GLP-1(7-37), Exendin-4, or Exendin-3. Preferably, a GLP-1 compound that is part of the heterologous fusion protein has glycine or valine at position 8.

The present invention also includes polynucleotides encoding the heterologous fusion proteins described herein, vectors comprising these polynucleotides and host cells transfected or transformed with the vectors described herein. Also included is a process for producing a heterologous fusion protein comprising the steps of transcribing and translating a polynucleotide described herein under conditions wherein the heterologous fusion protein is expressed in detectable amounts.

BSP molecules comprising at least one unnatural amino acid are provided in the invention. In certain embodiments of the invention, the BSP with at least one unnatural amino acid includes at least one post-translational modification. In one embodiment, the at least one post-translational modification comprises attachment of a molecule including but not limited to, a label, a dye, a polymer, a water-soluble polymer, a derivative of polyethylene glycol, a photocrosslinker, a radionuclide, a cytotoxic compound, a drug, an affinity label, a photoaffinity label, a reactive compound, a resin, a second protein or polypeptide or polypeptide analog, an antibody or antibody fragment, a metal chelator, a cofactor, a fatty acid, a carbohydrate, a polynucleotide, a DNA, a RNA, an antisense polynucleotide, a water-soluble dendrimer, a cyclodextrin, an inhibitory ribonucleic acid, a biomaterial, a nanoparticle, a spin label, a fluorophore, a metal-containing moiety, a radioactive moiety, a novel functional group, a group that covalently or noncovalently interacts with other molecules, a photocaged moiety, a photoisomerizable moiety, biotin, a derivative of biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, a small molecule, or any combination of the above or any other desirable compound or substance, comprising a second reactive group to at least one unnatural amino acid comprising a first reactive group utilizing chemistry methodology that is known to one of ordinary skill in the art to be suitable for the particular reactive groups. For example, the first reactive group is an alkynyl moiety (including but not limited to, in the unnatural amino acid p-propargyloxyphenylalanine, where the propargyl group is also sometimes referred to as an acetylene moiety) and the second reactive group is an azido moiety, and [3+2] cycloaddition chemistry methodologies are utilized. In another example, the first reactive group is the azido moiety (including but not limited to, in the unnatural amino acid p-azido-L-phenylalanine) and the second reactive group is the alkynyl moiety. In certain embodiments of the modified BSP of the present invention, at least one unnatural amino acid (including but not limited to, unnatural amino acid containing a keto functional group) comprising at least one post-translational modification, is used where the at least one post-translational modification comprises a saccharide moiety. In certain embodiments, the post-translational modification is made in vivo in a eukaryotic cell or in a non-eukaryotic cell.

In certain embodiments, the protein includes at least one post-translational modification that is made in vivo by one host cell, where the post-translational modification is not normally made by another host cell type. In certain embodiments, the protein includes at least one post-translational modification that is made in vivo by a eukaryotic cell, where the post-translational modification is not normally made by a non-eukaryotic cell. Examples of post-translational modifications include, but are not limited to, acetylation, acylation, lipid-modification, palmitoylation, palmitate addition, phosphorylation, glycolipid-linkage modification, and the like. In one embodiment, the post-translational modification comprises attachment of an oligosaccharide to an asparagine by a GlcNAc-asparagine linkage (including but not limited to, where the oligosaccharide comprises (GlcNAc-Man)$_2$-Man-GlcNAc-GlcNAc, and the like). In another embodiment, the post-translational modification comprises attachment of an oligosaccharide (including but not limited to, Gal-GalNAc, Gal-GlcNAc, etc.) to a serine or threonine by a GalNAc-serine, a GalNAc-threonine, a GlcNAc-serine, or a GlcNAc-threonine linkage. In certain embodiments, a protein or polypeptide of the invention can comprise a secretion or localization sequence or peptide, an epitope tag, a FLAG tag, a polyhistidine tag, a GST fusion, and/or the like. Examples of tags or linkers that may be used in the invention include, but are not limited to, a polypeptide, a polymer, an affinity tag, an antigen, a detection tag, an imaging tag, a member of a multiple-member binding complex, and a radio-isotope tag. Examples of affinity tags and detection tags include, but are not limited to, a poly-His tag, biotin, avidin, protein A, protein G, and an antigen including but not limited to, an immunoglobulin epitope. Examples of imaging tags include, but are not limited to, a metal, a radionuclide, and a magnetic molecule. Examples of multiple-member binding complex tags include, but are not limited to, streptavidin, avidin, biotin, protein A, and protein G.

The term "localization peptide" includes, but is not limited to, examples of secretion signal sequences. Examples of secretion signal sequences include, but are not limited to, a prokaryotic secretion signal sequence, an eukaryotic secretion signal sequence, an eukaryotic secretion signal sequence 5'-optimized for bacterial expression, a novel secretion signal sequence, pectate lyase secretion signal sequence, Omp A secretion signal sequence, and a phage secretion signal sequence. Examples of secretion signal sequences, include, but are not limited to, STII (prokaryotic), Fd GIII and M13 (phage), Bgl2 (yeast), and the signal sequence bla derived from a transposon. Secretion signal sequences include, but are not limited to, a bacterial secretion signal sequence, a yeast secretion signal sequence, an insect signal secretion sequence, a mammalian secretion signal sequence, and a unique secretion signal sequence. Another example of a "localization sequence" includes, but it not limited to, a TrpLE sequence.

The protein or polypeptide of interest can contain at least one, at least two, at least three, at least four, at least five, at least six, at least seven, at least eight, at least nine, or ten or more unnatural amino acids. The unnatural amino acids can be the same or different, for example, there can be 1, 2, 3, 4, 5, 6, 7, 8, 9, 10 or more different sites in the protein that comprise 1, 2, 3, 4, 5, 6, 7, 8, 9, 10 or more different unnatural amino acids. In certain embodiments, at least one, but fewer than all, of a particular amino acid present in a naturally occurring version of the protein is substituted with an unnatural amino acid.

Any BSP or fragment thereof with therapeutic activity may be used in this invention. Numerous examples of BSPs that may be used in this invention have been provided. However, the lists provided are not exhaustive and in no way limit the number or type of BSPs that may be used in this invention. Thus, any BSP and/or fragments produced from any BSP including novel BSPs may be modified according to the present invention, and used therapeutically.

The present invention provides methods and compositions based on BSPs comprising at least one non-naturally encoded amino acid. Introduction of at least one non-naturally encoded amino acid into BSP can allow for the application of conjugation chemistries that involve specific chemical reactions, including, but not limited to, with one or more non-naturally encoded amino acids while not reacting with the commonly occurring 20 amino acids. In some embodiments, the BSP, such as GLP-1, T-20, or PYY comprising the non-naturally encoded amino acid is linked to a water soluble polymer, such as polyethylene glycol (PEG), via the side chain of the non-naturally encoded amino acid. This invention provides a highly efficient method for the selective modification of proteins with PEG derivatives, which involves the selective incorporation of non-genetically encoded amino acids, including but not limited to, those amino acids containing functional groups or substituents not found in the 20 naturally incorporated amino acids, including but not limited to a ketone, an azide or acetylene moiety, into proteins in response to a selector codon and the subsequent modification of those amino acids with a suitably reactive PEG derivative. Once incorporated, the amino acid side chains can then be modified by utilizing chemistry methodologies known to those of ordinary skill in the art to be suitable for the particular functional groups or substituents present in the naturally encoded amino acid. Known chemistry methodologies of a wide variety are suitable for use in the present invention to incorporate a water soluble polymer into the protein. Such methodologies include but are not limited to a Huisgen [3+2] cycloaddition reaction (see, e.g., Padwa, A. in *Comprehensive Organic Synthesis*, Vol. 4, (1991) Ed. Trost, B. M., Pergamon, Oxford, p. 1069-1109; and, Huisgen, R. in 1,3-*Dipolar Cycloaddition Chemistry*, (1984) Ed. Padwa, A., Wiley, New York, p. 1-176) with, including but not limited to, acetylene or azide derivatives, respectively.

Because the Huisgen [3+2] cycloaddition method involves a cycloaddition rather than a nucleophilic substitution reaction, proteins can be modified with extremely high selectivity. The reaction can be carried out at room temperature in aqueous conditions with excellent regioselectivity (1,4>1,5) by the addition of catalytic amounts of Cu(I) salts to the reaction mixture. See, e.g., Tomoe, et al., (2002) *J. Org. Chem.* 67:3057-3064; and, Rostovtsev, et al., (2002) *Angew. Chem. Int. Ed.* 41:2596-2599; and WO 03/101972. A molecule that can be added to a protein of the invention through a [3+2] cycloaddition includes virtually any molecule with a suitable functional group or substituent including but not limited to an azido or acetylene derivative. These molecules can be added to an unnatural amino acid with an acetylene group, including but not limited to, p-propargyloxyphenylalanine, or azido group, including but not limited to p-azido-phenylalanine, respectively.

The five-membered ring that results from the Huisgen [3+2] cycloaddition is not generally reversible in reducing environments and is stable against hydrolysis for extended periods in aqueous environments. Consequently, the physical and chemical characteristics of a wide variety of substances can be modified under demanding aqueous conditions with the active PEG derivatives of the present invention. Even more important, because the azide and acetylene moieties are specific for one another (and do not, for example, react with any of the 20 common, genetically-encoded amino acids), proteins can be modified in one or more specific sites with extremely high selectivity.

The invention also provides water soluble and hydrolytically stable derivatives of PEG derivatives and related hydrophilic polymers having one or more acetylene or azide moieties. The PEG polymer derivatives that contain acetylene moieties are highly selective for coupling with azide moieties that have been introduced selectively into proteins in response to a selector codon. Similarly, PEG polymer derivatives that contain azide moieties are highly selective for coupling with acetylene moieties that have been introduced selectively into proteins in response to a selector codon.

More specifically, the azide moieties comprise, but are not limited to, alkyl azides, aryl azides and derivatives of these azides. The derivatives of the alkyl and aryl azides can include other substituents so long as the acetylene-specific reactivity is maintained. The acetylene moieties comprise alkyl and aryl acetylenes and derivatives of each. The derivatives of the alkyl and aryl acetylenes can include other substituents so long as the azide-specific reactivity is maintained.

The present invention provides conjugates of substances having a wide variety of functional groups, substituents or moieties, with other substances including but not limited to a label; a dye; a polymer; a water-soluble polymer; a derivative of polyethylene glycol; a photocrosslinker; a radionuclide; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a water-soluble dendrimer; a cyclodextrin; an inhibitory ribonucleic acid; a biomaterial; a nanoparticle; a spin label; a fluorophore, a metal-containing moiety; a radioactive moiety; a novel functional group; a group that covalently or noncovalently interacts with other molecules; a photocaged moiety; a photoisomerizable moiety; biotin; a derivative of biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; or any combination of the above, or any other desirable compound or substance). The present invention also includes conjugates of substances having azide or acetylene moieties with PEG polymer derivatives having the corresponding acetylene or azide moieties. For example, a PEG polymer containing an azide moiety can be coupled to a biologically active molecule at a position in the protein that contains a non-genetically encoded amino acid bearing an acetylene functionality. The linkage by which the PEG and the biologically active molecule are coupled includes but is not limited to the Huisgen [3+2] cycloaddition product.

It is well established in the art that PEG can be used to modify the surfaces of biomaterials (see, e.g., U.S. Pat. No. 6,610,281; Mehvar, R., J. Pharm Pharm Sci., 3(1):125-136 (2000) which are incorporated by reference herein). The invention also includes biomaterials comprising a surface having one or more reactive azide or acetylene sites and one or more of the azide- or acetylene-containing polymers of the invention coupled to the surface via the Huisgen [3+2] cycloaddition linkage. Biomaterials and other substances can also be coupled to the azide- or acetylene-activated polymer derivatives through a linkage other than the azide or acetylene linkage, such as through a linkage comprising a carboxylic acid, amine, alcohol or thiol moiety, to leave the azide or acetylene moiety available for subsequent reactions.

The invention includes a method of synthesizing the azide- and acetylene-containing polymers of the invention. In the case of the azide-containing PEG derivative, the azide can be bonded directly to a carbon atom of the polymer. Alternatively, the azide-containing PEG derivative can be prepared by attaching a linking agent that has the azide moiety at one terminus to a conventional activated polymer so that the resulting polymer has the azide moiety at its terminus. In the case of the acetylene-containing PEG derivative, the acetylene can be bonded directly to a carbon atom of the polymer. Alternatively, the acetylene-containing PEG derivative can be prepared by attaching a linking agent that has the acetylene moiety at one terminus to a conventional activated polymer so that the resulting polymer has the acetylene moiety at its terminus.

More specifically, in the case of the azide-containing PEG derivative, a water soluble polymer having at least one active hydroxyl moiety undergoes a reaction to produce a substituted polymer having a more reactive moiety, such as a mesylate, tresylate, tosylate or halogen leaving group, thereon. The preparation and use of PEG derivatives containing sulfonyl acid halides, halogen atoms and other leaving groups are well known to the skilled artisan. The resulting substituted polymer then undergoes a reaction to substitute for the more reactive moiety an azide moiety at the terminus of the polymer. Alternatively, a water soluble polymer having at least one active nucleophilic or electrophilic moiety undergoes a reaction with a linking agent that has an azide at one terminus so that a covalent bond is formed between the PEG polymer and the linking agent and the azide moiety is positioned at the terminus of the polymer. Nucleophilic and electrophilic moieties, including amines, thiols, hydrazides, hydrazines, alcohols, carboxylates, aldehydes, ketones, thioesters and the like, are well known to the skilled artisan.

More specifically, in the case of the acetylene-containing PEG derivative, a water soluble polymer having at least one active hydroxyl moiety undergoes a reaction to displace a halogen or other activated leaving group from a precursor that contains an acetylene moiety. Alternatively, a water soluble polymer having at least one active nucleophilic or electrophilic moiety undergoes a reaction with a linking agent that has an acetylene at one terminus so that a covalent bond is formed between the PEG polymer and the linking agent and the acetylene moiety is positioned at the terminus of the polymer. The use of halogen moieties, activated leaving group, nucleophilic and electrophilic moieties in the context of organic synthesis and the preparation and use of PEG derivatives is well established to practitioners in the art.

The invention also provides a method for the selective modification of proteins to add other substances to the modified protein, including but not limited to water soluble polymers such as PEG and PEG derivatives containing an azide or acetylene moiety. The azide- and acetylene-containing PEG derivatives can be used to modify the properties of surfaces and molecules where biocompatibility, stability, solubility and lack of immunogenicity are important, while at the same time providing a more selective means of attaching the PEG derivatives to proteins than was previously known in the art.

II Peptides and Polypeptides

BSPs that may be made utilizing the methods of the present invention may be any combination of amino acids, whether naturally occurring or non-naturally encoded, of any length or sequence. The only requirement is for at least one of the amino acids in the BSP chain to be a non-naturally encoded amino acid. If a polypeptide is made biosynthetically, then the non-naturally encoded amino acid is incorporated into the peptide chain as translated from an mRNA comprising at least one selector codon. The novel BSPs of the present invention that may be made by chemical synthesis may incorporate at least one non-naturally encoded amino acid during the synthesis process. The non-naturally encoded amino acid may be placed at any position in the amino acid chain, and may also be located in any portion of the finished BSP, including but not limited to, within the biologically active peptide, linker or fusion partner such as albumin or Fc.

Reference to GLP-1 polypeptides in this application is intended to use GLP-1 as an example of a peptide or polypeptide suitable for use in the present invention. Thus, it is understood that the modifications and chemistries described herein with reference to GLP-1 can be equally applied to any other BSPs, including but not limited to, those specifically listed herein.

GLP-1 released from the L-cells of the intestine, in response to food, enters portal circulation. It is rapidly cleaved by DPP IV (CD26) to release GLP-1(9-37) or GLP-1(9-36) amide, both of which are less active at GLP-1R. According to some reports, they may act as antagonists of GLP-1R and GLP-1 effects on gastrointestinal motility. The half-life of circulating GLP-1 was found to be about 4 minutes (Kreymann et al., 1987 Lancet. December 5; 2(8571): 1300-4). Dipeptidyl-peptidase IV (DPP IV, EC 3.4.14.5, CD26), designated CD26, is an extracellular membrane-bound enzyme, expressed on the surface of several cell types, in particular $CD4^+$ T-cells, as well as on kidney, placenta, blood plasma, liver, and intestinal cells. On T-cells, DPP IV has been shown to be identical to the antigen CD26. CD26 is expressed on a fraction of resting T cells at low density, but is strongly up-regulated following T-cell activation (Gorrell et al., 2001, Scand J. Immunol. 2001 September; 54(3):249-64). CD26 is a multifunctional molecule that may have an important functional role in T-cells and in overall immune system modulation. CD26 is associated with other receptors of immunological significance found on the cell surface, such as the protein tyrosine phosphatase CD45 and adenosine deaminase (ADA). DPP IV exerts a negative regulation of glucose disposal by degrading GLP-1 and GIP, thus lowering the incretin effect on beta cells of the pancreas.

DPP IV cleaves the Ala-Glu bond of the major circulating form of human GLP-1 (human GLP-1(7-36) NH2: His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-NH2) (SEQ ID NO: 1), releasing an N-terminal dipeptide. Substitution of Ala with Gly (Deacon et al., 1998, Diabetologia, 41:271-278; Burcelin et al. 1999, Metabolism; 48(2):252-258), Leu, D-Ala and other amino acids, was shown to protect GLP-1 from DPP IV degradation and potentiates its in-vitro and in-vivo insulinotropic actions (Xiao et al., 2001, Biochemistry, 40:2860-2869). Deletion of the amino-terminal histidine, or of the NH2 group of His7, decreased receptor affinity and potency of the analogue (Adelhorst et al., 1994, J. Biol. Chem., 269(9):6275-6278;

Xiao et al. 2001, supra; Siegel et al., 1999, Reg. Peptides, 79:93-102). U.S. Pat. No. 5,545,618 teaches that N-terminal modifications using alkyl and acyl modifications also produced DPP IV resistant analogues. More specifically, His7 substitution by N-alkylated ($C_1$-$C_6$) or N-acylated ($C_1$-$C_6$) L-/D-amino acids resulted in analogues possessing DPP IV-resistance. Covalent coupling of unsaturated organic acids, such as trans-3-hexenoic acid, also produces DPP IV-resistant GLP-1 analogs that potently reduce hyperglycemia in oral glucose tolerance tests in mice (Xiao et al. 2001, supra). Furthermore, His7 can be replaced by α-substituted carboxylic acids, one of the substituents being a 5- or 6-membered ring structure (e.g. imidazole), in order to confer DPP IV resistance (see WO 99/43707 which is incorporated by reference herein). Insertion of 6-aminohexanoic acid (AHA) after His7 was shown to confer DPP IV resistance, while retaining receptor affinity and insulinotropic efficacy in vivo (Doyle et al., 2001, Endocrinol., 142(10):4462-4468).

Numerous GLP-1 analogs demonstrating insulinotropic action are known in the art. These variants and analogs include, for example, GLP-1(7-36), Gln9-GLP-1(7-37), D-Gln9-GLP-1(7-37), acetyl-Lys9-GLP-1(7-37), Thr16-Lys 18-GLP-1(7-37), and Lys 18-GLP-1(7-37). Derivatives of GLP-1 include, for example, acid addition salts, carboxylate salts, lower alkyl esters, and amides (see WO 91/11457 (1991); EP 0 733,644 (1996); and U.S. Pat. No. 5,512,549 (1996)). It has also been demonstrated that the N-terminal histidine residue (His7) is very important to the insulinotropic activity of GLP-1 (Suzuki et al., 1988, Diabetes Research and Clinical Practice XIII Congress of the International Diabetes Federation, 5(Suppl. 1):S30 (abstract No. ORA-007-007)).

A group of GLP-1 compounds suitable for use in the present invention is disclosed in WO 91/11457 (U.S. Pat. No. 5,545,618) which are incorporated by reference herein, and consists essentially of GLP-1(7-34), GLP-1(7-35), GLP-1(7-36), or GLP-1(7-37), or the amide form thereof, and pharmaceutically-acceptable salts thereof, having at least one modification selected from the group consisting of: (a) substitution of glycine, serine, cysteine, threonine, asparagine, glutamine, tyrosine, alanine, valine, isoleucine, leucine, methionine, phenylalanine, arginine, or D-lysine for lysine at position 26 and/or position 34; or substitution of glycine, serine, cysteine, threonine, asparagine, glutamine, tyrosine, alanine, valine, isoleucine, leucine, methionine, phenylalanine, lysine, or a D-arginine for arginine at position 36; (b) substitution of an oxidation-resistant amino acid for tryptophan at position 31; (c) substitution of at least one of: tyrosine for valine at position 16; lysine for serine at position 18; aspartic acid for glutamic acid at position 21; serine for glycine at position 22; arginine for glutamine at position 23; arginine for alanine at position 24; and glutamine for lysine at position 26; and (d) substitution of at least one of: glycine, serine, or cysteine for alanine at position 8; aspartic acid, glycine, serine, cysteine, threonine, asparagine, glutamine, tyrosine, alanine, valine, isoleucine, leucine, methionine, or phenylalanine for glutamic acid at position 9; serine, cysteine, threonine, asparagine, glutamine, tyrosine, alanine, valine, isoleucine, leucine, methionine, or phenylalanine for glycine at position 10; and glutamic acid for aspartic acid at position 15; and (e) substitution of glycine, serine, cysteine, threonine, asparagine, glutamine, tyrosine, alanine, valine, isoleucine, leucine, methionine, or phenylalanine, or the D- or N-acylated or alkylated form of histidine for histidine at position 7; wherein, in the substitutions in (a), (b), (d), and (e), the substituted amino acids can optionally be in the D-form and the amino acids substituted at position 7 can optionally be in the N-acylated or N-alkylated form.

Because the enzyme, dipeptidyl-peptidase IV (DPP IV), may be responsible for the observed rapid in vivo inactivation of administered GLP-1, [see, e.g., Mentlein, R., et al., Eur. J. Biochem., 214:829-835 (1993)], GLP-1 analogs and derivatives that are protected from the activity of DPP IV in the context of a fusion protein are suitable, and fusion proteins wherein the GLP-1 compound is Gly8-GLP-1(7-37)OH, Val8-GLP-1(7-37)OH, α-methyl-Ala8-GLP-1(7-37)OH, or Gly8-Gly21-GLP-1(7-37)OH are also suitable.

Another preferred group of GLP-1 compounds for use in the present invention consists of the compounds disclosed in U.S. Pat. No. 5,512,549, which is expressly incorporated herein by reference.

Figure 2:
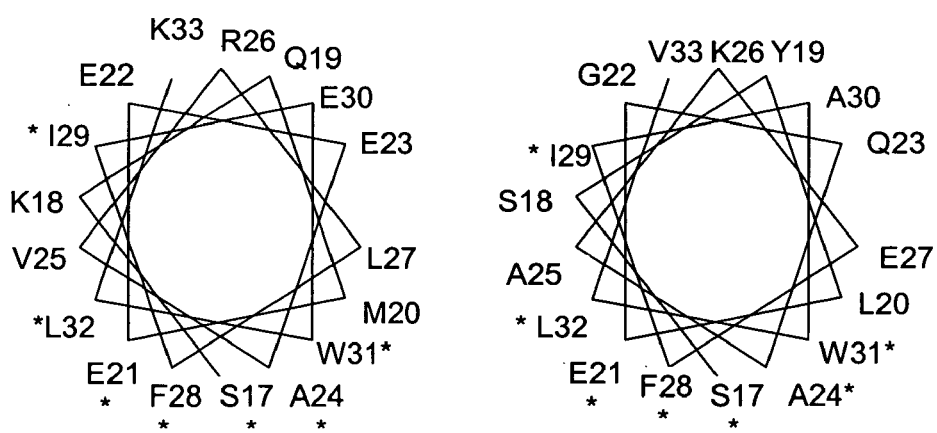
FIG. 2—A diagram of a helical comparison of GLP-1 (SEQ ID NO: 1) and Exendin-4 (SEQ ID NO: 21) is shown.
Figure 3:
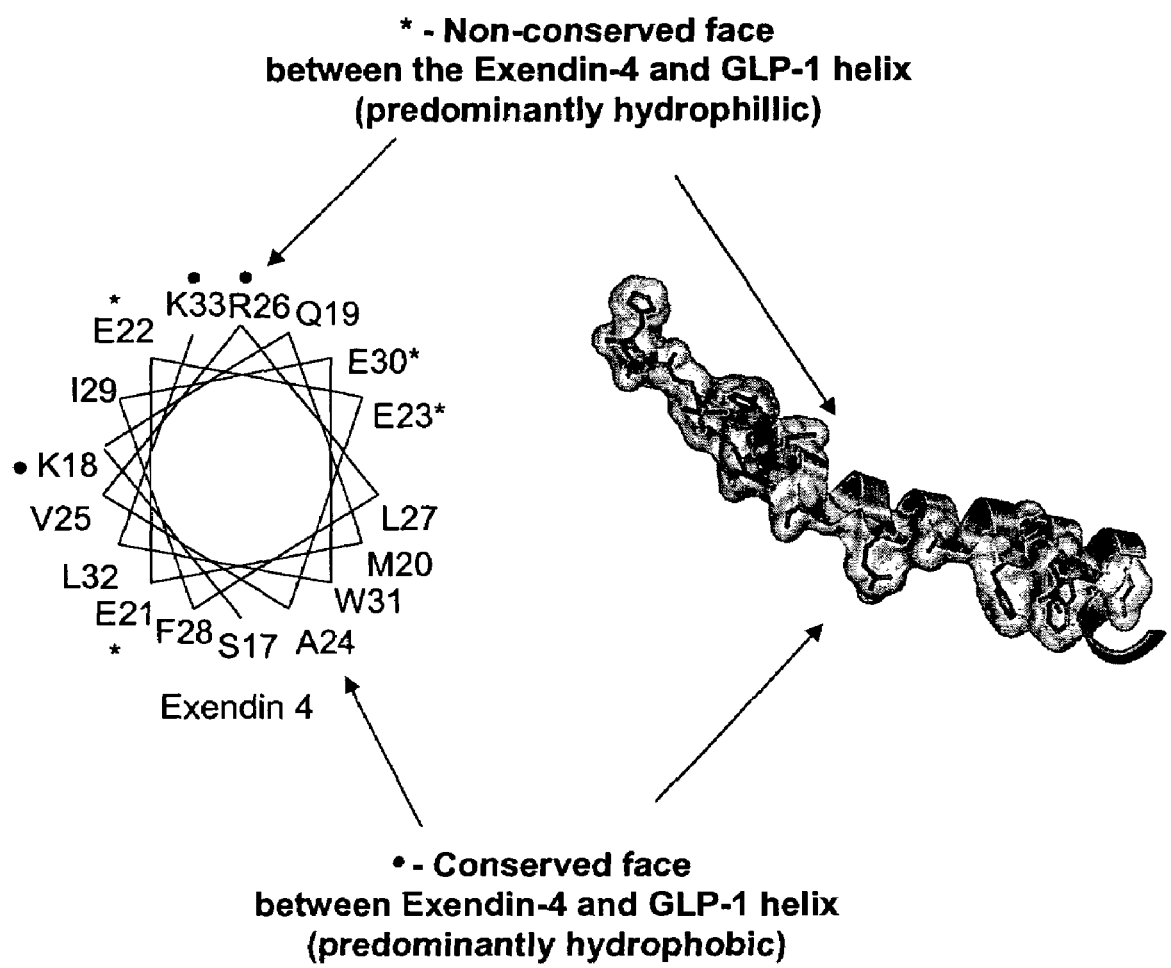
FIG. 3—A diagram of a comparison of the structures of GLP-1 and Exendin-4 is shown.

The GLP-1 compounds of the present invention also encompass Exendin compounds. Exendin-3 and Exendin-4 are biologically active peptides first isolated from Helodermatidae lizard venoms and have been shown to bind the GLP-1 receptor and stimulate cAMP-dependent $H^+$ production in mammalian parietal cells. Exendin-3 and Exendin-4 are both 39 amino acid peptides which are approximately 53% homologous to GLP-1. FIG. 2 is a helical comparison of the GLP-1 and Exendin-4 structures. Conserved residues are marked with an asterisk. FIG. 3 illustrates that the conserved face between Exendin-4 and GLP-1 is predominantly hydrophobic in nature, whereas the non-conserved face is predominantly hydrophilic.

They act as potent agonists of GLP-1 activity. Notably, an N-terminally truncated derivative of Exendin, known as Exendin(9-39 amino acids), is an inhibitor of Exendin-3, Exendin-4 and GLP-1. (Goke et al. (1993) J. Biol. Chem. 268(26)19650-19655)

An Exendin compound typically comprises a polypeptide having the amino acid sequence of Exendin-3, Exendin-4, or an analog or fragment thereof. Exendin-3 and Exendin-4 are disclosed in U.S. Pat. No. 5,424,286. Exendin-3 has the amino acid sequence of His-Ser-Asp-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser (SEQ ID NO: 21). Exendin-4 has the amino acid sequence of His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser (SEQ ID NO: 3).

GLP-1 compounds also include Exendin fragments which are polypeptides obtained after truncation of one or more amino acids from the N-terminus and/or C-terminus of Exendin or an Exendin analog. Furthermore, GLP-1 compounds include Exendin polypeptides in which one or more amino acids have been added to the N-terminus and/or C-terminus of Exendin or fragments thereof. Exendin compounds of this type have up to about forty-five amino acids.

GLP-1 compounds also include "Exendin analogs." An Exendin analog has sufficient homology to Exendin-4, Exendin-3, or a fragment thereof such that the analog has insulinotropic activity. The activity of Exendin fragments and/or analogs can be assessed using in vitro assays such as those described in EP 619,322 and U.S. Pat. No. 5,120,712, which are incorporated by reference herein. Additional Exendin-analogs that are useful for the present invention are described in PCT patent publications WO 99/25728 (Beeley et al.), WO 99/25727 (Beeley et al.), WO 98/05351 (Young et al.), WO 99/40788 (Young et al.), WO 99/07404 (Beeley et al.), and WO 99/43708 (Knudsen et al.), which are incorporated by reference herein. Examples of exendin as well as analogs, derivatives, and fragments thereof to be included within the present invention are those disclosed in WO 97/46584 and U.S. Pat. No. 5,424,286.

Heterologous Fc Fusion Proteins

The BSPs such as GLP-1 compounds described above may be fused directly or via a peptide linker to the Fc portion of an immunoglobulin. Immunoglobulins are molecules containing polypeptide chains held together by disulfide bonds, typically having two light chains and two heavy chains. In each chain, one domain (V) has a variable amino acid sequence depending on the antibody specificity of the molecule. The other domains (C) have a rather constant sequence common to molecules of the same class. One example of a GLP-1-Fc fusion compound is shown in FIG. 1.

As used herein, the Fc portion of an immunoglobulin has the meaning commonly given to the term in the field of immunology. Specifically, this term refers to an antibody fragment which is obtained by removing the two antigen binding regions (the Fab fragments) from the antibody. One way to remove the Fab fragments is to digest the immunoglobulin with papain protease. Thus, the Fc portion is formed from approximately equal sized fragments of the constant region from both heavy chains, which associate through non-covalent interactions and disulfide bonds. The Fc portion can include the hinge regions and extend through the CH2 and CH3 domains to the C-terminus of the antibody. Representative hinge regions for human and mouse immunoglobulins can be found in Antibody Engineering, A Practical Guide, Borrebaeck, C. A. K., ed., W. H. Freeman and Co., 1992, the teachings of which are herein incorporated by reference. The Fc portion can further include one or more glycosylation sites. The amino acid sequences of numerous representative Fc proteins containing a hinge region, CH2 and CH3 domains, and one N-glycosylation site are well known in the art.

There are five types of human immunoglobulin Fc regions with different effector functions and pharmacokinetic properties: IgG, IgA, IgM, IgD, and IgE. IgG is the most abundant immunoglobulin in serum. IgG also has the longest half-life in serum of any immunoglobulin (23 days). Unlike other immunoglobulins, IgG is efficiently recirculated following binding to an Fc receptor. There are four IgG subclasses G1, G2, G3, and G4, each of which has different effector functions. G1, G2, and G3 can bind C1q and fix complement while G4 cannot. Even though G3 is able to bind C1q more efficiently than G1, G 1 is more effective at mediating complement-directed cell lysis. G2 fixes complement very inefficiently. The C1q binding site in IgG is located at the carboxy terminal region of the CH2 domain.

All IgG subclasses are capable of binding to Fc receptors (CD16, CD32, CD64) with G1 and G3 being more effective than G2 and G4. The Fc receptor binding region of IgG is formed by residues located in both the hinge and the carboxy terminal regions of the CH2 domain.

IgA can exist both in a monomeric and dimeric form held together by a J-chain. IgA is the second most abundant Ig in serum, but it has a half-life of only 6 days. IgA has three effector functions. It binds to an IgA specific receptor on macrophages and eosinophils, which drives phagocytosis and degranulation, respectively. It can also fix complement via an unknown alternative pathway.

IgM is expressed as either a pentamer or a hexamer, both of which are held together by a J-chain. IgM has a serum half-life of 5 days. It binds weakly to C1q via a binding site located in its CH3 domain. IgD has a half-life of 3 days in serum. It is unclear what effector functions are attributable to this Ig. IgE is a monomeric Ig and has a serum half-life of 2.5 days. IgE binds to two Fc receptors which drives degranulation and results in the release of proinflammatory agents.

Depending on the desired in vivo effect, the heterologous fusion proteins of the present invention may contain any of the isotypes described above or may contain mutated Fc regions wherein the complement and/or Fc receptor binding functions have been altered. Thus, the heterologous fusion proteins of the present invention may contain the entire Fc portion of an immunoglobulin, fragments of the Fc portion of an immunoglobulin, or analogs thereof fused to a GLP-1 compound.

The fusion proteins of the present invention can consist of single chain proteins or as multi-chain polypeptides. Two or more Fc fusion proteins can be produced such that they interact through disulfide bonds that naturally form between Fc regions. These multimers can be homogeneous with respect to the GLP-1 compound or they may contain different GLP-1 compounds fused at the N-terminus of the Fc portion of the fusion protein.

Regardless of the final structure of the fusion protein, the Fc or Fc-like region may serve to prolong the in vivo plasma half-life of the GLP-1 compound fused at the N-terminus. Also, the GLP-1 component of a fusion protein compound should retain at least one biological activity of GLP-1. An increase in therapeutic or circulating half-life can be demonstrated using the method described herein or known in the art, wherein the half-life of the fusion protein is compared to the half-life of the GLP-1 compound alone. Biological activity can be determined by in vitro and in vivo methods known in the art.

Since the Fc region of IgG produced by proteolysis has the same in vivo half-life as the intact IgG molecule and Fab fragments are rapidly degraded, it is believed that the relevant sequence for prolonging half-life reside in the CH2 and/or CH3 domains. Further, it has been shown in the literature that the catabolic rates of IgG variants that do not bind the high-affinity Fc receptor or C1q are indistinguishable from the rate of clearance of the parent wild-type antibody, indicating that the catabolic site is distinct from the sites involved in Fc receptor or C1q binding. [Wawrzynczak et al., (1992) Molecular Immunology 29:221]. Site-directed mutagenesis studies using a murine IgG1 Fc region suggested that the site of the IgG1 Fc region that controls the catabolic rate is located at the CH2—CH3 domain interface. Fc regions can be modified at the catabolic site to optimize the half-life of the fusion proteins. The Fc region used for the fusion proteins of the present invention may be derived from an IgG1 or an IgG4 Fc region, and may contain both the CH2 and CH3 regions including the hinge region.

Heterologous Albumin Fusion Proteins

The BSPs such as GLP-1 compounds described herein may be fused directly or via a peptide linker, water soluble polymer, or prodrug linker to albumin or an analog, fragment, or derivative thereof. Generally, the albumin proteins that are part of the fusion proteins of the present invention may be derived from albumin cloned from any species, including human. Human serum albumin (HSA) consists of a single non-glycosylated polypeptide chain of 585 amino acids with a formula molecular weight of 66,500. The amino acid sequence of human HSA is known [See Meloun, et al. (1975) FEBS Letters 58:136; Behrens, et al. (1975) Fed. Proc. 34:591; Lawn, et al. (1981) Nucleic Acids Research 9:6102-6114; Minghetti, et al. (1986) J. Biol. Chem. 261:6747, each of which are incorporated by reference herein]. A variety of polymorphic variants as well as analogs and fragments of albumin have been described. [See Weitkamp, et al., (1973) Ann. Hum. Genet. 37:219]. For example, in EP 322,094, various shorter forms of HSA. Some of these fragments of HSA are disclosed, including HSA(1-373), HSA(1-388), HSA(1-389), HSA(1-369), and HSA(1-419) and fragments between 1-369 and 1-419. EP 399,666 discloses albumin fragments that include HSA(1-177) and HSA(1-200) and fragments between HSA(1-177) and HSA(1-200).

It is understood that the heterologous fusion proteins of the present invention include GLP-1 compounds that are coupled to any albumin protein including fragments, analogs, and derivatives wherein such fusion protein is biologically active and has a longer plasma half-life than the GLP-1 compound alone. Thus, the albumin portion of the fusion protein need not necessarily have a plasma half-life equal to that of native human albumin. Fragments, analogs, and derivatives are known or can be generated that have longer half-lives or have half-lives intermediate to that of native human albumin and the GLP-1 compound of interest.

The heterologous fusion proteins of the present invention encompass proteins having conservative amino acid substitutions in the GLP-1 compound and/or the Fc or albumin portion of the fusion protein. A "conservative substitution" is the replacement of an amino acid with another amino acid that has the same net electronic charge and approximately the same size and shape. Amino acids with aliphatic or substituted aliphatic amino acid side chains have approximately the same size when the total number carbon and heteroatoms in their side chains differs by no more than about four. They have approximately the same shape when the number of branches in their side chains differs by no more than one. Amino acids with phenyl or substituted phenyl groups in their side chains are considered to have about the same size and shape. Except as otherwise specifically provided herein, conservative substitutions are preferably made with naturally occurring amino acids.

Wild-type albumin and immunoglobulin proteins can be obtained from a variety of sources. For example, these proteins can be obtained from a cDNA library prepared from tissue or cells which express the mRNA of interest at a detectable level. Libraries can be screened with probes designed using the published DNA or protein sequence for the particular protein of interest. For example, immunoglobulin light or heavy chain constant regions are described in Adams, et al. (1980) Biochemistry 19:2711-2719; Goughet, et al. (1980) Biochemistry 19:2702-2710; Dolby, et al. (1980) Proc. Natl. Acad. Sci. USA 77:6027-6031; Rice et al. (1982) Proc. Natl. Acad. Sci. USA 79:7862-7862; Falkner, et al. (1982) Nature 298:286-288; and Morrison, et al. (1984) Ann. Rev. Immunol. 2:239-256. Some references disclosing albumin protein and DNA sequences include Meloun, et al. (1975) FEBS Letters 58:136; Behrens, et al. (1975) Fed. Proc. 34:591; Lawn, et al. (1981) Nucleic Acids Research 9:6102-6114; and Minghetti, et al. (1986) J. Biol. Chem. 261:6747.

The incorporation of non-natural amino acids, including synthetic non-native amino acids, substituted amino acids, or one or more D-amino acids into the heterologous fusion proteins of the present invention may be advantageous in a number of different ways. D-amino acid-containing peptides, etc., exhibit increased stability in vitro or in vivo compared to L-amino acid-containing counterparts. Thus, the construction of peptides, etc., incorporating D-amino acids can be particularly useful when greater intracellular stability is desired or required. More specifically, D-peptides, etc., are resistant to endogenous peptidases and proteases, thereby providing improved bioavailability of the molecule, and prolonged lifetimes in vivo when such properties are desirable. Additionally, D-peptides, etc., cannot be processed efficiently for major histocompatibility complex class II-restricted presentation to T helper cells, and are therefore, less likely to induce humoral immune responses in the whole organism.

Other peptides may be modified with non-naturally encoded amino acids, including but not limited, to T-20 (DP-178), PYY (3-36), and RANTES.

The polypeptide known as RANTES is a member of a large family of cytokines known as chemokines, and is classified as a β-chemokine. It has a sixty-eight amino acid sequence. A receptor for RANTES has recently been cloned (Gao, et al., J. Exp. Med. 177:1421-7 (1993); Neote, et al., Cell 72:415-25 (1993)), which has been shown to bind chemokines in the order of potency of MIP-1α>RANTES.

Chemokines have the ability to recruit and activate a wide variety of proinflammatory cell types, and RANTES has been shown to elicit an inflammatory response in vivo. RANTES, along with the natural ligands for the CCR5 chemokine receptor, MIP-1α, MIP-1β, were found to inhibit human immune deficiency virus type-1 ("HIV-1") infection (Cocchi, et al., Science 270:1811-1815 (1995)), leading to the identification of CCR5 as the major co-receptor for primary isolates of HIV-1, HIV-2 and SIV-1 (Deng, et al., Nature 381:661-666 (1996); Doranz, et al., Cell 85:1149-1158 (1996); Choe, et al., Cell 85:1135-1148 (1996); Chen, et al., J. Virol. 71:2705-2714 (1997); and Alkhatib, et al., Science 272:1955-1958 (1996)). However, although RANTES consistently inhibits HIV-1 replication in peripheral blood mononuclear cells, it does not block infection of primary macrophage cultures, which suggests that RANTES would not influence HIV replication in non-lymphocyte cell types.

N-terminal modifications of RANTES result in antagonists that can block HIV-1 infection without signaling calcium flux (Mack, et al., J. Exp. Med. 187:1215-1224 (1998) and Proudfoot, et al., J. Biol. Chem. 271:2599-2603 (1996)). These modifications include N-terminal truncation [RANTES 9-68] (Arenzana-Seisdedos, et al., Nature 383:400 (1996)), and addition of methionine ("Met-RANTES") or aminooxypentane ("AOP-RANTES") at the N-terminus of RANTES (Mack, et al., supra and Simmons, et al., Science 276:276-279 (1997)). It has been reported that the Met-RANTES and AOP-RANTES derivatives are antagonists of RANTES. Further, N-terminally modified RANTES, with a higher affinity for CCR5 than native RANTES are more potent than native RANTES in blocking infection (Simmons, et al., supra).

Chemokine receptor antagonists that are potent, selective, and achieve full receptor occupancy would clearly be useful for the treatment of HIV-1 in infected individuals. Surprisingly, compounds have been discovered with this spectrum of activity. These derivatives inhibited infection of many different cell types, including macrophages and lymphocytes. Additionally, antagonists of RANTES effectively block its inflammatory effects, and are thus useful for the treatment of asthma, allergic rhinitis, atopic dermatitis, viral diseases, atheroma/atheroschlerosis, rheumatoid arthritis and organ transplant rejection. Certain derivatives of RANTES are disclosed in Wells, et al., International Application WO 96/17935. U.S. Pat. No. 6,168,784, which is incorporated by reference herein, describes N-terminally modified RANTES derivatives produced by chemical synthesis. RANTES polypeptides comprising one or more non-naturally encoded amino acids may provide similar or improved therapeutic activities.

III. General Recombinant Nucleic Acid Methods for Use with the Invention

In numerous embodiments of the present invention, nucleic acids encoding a BSP of interest will be isolated, cloned and often altered using recombinant methods. Such embodiments are used, including but not limited to, for protein expression or during the generation of variants, derivatives, expression cassettes, or other sequences derived from a BSP. In some embodiments, the sequences encoding the polypeptides of the invention are operably linked to a heterologous promoter. Isolation of GLP-1 and production of GLP-1 in host cells is described in, e.g., U.S. Pat. No. 5,118,666, which is incorporated by reference herein.

A nucleotide sequence encoding a BSP comprising a non-naturally encoded amino acid may be synthesized on the basis of the amino acid sequence of the parent polypeptide, including but not limited to, having the amino acid sequence shown in SEQ ID NO: 1, 2, 3, 21 (GLP-1), SEQ ID NO: 22, 24 (T-20), or SEQ ID NO: 23 (PYY(3-36)) and then changing the nucleotide sequence so as to effect introduction (i.e., incorporation or substitution) or removal (i.e., deletion or substitution) of the relevant amino acid residue(s). The nucleotide sequence may be conveniently modified by site-directed mutagenesis in accordance with conventional methods. Alternatively, the nucleotide sequence may be prepared by chemical synthesis, including but not limited to, by using an oligonucleotide synthesizer, wherein oligonucleotides are designed based on the amino acid sequence of the desired polypeptide, and preferably selecting those codons that are favored in the host cell in which the recombinant polypeptide will be produced. For example, several small oligonucleotides coding for portions of the desired polypeptide may be synthesized and assembled by PCR, ligation or ligation chain reaction. See, e.g., Barany, et al., *Proc. Natl. Acad. Sci.* 88: 189-193 (1991); U.S. Pat. No. 6,521,427 which are incorporated by reference herein.

This invention utilizes routine techniques in the field of recombinant genetics. Basic texts disclosing the general methods of use in this invention include Sambrook et al., *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

General texts which describe molecular biological techniques include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (2nd Ed.), Vol. 1-3, Cold Spring Harbor Laboratory, Cold Spring Harbor, N.Y., 1989 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 1999) ("Ausubel")). These texts describe mutagenesis, the use of vectors, promoters and many other relevant topics related to, including but not limited to, the generation of genes that include selector codons for production of proteins that include unnatural amino acids, orthogonal tRNAs, orthogonal synthetases, and pairs thereof. Promoters include, but are not limited to, a prokaryotic promoter, a eukaryotic promoter, a bacterial promoter, a yeast promoter, an insect promoter, a mammalian promoter, a unique promoter, and an inducible promoter.

Various types of mutagenesis are used in the invention for a variety of purposes, including but not limited to, to produce libraries of tRNAs, to produce libraries of synthetases, to produce selector codons, to insert selector codons that encode unnatural amino acids in a protein or polypeptide of interest. They include but are not limited to site-directed, random point mutagenesis, homologous recombination, DNA shuffling or other recursive mutagenesis methods, chimeric construction, mutagenesis using uracil containing templates, oligonucleotide-directed mutagenesis, phosphorothioate-modified DNA mutagenesis, mutagenesis using gapped duplex DNA or the like, or any combination thereof. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, including but not limited to, involving chimeric constructs, are also included in the present invention. In one embodiment, mutagenesis can be guided by known information of the naturally occurring molecule or altered or mutated naturally occurring molecule, including but not limited to, sequence, sequence comparisons, physical properties, crystal structure or the like.

The texts and examples found herein describe these procedures. Additional information is found in the following publications and references cited within: Ling et al., Approaches to DNA mutagenesis: an overview, *Anal Biochem.* 254(2): 157-178 (1997); Dale et al., *Oligonucleotide-directed random mutagenesis using the phosphorothioate method*, Meth. ods Mol. Biol. 57:369-374 (1996); Smith, *In vitro mutagenesis*, Ann. Rev. Genet. 19:423462 (1985); Botstein & Shortle, *Strategies and applications of in vitro mutagenesis*, Science 229:1193-1201 (1985); Carter, *Site-directed mutagenesis*, Biochem. J. 237:1-7 (1986); Kunkel, *The efficiency of oligonucleotide directed mutagenesis*, in *Nucleic Acids & Molecular Biology* (Eckstein, F. and Lilley, D. M. J. eds., Springer Verlag, Berlin) (1987); Kunkel, *Rapid and efficient site-specific mutagenesis without phenotypic selection*, Proc. Natl. Acad. Sci. USA 82:488-492 (1985); Kunkel et al., *Rapid and efficient site-specific mutagenesis without phenotypic selection*, Methods in Enzymol. 154, 367-382 (1987); Bass et al., *Mutant Trp repressors with new DNA-binding specificities*, Science 242:240-245 (1988); Zoller & Smith, *Oligonucleotide-directed mutagenesis using M13-derived vectors: an efficient and general procedure for the production of point mutations in any DNA fragment*, Nucleic Acids Res. 10:6487-6500 (1982); Zoller & Smith, *Oligonucleotide-directed mutagenesis of DNA fragments cloned into M13 vectors*, Methods in Enzymol. 100:468-500 (1983); Zoller & Smith, *Oligonucleotide-directed mutagenesis: a simple method using two oligonucleotide primers and a single-stranded DNA template*, Methods in Enzymol. 154:329-350 (1987); Taylor et al., *The use of phosphorothioate-modified DNA in restriction enzyme reactions to prepare nicked DNA*, Nucl. Acids Res. 13: 8749-8764 (1985); Taylor et al., *The rapid generation of oligonucleotide-directed mutations at high frequency using phosphorothioate-modified DNA*, Nucl. Acids Res. 13: 8765-8785 (1985); Nakamaye & Eckstein, *Inhibition of restriction endonuclease Nci I cleavage by phosphorothioate groups and its application to oligonucleotide-directed mutagenesis*, Nucl. Acids Res. 14: 9679-9698 (1986); Sayers et al., *5'-3' Exonucleases in phosphorothioate-based oligonucleotide-directed mutagenesis*, Nucl. Acids Res. 16:791-802 (1988); Sayers et al., *Strand specific cleavage of phosphorothioate-containing DNA by reaction with restriction endonucleases in the presence of ethidium bromide*, (1988) Nucl. Acids Res. 16: 803-814; Kramer et al., *The gapped duplex DNA approach to oligonucleotide-directed mutation construction*, Nucl. Acids Res. 12: 9441-9456 (1984); Kramer & Fritz *Oligonucleotide-directed construction of mutations via gapped duplex DNA*, Methods in Enzymol. 154:350-367 (1987); Kramer et al., *Improved enzymatic in vitro reactions in the gapped duplex DNA approach to oligonucleotide-directed construction of mutations*, Nucl. Acids Res. 16: 7207 (1988); Fritz et al., *Oligonucleotide-directed construction of mutations: a gapped duplex DNA procedure without enzymatic reactions in vitro*, Nucl. Acids Res. 16: 6987-6999

(1988); Kramer et al., *Different base/base mismatches are corrected with different efficiencies by the methyl-directed DNA mismatch-repair system of E. coli*, Cell 38:879-887 (1984); Carter et al., *Improved oligonucleotide site-directed mutagenesis using M13 vectors*, Nucl. Acids Res. 13: 4431-4443 (1985); Carter, *Improved oligonucleotide-directed mutagenesis using M13 vectors*, Methods in Enzymol. 154: 382403 (1987); Eghtedarzadeh & Henikoff, *Use of oligonucleotides to generate large deletions*, Nucl. Acids Res. 14: 5115 (1986); Wells et al., *Importance of hydrogen-bond formation in stabilizing the transition state of subtilisin*, Phil. Trans. R. Soc. Lond. A 317: 415-423 (1986); Nambiar et al., *Total synthesis and cloning of a gene coding for the ribonuclease S protein*, Science 223: 1299-1301 (1984); Sakinar and Khorana, *Total synthesis and expression of a gene for the alpha-subunit of bovine rod outer segment guanine nucleotide-binding protein (transducin)*, Nucl. Acids Res. 14: 6361-6372 (1988); Wells et al., *Cassette mutagenesis: an efficient method for generation of multiple mutations at defined sites*, Gene 34:315-323 (1985); Grundström et al., *Oligonucleotide-directed mutagenesis by microscale 'shotgun' gene synthesis*, Nucl. Acids Res. 13: 3305-3316 (1985); Mandecki, *Oligonucleotide-directed double-strand break repair in plasmids of Escherichia coli: a method for site-specific mutagenesis*, Proc. Natl. Acad. Sci. USA, 83:7177-7181 (1986); Arnold, *Protein engineering for unusual environments*, Current Opinion in Biotechnology 4:450-455 (1993); Sieber, et al., Nature Biotechnology, 19:456-460 (2001); W. P. C. Stemmer, *Nature* 370, 389-91 (1994); and, I. A. Lorimer, I. Pastan, *Nucleic Acids Res.* 23, 3067-8 (1995). Additional details on many of the above methods can be found in *Methods in Enzymology* Volume 154, which also describes useful controls for trouble-shooting problems with various mutagenesis methods.

The invention also relates to eukaryotic host cells, non-eukaryotic host cells, and organisms for the in vivo incorporation of an unnatural amino acid via orthogonal tRNA/RS pairs. Host cells are genetically engineered (including but not limited to, transformed, transduced or transfected) with the polynucleotides of the invention or constructs which include a polynucleotide of the invention, including but not limited to, a vector of the invention, which can be, for example, a cloning vector or an expression vector. The vector can be, for example, in the form of a plasmid, a bacterium, a virus, a naked polynucleotide, or a conjugated polynucleotide. The vectors are introduced into cells and/or microorganisms by standard methods including electroporation (Fromm et al., *Proc. Natl. Acad. Sci. USA* 82, 5824 (1985), infection by viral vectors, high velocity ballistic penetration by small particles with the nucleic acid either within the matrix of small beads or particles, or on the surface (Klein et al., *Nature* 327, 70-73 (1987)).

The engineered host cells can be cultured in conventional nutrient media modified as appropriate for such activities as, for example, screening steps, activating promoters or selecting transformants. These cells can optionally be cultured into transgenic organisms. Other useful references, including but not limited to for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds.) (1995) *Plant Cell, Tissue and Organ Culture*; Fundamental Methods Springer Lab Manual, Springer-Verlag (Berlin Heidelberg N.Y.) and Atlas and Parks (eds.) *The Handbook of Microbiological Media* (1993) CRC Press, Boca Raton, Fla.

Several well-known methods of introducing target nucleic acids into cells are available, any of which can be used in the invention. These include: fusion of the recipient cells with bacterial protoplasts containing the DNA, electroporation, projectile bombardment, and infection with viral vectors (discussed further, below), etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, a plethora of kits are commercially available for the purification of plasmids from bacteria, (see, e.g., EasyPrep™, FlexiPrep™, both from Pharmacia Biotech; StrataClean™ from Stratagene; and, QIAprep™ from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (including but not limited to, shuttle vectors) and selection markers for both prokaryotic and eukaryotic systems. Vectors are suitable for replication and integration in prokaryotes, eukaryotes, or preferably both. See, Gillam & Smith, *Gene* 8:81 (1979); Roberts, et al., *Nature*, 328:731 (1987); Schneider, E., et al., *Protein Expr. Purif.* 6(1)10-14 (1995); Ausubel, Sambrook, Berger (all supra). A catalogue of bacteria and bacteriophages useful for cloning is provided, e.g., by the ATCC, e.g., *The ATCC Catalogue of Bacteria and Bacteriophage* (1992) Gherna et al. (eds) published by the ATCC. Additional basic procedures for sequencing, cloning and other aspects of molecular biology and underlying theoretical considerations are also found in Watson et al. (1992) *Recombinant DNA Second Edition* Scientific American Books, NY. In addition, essentially any nucleic acid (and virtually any labeled nucleic acid, whether standard or non-standard) can be custom or standard ordered from any of a variety of commercial sources, such as the Midland Certified Reagent Company (Midland, Tex. available on the World Wide Web at mcrc.com), The Great American Gene Company (Ramona, Calif. available on the World Wide Web at genco.com), ExpressGen Inc. (Chicago, Ill. available on the World Wide Web at expressgen.com), Operon Technologies Inc. (Alameda, Calif.) and many others.

Selector Codons

Selector codons of the invention expand the genetic codon framework of protein biosynthetic machinery. For example, a selector codon includes, but is not limited to, a unique three base codon, a nonsense codon, such as a stop codon, including but not limited to, an amber codon (UAG), or an opal codon (UGA), an unnatural codon, a four or more base codon, a rare codon, or the like. It is readily apparent to those of ordinary skill in the art that there is a wide range in the number of selector codons that can be introduced into a desired gene, including but not limited to, one or more, two or more, more than three, 4, 5, 6, 7, 8, 9, 10 or more in a single polynucleotide encoding at least a portion of the BSP.

In one embodiment, the methods involve the use of a selector codon that is a stop codon for the incorporation of unnatural amino acids in vivo in a eukaryotic cell. For example, an O-tRNA is produced that recognizes the stop codon, including but not limited to, UAG, and is aminoacylated by an O-RS with a desired unnatural amino acid. This O-tRNA is not recognized by the naturally occurring host's aminoacyl-tRNA synthetases. Conventional site-directed mutagenesis can be used to introduce the stop codon, including but not limited to, TAG, at the site of interest in a polypeptide of interest. See. e.g., Sayers, J. R., et al. (1988), 5'-3' *Exonucleases in phosphorothioate-based oligonucleotide-directed mutagenesis. Nucleic Acids Res* 16:791-802. When the O-RS, O-tRNA and the nucleic acid that encodes the polypeptide of interest are combined in vivo, the unnatural amino acid is incorporated in response to the UAG codon to give a polypeptide containing the unnatural amino acid at the specified position.

The incorporation of unnatural amino acids in vivo can be done without significant perturbation of the eukaryotic host cell. For example, because the suppression efficiency for the UAG codon depends upon the competition between the O-tRNA, including but not limited to, the amber suppressor tRNA, and a eukaryotic release factor (including but not limited to, eRF) (which binds to a stop codon and initiates release of the growing peptide from the ribosome), the suppression efficiency can be modulated by, including but not limited to, increasing the expression level of O-tRNA, and/or the suppressor tRNA.

Selector codons also comprise extended codons, including but not limited to, four or more base codons, such as, four, five, six or more base codons. Examples of four base codons include, including but not limited to, AGGA, CUAG, UAGA, CCCU and the like. Examples of five base codons include, but are not limited to, AGGAC, CCCCU, CCCUC, CUAGA, CUACU, UAGGC and the like. A feature of the invention includes using extended codons based on frameshift suppression. Four or more base codons can insert, including but not limited to, one or multiple unnatural amino acids into the same protein. For example, in the presence of mutated O-tRNAs, including but not limited to, a special frameshift suppressor tRNAs, with anticodon loops, for example, with at least 8-10 nt anticodon loops, the four or more base codon is read as single amino acid. In other embodiments, the anticodon loops can decode, including but not limited to, at least a four-base codon, at least a five-base codon, or at least a six-base codon or more. Since there are 256 possible four-base codons, multiple unnatural amino acids can be encoded in the same cell using a four or more base codon. See, Anderson et al., (2002) *Exploring the Limits of Codon and Anticodon Size, Chemistry and Biology*, 9:237-244; Magliery, (2001) *Expanding the Genetic Code: Selection of Efficient Suppressors of Four-base Codons and Identification of "Shifty" Four-base Codons with a Library Approach in Escherichia coli, J. Mol. Biol.* 307: 755-769.

For example, four-base codons have been used to incorporate unnatural amino acids into proteins using in vitro biosynthetic methods. See, e.g., Ma et al., (1993) *Biochemistry*, 32:7939; and Hohsaka et al., (1999) *J. Am. Chem. Soc.*, 121: 34. CGGG and AGGU were used to simultaneously incorporate 2-naphthylalanine and an NBD derivative of lysine into streptavidin in vitro with two chemically acylated frameshift suppressor tRNAs. See, e.g., Hohsaka et al., (1999) *J. Am. Chem. Soc.*, 121:12194. In an in vivo study, Moore et al. examined the ability of tRNALeu derivatives with NCUA anticodons to suppress UAGN codons (N can be U, A, G, or C), and found that the quadruplet UAGA can be decoded by a tRNALeu with a UCUA anticodon with an efficiency of 13 to 26% with little decoding in the 0 or –1 frame. See, Moore et al., (2000) *J. Mol. Biol.*, 298:195. In one embodiment, extended codons based on rare codons or nonsense codons can be used in the present invention, which can reduce missense readthrough and frameshift suppression at other unwanted sites.

For a given system, a selector codon can also include one of the natural three base codons, where the endogenous system does not use (or rarely uses) the natural base codon. For example, this includes a system that is lacking a tRNA that recognizes the natural three base codon, and/or a system where the three base codon is a rare codon.

Selector codons optionally include unnatural base pairs. These unnatural base pairs further expand the existing genetic alphabet. One extra base pair increases the number of triplet codons from 64 to 125. Properties of third base pairs include stable and selective base pairing, efficient enzymatic incorporation into DNA with high fidelity by a polymerase, and the efficient continued primer extension after synthesis of the nascent unnatural base pair. Descriptions of unnatural base pairs which can be adapted for methods and compositions include, e.g., Hirao, et al., (2002) *An unnatural base pair for incorporating amino acid analogues into protein, Nature Biotechnology*, 20:177-182. Other relevant publications are listed below.

For in vivo usage, the unnatural nucleoside is membrane permeable and is phosphorylated to form the corresponding triphosphate. In addition, the increased genetic information is stable and not destroyed by cellular enzymes. Previous efforts by Benner and others took advantage of hydrogen bonding patterns that are different from those in canonical Watson-Crick pairs, the most noteworthy example of which is the iso-C:iso-G pair. See, e.g., Switzer et al., (1989) *J. Am. Chem. Soc.*, 111:8322; and Piccirilli et al., (1990) *Nature*, 343:33; Kool, (2000) *Curr. Opin. Chem. Biol.*, 4:602. These bases in general mispair to some degree with natural bases and cannot be enzymatically replicated. Kool and co-workers demonstrated that hydrophobic packing interactions between bases can replace hydrogen bonding to drive the formation of base pair. See, Kool, (2000) *Curr. Opin. Chem. Biol.*, 4:602; and Guckian and Kool, (1998) *Angew. Chem. Int. Ed. Engl.*, 36, 2825. In an effort to develop an unnatural base pair satisfying all the above requirements, Schultz, Romesberg and co-workers have systematically synthesized and studied a series of unnatural hydrophobic bases. A PICS:PICS self-pair is found to be more stable than natural base pairs, and can be efficiently incorporated into DNA by Klenow fragment of *Escherichia coli* DNA polymerase I (KF). See, e.g., McMinn et al., (1999) *J. Am. Chem. Soc.*, 121:11585-6; and Ogawa et al., (2000) *J. Am. Chem. Soc.*, 122:3274. A 3MN:3MN self-pair can be synthesized by KF with efficiency and selectivity sufficient for biological function. See, e.g., Ogawa et al., (2000) *J. Am. Chem. Soc.*, 122:8803. However, both bases act as a chain terminator for further replication. A mutant DNA polymerase has been recently evolved that can be used to replicate the PICS self pair. In addition, a 7AI self pair can be replicated. See, e.g., Tae et al., (2001) *J. Am. Chem. Soc.*, 123:7439. A novel metallobase pair, Dipic:Py, has also been developed, which forms a stable pair upon binding Cu(II). See, Meggers et al., (2000) *J. Am. Chem. Soc.*, 122:10714. Because extended codons and unnatural codons are intrinsically orthogonal to natural codons, the methods of the invention can take advantage of this property to generate orthogonal tRNAs for them.

A translational bypassing system can also be used to incorporate an unnatural amino acid in a desired polypeptide. In a translational bypassing system, a large sequence is incorporated into a gene but is not translated into protein. The sequence contains a structure that serves as a cue to induce the ribosome to hop over the sequence and resume translation downstream of the insertion.

In certain embodiments, the protein or polypeptide of interest (or portion thereof) in the methods and/or compositions of the invention is encoded by a nucleic acid. Typically, the nucleic acid comprises at least one selector codon, at least two selector codons, at least three selector codons, at least four selector codons, at least five selector codons, at least six selector codons, at least seven selector codons, at least eight selector codons, at least nine selector codons, ten or more selector codons.

Genes coding for proteins or polypeptides of interest can be mutagenized using methods well-known to one of skill in the art and described herein to include, for example, one or more selector codon for the incorporation of an unnatural amino acid. For example, a nucleic acid for a protein of interest is mutagenized to include one or more selector codon, providing for the incorporation of one or more unnatural amino acids. The invention includes any such variant, including but not limited to, mutant, versions of any protein, for example, including at least one unnatural amino acid. Similarly, the invention also includes corresponding nucleic acids, i.e., any nucleic acid with one or more selector codon that encodes one or more unnatural amino acid.

Nucleic acid molecules encoding a BSP such as GLP-1, T-20, or PYY(3-36) may be readily mutated to introduce a cysteine at any desired position of the polypeptide. Cysteine is widely used to introduce reactive molecules, water soluble polymers, proteins, or a wide variety of other molecules, onto a protein of interest. Methods suitable for the incorporation of cysteine into a desired position of a polypeptide are well known in the art, such as those described in U.S. Pat. No. 6,608,183, and include standard mutagenesis techniques.

IV. Non-Naturally Encoded Amino Acids

A very wide variety of non-naturally encoded amino acids are suitable for use in the present invention. Any number of non-naturally encoded amino acids can be introduced into a BSP. In general, the introduced non-naturally encoded amino acids are substantially chemically inert toward the 20 common, genetically-encoded amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine). In some embodiments, the non-naturally encoded amino acids include side chain functional groups that react efficiently and selectively with functional groups not found in the 20 common amino acids (including but not limited to, azido, ketone, aldehyde and aminooxy groups) to form stable conjugates. For example, a BSP that includes a non-naturally encoded amino acid containing an azido functional group can be reacted with a polymer (including but not limited to, poly(ethylene glycol) or, alternatively, a second polypeptide containing an alkyne moiety to form a stable conjugate resulting for the selective reaction of the azide and the alkyne functional groups to form a Huisgen [3+2] cycloaddition product.

The generic structure of an alpha-amino acid is illustrated as follows (Formula I):

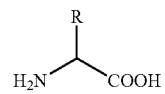

A non-naturally encoded amino acid is typically any structure having the above-listed formula wherein the R group is any substituent other than one used in the twenty natural amino acids, and may be suitable for use in the present invention. Because the non-naturally encoded amino acids of the invention typically differ from the natural amino acids only in the structure of the side chain, the non-naturally encoded amino acids form amide bonds with other amino acids, including but not limited to, natural or non-naturally encoded, in the same manner in which they are formed in naturally occurring polypeptides. However, the non-naturally encoded amino acids have side chain groups that distinguish them from the natural amino acids. For example, R optionally comprises an alkyl-, aryl-, acyl-, keto-, azido-, hydroxyl-, hydrazine, cyano-, halo-, hydrazide, alkenyl, alkynl, ether, thiol, seleno-, sulfonyl-, borate, boronate, phospho, phosphono, phosphine, heterocyclic, enone, imine, aldehyde, ester, thioacid, hydroxylamine, amino group, or the like or any combination thereof. Other non-naturally occurring amino acids of interest that may be suitable for use in the present invention include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, amino acids comprising biotin or a biotin analogue, glycosylated amino acids such as a sugar substituted serine, other carbohydrate modified amino acids, keto-containing amino acids, amino acids comprising polyethylene glycol or polyether, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety.

Exemplary non-naturally encoded amino acids that may be suitable for use in the present invention and that are useful for reactions with water soluble polymers include, but are not limited to, those with carbonyl, aminooxy, hydrazine, hydrazide, semicarbazide, azide and alkyne reactive groups. In some embodiments, non-naturally encoded amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature—including but not limited to, an alkene, an oxime, a thioether, an amide and the like. Examples of such amino acids also include saccharides that are not commonly found in naturally-occurring proteins such as 2-deoxy-glucose, 2-deoxygalactose and the like.

Many of the non-naturally encoded amino acids provided herein are commercially available, e.g., from Sigma-Aldrich (St. Louis, Mo., USA), Novabiochem (a division of EMD Biosciences, Darmstadt, Germany), or Peptech (Burlington, Mass., USA). Those that are not commercially available are optionally synthesized as provided herein or using standard methods known to those of skill in the art. For organic synthesis techniques, see, e.g., *Organic Chemistry* by Fessendon and Fessendon, (1982, Second Edition, Willard Grant Press, Boston Mass.); *Advanced Organic Chemistry* by March (Third Edition, 1985, Wiley and Sons, New York); and *Advanced Organic Chemistry* by Carey and Sundberg (Third Edition, Parts A and B, 1990, Plenum Press, New York). See, also, U.S. Patent Application Publications 2003/0082575 and 2003/0108885, which is incorporated by reference herein. In addition to unnatural amino acids that contain novel side chains, unnatural amino acids that may be suitable for use in the present invention also optionally comprise modified backbone structures, including but not limited to, as illustrated by the structures of Formula II and III:

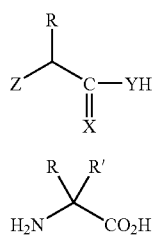

wherein Z typically comprises OH, $NH_2$, SH, NH—R', or S—R'; X and Y, which can be the same or different, typically comprise S or O, and R and R', which are optionally the same or different, are typically selected from the same list of constituents for the R group described above for the unnatural amino acids having Formula I as well as hydrogen. For example, unnatural amino acids of the invention optionally comprise substitutions in the amino or carboxyl group as illustrated by Formulas II and III. Unnatural amino acids of this type include, but are not limited to, α-hydroxy acids, α-thioacids, α-aminothiocarboxylates, including but not limited to, with side chains corresponding to the common twenty natural amino acids or unnatural side chains. In addition, substitutions at the α-carbon optionally include, but are not limited to, L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3, 4, 6, 7, 8, and 9 membered ring proline analogues, β and γ amino acids such as substituted β-alanine and γ-amino butyric acid.

Many unnatural amino acids are based on natural amino acids, such as tyrosine, glutamine, phenylalanine, and the like, and are suitable for use in the present invention. Tyrosine analogs include, but are not limited to, para-substituted tyrosines, ortho-substituted tyrosines, and meta substituted tyrosines, where the substituted tyrosine comprises, including but not limited to, a keto group (including but not limited to, an acetyl group), a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, an alkynyl group or the like. In addition, multiply substituted aryl rings are also contemplated. Glutamine analogs that may be suitable for use in the present invention include, but are not limited to, α-hydroxy derivatives, γ-substituted derivatives, cyclic derivatives, and amide substituted glutamine derivatives. Example phenylalanine analogs that may be suitable for use in the present invention include, but are not limited to, para-substituted phenylalanines, ortho-substituted phenylalanines, and meta-substituted phenylalanines, where the substituent comprises, including but not limited to, a hydroxy group, a methoxy group, a methyl group, an allyl group, an aldehyde, an azido, an iodo, a bromo, a keto group (including but not limited to, an acetyl group), a benzoyl, an alkynyl group, or the like. Specific examples of unnatural amino acids that may be suitable for use in the present invention include, but are not limited to, a p-acetyl-L-phenylalanine, an O-methyl-L-tyrosine, an L-3-(2-naphthyl)alanine, a 3-methyl-phenylalanine, an 0-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, and a p-propargyloxy-phenylalanine, and the like. Examples of structures of a variety of unnatural amino acids that may be suitable for use in the present invention are provided in, for example, WO 2002/085923 entitled "In vivo incorporation of unnatural amino acids." See also Kiick et al., (2002) *Incorporation of azides into recombinant proteins for chemoselective modification by the Staudinger ligation*, PNAS 99:19-24, for additional methionine analogs.

In one embodiment, compositions of BSP that include an unnatural amino acid (such as p-(propargyloxy)-phenylalanine) are provided. Various compositions comprising p-(propargyloxy)-phenylalanine and, including but not limited to, proteins and/or cells, are also provided. In one aspect, a composition that includes the p-(propargyloxy)-phenylalanine unnatural amino acid, further includes an orthogonal tRNA. The unnatural amino acid can be bonded (including but not limited to, covalently) to the orthogonal tRNA, including but not limited to, covalently bonded to the orthogonal tRNA though an amino-acyl bond, covalently bonded to a 3'OH or a 2'OH of a terminal ribose sugar of the orthogonal tRNA, etc.

The chemical moieties via unnatural amino acids that can be incorporated into proteins offer a variety of advantages and manipulations of the protein. For example, the unique reactivity of a keto functional group allows selective modification of proteins with any of a number of hydrazine- or hydroxylamine-containing reagents in vitro and in vivo. A heavy atom unnatural amino acid, for example, can be useful for phasing X-ray structure data. The site-specific introduction of heavy atoms using unnatural amino acids also provides selectivity and flexibility in choosing positions for heavy atoms. Photoreactive unnatural amino acids (including but not limited to, amino acids with benzophenone and arylazides (including but not limited to, phenylazide) side chains), for example, allow for efficient in vivo and in vitro photocrosslinking of protein. Examples of photoreactive unnatural amino acids include, but are not limited to, p-azido-phenylalanine and p-benzoyl-phenylalanine. The protein with the photoreactive unnatural amino acids can then be crosslinked at will by excitation of the photoreactive group-providing temporal control. In one example, the methyl group of an unnatural amino can be substituted with an isotopically labeled, including but not limited to, methyl group, as a probe of local structure and dynamics, including but not limited to, with the use of nuclear magnetic resonance and vibrational spectroscopy. Alkynyl or azido functional groups, for example, allow the selective modification of proteins with molecules through a [3+2] cycloaddition reaction.

A non-natural amino acid incorporated into a polypeptide at the amino terminus can be composed of an R group that is any substituent other than one used in the twenty natural amino acids and a $2^{nd}$ reactive group different from the $NH_2$ group normally present in α-amino acids (see Formula I). A similar non-natural amino acid can be incorporated at the carboxyl terminus with a $2^{nd}$ reactive group different from the COOH group normally present in α-amino acids (see Formula I).

Chemical Synthesis of Unnatural Amino Acids

Many of the unnatural amino acids suitable for use in the present invention are commercially available, e.g., from Sigma (USA) or Aldrich (Milwaukee, Wis., USA). Those that are not commercially available are optionally synthesized as provided herein or as provided in various publications or using standard methods known to those of skill in the art. For organic synthesis techniques, see, e.g., *Organic Chemistry* by Fessendon and Fessendon, (1982, Second Edition, Willard Grant Press, Boston Mass.); *Advanced Organic Chemistry* by March (Third Edition, 1985, Wiley and Sons, New York); and *Advanced Organic Chemistry* by Carey and Sundberg (Third Edition, Parts A and B, 1990, Plenum Press, New York). Additional publications describing the synthesis of unnatural amino acids include, e.g., WO 2002/085923 entitled "In vivo incorporation of Unnatural Amino Acids;" Matsoukas et al., (1995) *J. Med. Chem.*, 38, 4660-4669; King, F. E. & Kidd, D. A. A. (1949) *A New Synthesis of Glutamine and of γ-Dipeptides of Glutamic Acid from Phthylated Intermediates. J. Chem. Soc.*, 3315-3319; Friedman, O. M. & Chattenji, R. (1959) *Synthesis of Derivatives of Glutamine as Model Substrates for Anti-Tumor Agents. J. Am. Chem. Soc.* 81, 3750-3752; Craig, J. C. et al. (1988) *Absolute Configuration of the Enantiomers of 7-Chloro-4 [[4-(diethylamino)-]-methylbutyl]amino]quinoline (Chloroquine). J. Org. Chem.* 53, 1167-1170; Azoulay, M., Vilmont, M. & Frappier, F. (1991) *Glutamine analogues as Potential Antimalarials, Eur. J. Med. Chem.* 26, 201-5; Koskinen, A. M. P. & Rapoport, H. (1989) *Synthesis of 4-Substituted Prolines as Conformationally Constrained Amino Acid Analogues. J. Org. Chem.* 54, 1859-1866; Christie, B. D. & Rapoport, H. (1985) *Synthesis of Optically Pure Pipecolates from L-Asparagine. Application to the Total Synthesis of (+)-Apovincamine through Amino Acid Decarbonylation and Iminium Ion Cyclization. J. Org. Chem.* 50:1239-1246; Barton et al., (1987) *Synthesis of Novel alpha-Amino-Acids and Derivatives Using Radical Chemistry: Synthesis of L- and D-alpha-Amino-Adipic Acids, L-alpha-aminopimelic Acid and Appropriate Unsaturated Derivatives. Tetrahedron* 43:4297-4308; and, Subasinghe et al., (1992) *Quisqualic acid analogues: synthesis of beta-heterocyclic 2-aminopropanoic acid derivatives and their activity at a novel quisqualate-sensitized site. J. Med. Chem.* 35:4602-7. See also, patent applications entitled "Protein Arrays," filed Dec. 22, 2003, Ser. No. 10/744,899 and Ser. No. 60/435,821 filed on Dec. 22, 2002.

A. Carbonyl Reactive Groups

Amino acids with a carbonyl reactive group allow for a variety of reactions to link molecules (including but not limited to, PEG or other water soluble molecules) via nucleophilic addition or aldol condensation reactions among others.

Exemplary carbonyl-containing amino acids can be represented as follows:

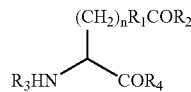

wherein n is 0-10; $R_1$ is an alkyl, aryl, substituted alkyl, or substituted aryl; $R_2$ is H, alkyl, aryl, substituted alkyl, and substituted aryl; and $R_3$ is H, an amino acid, a polypeptide, or an amino terminus modification group, and $R_4$ is H, an amino acid, a polypeptide, or a carboxy terminus modification group. In some embodiments, n is 1, $R_1$ is phenyl and $R_2$ is a simple alkyl (i.e., methyl, ethyl, or propyl) and the ketone moiety is positioned in the para position relative to the alkyl side chain. In some embodiments, n is 1, $R_1$ is phenyl and $R_2$ is a simple alkyl (i.e., methyl, ethyl, or propyl) and the ketone moiety is positioned in the meta position relative to the alkyl side chain.

The synthesis of p-acetyl-(+/−)-phenylalanine and m-acetyl-(+/−)-phenylalanine is described in Zhang, Z., et al., Biochemistry 42: 6735-6746 (2003), which is incorporated by reference herein. Other carbonyl-containing amino acids can be similarly prepared by one skilled in the art.

In some embodiments, a polypeptide comprising a non-naturally encoded amino acid is chemically modified to generate a reactive carbonyl functional group. For instance, an aldehyde functionality useful for conjugation reactions can be generated from a functionality having adjacent amino and hydroxyl groups. Where the biologically active molecule is a polypeptide, for example, an N-terminal serine or threonine (which may be normally present or may be exposed via chemical or enzymatic digestion) can be used to generate an aldehyde functionality under mild oxidative cleavage conditions using periodate. See, e.g., Gaertner, et al., *Bioconjug. Chem.* 3: 262-268 (1992); Geoghegan, K. & Stroh, J., *Bioconjug. Chem.* 3:138-146 (1992); Gaertner et al., *J. Biol. Chem.* 269:7224-7230 (1994). However, methods known in the art are restricted to the amino acid at the N-terminus of the peptide or protein.

In the present invention, a non-naturally encoded amino acid bearing adjacent hydroxyl and amino groups can be incorporated into the polypeptide as a "masked" aldehyde functionality. For example, 5-hydroxylysine bears a hydroxyl group adjacent to the epsilon amine. Reaction conditions for generating the aldehyde typically involve addition of molar excess of sodium metaperiodate under mild conditions to avoid oxidation at other sites within the polypeptide. The pH of the oxidation reaction is typically about 7.0. A typical reaction involves the addition of about 1.5 molar excess of sodium meta periodate to a buffered solution of the polypeptide, followed by incubation for about 10 minutes in the dark. See, e.g. U.S. Pat. No. 6,423,685, which is incorporated by reference herein.

The carbonyl functionality can be reacted selectively with a hydrazine-, hydrazide-, hydroxylamine-, or semicarbazide-containing reagent under mild conditions in aqueous solution to form the corresponding hydrazone, oxime, or semicarbazone linkages, respectively, that are stable under physiological conditions. See, e.g., Jencks, W. P., *J. Am. Chem. Soc.* 81, 475-481 (1959); Shao, J. and Tam, J. P., *J. Am. Chem. Soc.* 117:3893-3899 (1995). Moreover, the unique reactivity of the carbonyl group allows for selective modification in the presence of the other amino acid side chains. See, e.g., Cornish, V. W., et al., *J. Am. Chem. Soc.* 118:8150-8151 (1996); Geoghegan, K. F. & Stroh, J. G., *Bioconjug. Chem.* 3:138-146 (1992); Mahal, L. K., et al., *Science* 276:1125-1128 (1997).

B. Hydrazine, Hydrazide or Semicarbazide Reactive Groups

Non-naturally encoded amino acids containing a nucleophilic group, such as a hydrazine, hydrazide or semicarbazide, allow for reaction with a variety of electrophilic groups to form conjugates (including but not limited to, with PEG or other water soluble polymers).

Exemplary hydrazine, hydrazide or semicarbazide-containing amino acids can be represented as follows:

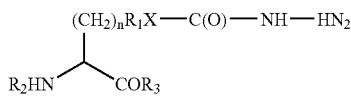

wherein n is 0-10; $R_1$ is an alkyl, aryl, substituted alkyl, or substituted aryl or not present; X, is O, N, or S or not present; $R_2$ is H, an amino acid, a polypeptide, or an amino terminus modification group, and $R_3$ is H, an amino acid, a polypeptide, or a carboxy terminus modification group.

In some embodiments, n is 4, $R_1$ is not present, and X is N. In some embodiments, n is 2, $R_1$ is not present, and X is not present. In some embodiments, n is 1, $R_1$ is phenyl, X is O, and the oxygen atom is positioned para to the alphatic group on the aryl ring.

Hydrazide-, hydrazine-, and semicarbazide-containing amino acids are available from commercial sources. For instance, L-glutamate-γ-hydrazide is available from Sigma Chemical (St. Louis, Mo.). Other amino acids not available commercially can be prepared by one skilled in the art See, e.g., U.S. Pat. No. 6,281,211, which is incorporated by reference herein.

Polypeptides containing non-naturally encoded amino acids that bear hydrazide, hydrazine or semicarbazide functionalities can be reacted efficiently and selectively with a variety of molecules that contain aldehydes or other functional groups with similar chemical reactivity. See, e.g., Shao, J. and Tam, J., *J. Am. Chem. Soc.* 117:3893-3899 (1995). The unique reactivity of hydrazide, hydrazine and semicarbazide functional groups makes them significantly more reactive toward aldehydes, ketones and other electrophilic groups as compared to the nucleophilic groups present on the 20 common amino acids (including but not limited to, the hydroxyl group of serine or threonine or the amino groups of lysine and the N-terminus).

C. Aminooxy-Containing Amino Acids

Non-naturally encoded amino acids containing an aminooxy (also called a hydroxylamine) group allow for reaction with a variety of electrophilic groups to form conjugates (including but not limited to, with PEG or other water soluble polymers). Like hydrazines, hydrazides and semicarbazides, the enhanced nucleophilicity of the aminooxy group permits it to react efficiently and selectively with a variety of molecules that contain aldehydes or other functional groups with similar chemical reactivity. See, e.g., Shao, J. and Tam, J., *J. Am. Chem. Soc.* 117:3893-3899 (1995); H. Hang and C. Bertozzi, *Acc. Chem. Res.* 34: 727-736 (2001). Whereas the result of reaction with a hydrazine group is the corresponding hydrazone, however, an oxime results generally from the reaction of an aminooxy group with a carbonyl-containing group such as a ketone.

Exemplary amino acids containing aminooxy groups can be represented as follows:

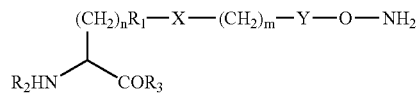

wherein n is 0-10; $R_1$ is an alkyl, aryl, substituted alkyl, or substituted aryl or not present; X is O, N, S or not present; m is 0-10; Y=C(O) or not present; $R_2$ is H, an amino acid, a polypeptide, or an amino terminus modification group, and $R_3$ is H, an amino acid, a polypeptide, or a carboxy terminus modification group. In some embodiments, n is 1, $R_1$ is phenyl, X is O, m is 1, and Y is present. In some embodiments, n is 2, $R_1$ and X are not present, m is 0, and Y is not present.

Aminooxy-containing amino acids can be prepared from readily available amino acid precursors (homoserine, serine and threonine). See, e.g., M. Carrasco and R. Brown, *J. Org. Chem.* 68: 8853-8858 (2003). Certain aminooxy-containing amino acids, such as L-2-amino-4-(aminooxy)butyric acid), have been isolated from natural sources (Rosenthal, G., Life Sci. 60: 1635-1641 (1997). Other aminooxy-containing amino acids can be prepared by one skilled in the art.

D. Azide and Alkyne Reactive Groups

The unique reactivity of azide and alkyne functional groups makes them extremely useful for the selective modification of polypeptides and other biological molecules. Organic azides, particularly alphatic azides, and alkynes are generally stable toward common reactive chemical conditions. In particular, both the azide and the alkyne functional groups are inert toward the side chains (i.e., R groups) of the 20 common amino acids found in naturally-occurring polypeptides. When brought into close proximity, however, the "spring-loaded" nature of the azide and alkyne groups is revealed and they react selectively and efficiently via Huisgen [3+2] cycloaddition reaction to generate the corresponding triazole. See, e.g., Chin J., et al., *Science* 301:964-7 (2003); Wang, Q., et al., *J. Am. Chem. Soc.* 125, 3192-3193 (2003); Chin, J. W., et al., *J. Am. Chem. Soc.* 124:9026-9027 (2002).

Because the Huisgen cycloaddition reaction involves a selective cycloaddition reaction (see, e.g., Padwa, A., in Comprehensive Organic Synthesis, Vol. 4, (ed. Trost, B. M., 1991), p. 1069-1109; Huisgen, R. in 1,3-Dipolar Cycloaddition Chemistry, (ed. Padwa, A., 1984), p. 1-176) rather than a nucleophilic substitution, the incorporation of non-naturally encoded amino acids bearing azide and alkyne-containing side chains permits the resultant polypeptides to be modified selectively at the position of the non-naturally encoded amino acid. Cycloaddition reaction involving azide or alkyne-containing BSP can be carried out at room temperature under aqueous conditions by the addition of Cu(II) (including but not limited to, in the form of a catalytic amount of $CuSO_4$) in the presence of a reducing agent for reducing Cu(II) to Cu(I), in situ, in catalytic amount. See, e.g., Wang, Q., et al., *J. Am. Chem. Soc.* 125, 3192-3193 (2003); Tomoe, C. W., et al., *J. Org. Chem.* 67:3057-3064 (2002); Rostovtsev, et al., *Angew. Chem. Int. Ed.* 41:2596-2599 (2002). Exemplary reducing agents include, including but not limited to, ascorbate, metallic copper, quinine, hydroquinone, vitamin K, glutathione, cysteine, $Fe^{2+}$, $Co^{2+}$, and an applied electric potential.

In some cases, where a Huisgen [3+2] cycloaddition reaction between an azide and an alkyne is desired, the BSP comprises a non-naturally encoded amino acid comprising an alkyne moiety and the water soluble polymer to be attached to the amino acid comprises an azide moiety. Alternatively, the converse reaction (i.e., with the azide moiety on the amino acid and the alkyne moiety present on the water soluble polymer) can also be performed.

The azide functional group can also be reacted selectively with a water soluble polymer containing an aryl ester and appropriately functionalized with an aryl phosphine moiety to generate an amide linkage. The aryl phosphine group reduces the azide in situ and the resulting amine then reacts efficiently with a proximal ester linkage to generate the corresponding amide. See, e.g., E. Saxon and C. Bertozzi, *Science* 287, 2007-2010 (2000). The azide-containing amino acid can be either an alkyl azide (including but not limited to, 2-amino-6-azido-1-hexanoic acid) or an aryl azide (p-azidophenylalanine).

Exemplary water soluble polymers containing an aryl ester and a phosphine moiety can be represented as follows:

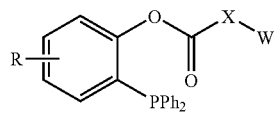

wherein X can be O, N, S or not present, Ph is phenyl, W is a water soluble polymer and R can be H, alkyl, aryl, substituted alkyl and substituted aryl groups. Exemplary R groups include but are not limited to —CH$_2$, —C(CH$_3$)$_3$, —OR', —NR'R", —SR', -halogen, —C(O)R', —CONR'R", —S(O)$_2$R', —S(O)$_2$NR'R", —CN and —NO$_2$. R', R", R'" and R"" each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, —CF$_3$ and —CH$_2$CF$_3$) and acyl (including but not limited to, —C(O)CH$_3$, —C(O)CF$_3$, —C(O)CH$_2$OCH$_3$, and the like).

The azide functional group can also be reacted selectively with a water soluble polymer containing a thioester and appropriately functionalized with an aryl phosphine moiety to generate an amide linkage. The aryl phosphine group reduces the azide in situ and the resulting amine then reacts efficiently with the thioester linkage to generate the corresponding amide. Exemplary water soluble polymers containing a thioester and a phosphine moiety can be represented as follows:

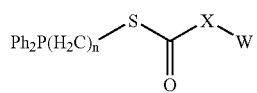

wherein n is 1-10; X can be O, N, S or not present, Ph is phenyl, and W is a water soluble polymer.

Exemplary alkyne-containing amino acids can be represented as follows:

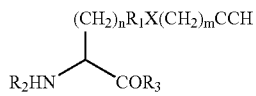

wherein n is 0-10; R$_1$ is an alkyl, aryl, substituted alkyl, or substituted aryl or not present; X is O, N, S or not present; m is 0-10, R$_2$ is H, an amino acid, a polypeptide, or an amino terminus modification group, and R$_3$ is H, an amino acid, a polypeptide, or a carboxy terminus modification group. In some embodiments, n is 1, R$_1$ is phenyl, X is not present, m is 0 and the acetylene moiety is positioned in the para position relative to the alkyl side chain. In some embodiments, n is 1, R$_1$ is phenyl, X is O, m is 1 and the propargyloxy group is positioned in the para position relative to the alkyl side chain (i.e., O-propargyl-tyrosine). In some embodiments, n is 1, R$_1$ and X are not present and m is 0 (i.e., proparylglycine).

Alkyne-containing amino acids are commercially available. For example, propargyiglycine is commercially available from Peptech (Burlington, Mass.). Alternatively, alkyne-containing amino acids can be prepared according to standard methods. For instance, p-propargyloxyphenylalanine can be synthesized, for example, as described in Deiters, A., et al., *J. Am. Chem. Soc.* 125: 11782-11783 (2003), and 4-alkynyl-L-phenylalanine can be synthesized as described in Kayser, B., et al., *Tetrahedron* 53(7): 2475-2484 (1997). Other alkyne-containing amino acids can be prepared by one skilled in the art.

Exemplary azide-containing amino acids can be represented as follows:

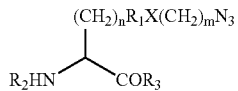

wherein n is 0-10; R$_1$ is an alkyl, aryl, substituted alkyl, substituted aryl or not present; X is O, N, S or not present; m is 0-10; R$_2$ is H, an amino acid, a polypeptide, or an amino terminus modification group, and R$_3$ is H, an amino acid, a polypeptide, or a carboxy terminus modification group. In some embodiments, n is 1, R$_1$ is phenyl, X is not present, m is 0 and the azide moiety is positioned para to the alkyl side chain. In some embodiments, n is 0-4 and R$_1$ and X are not present, and m=0. In some embodiments, n is 1, R$_1$ is phenyl, X is O, m is 2 and the β-azidoethoxy moiety is positioned in the para position relative to the alkyl side chain.

Azide-containing amino acids are available from commercial sources. For instance, 4-azidophenylalanine can be obtained from Chem-Impex International, Inc. (Wood Dale, Ill.). For those azide-containing amino acids that are not commercially available, the azide group can be prepared relatively readily using standard methods known to those of skill in the art, including but not limited to, via displacement of a suitable leaving group (including but not limited to, halide, mesylate, tosylate) or via opening of a suitably protected lactone. See, e.g., *Advanced Organic Chemistry* by March (Third Edition, 1985, Wiley and Sons, New York).

E. Aminothiol Reactive Groups

The unique reactivity of beta-substituted aminothiol functional groups makes them extremely useful for the selective modification of polypeptides and other biological molecules that contain aldehyde groups via formation of the thiazolidine. See, e.g., J. Shao and J. Tam, *J. Am. Chem. Soc.* 1995, 117 (14) 3893-3899. In some embodiments, beta-substituted aminothiol amino acids can be incorporated into BSPs and then reacted with water soluble polymers comprising an aldehyde functionality. In some embodiments, a water soluble polymer, drug conjugate or other payload can be coupled to a BSP comprising a beta-substituted aminothiol amino acid via formation of the thiazolidine.

Cellular Uptake of Unnatural Amino Acids

Unnatural amino acid uptake by a eukaryotic cell is one issue that is typically considered when designing and selecting unnatural amino acids, including but not limited to, for incorporation into a protein. For example, the high charge density of α-amino acids suggests that these compounds are unlikely to be cell permeable. Natural amino acids are taken up into the eukaryotic cell via a collection of protein-based transport systems. A rapid screen can be done which assesses which unnatural amino acids, if any, are taken up by cells. See, e.g., the toxicity assays in, e.g., the applications entitled "Protein Arrays," filed Dec. 22, 2003, Ser. No. 10/744,899 and Ser. No. 60/435,821 filed on Dec. 22, 2002; and Liu, D. R. & Schultz, P. G. (1999) *Progress toward the evolution of an organism with an expanded genetic code. PNAS United States* 96:4780-4785. Although uptake is easily analyzed with various assays, an alternative to designing unnatural amino acids that are amenable to cellular uptake pathways is to provide biosynthetic pathways to create amino acids in vivo.

Biosynthesis of Unnatural Amino Acids

Many biosynthetic pathways already exist in cells for the production of amino acids and other compounds. While a biosynthetic method for a particular unnatural amino acid may not exist in nature, including but not limited to, in a eukaryotic cell, the invention provides such methods. For example, biosynthetic pathways for unnatural amino acids are optionally generated in host cell by adding new enzymes or modifying existing host cell pathways. Additional new enzymes are optionally naturally occurring enzymes or artificially evolved enzymes. For example, the biosynthesis of p-aminophenylalanine (as presented in an example in WO 2002/085923 entitled "In vivo incorporation of unnatural amino acids") relies on the addition of a combination of known enzymes from other organisms. The genes for these enzymes can be introduced into a eukaryotic cell by transforming the cell with a plasmid comprising the genes. The genes, when expressed in the cell, provide an enzymatic pathway to synthesize the desired compound. Examples of the types of enzymes that are optionally added are provided in the examples below. Additional enzymes sequences are found, for example, in Genbank. Artificially evolved enzymes are also optionally added into a cell in the same manner. In this manner, the cellular machinery and resources of a cell are manipulated to produce unnatural amino acids.

A variety of methods are available for producing novel enzymes for use in biosynthetic pathways or for evolution of existing pathways. For example, recursive recombination, including but not limited to, as developed by Maxygen, Inc. (available on the World Wide Web at maxygen.com), is optionally used to develop novel enzymes and pathways. See, e.g., Stemmer (1994), *Rapid evolution of a protein in vitro by DNA shuffling, Nature* 370(4):389-391; and, Stemmer, (1994), *DNA shuffling by random fragmentation and reassembly: In vitro recombination for molecular evolution, Proc. Natl. Acad. Sci. USA.*, 91:10747-10751. Similarly DesignPath™, developed by Genencor (available on the World Wide Web at genencor.com) is optionally used for metabolic pathway engineering, including but not limited to, to engineer a pathway to create O-methyl-L-tyrosine in a cell. This technology reconstructs existing pathways in host organisms using a combination of new genes, including but not limited to, identified through functional genomics, and molecular evolution and design. Diversa Corporation (available on the World Wide Web at diversa.com) also provides technology for rapidly screening libraries of genes and gene pathways, including but not limited to, to create new pathways.

Typically, the unnatural amino acid produced with an engineered biosynthetic pathway of the invention is produced in a concentration sufficient for efficient protein biosynthesis, including but not limited to, a natural cellular amount, but not to such a degree as to affect the concentration of the other amino acids or exhaust cellular resources. Typical concentrations produced in vivo in this manner are about 10 mM to about 0.05 mM. Once a cell is transformed with a plasmid comprising the genes used to produce enzymes desired for a specific pathway and an unnatural amino acid is generated, in vivo selections are optionally used to further optimize the production of the unnatural amino acid for both ribosomal protein synthesis and cell growth.

Polypeptides with Unnatural Amino Acids

The incorporation of an unnatural amino acid can be done for a variety of purposes, including but not limited to, tailoring changes in protein structure and/or function, changing size, acidity, nucleophilicity, hydrogen bonding, hydrophobicity, accessibility of protease target sites, targeting to a moiety (including but not limited to, for a protein array), adding a biologically active molecule, attaching a polymer, attaching a radionuclide, modulating serum half-life, modulating tissue penetration (e.g. tumors), modulating active transport, modulating tissue, cell or organ specificity or distribution, modulating immunogenicity, modulating protease resistance, etc. Proteins that include an unnatural amino acid can have enhanced or even entirely new catalytic or biophysical properties. For example, the following properties are optionally modified by inclusion of an unnatural amino acid into a protein: toxicity, biodistribution, structural properties, spectroscopic properties, chemical and/or photochemical properties, catalytic ability, half-life (including but not limited to, serum half-life), ability to react with other molecules, including but not limited to, covalently or noncovalently, and the like. The compositions including proteins that include at least one unnatural amino acid are useful for, including but not limited to, novel therapeutics, diagnostics, catalytic enzymes, industrial enzymes, binding proteins (including but not limited to, antibodies), and including but not limited to, the study of protein structure and function. See, e.g., Dougherty, (2000) *Unnatural Amino Acids as Probes of Protein Structure and Function, Current Opinion in Chemical Biology*, 4:645-652.

In one aspect of the invention, a composition includes at least one protein with at least one, including but not limited to, at least two, at least three, at least four, at least five, at least six, at least seven, at least eight, at least nine, or at least ten or more unnatural amino acids. The unnatural amino acids can be the same or different, including but not limited to, there can be 1, 2, 3, 4, 5, 6, 7, 8, 9, or 10 or more different sites in the protein that comprise 1, 2, 3, 4, 5, 6, 7, 8, 9, or 10 or more different unnatural amino acids. In another aspect, a composition includes a protein with at least one, but fewer than all, of a particular amino acid present in the protein is substituted with the unnatural amino acid. For a given protein with more than one unnatural amino acids, the unnatural amino acids can be identical or different (including but not limited to, the protein can include two or more different types of unnatural amino acids, or can include two of the same unnatural amino acid). For a given protein with more than two unnatural amino acids, the unnatural amino acids can be the same, different or a combination of a multiple unnatural amino acid of the same kind with at least one different unnatural amino acid.

Proteins or polypeptides of interest with at least one unnatural amino acid are a feature of the invention. The invention also includes polypeptides or proteins with at least one unnatural amino acid produced using the compositions and methods of the invention. An excipient (including but not limited to, a pharmaceutically acceptable excipient) can also be present with the protein.

By producing proteins or polypeptides of interest with at least one unnatural amino acid in eukaryotic cells, proteins or polypeptides will typically include eukaryotic post-translational modifications. In certain embodiments, a protein includes at least one unnatural amino acid and at least one post-translational modification that is made in vivo by a eukaryotic cell, where the post-translational modification is not made by a prokaryotic cell. For example, the post-translation modification includes, including but not limited to, acetylation, acylation, lipid-modification, palmitoylation, palmitate addition, phosphorylation, glycolipid-linkage modification, glycosylation, and the like. In one aspect, the post-translational modification includes attachment of an oligosaccharide (including but not limited to, $(GlcNAc-Man)_2$-Man-GlcNAc-GlcNAc)) to an asparagine by a GlcNAc-asparagine linkage. See Table 1 which lists some examples of N-linked oligosaccharides of eukaryotic proteins (additional residues can also be present, which are not shown). In another aspect, the post-translational modification includes attachment of an oligosaccharide (including but not limited to, Gal-GalNAc, Gal-GlcNAc, etc.) to a serine or threonine by a GalNAc-serine or GalNAc-threonine linkage, or a GlcNAc-serine or a GlcNAc-threonine linkage.

cell (including but not limited to, to organelles, such as the endoplasmic reticulum, the Golgi apparatus, the nucleus, lysosomes, peroxisomes, mitochondria, chloroplasts, vacuoles, etc., or through the secretory pathway). In certain embodiments, the protein comprises a secretion or localization sequence, an epitope tag, a FLAG tag, a polyhistidine tag, a GST fusion, or the like.

One advantage of an unnatural amino acid is that it presents additional chemical moieties that can be used to add additional molecules. These modifications can be made in vivo in a eukaryotic or non-eukaryotic cell, or in vitro. Thus, in certain embodiments, the post-translational modification is through the unnatural amino acid. For example, the post-translational modification can be through a nucleophilic-electrophilic reaction. Most reactions currently used for the selective modification of proteins involve covalent bond formation between nucleophilic and electrophilic reaction partners, including but not limited to the reaction of α-haloketones with histidine or cysteine side chains. Selectivity in these cases is determined by the number and accessibility of the nucleophilic residues in the protein. In proteins of the invention, other more selective reactions can be used such as the reaction of an unnatural keto-amino acid with hydrazides or aminooxy compounds, in vitro and in vivo. See, e.g., Cornish, et al., (1996) *J. Am. Chem. Soc.,* 118:8150-8151; Mahal, et al., (1997) *Science,* 276:1125-1128; Wang, et al., (2001) *Science* 292:498-500; Chin, et al., (2002) *J. Am. Chem. Soc.* 124:9026-9027; Chin, et al., (2002) *Proc. Natl. Acad. Sci.,* 99:11020-11024; Wang, et al., (2003) *Proc. Natl. Acad. Sci.,* 100:56-61; Zhang, et al., (2003) *Biochemistry,* 42:6735-6746; and, Chin, et al., (2003) *Science,* 301:964-7. This allows the selective labeling of virtually any protein with a host of reagents including fluorophores, crosslinking agents, saccharide derivatives and cytotoxic molecules. See also, U.S. patent application Ser. No. 10/686,944 entitled "Glycoprotein synthesis" filed Oct. 15, 2003 based on U.S. provisional patent application Ser. No. 60/419,265, filed Oct. 16,

TABLE 1

EXAMPLES OF OLIGOSACCHARIDES THROUGH GlcNAc-LINKAGE

| Type | Base Structure |
|---|---|
| High-mannose | Manα1-6 \\ Manα1-3 / Manα1-6 \\ Manα1-3 / Manβ1-4GlcNAcβ1-4GlcNAcβ1-Asn |
| Hybrid | Manα1-6 \\ GlcNAcβ1-2 —— Manα1-3 / Manβ1-4GlcNAcβ1-4GlcNAcβ1-Asn |
| Complex | GlcNAcβ1-2 —— Manα1-6 \\ GlcNAcβ1-2 —— Manα1-3 / Manβ1-4GlcNAcβ1-4GlcNAcβ1-Asn |
| Xylose | Manα1-6 \\ Xylβ1-2 / Manβ1-4GlcNAcβ1-4GlcNAcβ1-Asn |

In yet another aspect, the post-translation modification includes proteolytic processing of precursors (including but not limited to, calcitonin precursor, calcitonin gene-related peptide precursor, preproparathyroid hormone, preproinsulin, proinsulin, prepro-opiomelanocortin, pro-opiomelanocortin and the like), assembly into a multisubunit protein or macromolecular assembly, translation to another site in the 2002, U.S. provisional patent application Ser. No. 60/420,990, filed Oct. 23, 2002, and U.S. provisional patent application Ser. No. 60/441,450, filed Jan. 16, 2003, which are incorporated by reference herein. Post-translational modifications, including but not limited to, through an azido amino acid, can also made through the Staudinger ligation (including but not limited to, with triarylphosphine reagents). See, e.g., Kiick et al., (2002) *Incorporation of azides into recombinant proteins for chemoselective modification by the Staudinger ligation*, PNAS 99:19-24.

This invention provides another highly efficient method for the selective modification of proteins, which involves the genetic incorporation of unnatural amino acids, including but not limited to, containing an azide or alkynyl moiety into proteins in response to a selector codon. These amino acid side chains can then be modified by, including but not limited to, a Huisgen [3+2] cycloaddition reaction (see, e.g., Padwa, A. in *Comprehensive Organic Synthesis*, Vol. 4, (1991) Ed. Trost, B. M., Pergamon, Oxford, p. 1069-1109; and, Huisgen, R. in 1,3-*Dipolar Cycloaddition Chemistry*, (1984) Ed. Padwa, A., Wiley, New York, p. 1-176) with, including but not limited to, alkynyl or azide derivatives, respectively. Because this method involves a cycloaddition rather than a nucleophilic substitution, proteins can be modified with extremely high selectivity. This reaction can be carried out at room temperature in aqueous conditions with excellent regioselectivity (1,4>1,5) by the addition of catalytic amounts of Cu(I) salts to the reaction mixture. See, e.g., Tornoe, et al., (2002) *J. Org. Chem.* 67:3057-3064; and, Rostovtsev, et al., (2002) *Angew. Chem. Int. Ed.* 41:2596-2599. Another method that can be used is the ligand exchange on a bisarsenic compound with a tetracysteine motif, see, e.g., Griffin, et al., (1998) *Science* 281:269-272.

A molecule that can be added to a protein of the invention through a [3+2] cycloaddition includes virtually any molecule with an azide or alkynyl derivative. Molecules include, but are not limited to, dyes, fluorophores, crosslinking agents, saccharide derivatives, polymers (including but not limited to, derivatives of polyethylene glycol), photocrosslinkers, cytotoxic compounds, affinity labels, derivatives of biotin, resins, beads, a second protein or polypeptide (or more), polynucleotide(s) (including but not limited to, DNA, RNA, etc.), metal chelators, cofactors, fatty acids, carbohydrates, and the like. These molecules can be added to an unnatural amino acid with an alkynyl group, including but not limited to, p-propargyloxyphenylalanine, or azido group, including but not limited to, p-azido-phenylalanine, respectively.

V. In Vivo Generation of a BSP Comprising Non-Genetically-Encoded Amino Acids The BSPs of the invention can be generated in vivo using modified tRNA and tRNA synthetases to add to or substitute amino acids that are not encoded in naturally-occurring systems.

Methods for generating tRNAs and tRNA synthetases which use amino acids that are not encoded in naturally-occurring systems are described in, e.g., U.S. Patent Application Publications 2003/0082575 (Ser. No. 10/126,927) and 2003/0108885 (Ser. No. 10/126,931) which are incorporated by reference herein. These methods involve generating a translational machinery that functions independently of the synthetases and tRNAs endogenous to the translation system (and are therefore sometimes referred to as "orthogonal"). Typically, the translation system comprises an orthogonal tRNA (O-tRNA) and an orthogonal aminoacyl tRNA synthetase (O-RS). Typically, the O-RS preferentially aminoacylates the O-tRNA with at least one non-naturally occurring amino acid in the translation system and the O-tRNA recognizes at least one selector codon that is not recognized by other tRNAs in the system. The translation system thus inserts the non-naturally-encoded amino acid into a protein produced in the system, in response to an encoded selector codon, thereby "substituting" an amino acid into a position in the encoded polypeptide.

A wide variety of orthogonal tRNAs and aminoacyl tRNA synthetases have been described in the art for inserting particular synthetic amino acids into polypeptides, and are generally suitable for use in the present invention. For example, keto-specific O-tRNA/aminoacyl-tRNA synthetases are described in Wang, L., et al., *Proc. Natl. Acad. Sci. USA* 100:56-61 (2003) and Zhang, Z. et al., *Biochem.* 42(22): 6735-6746 (2003). Exemplary O-RS, or portions thereof, are encoded by polynucleotide sequences and include amino acid sequences disclosed in U.S. Patent Application Publications 2003/0082575 and 2003/0108885, each incorporated herein by reference. Corresponding O-tRNA molecules for use with the O-RSs are also described in U.S. Patent Application Publications 2003/0082575 (Ser. No. 10/126,927) and 2003/0108885 (Ser. No. 10/126,931) which are incorporated by reference herein.

An example of an azide-specific O-tRNA/aminoacyl-tRNA synthetase system is described in Chin, J. W., et al., *J. Am. Chem. Soc.* 124:9026-9027 (2002). Exemplary O-RS sequences for p-azido-L-Phe include, but are not limited to, nucleotide sequences SEQ ID NOs: 14-16 and 29-32 and amino acid sequences SEQ ID NOs: 46-48 and 61-64 as disclosed in U.S. Patent Application Publication 2003/0108885 (Ser. No. 10/126,931) which is incorporated by reference herein. Exemplary O-tRNA sequences suitable for use in the present invention include, but are not limited to, nucleotide sequences SEQ ID NOs: 1-3 as disclosed in U.S. Patent Application Publication 2003/0108885 (Ser. No. 10/126,931) which is incorporated by reference herein. Other examples of O-tRNA/aminoacyl-tRNA synthetase pairs specific to particular non-naturally encoded amino acids are described in U.S. Patent Application Publication 2003/0082575 (Ser. No. 10/126,927) which is incorporated by reference herein. O-RS and O-tRNA that incorporate both keto- and azide-containing amino acids in *S. cerevisiae* are described in Chin, J. W., et al., *Science* 301:964-967 (2003).

Use of O-tRNA/aminoacyl-tRNA synthetases involves selection of a specific codon which encodes the non-naturally encoded amino acid. While any codon can be used, it is generally desirable to select a codon that is rarely or never used in the cell in which the O-tRNA/aminoacyl-tRNA synthetase is expressed. For example, exemplary codons include nonsense codon such as stop codons (amber, ochre, and opal), four or more base codons and other natural three-base codons that are rarely or unused.

Specific selector codon(s) can be introduced into appropriate positions in the GLP-1 polynucleotide coding sequence using mutagenesis methods known in the art (including but not limited to, site-specific mutagenesis, cassette mutagenesis, restriction selection mutagenesis, etc.).

Methods for generating components of the protein biosynthetic machinery, such as O-RSs, O-tRNAs, and orthogonal O-tRNA/O-RS pairs that can be used to incorporate a non-naturally encoded amino acid are described in Wang, L., et al., *Science* 292: 498-500 (2001); Chin, J. W., et al., *J. Am. Chem. Soc.* 124:9026-9027 (2002); Zhang, Z. et al., *Biochemistry* 42: 6735-6746 (2003). Methods and compositions for the in vivo incorporation of non-naturally encoded amino acids are described in U.S. Patent Application Publication 2003/0082575 (Ser. No. 10/126,927) which is incorporated by reference herein. Methods for selecting an orthogonal tRNA-tRNA synthetase pair for use in in vivo translation system of an organism are also described in U.S. Patent Application Publications 2003/0082575 (Ser. No. 10/126,927) and 2003/0108885 (Ser. No. 10/126,931) which are incorporated by reference herein.

Methods for producing at least one recombinant orthogonal aminoacyl-tRNA synthetase (O-RS) comprise: (a) generating a library of (optionally mutant) RSs derived from at least one aminoacyl-tRNA synthetase (RS) from a first organism, including but not limited to, a prokaryotic organism, such as *Methanococcus jannaschii, Methanobacterium thermoautotrophicum, Halobacterium, Escherichia coli, A. fulgidus, P. furiosus, P. horikoshii, A. pernix, T. thermophilus,* or the like, or a eukaryotic organism; (b) selecting (and/or screening) the library of RSs (optionally mutant RSs) for members that aminoacylate an orthogonal tRNA (O-tRNA) in the presence of a non-naturally encoded amino acid and a natural amino acid, thereby providing a pool of active (optionally mutant) RSs; and/or, (c) selecting (optionally through negative selection) the pool for active RSs (including but not limited to, mutant RSs) that preferentially aminoacylate the O-tRNA in the absence of the non-naturally encoded amino acid, thereby providing the at least one recombinant O-RS; wherein the at least one recombinant O-RS preferentially aminoacylates the O-tRNA with the non-naturally encoded amino acid.

In one embodiment, the RS is an inactive RS. The inactive RS can be generated by mutating an active RS. For example, the inactive RS can be generated by mutating at least about 1, at least about 2, at least about 3, at least about 4, at least about 5, at least about 6, or at least about 10 or more amino acids to different amino acids, including but not limited to, alanine.

Libraries of mutant RSs can be generated using various techniques known in the art, including but not limited to rational design based on protein three dimensional RS structure, or mutagenesis of RS nucleotides in a random or rational design technique. For example, the mutant RSs can be generated by site-specific mutations, random mutations, diversity generating recombination mutations, chimeric constructs, rational design and by other methods described herein or known in the art.

In one embodiment, selecting (and/or screening) the library of RSs (optionally mutant RSs) for members that are active, including but not limited to, that aminoacylate an orthogonal tRNA (O-tRNA) in the presence of a non-naturally encoded amino acid and a natural amino acid, includes: introducing a positive selection or screening marker, including but not limited to, an antibiotic resistance gene, or the like, and the library of (optionally mutant) RSs into a plurality of cells, wherein the positive selection and/or screening marker comprises at least one selector codon, including but not limited to, an amber, ochre, or opal codon; growing the plurality of cells in the presence of a selection agent; identifying cells that survive (or show a specific response) in the presence of the selection and/or screening agent by suppressing the at least one selector codon in the positive selection or screening marker, thereby providing a subset of positively selected cells that contains the pool of active (optionally mutant) RSs. Optionally, the selection and/or screening agent concentration can be varied.

In one aspect, the positive selection marker is a chloramphenicol acetyltransferase (CAT) gene and the selector codon is an amber stop codon in the CAT gene. Optionally, the positive selection marker is a β-lactamase gene and the selector codon is an amber stop codon in the β-lactamase gene. In another aspect the positive screening marker comprises a fluorescent or luminescent screening marker or an affinity based screening marker (including but not limited to, a cell surface marker).

In one embodiment, negatively selecting or screening the pool for active RSs (optionally mutants) that preferentially aminoacylate the O-tRNA in the absence of the non-naturally encoded amino acid includes: introducing a negative selection or screening marker with the pool of active (optionally mutant) RSs from the positive selection or screening into a plurality of cells of a second organism, wherein the negative selection or screening marker comprises at least one selector codon (including but not limited to, an antibiotic resistance gene, including but not limited to, a chloramphenicol acetyltransferase (CAT) gene); and, identifying cells that survive or show a specific screening response in a first medium supplemented with the non-naturally encoded amino acid and a screening or selection agent, but fail to survive or to show the specific response in a second medium not supplemented with the non-naturally encoded amino acid and the selection or screening agent, thereby providing surviving cells or screened cells with the at least one recombinant O-RS. For example, a CAT identification protocol optionally acts as a positive selection and/or a negative screening in determination of appropriate O-RS recombinants. For instance, a pool of clones is optionally replicated on growth plates containing CAT (which comprises at least one selector codon) either with or without one or more non-naturally encoded amino acid. Colonies growing exclusively on the plates containing non-naturally encoded amino acids are thus regarded as containing recombinant O-RS. In one aspect, the concentration of the selection (and/or screening) agent is varied. In some aspects the first and second organisms are different. Thus, the first and/or second organism optionally comprises: a prokaryote, a eukaryote, a mammal, an *Escherichia coli,* a fungi, a yeast, an archaebacterium, a *eubacterium,* a plant, an insect, a protist, etc. In other embodiments, the screening marker comprises a fluorescent or luminescent screening marker or an affinity based screening marker.

In another embodiment, screening or selecting (including but not limited to, negatively selecting) the pool for active (optionally mutant) RSs includes: isolating the pool of active mutant RSs from the positive selection step (b); introducing a negative selection or screening marker, wherein the negative selection or screening marker comprises at least one selector codon (including but not limited to, a toxic marker gene, including but not limited to, a ribonuclease barnase gene, comprising at least one selector codon), and the pool of active (optionally mutant) RSs into a plurality of cells of a second organism; and identifying cells that survive or show a specific screening response in a first medium not supplemented with the non-naturally encoded amino acid, but fail to survive or show a specific screening response in a second medium supplemented with the non-naturally encoded amino acid, thereby providing surviving or screened cells with the at least one recombinant O-RS, wherein the at least one recombinant O-RS is specific for the non-naturally encoded amino acid. In one aspect, the at least one selector codon comprises about two or more selector codons. Such embodiments optionally can include wherein the at least one selector codon comprises two or more selector codons, and wherein the first and second organism are different (including but not limited to, each organism is optionally, including but not limited to, a prokaryote, a eukaryote, a mammal, an *Escherichia coli,* a fungi, a yeast, an archaebacteria, a eubacteria, a plant, an insect, a protist, etc.). Also, some aspects include wherein the negative selection marker comprises a ribonuclease barnase gene (which comprises at least one selector codon). Other aspects include wherein the screening marker optionally comprises a fluorescent or luminescent screening marker or an affinity based screening marker. In the embodiments herein, the screenings and/or selections optionally include variation of the screening and/or selection stringency.

In one embodiment, the methods for producing at least one recombinant orthogonal aminoacyl-tRNA synthetase (O-RS) can further comprise: (d) isolating the at least one recombinant O-RS; (e) generating a second set of O-RS (optionally mutated) derived from the at least one recombinant O-RS; and, (f) repeating steps (b) and (c) until a mutated O-RS is obtained that comprises an ability to preferentially aminoacylate the O-tRNA. Optionally, steps (d)-(f) are repeated, including but not limited to, at least about two times. In one aspect, the second set of mutated O-RS derived from at least one recombinant O-RS can be generated by mutagenesis, including but not limited to, random mutagenesis, site-specific mutagenesis, recombination or a combination thereof.

The stringency of the selection/screening steps, including but not limited to, the positive selection/screening step (b), the negative selection/screening step (c) or both the positive and negative selection/screening steps (b) and (c), in the above-described methods, optionally includes varying the selection/screening stringency. In another embodiment, the positive selection/screening step (b), the negative selection/screening step (c) or both the positive and negative selection/screening steps (b) and (c) comprise using a reporter, wherein the reporter is detected by fluorescence-activated cell sorting (FACS) or wherein the reporter is detected by luminescence. Optionally, the reporter is displayed on a cell surface, on a phage display or the like and selected based upon affinity or catalytic activity involving the non-naturally encoded amino acid or an analogue. In one embodiment, the mutated synthetase is displayed on a cell surface, on a phage display or the like.

Methods for producing a recombinant orthogonal tRNA (O-tRNA) include: (a) generating a library of mutant tRNAs derived from at least one tRNA, including but not limited to, a suppressor tRNA, from a first organism; (b) selecting (including but not limited to, negatively selecting) or screening the library for (optionally mutant) tRNAs that are aminoacylated by an aminoacyl-tRNA synthetase (RS) from a second organism in the absence of a RS from the first organism, thereby providing a pool of tRNAs (optionally mutant); and, (c) selecting or screening the pool of tRNAs (optionally mutant) for members that are aminoacylated by an introduced orthogonal RS(O-RS), thereby providing at least one recombinant O-tRNA; wherein the at least one recombinant O-tRNA recognizes a selector codon and is not efficiency recognized by the RS from the second organism and is preferentially aminoacylated by the O-RS. In some embodiments the at least one tRNA is a suppressor tRNA and/or comprises a unique three base codon of natural and/or unnatural bases, or is a nonsense codon, a rare codon, an unnatural codon, a codon comprising at least 4 bases, an amber codon, an ochre codon, or an opal stop codon. In one embodiment, the recombinant O-tRNA possesses an improvement of orthogonality. It will be appreciated that in some embodiments, O-tRNA is optionally imported into a first organism from a second organism without the need for modification. In various embodiments, the first and second organisms are either the same or different and are optionally chosen from, including but not limited to, prokaryotes (including but not limited to, *Methanococcus jannaschii, Methanobacteium thermoautotrophicum, Escherichia coli, Halobacterium,* etc.), eukaryotes, mammals, fungi, yeasts, archaebacteria, eubacteria, plants, insects, protists, etc. Additionally, the recombinant tRNA is optionally aminoacylated by a non-naturally encoded amino acid, wherein the non-naturally encoded amino acid is biosynthesized in vivo either naturally or through genetic manipulation. The non-naturally encoded amino acid is optionally added to a growth medium for at least the first or second organism.

In one aspect, selecting (including but not limited to, negatively selecting) or screening the library for (optionally mutant) tRNAs that are aminoacylated by an aminoacyl-tRNA synthetase (step (b)) includes: introducing a toxic marker gene, wherein the toxic marker gene comprises at least one of the selector codons (or a gene that leads to the production of a toxic or static agent or a gene essential to the organism wherein such marker gene comprises at least one selector codon) and the library of (optionally mutant) tRNAs into a plurality of cells from the second organism; and, selecting surviving cells, wherein the surviving cells contain the pool of (optionally mutant) tRNAs comprising at least one orthogonal tRNA or nonfunctional tRNA. For example, surviving cells can be selected by using a comparison ratio cell density assay.

In another aspect, the toxic marker gene can include two or more selector codons. In another embodiment of the methods, the toxic marker gene is a ribonuclease barnase gene, where the ribonuclease barnase gene comprises at least one amber codon. Optionally, the ribonuclease barnase gene can include two or more amber codons.

In one embodiment, selecting or screening the pool of (optionally mutant) tRNAs for members that are aminoacylated by an introduced orthogonal RS(O-RS) can include: introducing a positive selection or screening marker gene, wherein the positive marker gene comprises a drug resistance gene (including but not limited to, β-lactamase gene, comprising at least one of the selector codons, such as at least one amber stop codon) or a gene essential to the organism, or a gene that leads to detoxification of a toxic agent, along with the O-RS, and the pool of (optionally mutant) tRNAs into a plurality of cells from the second organism; and, identifying surviving or screened cells grown in the presence of a selection or screening agent, including but not limited to, an antibiotic, thereby providing a pool of cells possessing the at least one recombinant tRNA, where the at least one recombinant tRNA is aminoacylated by the O-RS and inserts an amino acid into a translation product encoded by the positive marker gene, in response to the at least one selector codons. In another embodiment, the concentration of the selection and/or screening agent is varied.

Methods for generating specific O-tRNA/O-RS pairs are provided. Methods include: (a) generating a library of mutant tRNAs derived from at least one tRNA from a first organism; (b) negatively selecting or screening the library for (optionally mutant) tRNAs that are aminoacylated by an aminoacyl-tRNA synthetase (RS) from a second organism in the absence of a RS from the first organism, thereby providing a pool of (optionally mutant) tRNAs; (c) selecting or screening the pool of (optionally mutant) tRNAs for members that are aminoacylated by an introduced orthogonal RS(O-RS), thereby providing at least one recombinant O-tRNA. The at least one recombinant O-tRNA recognizes a selector codon and is not efficiency recognized by the RS from the second organism and is preferentially aminoacylated by the O-RS. The method also includes (d) generating a library of (optionally mutant) RSs derived from at least one aminoacyl-tRNA synthetase (RS) from a third organism; (e) selecting or screening the library of mutant RSs for members that preferentially aminoacylate the at least one recombinant O-tRNA in the presence of a non-naturally encoded amino acid and a natural amino acid, thereby providing a pool of active (optionally mutant) RSs; and, (f) negatively selecting or screening the pool for active (optionally mutant) RSs that preferentially aminoacylate the at least one recombinant O-tRNA in the absence of the non-naturally encoded amino acid, thereby providing the at least one specific O-tRNA/O-RS pair, wherein the at least one specific O-tRNA/O-RS pair comprises at least one recombinant O-RS that is specific for the non-naturally encoded amino acid and the at least one recombinant O-tRNA. Specific O-tRNA/O-RS pairs produced by the methods are included. For example, the specific O-tRNA/O-RS pair can include, including but not limited to, a mutR-NATyr-mutTyrRS pair, such as a mutRNATyr-SS12TyrRS pair, a mutRNALeu-mutLeuRS pair, a mutRNAThr-mutThrRS pair, a mutRNAGlu-mutGluRS pair, or the like. Additionally, such methods include wherein the first and third organism are the same (including but not limited to, *Methanococcus jannaschii*).

Methods for selecting an orthogonal tRNA-tRNA synthetase pair for use in an in vivo translation system of a second organism are also included in the present invention. The methods include: introducing a marker gene, a tRNA and an aminoacyl-tRNA synthetase (RS) isolated or derived from a first organism into a first set of cells from the second organism; introducing the marker gene and the tRNA into a duplicate cell set from a second organism; and, selecting for surviving cells in the first set that fail to survive in the duplicate cell set or screening for cells showing a specific screening response that fail to give such response in the duplicate cell set, wherein the first set and the duplicate cell set are grown in the presence of a selection or screening agent, wherein the surviving or screened cells comprise the orthogonal tRNA-tRNA synthetase pair for use in the in the in vivo translation system of the second organism. In one embodiment, comparing and selecting or screening includes an in vivo complementation assay. The concentration of the selection or screening agent can be varied.

The organisms of the present invention comprise a variety of organism and a variety of combinations. For example, the first and the second organisms of the methods of the present invention can be the same or different. In one embodiment, the organisms are optionally a prokaryotic organism, including but not limited to, *Methanococcus jannaschii, Methanobacterium thermoautotrophicum, Halobacterium, Escherichia coli, A. fulgidus, P. furiosus, P. horikoshii, A. pernix, T. thermophilus*, or the like. Alternatively, the organisms optionally comprise a eukaryotic organism, including but not limited to, plants (including but not limited to, complex plants such as monocots, or dicots), algae, protists, fungi (including but not limited to, yeast, etc), animals (including but not limited to, mammals, insects, arthropods, etc.), or the like. In another embodiment, the second organism is a prokaryotic organism, including but not limited to, *Methanococcus jannaschii, Methanobacterium thermoautotrophicum, Halobacterium, Escherichia coli, A. fulgidus, Halobacterium, P. furiosus, P. horikoshii, A. pernix, T. thermophilus*, or the like. Alternatively, the second organism can be a eukaryotic organism, including but not limited to, a yeast, a animal cell, a plant cell, a fungus, a mammalian cell, or the like. In various embodiments the first and second organisms are different.

VI. Location of Non-Naturally-Occurring Amino Acids in a BSP

The present invention contemplates incorporation of one or more non-naturally-occurring amino acids into a BSP. One or more non-naturally-occurring amino acids may be incorporated at a particular position which does not disrupt activity of the polypeptide. This can be achieved by making "conservative" substitutions, including but not limited to, substituting hydrophobic amino acids with hydrophobic amino acids, bulky amino acids for bulky amino acids, hydrophilic amino acids for hydrophilic amino acids) and/or inserting the non-naturally-occurring amino acid in a location that is not required for activity.

A variety of biochemical and structural approaches can be employed to select the desired sites for substitution with a non-naturally encoded amino acid within the BSP. It is readily apparent to those of ordinary skill in the art that any position of the polypeptide chain is suitable for selection to incorporate a non-naturally encoded amino acid, and selection may be based on rational design or by random selection for any or no particular desired purpose. Selection of desired sites may be for producing a BSP molecule having any desired property or activity, including but not limited to, agonists, super-agonists, inverse agonists, antagonists, receptor binding modulators, receptor activity modulators, modulators of binding to binding partners, binding partner activity modulators, binding partner conformation modulators, dimer or multimer formation, no change to activity or property compared to the native molecule, or manipulating any physical or chemical property of the polypeptide such as solubility, aggregation, or stability. For example, locations in the polypeptide required for biological activity of BSP can be identified using point mutation analysis, alanine scanning or homolog scanning methods known in the art. See, Adelhorst et al. J. of Biol. Chem. 1994 269(9):6275-6278 for GLP-1. Residues other than those identified as critical to biological activity by alanine or homolog scanning mutagenesis may be good candidates for substitution with a non-naturally encoded amino acid depending on the desired activity sought for the polypeptide. Alternatively, the sites identified as critical to biological activity may also be good candidates for substitution with a non-naturally encoded amino acid, again depending on the desired activity sought for the polypeptide. Another alternative would be to simply make serial substitutions in each position on the polypeptide chain with a non-naturally encoded amino acid and observe the effect on the activities of the polypeptide. It is readily apparent to those of ordinary skill in the art that any means, technique, or method for selecting a position for substitution with a non-natural amino acid into any polypeptide is suitable for use in the present invention.

The structure and activity of naturally-occurring mutants of BSP that contain deletions can also be examined to determine regions of the protein that are likely to be tolerant of substitution with a non-naturally encoded amino acid. In a similar manner, protease digestion and monoclonal antibodies can be used to identify regions of BSP that are responsible for binding the BSP receptor or binding partners. Once residues that are likely to be intolerant to substitution with non-naturally encoded amino acids have been eliminated, the impact of proposed substitutions at each of the remaining positions can be examined from the structure of BSP and its receptor or binding partners. Thus, those of skill in the art can readily identify amino acid positions that can be substituted with non-naturally encoded amino acids.

In some embodiments, the BSPs of the invention comprise one or more non-naturally occurring amino acids positioned in a region of the protein that does not disrupt the helices or beta sheet secondary structure of the polypeptide.

In some embodiments, one or more non-naturally encoded amino acids are incorporated at any position in GLP-1, before the first amino acid (at the amino terminus), an addition at the carboxy terminus, or any combination thereof. In some embodiments, one or more non-naturally encoded amino acids are incorporated at any position in GLP-1, including but not limited to, the residues as follows: before the first amino acid at position 7 (i.e. at the N terminus), 7H, 8A, 9E, V16, 17S, 18S, 19Y, 20L, 21E, 22G, 23Q, 24A, 25A, 26K, 27E, 28F, 29I, 30A, 31W, 32L, 33V, 34K, 35G, 36R, 37G, an addition at position 38 (i.e. at the carboxyl terminus), or any combination thereof.

In some embodiments, the non-naturally occurring amino acid at these or other positions is linked to a water soluble molecule, including but not limited to positions: before the first amino acid at position 7 (i.e. at the N terminus), 7H, 8A, 9E, V16, 17S, 18S, 19Y, 20L, 21E, 22G, 23Q, 24A, 25A, 26K, 27E, 28F, 29I, 30A, 31W, 32L, 33V, 34K, 35G, 36R, 37G, an addition at position 38 (i.e. at the carboxyl terminus), or any combination thereof. In some embodiments, the GLP-1 polypeptides of the invention comprise one or more non-naturally occurring amino acids at one or more of the following positions providing an antagonist: 7, 8, 9, 22, 18, 29, 25, 32, 21, 28, 17, 24, 31, 20, or any combination thereof.

In some embodiments, one or more non-naturally encoded amino acids are incorporated at any position in T-20 (including TEX), before the first amino acid (at the amino terminus), an addition at the carboxy terminus, or any combination thereof. In some embodiments, one or more non-naturally encoded amino acids are incorporated at any position in T-20 (including TEX), including but not limited to, the residues as follows: W631, D632, I635, N636, N637, Y638, T639, S640, L641, L645, N651, or any combination thereof.

In some embodiments, one or more non-naturally encoded amino acids are incorporated at any position in Peptide YY, before the first amino acid (at the amino terminus), an addition at the carboxy terminus, or any combination thereof.

Exemplary residues of incorporation of a non-naturally encoded amino acid may be those that are excluded from potential receptor binding regions or regions for binding to binding partners, may be fully or partially solvent exposed, have minimal or no hydrogen-bonding interactions with nearby residues, may be minimally exposed to nearby reactive residues, may be on one or more of the exposed faces of the BSP, may be in regions that are highly flexible, or structurally rigid, as predicted by the three-dimensional, secondary, tertiary, or quaternary structure of the BSP, bound or unbound to its receptor or binding partner, or coupled or not coupled to another BSP or other biologically active molecule, or may modulate the conformation of the BSP itself or a dimer or multimer comprising one or more BSP, by altering the flexibility or rigidity of the complete structure as desired.

In some embodiments, the GLP-1 antagonist comprises a non-naturally encoded amino acid linked to a water soluble polymer that is present in a receptor binding region of the GLP-1 molecule. In some embodiments the water soluble polymer is coupled to the GLP-1 polypeptide at one or more of the amino acid positions: 7, 8, 9, 22, 18, 29, 25, 32, 21, 28, 17, 24, 31, and 20. (SEQ ID NO: 1, 2, 3, 21, or any other GLP-1 polypeptide).

A wide variety of non-naturally encoded amino acids can be substituted for, or incorporated into, a given position in BSP. In general, a particular non-naturally encoded amino acid is selected for incorporation based on an examination of the structure of BSP with or without its receptor or binding partners, a preference for conservative substitutions (i.e., aryl-based non-naturally encoded amino acids, such as p-acetylphenylalanine or O-propargyltyrosine substituting for Phe, Tyr or Trp), and the specific conjugation chemistry that one desires to introduce into the BSP (e.g., the introduction of 4-azidophenylalanine if one wants to effect a Huisgen [3+2] cycloaddition with a water soluble polymer bearing an alkyne moiety or a amide bond formation with a water soluble polymer that bears an aryl ester that, in turn, incorporates a phosphine moiety).

In one embodiment, the method further includes incorporating into the protein the unnatural amino acid, where the unnatural amino acid comprises a first reactive group; and contacting the protein with a molecule (including but not limited to, a label, a dye, a polymer, a water-soluble polymer, a derivative of polyethylene glycol, a photocrosslinker, a radionuclide, a cytotoxic compound, a drug, an affinity label, a photoaffinity label, a reactive compound, a resin, a second protein or polypeptide or polypeptide analog, an antibody or antibody fragment, a metal chelator, a cofactor, a fatty acid, a carbohydrate, a polynucleotide, a DNA, a RNA, an antisense polynucleotide, a water soluble dendimer, a cyclodextrin, an inhibitory ribonucleic acid, a biomaterial, a nanoparticle, a spin label, a fluorophore, a metal-containing moiety, a radioactive moiety, a novel functional group, a group that covalently or noncovalently interacts with other molecules, a photocaged moiety, a photoisomerizable moiety, biotin, a derivative of biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, a small molecule, or any combination of the above, or any other desirable compound or substance) that comprises a second reactive group. The first reactive group reacts with the second reactive group to attach the molecule to the unnatural amino acid through a [3+2] cycloaddition. In one embodiment, the first reactive group is an alkynyl or azido moiety and the second reactive group is an azido or alkynyl moiety. For example, the first reactive group is the alkynyl moiety (including but not limited to, in unnatural amino acid p-propargyloxyphenylalanine) and the second reactive group is the azido moiety. In another example, the first reactive group is the azido moiety (including but not limited to, in the unnatural amino acid p-azido-L-phenylalanine) and the second reactive group is the alkynyl moiety.

In some cases, the non-naturally encoded amino acid substitution(s) will be combined with other additions, substitutions or deletions within the BSP to affect other biological traits of the BSP. In some cases, the other additions, substitutions or deletions may increase the stability (including but not limited to, resistance to proteolytic degradation) of the BSP or increase affinity of the BSP for its receptor or binding partner. In some cases, the other additions, substitutions or deletions may increase the solubility (including but not limited to, when expressed in *E. Coli* or other host cells) of the BSP. In some embodiments additions, substitutions or deletions may increase the polypeptide solubility following expression in *E. coli* recombinant host cells. In some embodiments sites are selected for substitution with a naturally encoded or non-natural amino acid in addition to another site for incorporation of a non-natural amino acid that results in increasing the polypeptide solubility following expression in *E. coli* recombinant host cells. In some embodiments, the BSPs comprise another addition, substitution or deletion that modulates affinity for the BSP receptor or binding partner, modulates (including but not limited to, increases or decreases) receptor dimerization, stabilizes receptor dimers, modulates the conformation or one or biological activities of a binding partner, modulates circulating half-life, modulates release or bio-availability, facilitates purification, or improves or alters a particular route of administration. Similarly, BSPs can comprise protease cleavage sequences, reactive groups, antibody-binding domains (including but not limited to, FLAG or poly-His) or other affinity based sequences (including, but not limited to, FLAG, poly-His GST, etc.) or linked molecules (including, but not limited to, biotin) that improve detection (including, but not limited to, GFP), purification, transport through tissues or cell membranes, prodrug release or activation, BSP size reduction, or other traits of the polypeptide.

In some embodiments, the substitution of a non-naturally encoded amino acid generates a BSP antagonist. A subset of exemplary sites for incorporation of a non-naturally encoded amino acid include: 7, 8, 9, 22, 18, 29, 25, 32, 21, 28, 17, 24, 31, and 20 of GLP-1. In other embodiments, the above-listed substitutions are combined with additional substitutions that cause the GLP-1 polypeptide to be a GLP-1 antagonist. In some embodiments, the GLP-1 antagonist comprises a non-naturally encoded amino acid linked to a water soluble polymer that is present in a receptor binding region of the GLP-1 molecule.

In some cases, 1, 2, 3, 4, 5, 6, 7, 8, 9, 10, or more amino acids are substituted with one or more non-naturally-encoded amino acids. In some cases, the BSP further includes 1, 2, 3, 4, 5, 6, 7, 8, 9, 10, or more substitutions of one or more non-naturally encoded amino acids for naturally-occurring amino acids. For example, in some embodiments, at least two residues in the following regions of GLP-1 are substituted with a non-naturally encoded amino acid: before the first amino acid at position 7 (i.e. at the N terminus), 7H, 8A, 9E, V16, 17S, 18S, 19Y, 20L, 21E, 22G, 23Q, 24A, 25A, 26K, 27E, 28F, 291,30A, 31W, 32L, 33V, 34K, 35G, 36R, 37G, an addition at position 38 (i.e. at the carboxyl terminus) or any combination thereof. In some embodiments, at least two residues of T-20 polypeptides are substituted with a non-naturally encoded amino acid including but not limited to: W631, D632, I635, N636, N637, Y638, T639, S640, L641, L645, N651. In some embodiments, one or more non-naturally encoded amino acids are incorporated at any position in Peptide YY, before the first amino acid (at the amino terminus), an addition at the carboxy terminus, or any combination thereof.

In some cases, the one or more non-naturally encoded residues are linked to one or more lower molecular weight linear or branched PEGs (approximately ~5-20 kDa in mass or less), thereby enhancing binding affinity and comparable serum half-life relative to the species attached to a single, higher molecular weight PEG.

VII. Expression in Non-Eukaryotes and Eukaryotes

To obtain high level expression of a cloned BSP, one typically subclones polynucleotides encoding a BSP of the invention into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al.

Bacterial expression systems for expressing BSPs of the invention are available in, including but not limited to, *E. coli*, *Bacillus* sp., and *Salmonella* (Palva et al., *Gene* 22:229-235 (1983); Mosbach et al., *Nature* 302:543-545 (1983)). Kits for such expression systems are commercially available. Eukaryotic expression systems for mammalian cells, yeast, and insect cells are well known in the art and are also commercially available. In cases where orthogonal tRNAs and aminoacyl tRNA synthetases (described above) are used to express the BSPs of the invention, host cells for expression are selected based on their ability to use the orthogonal components. Exemplary host cells include Gram-positive bacteria (including but not limited to *B. brevis, B. subtilis*, or *Streptomyces*) and Gram-negative bacteria (*E. coli, Pseudomonas fluorescens, Pseudomonas aeruginosa, Pseudomonas putida*), as well as yeast and other eukaryotic cells. Cells comprising O-tRNA/O-RS pairs can be used as described herein.

A eukaryotic host cell or non-eukaryotic host cell of the present invention provides the ability to synthesize proteins that comprise unnatural amino acids in large useful quantities. In one aspect, the composition optionally includes, including but not limited to, at least 10 micrograms, at least 50 micrograms, at least 75 micrograms, at least 100 micrograms, at least 200 micrograms, at least 250 micrograms, at least 500 micrograms, at least 1 milligram, at least 10 milligrams, at least 100 milligrams, at least one gram, or more of the protein that comprises an unnatural amino acid, or an amount that can be achieved with in vivo protein production methods (details on recombinant protein production and purification are provided herein). In another aspect, the protein is optionally present in the composition at a concentration of, including but not limited to, at least 10 micrograms of protein per liter, at least 50 micrograms of protein per liter, at least 75 micrograms of protein per liter, at least 100 micrograms of protein per liter, at least 200 micrograms of protein per liter, at least 250 micrograms of protein per liter, at least 500 micrograms of protein per liter, at least 1 milligram of protein per liter, or at least 10 milligrams of protein per liter or more, in, including but not limited to, a cell lysate, a buffer, a pharmaceutical buffer, or other liquid suspension (including but not limited to, in a volume of, including but not limited to, anywhere from about 1 nl to about 100 L). The production of large quantities (including but not limited to, greater that that typically possible with other methods, including but not limited to, in vitro translation) of a protein in a eukaryotic cell including at least one unnatural amino acid is a feature of the invention.

A eukaryotic host cell or non-eukaryotic host cell of the present invention provides the ability to biosynthesize proteins that comprise unnatural amino acids in large useful quantities. For example, proteins comprising an unnatural amino acid can be produced at a concentration of, including but not limited to, at least 10 μg/liter, at least 50 μg/liter, at least 75 μg/liter, at least 100 μg/liter, at least 200 μg/liter, at least 250 μg/liter, or at least 500 μg/liter, at least 1 mg/liter, at least 2 mg/liter, at least 3 mg/liter, at least 4 mg/liter, at least 5 mg/liter, at least 6 mg/liter, at least 7 mg/liter, at least 8 mg/liter, at least 9 mg/liter, at least 10 mg/liter, at least 20, 30, 40, 50, 60, 70, 80, 90, 100, 200, 300, 400, 500, 600, 700, 800, 900 mg/liter, 1 g/liter, 5 g/liter, 10 g/liter or more of protein in a cell extract, cell lysate, culture medium, a buffer, and/or the like.

I. Expression Systems, Culture, and Isolation

BSPs may be expressed in any number of suitable expression systems including, for example, yeast, insect cells, mammalian cells, and bacteria. A description of exemplary expression systems is provided below.

Yeast As used herein, the term "yeast" includes any of the various yeasts capable of expressing a gene encoding a BSP. Such yeasts include, but are not limited to, ascosporogenous yeasts (*Endomycetales*), basidiosporogenous yeasts and yeasts belonging to the Fungi imperfecti (*Blastomycetes*) group. The ascosporogenous yeasts are divided into two families, *Spennophthoraceae* and *Saccharomycetaceae*. The latter is comprised of four subfamilies, *Schizosaccharomycoideae*

(e.g., genus *Schizosaccharomyces*), Nadsonioideae, Lipomycoideae and Saccharomycoideae (e.g., genera *Pichia*, *Kluyveromyces* and *Saccharomyces*). The basidiosporogenous yeasts include the genera *Leucosporidium*, *Rhodosporidium*, *Sporidiobolus*, *Filobasidium*, and *Filobasidiella*. Yeasts belonging to the Fungi Imperfecti (*Blastomycetes*) group are divided into two families, Sporobolomycetaceae (e.g., genera *Sporobolomyces* and *Bullera*) and Cryptococcaceae (e.g., genus *Candida*).

Of particular interest for use with the present invention are species within the genera *Pichia*, *Kluyveromyces*, *Saccharomyces*, *Schizosaccharomyces*, *Hansenula*, *Torulopsis*, and *Candida*, including, but not limited to, *P. pastoris*, *P. guillerimondii*, *S. cerevisiae*, *S. carlsbergensis*, *S. diastaticus*, *S. douglasii*, *S. kluyveri*, *S. norbensis*, *S. oviformis*, *K. lactis*, *K. fragilis*, *C. albicans*, *C. maltosa*, and *H. polymorpha*.

The selection of suitable yeast for expression of BSP is within the skill of one of ordinary skill in the art. In selecting yeast hosts for expression, suitable hosts may include those shown to have, for example, good secretion capacity, low proteolytic activity, good soluble protein production, and overall robustness. Yeast are generally available from a variety of sources including, but not limited to, the Yeast Genetic Stock Center, Department of Biophysics and Medical Physics, University of California (Berkeley, Calif.), and the American Type Culture Collection ("ATCC") (Manassas, Va.).

The term "yeast host" or "yeast host cell" includes yeast that can be, or has been, used as a recipient for recombinant vectors or other transfer DNA. The term includes the progeny of the original yeast host cell that has received the recombinant vectors or other transfer DNA. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding BSP, are included in the progeny intended by this definition.

Expression and transformation vectors, including extrachromosomal replicons or integrating vectors, have been developed for transformation into many yeast hosts. For example, expression vectors have been developed for *S. cerevisiae* (Sikorski et al., GENETICS (1989) 122:19; Ito et al., J. BACTERIOL. (1983) 153:163; Hinnen et al., PROC. NATL. ACAD. SCI. USA (1978) 75:1929); *C. albicans* (Kurtz et al., MOL. CELL. BIOL. (1986) 6:142); *C. maltosa* (Kunze et al., J. BASIC MICROBIOL. (1985) 25:141); *H. polymorpha* (Gleeson et al., J. GEN. MICROBIOL. (1986) 132:3459; Roggenkamp et al., MOL. GENETICS AND GENOMICS (1986) 202:302); *K. fragilis* (Das et al., J. BACTERIOL. (1984) 158:1165); *K. lactis* (De Louvencourt et al., J. BACTERIOL. (1983) 154:737; Van den Berg et al., BIOTECHNOLOGY (NY) (1990) 8:135); *P. guillerimondii* (Kunze et al., J. BASIC MICROBIOL. (1985) 25:141); *P. pastoris* (U.S. Pat. Nos. 5,324,639; 4,929,555; and 4,837,148; Cregg et al., MOL. CELL. BIOL. (1985) 5:3376); *Schizosaccharomyces pombe* (Beach et al., NATURE (1982) 300:706); and *Y. lipolytica* (Davidow et al., CURR. GENET. (1985) 10:380 (1985); Gaillardin et al., CURR. GENET. (1986) 10:49); *A. nidulans* (Ballance et al., BIOCHEM. BIOPHYS. RES. COMMUN. (1983) 112:284-89; Tilburn et al., GENE (1983) 26:205-221; and Yelton et al., PROC. NATL. ACAD. SCI. USA (1984) 81:1470-74); *A. niger* (Kelly and Hynes, EMBO J. (1985) 4:475-479); *T. reesia* (EP 0 244 234); and filamentous fungi such as, e.g., *Neurospora*, *Penicillium*, *Tolypocladium* (WO 91/00357), each incorporated by reference herein.

Control sequences for yeast vectors are well known to those of ordinary skill in the art and include, but are not limited to, promoter regions from genes such as alcohol dehydrogenase (ADH) (EP 0 284 044); enolase; glucokinase; glucose-6-phosphate isomerase; glyceraldehydes-3-phosphate-dehydrogenase (GAP or GAPDH); hexokinase; phosphofructokinase; 3-phosphoglycerate mutase; and pyruvate kinase (PyK) (EP 0 329 203). The yeast PHO5 gene, encoding acid phosphatase, also may provide useful promoter sequences (Miyanohara et al., PROC. NATL. ACAD. SCI. USA (1983) 80:1). Other suitable promoter sequences for use with yeast hosts may include the promoters for 3-phosphoglycerate kinase (Hitzeman et al., J. BIOL. CHEM. (1980) 255:12073); and other glycolytic enzymes, such as pyruvate decarboxylase, triosephosphate isomerase, and phosphoglucose isomerase (Holland et al., BIOCHEMISTRY (1978) 17:4900; Hess et al., J. ADV. ENZYME REG. (1969) 7:149). Inducible yeast promoters having the additional advantage of transcription controlled by growth conditions may include the promoter regions for alcohol dehydrogenase 2; isocytochrome C; acid phosphatase; metallothionein; glyceraldehyde-3-phosphate dehydrogenase; degradative enzymes associated with nitrogen metabolism; and enzymes responsible for maltose and galactose utilization. Suitable vectors and promoters for use in yeast expression are further described in EP 0 073 657.

Yeast enhancers also may be used with yeast promoters. In addition, synthetic promoters may also function as yeast promoters. For example, the upstream activating sequences (UAS) of a yeast promoter may be joined with the transcription activation region of another yeast promoter, creating a synthetic hybrid promoter. Examples of such hybrid promoters include the ADH regulatory sequence linked to the GAP transcription activation region. See U.S. Pat. Nos. 4,880,734 and 4,876,197, which are incorporated by reference herein. Other examples of hybrid promoters include promoters that consist of the regulatory sequences of the ADH2, GAL4, GAL10, or PHO5 genes, combined with the transcriptional activation region of a glycolytic enzyme gene such as GAP or PyK. See EP 0 164 556. Furthermore, a yeast promoter may include naturally occurring promoters of non-yeast origin that have the ability to bind yeast RNA polymerase and initiate transcription.

Other control elements that may comprise part of the yeast expression vectors include terminators, for example, from GAPDH or the enolase genes (Holland et al., J. BIOL. CHEM. (1981) 256:1385). In addition, the origin of replication from the 2μ plasmid origin is suitable for yeast. A suitable selection gene for use in yeast is the trp1 gene present in the yeast plasmid. See Tschumper et al., GENE (1980) 10:157; Kingsman et al., GENE (1979) 7:141. The trp1 gene provides a selection marker for a mutant strain of yeast lacking the ability to grow in tryptophan. Similarly, Leu2-deficient yeast strains (ATCC 20,622 or 38,626) are complemented by known plasmids bearing the Leu2 gene.

Methods of introducing exogenous DNA into yeast hosts are well known to those of ordinary skill in the art, and typically include, but are not limited to, either the transformation of spheroplasts or of intact yeast host cells treated with alkali cations. For example, transformation of yeast can be carried out according to the method described in Hsiao et al., PROC. NATL. ACAD. SCI. USA (1979) 76:3829 and Van Solingen et al., J. BACT. (1977) 130:946. However, other methods for introducing DNA into cells such as by nuclear injection, electroporation, or protoplast fusion may also be used as described generally in SAMBROOK ET AL., MOLECULAR CLONING:

A LAB. MANUAL (2001). Yeast host cells may then be cultured using standard techniques known to those of ordinary skill in the art.

Other methods for expressing heterologous proteins in yeast host cells are well known to those of ordinary skill in the art. See generally U.S. Patent Publication No. 20020055169, U.S. Pat. Nos. 6,361,969; 6,312,923; 6,183,985; 6,083,723; 6,017,731; 5,674,706; 5,629,203; 5,602,034; and 5,089,398; U.S. Reexamined Patent Nos. RE37,343 and RE35,749; PCT Published Patent Applications WO 99/07862; WO 98/37208; and WO 98/26080; European Patent Applications EP 0 946 736; EP 0 732 403; EP 0 480 480; EP 0 460 071; EP 0 340 986; EP 0 329 203; EP 0 324 274; and EP 0 164 556. See also Gellissen et al., ANTONIE VAN LEEUWENHOEK (1992) 62(1-2):79-93; Romanos et al., YEAST (1992) 8(6):423-488; Goeddel, METHODS IN ENZYMOLOGY (1990) 185:3-7, each incorporated by reference herein.

The yeast host strains may be grown in fermentors during the amplification stage using standard feed batch fermentation methods well known to those of ordinary skill in the art. The fermentation methods may be adapted to account for differences in a particular yeast host's carbon utilization pathway or mode of expression control. For example, fermentation of a *Saccharomyces* yeast host may require a single glucose feed, complex nitrogen source (e.g., casein hydrolysates), and multiple vitamin supplementation. In contrast, the methylotrophic yeast *P. pastoris* may require glycerol, methanol, and trace mineral feeds, but only simple ammonium (nitrogen) salts for optimal growth and expression. See, e.g., U.S. Pat. No. 5,324,639; Elliott et al., J. PROTEIN CHEM. (1990) 9:95; and Fieschko et al., BIOTECH. BIOENG. (1987) 29:1113, incorporated by reference herein.

Such fermentation methods, however, may have certain common features independent of the yeast host strain employed. For example, a growth limiting nutrient, typically carbon, may be added to the fermentor during the amplification phase to allow maximal growth. In addition, fermentation methods generally employ a fermentation medium designed to contain adequate amounts of carbon, nitrogen, basal salts, phosphorus, and other minor nutrients (vitamins, trace minerals and salts, etc.). Examples of fermentation media suitable for use with *Pichia* are described in U.S. Pat. Nos. 5,324,639 and 5,231,178, which are incorporated by reference herein.

Baculovirus-Infected Insect Cells The term "insect host" or "insect host cell" refers to a insect that can be, or has been, used as a recipient for recombinant vectors or other transfer DNA. The term includes the progeny of the original insect host cell that has been transfected. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding a BSP, are included in the progeny intended by this definition.

The selection of suitable insect cells for expression of BSP is well known to those of ordinary skill in the art. Several insect species are well described in the art and are commercially available including *Aedes aegypti, Bombyx mori, Drosophila melanogaster, Spodoptera frugiperda*, and *Trichoplusia ni*. In selecting insect hosts for expression, suitable hosts may include those shown to have, inter alia, good secretion capacity, low proteolytic activity, and overall robustness. Insect are generally available from a variety of sources including, but not limited to, the Insect Genetic Stock Center, Department of Biophysics and Medical Physics, University of California (Berkeley, Calif.); and the American Type Culture Collection ("ATCC") (Manassas, Va.).

Generally, the components of a baculovirus-infected insect expression system include a transfer vector, usually a bacterial plasmid, which contains both a fragment of the baculovirus genome, and a convenient restriction site for insertion of the heterologous gene to be expressed; a wild type baculovirus with sequences homologous to the baculovirus-specific fragment in the transfer vector (this allows for the homologous recombination of the heterologous gene in to the baculovirus genome); and appropriate insect host cells and growth media. The materials, methods and techniques used in constructing vectors, transfecting cells, picking plaques, growing cells in culture, and the like are known in the art and manuals are available describing these techniques.

After inserting the heterologous gene into the transfer vector, the vector and the wild type viral genome are transfected into an insect host cell where the vector and viral genome recombine. The packaged recombinant virus is expressed and recombinant plaques are identified and purified. Materials and methods for baculovirus/insect cell expression systems are commercially available in kit form from, for example, Invitrogen Corp. (Carlsbad, Calif.). These techniques are generally known to those skilled in the art and fully described in SUMMERS AND SMITH, TEXAS AGRICULTURAL EXPERIMENT STATION BULLETIN No. 1555 (1987), herein incorporated by reference. See also, RICHARDSON, 39 METHODS IN MOLECULAR BIOLOGY: BACULOVIRUS EXPRESSION PROTOCOLS (1995); AUSUBEL ET AL., CURRENT PROTOCOLS IN MOLECULAR BIOLOGY 16.9-16.11 (1994); KING AND POSSEE, THE BACULOVIRUS SYSTEM: A LABORATORY GUIDE (1992); and O'REILLY ET AL., BACULOVIRUS EXPRESSION VECTORS: A LABORATORY MANUAL (1992).

Indeed, the production of various heterologous proteins using baculovirus/insect cell expression systems is well known in the art. See, e.g., U.S. Pat. Nos. 6,368,825; 6,342,216; 6,338,846; 6,261,805; 6,245,528, 6,225,060; 6,183,987; 6,168,932; 6,126,944; 6,096,304; 6,013,433; 5,965,393; 5,939,285; 5,891,676; 5,871,986; 5,861,279; 5,858,368; 5,843,733; 5,762,939; 5,753,220; 5,605,827; 5,583,023; 5,571,709; 5,516,657; 5,290,686; WO 02/06305; WO 01/90390; WO 01/27301; WO 01/05956; WO 00/55345; WO 00/20032 WO 99/51721; WO 99/45130; WO 99/31257; WO 99/10515; WO 99/09193; WO 97/26332; WO 96/29400; WO 96/25496; WO 96/06161; WO 95/20672; WO 93/03173; WO 92/16619; WO 92/03628; WO 92/01801; WO 90/14428; WO 90/10078; WO 90/02566; WO 90/02186; WO 90/01556; WO 89/01038; WO 89/01037; WO 88/07082, which are incorporated by reference herein.

Vectors that are useful in baculovirus/insect cell expression systems are known in the art and include, for example, insect expression and transfer vectors derived from the baculovirus *Autographacalifornica* nuclear polyhedrosis virus (AcNPV), which is a helper-independent, viral expression vector. Viral expression vectors derived from this system usually use the strong viral polyhedrin gene promoter to drive expression of heterologous genes. See generally, O'Reilly ET AL., BACULOVIRUS EXPRESSION VECTORS: A LABORATORY MANUAL (1992).

Prior to inserting the foreign gene into the baculovirus genome, the above-described components, comprising a promoter, leader (if desired), coding sequence of interest, and transcription termination sequence, are typically assembled into an intermediate transplacement construct (transfer vector). Intermediate transplacement constructs are often maintained in a replicon, such as an extra chromosomal element (e.g., plasmids) capable of stable maintenance in a host, such as bacteria. The replicon will have a replication system, thus allowing it to be maintained in a suitable host for cloning and amplification. More specifically, the plasmid may contain the polyhedrin polyadenylation signal (Miller, ANN. REV. MICROBIOL. (1988) 42:177) and a prokaryotic ampicillin-resistance (amp) gene and origin of replication for selection and propagation in *E. coli*.

One commonly used transfer vector for introducing foreign genes into AcNPV is pAc373. Many other vectors, known to those of skill in the art, have also been designed including, for example, pVL985, which alters the polyhedrin start codon from ATG to ATT, and which introduces a BamHI cloning site 32 base pairs downstream from the ATT. See Luckow and Summers, VIROLOGY 170:31 (1989). Other commercially available vectors include, for example, PBlue-Bac4.5/V5-His; pBlueBacHis2; pMelBac; pBlueBac4.5 (Invitrogen Corp., Carlsbad, Calif.).

After insertion of the heterologous gene, the transfer vector and wild type baculoviral genome are co-transfected into an insect cell host. Methods for introducing heterologous DNA into the desired site in the baculovirus virus are known in the art. See SUMMERS AND SMITH, TEXAS AGRICULTURAL EXPERIMENT STATION BULLETIN No. 1555 (1987); Smith et al., MOL. CELL. BIOL. (1983) 3:2156; Luckow and Summers, VIROLOGY (1989) 170:31. For example, the insertion can be into a gene such as the polyhedrin gene, by homologous double crossover recombination; insertion can also be into a restriction enzyme site engineered into the desired baculovirus gene. See Miller et al., BIOESSAYS (1989) 11(4):91.

Transfection may be accomplished by electroporation. See TROTTER AND WOOD, 39 METHODS IN MOLECULAR BIOLOGY (1995); Mann and King, J. GEN. VIROL. (1989) 70:3501. Alternatively, liposomes may be used to transfect the insect cells with the recombinant expression vector and the baculovirus. See, e.g., Liebman et al., BIOTECHNIQUES (1999) 26(1):36; Graves et al., BIOCHEMISTRY (1998) 37:6050; Nomura et al., J. BIOL. CHEM. (1998) 273(22): 13570; Schmidt et al., PROTEIN EXPRESSION AND PURIFICATION (1998) 12:323; Siffert et al., NATURE GENETICS (1998) 18:45; TILKINS ET AL., CELL BIOLOGY: A LABORATORY HANDBOOK 145-154 (1998); Cai et al., PROTEIN EXPRESSION AND PURIFICATION (1997) 10:263; Dolphin et al., NATURE GENETICS (1997) 17:491; Kost et al., GENE (1997) 190:139; Jakobsson et al., J. BIOL. CHEM. (1996) 271:22203; Rowles et al., J. BIOL. CHEM. (1996) 271(37):22376; Reverey et al., J. BIOL. CHEM. (1996) 271(39):23607-10; Stanley et al., J. BIOL. CHEM. (1995) 270:4121; Sisk et al., J. VIROL. (1994) 68(2):766; and Peng et al., BIOTECHNIQUES (1993) 14(2):274. Commercially available liposomes include, for example, Cellfectin® and Lipofectin® (Invitrogen, Corp., Carlsbad, Calif.). In addition, calcium phosphate transfection may be used. See TROTTER AND WOOD, 39 METHODS IN MOLECULAR BIOLOGY (1995); Kitts, NAR (1990) 18(19):5667; and Mann and King, J. GEN. VIROL. (1989) 70:3501.

Baculovirus expression vectors usually contain a baculovirus promoter. A baculovirus promoter is any DNA sequence capable of binding a baculovirus RNA polymerase and initiating the downstream (3') transcription of a coding sequence (e.g., structural gene) into mRNA. A promoter will have a transcription initiation region which is usually placed proximal to the 5' end of the coding sequence. This transcription initiation region typically includes an RNA polymerase binding site and a transcription initiation site. A baculovirus promoter may also have a second domain called an enhancer, which, if present, is usually distal to the structural gene. Moreover, expression may be either regulated or constitutive.

Structural genes, abundantly transcribed at late times in the infection cycle, provide particularly useful promoter sequences. Examples include sequences derived from the gene encoding the viral polyhedron protein (FRIESEN ET AL., *The Regulation of Baculovirus Gene Expression in* THE MOLECULAR BIOLOGY OF BACULOVIRUSES (1986); EP 0 127 839 and 0 155 476) and the gene encoding the p10 protein (Vlak et al., J. GEN. VIROL. (1988) 69:765).

The newly formed baculovirus expression vector is packaged into an infectious recombinant baculovirus and subsequently grown plaques may be purified by techniques known to those skilled in the art. See Miller et al., BIOESSAYS (1989) 11(4):91; SUMMERS AND SMITH, TEXAS AGRICULTURAL EXPERIMENT STATION BULLETIN No. 1555 (1987).

Recombinant baculovirus expression vectors have been developed for infection into several insect cells. For example, recombinant baculoviruses have been developed for, inter alia, *Aedes aegypti* (ATCC No. CCL-125), *Bombyx mori* (ATCC No. CRL-8910), *Drosophila melanogaster* (ATCC No. 1963), *Spodoptera frugiperda*, and *Trichoplusia ni*. See WO 89/046,699; Wright, NATURE (1986) 321:718; Carbonell et al., J. VIROL. (1985) 56:153; Smith et al., MOL. CELL. BIOL. (1983) 3:2156. See generally, Fraser et al., IN VITRO CELL. DEV. BIOL. (1989) 25:225. More specifically, the cell lines used for baculovirus expression vector systems commonly include, but are not limited to, Sf9 (*Spodoptera frugiperda*) (ATCC No. CRL-1711), Sf21 (*Spodoptera frugiperda*) (Invitrogen Corp., Cat. No. 11497-013 (Carlsbad, Calif.)), Tri-368 (*Trichopulsia ni*), and High-Five™ BTI-TN-5B1-4 (*Trichopulsia ni*).

Cells and culture media are commercially available for both direct and fusion expression of heterologous polypeptides in a baculovirus/expression, and cell culture technology is generally known to those skilled in the art.

*E. Coli, Pseudomonas* species, and other Prokaryotes Bacterial expression techniques are well known in the art. A wide variety of vectors are available for use in bacterial hosts. The vectors may be single copy or low or high multicopy vectors. Vectors may serve for cloning and/or expression. In view of the ample literature concerning vectors, commercial availability of many vectors, and even manuals describing vectors and their restriction maps and characteristics, no extensive discussion is required here. As is well-known, the vectors normally involve markers allowing for selection, which markers may provide for cytotoxic agent resistance, prototrophy or immunity. Frequently, a plurality of markers is present, which provide for different characteristics.

A bacterial promoter is any DNA sequence capable of binding bacterial RNA polymerase and initiating the downstream (3') transcription of a coding sequence (e.g. structural gene) into mRNA. A promoter will have a transcription initiation region which is usually placed proximal to the 5' end of the coding sequence. This transcription initiation region typically includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*) [Raibaud et al., ANNU. REV. GENET. (1984)

18:173]. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et al., NATURE (1977) 198:1056], and maltose. Additional examples include promoter sequences derived from biosynthetic enzymes such as tryptophan (trp) [Goeddel et al., NUC. ACIDS RES. (1980) 8:4057; Yelverton et al., NUCL. ACIDS RES. (1981) 9:731; U.S. Pat. No. 4,738,921; EP Pub. Nos. 036 776 and 121 775, which are incorporated by reference herein]. The β-galactosidase (bla) promoter system [Weissmann (1981) "The cloning of interferon and other mistakes." In Interferon 3 (Ed. I. Gresser)], bacteriophage lambda PL [Shimatake et al., NATURE (1981) 292:128] and T5 [U.S. Pat. No. 4,689,406, which are incorporated by reference herein] promoter systems also provide useful promoter sequences. Preferred methods of the present invention utilize strong promoters, such as the T7 promoter to induce BSP at high levels. Examples of such vectors are well known in the art and include the pET29 series from Novagen, and the pPOP vectors described in WO99/05297, which is incorporated by reference herein. Such expression systems produce high levels of BSP in the host without compromising host cell viability or growth parameters.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551,433, which is incorporated by reference herein]. For example, the tac promoter is a hybrid trp-lac promoter comprised of both trp promoter and lac operon sequences that is regulated by the lac repressor [Amann et al., GENE (1983) 25:167; de Boer et al., PROC. NATL. ACAD. SCI. (1983) 80:21]. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system [Studier et al., J. MOL. BIOL. (1986) 189:113; Tabor et al., Proc Natl. Acad. Sci. (1985) 82:1074]. In addition, a hybrid promoter can also be comprised of a bacteriophage promoter and an *E. coli* operator region (EP Pub. No. 267 851).

In addition to a functioning promoter sequence, an efficient ribosome binding site is also useful for the expression of foreign genes in prokaryotes. In *E. coli*, the ribosome binding site is called the Shine-Dalgarno (SD) sequence and includes an initiation codon (ATG) and a sequence 3-9 nucleotides in length located 3-11 nucleotides upstream of the initiation codon [Shine et al., NATURE (1975) 254:34]. The SD sequence is thought to promote binding of mRNA to the ribosome by the pairing of bases between the SD sequence and the 3' and of *E. coli* 16S rRNA [Steitz et al. "Genetic signals and nucleotide sequences in messenger RNA", In Biological Regulation and Development: Gene Expression (Ed. R. F. Goldberger, 1979)]. To express eukaryotic genes and prokaryotic genes with weak ribosome-binding site [Sambrook et al. "Expression of cloned genes in *Escherichia coli*", Molecular Cloning: A Laboratory Manual, 1989].

The term "bacterial host" or "bacterial host cell" refers to a bacterial that can be, or has been, used as a recipient for recombinant vectors or other transfer DNA. The term includes the progeny of the original bacterial host cell that has been transfected. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding a BSP, are included in the progeny intended by this definition.

The selection of suitable host bacteria for expression of BSP is well known to those of ordinary skill in the art. In selecting bacterial hosts for expression, suitable hosts may include those shown to have, inter alia, good inclusion body formation capacity, low proteolytic activity, and overall robustness. Bacterial hosts are generally available from a variety of sources including, but not limited to, the Bacterial Genetic Stock Center, Department of Biophysics and Medical Physics, University of California (Berkeley, Calif.); and the American Type Culture Collection ("ATCC") (Manassas, Va.). Industrial/pharmaceutical fermentation generally use bacterial derived from K strains (e.g. W3110) or from bacteria derived from B strains (e.g. BL21). These strains are particularly useful because their growth parameters are extremely well known and robust. In addition, these strains are non-pathogenic, which is commercially important for safety and environmental reasons. In one embodiment of the methods of the present invention, the *E. coli* host is a strain of BL21. In another embodiment of the methods of the present invention, the *E. coli* host is a protease minus strain including, but not limited to, OMP- and LON-. In another embodiment of the methods of the present invention, the host cell strain is a species of *Pseudomonas*, including but not limited to, *Pseudomonas fluorescens*, *Pseudomonas aeruginosa*, and *Pseudomonas putida*. *Pseudomonas fluorescens* biovar 1, designated strain MB101, is known to be useful for recombinant production and is available for therapeutic protein production processes. Examples of a *Pseudomonas* expression system include the system available by The Dow Chemical Company as a host strain (Midland, Mich. available on the World Wide Web at dow.com). U.S. Pat. Nos. 4,755,465 and 4,859,600, which are incorporated by reference herein, describe the use of *Pseudomonas* strains as a host cell for hGH production.

Once a recombinant host cell strain has been established (i.e., the expression construct has been introduced into the host cell and host cells with the proper expression construct are isolated), the recombinant host cell strain is cultured under conditions appropriate for production of BSP. As will be apparent to one of skill in the art, the method of culture of the recombinant host cell strain will be dependent on the nature of the expression construct utilized and the identity of the host cell. Recombinant host strains are normally cultured using methods that are well known to the art. Recombinant host cells are typically cultured in liquid medium containing assimilatable sources of carbon, nitrogen, and inorganic salts and, optionally, containing vitamins, amino acids, growth factors, and other proteinaceous culture supplements well known to the art. Liquid media for culture of host cells may optionally contain antibiotics or anti-fungals to prevent the growth of undesirable microorganisms and/or compounds including, but not limited to, antibiotics to select for host cells containing the expression vector.

Recombinant host cells may be cultured in batch or continuous formats, with either cell harvesting (in the case where BSP accumulates intracellularly) or harvesting of culture supernatant in either batch or continuous formats. For production in prokaryotic host cells, batch culture and cell harvest are preferred.

The BSPs of the present invention are normally purified after expression in recombinant systems. The BSP may be purified from host cells by a variety of methods known to the art. Normally, BSP produced in bacterial host cells may be poorly soluble or insoluble (in the form of inclusion bodies). In one embodiment of the present invention, amino acid substitutions may readily be made in the BSP that are selected for the purpose of increasing the solubility of the recombinantly produced protein utilizing the methods disclosed herein as well as those known in the art. In the case of insoluble protein, the protein may be collected from host cell lysates by centrifugation and may further be followed by homogenization of the cells. In the case of poorly soluble protein, compounds including, but not limited to, polyethylene imine (PEI) may be added to induce the precipitation of partially soluble protein. The precipitated protein may then be conveniently collected by centrifugation. Recombinant host cells may be disrupted or homogenized to release the inclusion bodies from within the cells using a variety of methods well known to those of ordinary skill in the art. Host cell disruption or homogenization may be performed using well known techniques including, but not limited to, enzymatic cell disruption, sonication, dounce homogenization, or high pressure release disruption. In one embodiment of the method of the present invention, the high pressure release technique may be used to disrupt the E. coli host cells to release the inclusion bodies of BSP. When handling inclusion bodies of BSP, it may be advantageous to minimize the homogenization time on repetitions in order to maximize the yield of inclusion bodies without loss due to factors such as solubilization, mechanical shearing or proteolysis. The tendency for the formation of inclusion bodies may be enhanced by fusion of the target protein to certain other proteins, such as TrpLE [Georgiou, G. (1996) in Protein engineering: Principles and Practice (Cleland, J. L. and Craik, C. S., eds.), pp. 101-127, Wiley-Liss, New York, Ford, C. F., Suominen, I. and Glatz, C. E. (1991) Protein Expression Purif. 2, 95-107], and by cultivation at elevated temperatures or at a pH other than 7.0.

Insoluble or precipitated BSP may then be solubilized using any of a number of suitable solubilization agents known to the art. Preferably, BSP is solubilized with urea or guanidine hydrochloride. The volume of the solubilized BSP should be minimized so that large batches may be produced using conveniently manageable batch sizes. This factor may be significant in a large-scale commercial setting where the recombinant host may be grown in batches that are thousands of liters in volume. In addition, when manufacturing BSP in a large-scale commercial setting, in particular for human pharmaceutical uses, the avoidance of harsh chemicals that can damage the machinery and container, or the protein product itself, should be avoided, if possible. It has been shown in the method of the present invention that the milder denaturing agent urea can be used to solubilize the BSP inclusion bodies in place of the harsher denaturing agent guanidine hydrochloride. The use of urea significantly reduces the risk of damage to stainless steel equipment utilized in the manufacturing and purification process of BSP while efficiently solubilizing the BSP inclusion bodies.

In the case of soluble BSP, the BSP may be secreted into the periplasmic space or into the culture medium. In addition, soluble BSP may be present in the cytoplasm of the host cells. It may be desired to concentrate soluble BSP prior to performing purification steps. Standard techniques known to those skilled in the art may be used to concentrate soluble BSP from, for example, cell lysates or culture medium. In addition, standard techniques known to those skilled in the art may be used to disrupt host cells and release soluble BSP from the cytoplasm or periplasmic space of the host cells.

When BSP is produced as a fusion protein, the fusion sequence is preferably removed. Removal of a fusion sequence may be accomplished under a number of different conditions, including but not limited to, by enzymatic or chemical cleavage. Enzymatic removal of fusion sequences may be accomplished using methods well known to those in the art. The choice of enzyme for removal of the fusion sequence will be determined by the identity of the fusion, and the reaction conditions will be specified by the choice of enzyme as will be apparent to one skilled in the art. Chemical cleavage may be accomplished using reagents well known to those in the art. One such reagent is cyanogen bromide which cleaves at methionine residues. The cleaved BSP is preferably purified from the cleaved fusion sequence by well known methods. Such methods will be determined by the identity and properties of the fusion sequence and BSP, as will be apparent to one skilled in the art. Peptide bonds for removal of fusion sequence, for example, may be cleaved under exposure to photon energy, increased temperature, decreased temperature, increased pH, decreased pH, exposure to sub-atomic particles, addition of a catalyst, incubation with an enzyme, contact with another chemical functional group, and/or other conditions. For a peptide bond to be cleaved under one or more of these conditions, the non-naturally encoded amino acid may have a functional group with one or more characteristics including, but not limited to, a photo-activated functional group, pH activated functional group, temperature activated functional group, functional group that requires a catalyst, and a functional group that is recognized by a protease, enzyme, or another chemical functional group. Methods for purification may include, but are not limited to, size-exclusion chromatography, hydrophobic interaction chromatography, ion-exchange chromatography or dialysis or any combination thereof.

The BSP is also preferably purified to remove DNA from the protein solution. DNA may be removed by any suitable method known to the art, such as precipitation or ion exchange chromatography, but is preferably removed by precipitation with a nucleic acid precipitating agent, such as, but not limited to, protamine sulfate. BSP may be separated from the precipitated DNA using standard well known methods including, but not limited to, centrifugation or filtration. Removal of host nucleic acid molecules is an important factor in a setting where BSP is to be used to treat humans and the methods of the present invention reduce host cell DNA to pharmaceutically acceptable levels.

Methods for small-scale or large-scale fermentation can also be used in protein expression, including but not limited to, fermentors, shake flasks, fluidized bed bioreactors, hollow fiber bioreactors, roller bottle culture systems, and stirred tank bioreactor systems. Each of these methods can be performed in a batch, fed-batch, or continuous mode process.

Human BSPs of the invention can generally be recovered using methods standard in the art. For example, culture medium or cell lysate can be centrifuged or filtered to remove cellular debris. The supernatant may be concentrated or diluted to a desired volume or diafiltered into a suitable buffer to condition the preparation for further purification. Further purification of the BSP of the present invention includes separating deamidated and clipped forms of the BSP variant from the intact form.

Any of the following exemplary procedures can be employed for purification of BSPs of the invention: affinity chromatography; anion- or cation-exchange chromatography (using, including but not limited to, DEAE SEPHAROSE); chromatography on silica; reverse phase HPLC; gel filtration (using, including but not limited to, SEPHADEX G-75); hydrophobic interaction chromatography; size-exclusion chromatography, metal-chelate chromatography; ultrafiltration/diafiltration; ethanol precipitation; ammonium sulfate precipitation; chromatofocusing; displacement chromatography; electrophoretic procedures (including but not limited to preparative isoelectric focusing), differential solubility (including but not limited to ammonium sulfate precipitation), SDS-PAGE, or extraction.

Proteins of the present invention, including but not limited to, proteins comprising unnatural amino acids, peptides comprising unnatural amino acids, antibodies to proteins comprising unnatural amino acids, binding partners for proteins comprising unnatural amino acids, etc., can be purified, either partially or substantially to homogeneity, according to standard procedures known to and used by those of skill in the art. Accordingly, polypeptides of the invention can be recovered and purified by any of a number of methods well known in the art, including but not limited to, ammonium sulfate or ethanol precipitation, acid or base extraction, column chromatography, affinity column chromatography, anion or cation exchange chromatography, phosphocellulose chromatography, hydrophobic interaction chromatography, hydroxylapatite chromatography, lectin chromatography, gel electrophoresis and the like. Protein refolding steps can be used, as desired, in making correctly folded mature proteins. High performance liquid chromatography (HPLC), affinity chromatography or other suitable methods can be employed in final purification steps where high purity is desired. In one embodiment, antibodies made against unnatural amino acids (or proteins or peptides comprising unnatural amino acids) are used as purification reagents, including but not limited to, for affinity-based purification of proteins or peptides comprising one or more unnatural amino acids(s). Once purified, partially or to homogeneity, as desired, the polypeptides are optionally used for a wide variety of utilities, including but not limited to, as assay components, therapeutics, prophylaxis, diagnostics, research reagents, and/or as immunogens for antibody production.

In addition to other references noted herein, a variety of purification/protein folding methods are well known in the art, including, but not limited to, those set forth in R. Scopes, *Protein Purification*, Springer-Verlag, N.Y. (1982); Deutscher, *Methods in Enzymology* Vol. 182: *Guide to Protein Purification*, Academic Press, Inc. N.Y. (1990); Sandana, (1997) *Bioseparation of Proteins*, Academic Press, Inc.; Bollag et al. (1996) *Protein Methods*, 2nd Edition Wiley-Liss, NY; Walker, (1996) *The Protein Protocols Handbook* Humana Press, NJ, Harris and Angal, (1990) *Protein Purification Applications: A Practical Approach* IRL Press at Oxford, Oxford, England; Harris and Angal, *Protein Purification Methods: A Practical Approach* IRL Press at Oxford, Oxford, England; Scopes, (1993) *Protein Purification: Principles and Practice* 3rd Edition Springer Verlag, NY; Janson and Ryden, (1998) *Protein Purification: Principles, High Resolution Methods and Applications*, Second Edition Wiley-VCH, NY; and Walker (1998), *Protein Protocols on CD-ROM* Humana Press, NJ; and the references cited therein.

One advantage of producing a protein or polypeptide of interest with an unnatural amino acid in a eukaryotic host cell or non-eukaryotic host cell is that typically the proteins or polypeptides will be folded in their native conformations. However, in certain embodiments of the invention, those of skill in the art will recognize that, after synthesis, expression and/or purification, proteins, or peptides can possess a conformation different from the desired conformations of the relevant polypeptides. In one aspect of the invention, the expressed protein or polypeptide is optionally denatured and then renatured. This is accomplished utilizing methods known in the art, including but not limited to, by adding a chaperonin to the protein or polypeptide of interest, by solubilizing the proteins in a chaotropic agent such as guanidine HCl, utilizing protein disulfide isomerase, etc.

In general, it is occasionally desirable to denature and reduce expressed polypeptides and then to cause the polypeptides to re-fold into the preferred conformation. For example, guanidine, urea, DTT, DTE, and/or a chaperonin can be added to a translation product of interest. Methods of reducing, denaturing and renaturing proteins are well known to those of skill in the art (see, the references above, and Debinski, et al. (1993) *J. Biol. Chem.*, 268: 14065-14070; Kreitman and Pastan (1993) *Bioconjug. Chem.*, 4: 581-585; and Buchner, et al., (1992) *Anal. Biochem.*, 205: 263-270). Debinski, et al., for example, describe the denaturation and reduction of inclusion body proteins in guanidine-DTE. The proteins can be refolded in a redox buffer containing, including but not limited to, oxidized glutathione and L-arginine. Refolding reagents can be flowed or otherwise moved into contact with the one or more polypeptide or other expression product, or vice-versa.

In the case of prokaryotic production of BSP, the BSP thus produced may be misfolded and thus lacks or has reduced biological activity. The bioactivity of the protein may be restored by "refolding". In general, misfolded BSP is refolded by solubilizing (where the BSP is also insoluble), unfolding and reducing the polypeptide chain using, for example, one or more chaotropic agents (e.g. urea and/or guanidine) and a reducing agent capable of reducing disulfide bonds (e.g. dithiothreitol, DTT or 2-mercaptoethanol, 2-ME). At a moderate concentration of chaotrope, an oxidizing agent is then added (e.g., oxygen, cystine or cystamine), which allows the reformation of disulfide bonds. BSP may be refolded using standard methods known in the art, such as those described in U.S. Pat. Nos. 4,511,502, 4,511,503, and 4,512,922, which are incorporated by reference herein. The BSP may also be cofolded with other proteins to form heterodimers or heteromultimers. After refolding or cofolding, the BSP is preferably further purified.

General Purification Methods Any one of a variety of isolation steps may be performed on the cell lysate comprising BSP or on any BSP mixtures resulting from any isolation steps including, but not limited to, affinity chromatography, ion exchange chromatography, hydrophobic interaction chromatography, gel filtration chromatography, high performance liquid chromatography ("HPLC"), reversed phase-HPLC ("RP-HPLC"), expanded bed adsorption, or any combination and/or repetition thereof and in any appropriate order.

Equipment and other necessary materials used in performing the techniques described herein are commercially available. Pumps, fraction collectors, monitors, recorders, and entire systems are available from, for example, Applied Biosystems (Foster City, Calif.), Bio-Rad Laboratories, Inc. (Hercules, Calif.), and Amersham Biosciences, Inc. (Piscataway, N.J.). Chromatographic materials including, but not limited to, exchange matrix materials, media, and buffers are also available from such companies.

Equilibration, and other steps in the column chromatography processes described herein such as washing and elution, may be more rapidly accomplished using specialized equipment such as a pump. Commercially available pumps include, but are not limited to, HILOAD® Pump P-50, Peristaltic Pump P-1, Pump P-901, and Pump P-903 (Amersham Biosciences, Piscataway, N.J.).

Examples of fraction collectors include RediFrac Fraction Collector, FRAC-100 and FRAC-200 Fraction Collectors, and SUPERFRAC® Fraction Collector (Amersham Biosciences, Piscataway, N.J.). Mixers are also available to form pH and linear concentration gradients. Commercially available mixers include Gradient Mixer GM-1 and In-Line Mixers (Amersham Biosciences, Piscataway, N.J.).

The chromatographic process may be monitored using any commercially available monitor. Such monitors may be used to gather information like UV, pH, and conductivity. Examples of detectors include Monitor UV-1, UVICORD® S II, Monitor UV-M II, Monitor UV-900, Monitor UPC-900, Monitor pH/C-900, and Conductivity Monitor (Amersham Biosciences, Piscataway, N.J.). Indeed, entire systems are commercially available including the various AKTA® systems from Amersham Biosciences (Piscataway, N.J.).

In one embodiment of the present invention, for example, the BSP may be reduced and denatured by first denaturing the resultant purified BSP in urea, followed by dilution into TRIS buffer containing a reducing agent (such as DTT) at a suitable pH. In another embodiment, the BSP is denatured in urea in a concentration range of between about 2 M to about 9 M, followed by dilution in TRIS buffer at a pH in the range of about 5.0 to about 8.0. The refolding mixture of this embodiment may then be incubated. In one embodiment, the refolding mixture is incubated at room temperature for four to twenty-four hours. The reduced and denatured BSP mixture may then be further isolated or purified.

As stated herein, the pH of the first BSP mixture may be adjusted prior to performing any subsequent isolation steps. In addition, the first BSP mixture or any subsequent mixture thereof may be concentrated using techniques known in the art. Moreover, the elution buffer comprising the first BSP mixture or any subsequent mixture thereof may be exchanged for a buffer suitable for the next isolation step using techniques well known to those of ordinary skill in the art.

Ion Exchange Chromatography In one embodiment, and as an optional, additional step, ion exchange chromatography may be performed on the first BSP mixture. See generally ION EXCHANGE CHROMATOGRAPHY:PRINCIPLES AND METHODS (Cat. No. 18-1114-21, Amersham Biosciences (Piscataway, N.J.)). Commercially available ion exchange columns include HITRAP®, HIPREP®, and HILOAD® Columns (Amersham Biosciences, Piscataway, N.J.). Such columns utilize strong anion exchangers such as Q SEPHAROSE® Fast Flow, Q SEPHAROSE® High Performance, and Q SEPHAROSE® XL; strong cation exchangers such as SP SEPHAROSE® High Performance, SP SEPHAROSE® Fast Flow, and SP SEPHAROSE® XL; weak anion exchangers such as DEAE SEPHAROSE® Fast Flow; and weak cation exchangers such as CM SEPHAROSE® Fast Flow (Amersham Biosciences, Piscataway, N.J.). Anion or cation exchange column chromatography may be performed on the BSP at any stage of the purification process to isolate substantially purified BSP. The cation exchange chromatography step may be performed using any suitable cation exchange matrix. Useful cation exchange matrices include, but are not limited to, fibrous, porous, non-porous, microgranular, beaded, or cross-linked cation exchange matrix materials. Such cation exchange matrix materials include, but are not limited to, cellulose, agarose, dextran, polyacrylate, polyvinyl, polystyrene, silica, polyether, or composites of any of the foregoing.

The cation exchange matrix may be any suitable cation exchanger including strong and weak cation exchangers. Strong cation exchangers may remain ionized over a wide pH range and thus, may be capable of binding BSP over a wide pH range. Weak cation exchangers, however, may lose ionization as a function of pH. For example, a weak cation exchanger may lose charge when the pH drops below about pH 4 or pH 5. Suitable strong cation exchangers include, but are not limited to, charged functional groups such as sulfopropyl (SP), methyl sulfonate (S), or sulfoethyl (SE). The cation exchange matrix may be a strong cation exchanger, preferably having a BSP binding pH range of about 2.5 to about 6.0. Alternatively, the strong cation exchanger may have a BSP binding pH range of about pH 2.5 to about pH 5.5. The cation exchange matrix may be a strong cation exchanger having a BSP binding pH of about 3.0. Alternatively, the cation exchange matrix may be a strong cation exchanger, preferably having a BSP binding pH range of about 6.0 to about 8.0. The cation exchange matrix may be a strong cation exchanger preferably having a BSP binding pH range of about 8.0 to about 12.5. Alternatively, the strong cation exchanger may have a BSP binding pH range of about pH 8.0 to about pH 12.0.

Prior to loading the BSP, the cation exchange matrix may be equilibrated, for example, using several column volumes of a dilute, weak acid, e.g., four column volumes of 20 mM acetic acid, pH 3. Following equilibration, the BSP may be added and the column may be washed one to several times, prior to elution of substantially purified BSP, also using a weak acid solution such as a weak acetic acid or phosphoric acid solution. For example, approximately 2-4 column volumes of 20 mM acetic acid, pH 3, may be used to wash the column. Additional washes using, e.g., 2-4 column volumes of 0.05 M sodium acetate, pH 5.5, or 0.05 M sodium acetate mixed with 0.1 M sodium chloride, pH 5.5, may also be used. Alternatively, using methods known in the art, the cation exchange matrix may be equilibrated using several column volumes of a dilute, weak base.

Alternatively, substantially purified BSP may be eluted by contacting the cation exchanger matrix with a buffer having a sufficiently low pH or ionic strength to displace the BSP from the matrix. The pH of the elution buffer may range from about pH 2.5 to about pH 6.0. More specifically, the pH of the elution buffer may range from about pH 2.5 to about pH 5.5, about pH 2.5 to about pH 5.0. The elution buffer may have a pH of about 3.0. In addition, the quantity of elution buffer may vary widely and will generally be in the range of about 2 to about 10 column volumes.

Following adsorption of BSP to the cation exchanger matrix, substantially purified BSP may be eluted by contacting the matrix with a buffer having a sufficiently high pH or ionic strength to displace BSP from the matrix. Suitable buffers for use in high pH elution of substantially purified BSP include, but are not limited to, citrate, phosphate, formate, acetate, HEPES, and MES buffers ranging in concentration from at least about 5 mM to at least about 100 mM.

Reverse-Phase Chromatography RP-HPLC may be performed to purify proteins following suitable protocols that are known to those of ordinary skill in the art. See, e.g., Pearson et al., ANAL BIOCHEM. (1982) 124:217-230 (1982); Rivier et al., J. CHROM. (1983) 268:112-119; Kunitani et al., J. CHROM. (1986) 359:391-402. RP-HPLC may be performed on the BSP to isolate substantially purified BSP. In this regard, silica derivatized resins with alkyl functionalities with a wide variety of lengths, including, but not limited to, at least about $C_3$ to at least about $C_{30}$, at least about $C_3$ to at least about $C_{20}$, or at least about $C_3$ to at least about $C_{18}$, resins may be used.

Alternatively, a polymeric resin may be used. For example, TosoHaas Amberchrome CG1000sd resin may be used, which is a styrene polymer resin. Cyano or polymeric resins with a wide variety of alkyl chain lengths may also be used. Furthermore, the RP-HPLC column may be washed with a solvent such as ethanol. The Source RP column is another example of a RP-HPLC column A suitable elution buffer containing an ion pairing agent and an organic modifier such as methanol, isopropanol, tetrahydrofuran, acetonitrile or ethanol, may be used to elute the BSP from the RP-HPLC column. The most commonly used ion pairing agents include, but are not limited to, acetic acid, formic acid, perchloric acid, phosphoric acid, trifluoroacetic acid, heptafluorobutyric acid, triethylamine, tetramethylammonium, tetrabutylammonium, triethylammonium acetate. Elution may be performed using one or more gradients or isocratic conditions, with gradient conditions preferred to reduce the separation time and to decrease peak width. Another method involves the use of two gradients with different solvent concentration ranges. Examples of suitable elution buffers for use herein may include, but are not limited to, ammonium acetate and acetonitrile solutions.

Hydrophobic Interaction Chromatography Purification Techniques Hydrophobic interaction chromatography (HIC) may be performed on the BSP. See generally HYDROPHOBIC INTERACTION CHROMATOGRAPHY HANDBOOK: PRINCIPLES AND METHODS (Cat. No. 18-1020-90, Amersham Biosciences (Piscataway, N.J.) which is incorporated by reference herein. Suitable HIC matrices may include, but are not limited to, alkyl- or aryl-substituted matrices, such as butyl-, hexyl-, octyl- or phenyl-substituted matrices including agarose, cross-linked agarose, sepharose, cellulose, silica, dextran, polystyrene, poly(methacrylate) matrices, and mixed mode resins, including but not limited to, a polyethyleneamine resin or a butyl- or phenyl-substituted poly(methacrylate) matrix. Commercially available sources for hydrophobic interaction column chromatography include, but are not limited to, HITRAP®, HIPREP®, and HILOAD® columns (Amersham Biosciences, Piscataway, N.J.).

Briefly, prior to loading, the HIC column may be equilibrated using standard buffers known to those of ordinary skill in the art, such as an acetic acid/sodium chloride solution or HEPES containing ammonium sulfate. After loading the BSP, the column may then washed using standard buffers and conditions to remove unwanted materials but retaining the BSP on the HIC column. BSP may be eluted with about 3 to about 10 column volumes of a standard buffer, such as a HEPES buffer containing EDTA and lower ammonium sulfate concentration than the equilibrating buffer, or an acetic acid/sodium chloride buffer, among others. A decreasing linear salt gradient using, for example, a gradient of potassium phosphate, may also be used to elute the BSP molecules. The eluant may then be concentrated, for example, by filtration such as diafiltration or ultrafiltration. Diafiltration may be utilized to remove the salt used to elute BSP.

Other Purification Techniques Yet another isolation step using, for example, gel filtration (GEL FILTRATION: PRINCIPLES AND METHODS (Cat. No. 18-1022-18, Amersham Biosciences, Piscataway, N.J.) which is incorporated by reference herein, hydroxyapatite chromatography (suitable matrices include, but are not limited to, HA-Ultrogel, High Resolution (Calbiochem), CHT Ceramic Hydroxyapatite (BioRad), Bio—Gel HTP Hydroxyapatite (BioRad)), HPLC, expanded bed adsorption, ultrafiltration, diafiltration, lyophilization, and the like, may be performed on the first BSP mixture or any subsequent mixture thereof, to remove any excess salts and to replace the buffer with a suitable buffer for the next isolation step or even formulation of the final drug product.

The yield of BSP, including substantially purified BSP, may be monitored at each step described herein using techniques known to those of ordinary skill in the art. Such techniques may also used to assess the yield of substantially purified BSP following the last isolation step. For example, the yield of BSP may be monitored using any of several reverse phase high pressure liquid chromatography columns, having a variety of alkyl chain lengths such as cyano RP-HPLC, $C_{18}$RP-HPLC; as well as cation exchange HPLC and gel filtration HPLC.

In specific embodiments of the present invention, the yield of BSP after each purification step may be at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99.9%, or at least about 99.99%, of the BSP in the starting material for each purification step.

Purity may be determined using standard techniques, such as SDS-PAGE, or by measuring BSP using Western blot and ELISA assays. For example, polyclonal antibodies may be generated against proteins isolated from negative control yeast fermentation and the cation exchange recovery. The antibodies may also be used to probe for the presence of contaminating host cell proteins.

RP-HPLC material Vydac C4 (Vydac) consists of silica gel particles, the surfaces of which carry C4-alkyl chains. The separation of BSP from the proteinaceous impurities is based on differences in the strength of hydrophobic interactions. Elution is performed with an acetonitrile gradient in diluted trifluoroacetic acid. Preparative HPLC is performed using a stainless steel column (filled with 2.8 to 3.2 liter of Vydac C4 silicagel). The Hydroxyapatite Ultrogel eluate is acidified by adding trifluoroacetic acid and loaded onto the Vydac C4 column. For washing and elution an acetonitrile gradient in diluted trifluoroacetic acid is used. Fractions are collected and immediately neutralized with phosphate buffer. The BSP fractions which are within the IPC limits are pooled.

DEAE Sepharose (Pharmacia) material consists of diethylaminoethyl (DEAE)-groups which are covalently bound to the surface of Sepharose beads. The binding of BSP to the DEAE groups is mediated by ionic interactions. Acetonitrile and trifluoroacetic acid pass through the column without being retained. After these substances have been washed off, trace impurities are removed by washing the column with acetate buffer at a low pH. Then the column is washed with neutral phosphate buffer and BSP is eluted with a buffer with increased ionic strength. The column is packed with DEAE Sepharose fast flow. The column volume is adjusted to assure a BSP load in the range of 3-10 mg BSP/ml gel. The column is washed with water and equilibration buffer (sodium/potassium phosphate). The pooled fractions of the HPLC eluate are loaded and the column is washed with equilibration buffer. Then the column is washed with washing buffer (sodium acetate buffer) followed by washing with equilibration buffer. Subsequently, BSP is eluted from the column with elution buffer (sodium chloride, sodium/potassium phosphate) and collected in a single fraction in accordance with the master elution profile. The eluate of the DEAE Sepharose column is adjusted to the specified conductivity. The resulting drug substance is sterile filtered into Teflon bottles and stored at −70° C.

Additional methods that may be employed include, but are not limited to, steps to remove endotoxins. Endotoxins are lipopoly-saccharides (LPSs) which are located on the outer membrane of Gram-negative host cells, such as, for example, *Escherichia coli*. Methods for reducing endotoxin levels are known to one skilled in the art and include, but are not limited to, purification techniques using silica supports, glass powder or hydroxyapatite, reverse-phase, affinity, size-exclusion, anion-exchange chromatography, hydrophobic interaction chromatography, a combination of these methods, and the like. Modifications or additional methods may be required to remove contaminants such as co-migrating proteins from the polypeptide of interest.

A wide variety of methods and procedures can be used to assess the yield and purity of a BSP comprising one or more non-naturally encoded amino acids, including but not limited to, the Bradford assay, SDS-PAGE, silver stained SDS-PAGE, coomassie stained SDS-PAGE, mass spectrometry (including but not limited to, MALDI-TOF) and other methods for characterizing proteins known to one skilled in the art.

Characterization of the Heterologous Fusion Proteins of the Present Invention

Numerous methods exist to characterize the fusion proteins of the present invention. Some of these methods include, but are not limited to: SDS-PAGE coupled with protein staining methods or immunoblotting using anti-IgG or anti-HSA antibodies. Other methods include matrix assisted laser desorption/ionization-mass spectrometry (MALDI-MS), liquid chromatography/mass spectrometry, isoelectric focusing, analytical anion exchange, chromatofocusing, and circular dichroism, for example.

VIII. Expression in Alternate Systems

Several strategies have been employed to introduce unnatural amino acids into proteins in non-recombinant host cells, mutagenized host cells, or in cell-free systems. These systems are also suitable for use in making the BSPs of the present invention. Derivatization of amino acids with reactive side-chains such as Lys, Cys and Tyr resulted in the conversion of lysine to $N^2$-acetyl-lysine. Chemical synthesis also provides a straightforward method to incorporate unnatural amino acids. With the recent development of enzymatic ligation and native chemical ligation of peptide fragments, it is possible to make larger proteins. See, e.g., P. E. Dawson and S. B. H. Kent, *Annu. Rev. Biochem*, 69:923 (2000). A general in vitro biosynthetic method in which a suppressor tRNA chemically acylated with the desired unnatural amino acid is added to an in vitro extract capable of supporting protein biosynthesis, has been used to site-specifically incorporate over 100 unnatural amino acids into a variety of proteins of virtually any size. See, e.g., V. W. Cornish, D. Mendel and P. G. Schultz, *Angew. Chem. Int. Ed. Engl.*, 1995, 34:621 (1995); C. J. Noren, S. J. Anthony-Cahill, M.C. Griffith, P. G. Schultz, *A general method for site-specific incorporation of unnatural amino acids into proteins, Science* 244:182-188 (1989); and, J. D. Bain, C. G. Glabe, T. A. Dix, A. R. Chamberlin, E. S. Diala, *Biosynthetic site-specific incorporation of a non-natural amino acid into a polypeptide, J. Am. Chem. Soc.* 111:8013-8014 (1989). A broad range of functional groups has been introduced into proteins for studies of protein stability, protein folding, enzyme mechanism, and signal transduction.

An in vivo method, termed selective pressure incorporation, was developed to exploit the promiscuity of wild-type synthetases. See, e.g., N. Budisa, C. Minks, S. Alefelder, W. Wenger, F. M. Dong, L. Moroder and R. Huber, *FASEB J.*, 13:41 (1999). An auxotrophic strain, in which the relevant metabolic pathway supplying the cell with a particular natural amino acid is switched off, is grown in minimal media containing limited concentrations of the natural amino acid, while transcription of the target gene is repressed. At the onset of a stationary growth phase, the natural amino acid is depleted and replaced with the unnatural amino acid analog. Induction of expression of the recombinant protein results in the accumulation of a protein containing the unnatural analog. For example, using this strategy, o, m and p-fluorophenylalanines have been incorporated into proteins, and exhibit two characteristic shoulders in the UV spectrum which can be easily identified, see, e.g., C. Minks, R. Huber, L. Moroder and N. Budisa, *Anal. Biochem.*, 284:29 (2000); trifluoromethionine has been used to replace methionine in bacteriophage T4 lysozyme to study its interaction with chitooligosaccharide ligands by $^{19}$F NMR, see, e.g., H. Duewel, E. Daub, V. Robinson and J. F. Honek, *Biochemistry*, 36:3404 (1997); and trifluoroleucine has been incorporated in place of leucine, resulting in increased thermal and chemical stability of a leucine-zipper protein. See, e.g., Y. Tang, G. Ghirlanda, W. A. Petka, T. Nakajima, W. F. DeGrado and D. A. Tirrell, *Angew. Chem. Int. Ed. Engl.*, 40:1494 (2001). Moreover, selenomethionine and telluromethionine are incorporated into various recombinant proteins to facilitate the solution of phases in X-ray crystallography. See, e.g., W. A. Hendrickson, J. R. Horton and D. M. Lemaster, *EMBO J.*, 9:1665 (1990); J. O. Boles, K. Lewinski, M. Kunkle, J. D. Odom, B. Dunlap, L. Lebioda and M. Hatada, *Nat. Struct. Biol.*, 1:283 (1994); N. Budisa, B. Steipe, P. Demange, C. Eckerskorn, J. Kellermann and R. Huber, *Eur. J. Biochem.*, 230:788 (1995); and, N. Budisa, W. Kambrock, S. Steinbacher, A. Humm, L. Prade, T. Neuefeind, L. Moroder and R. Huber, *J. Mol. Biol.*, 270:616 (1997). Methionine analogs with alkene or alkyne functionalities have also been incorporated efficiently, allowing for additional modification of proteins by chemical means. See, e.g., J. C. van Hest and D. A. Tirrell, *FEBS Lett.*, 428:68 (1998); J. C. van Hest, K. L. Kiick and D. A. Tirrell, *J. Am. Chem. Soc.*, 122:1282 (2000); and, K. L. Kiick and D. A. Tirrell, Tetrahedron, 56:9487 (2000); U.S. Pat. No. 6,586,207; U.S. Patent Publication 2002/0042097, which are incorporated by reference herein.

The success of this method depends on the recognition of the unnatural amino acid analogs by aminoacyl-tRNA synthetases, which, in general, require high selectivity to insure the fidelity of protein translation. One way to expand the scope of this method is to relax the substrate specificity of aminoacyl-tRNA synthetases, which has been achieved in a limited number of cases. For example, replacement of $Ala^{294}$ by Gly in *Escherichia coli* phenylalanyl-tRNA synthetase (PheRS) increases the size of substrate binding pocket, and results in the acylation of tRNAPhe by p-Cl-phenylalanine (p-Cl-Phe). See, M. Ibba, P. Kast and H. Hennecke, *Biochemistry*, 33:7107 (1994). An *Escherichia coli* strain harboring this mutant PheRS allows the incorporation of p-Cl-phenylalanine or p-Br-phenylalanine in place of phenylalanine. See, e.g., M. Ibba and H. Hennecke, *FEBS Lett.*, 364:272 (1995); and, N. Sharma, R. Furter, P. Kast and D. A. Tirrell, *FEBS Lett.*, 467:37 (2000). Similarly, a point mutation Phe130Ser near the amino acid binding site of *Escherichia coli* tyrosyl-tRNA synthetase was shown to allow azatyrosine to be incorporated more efficiently than tyrosine. See, F. Hamano-Takaku, T. Iwama, S. Saito-Yano, K. Takaku, Y. Monden, M. Kitabatake, D. Soll and S. Nishimura, *J. Biol. Chem.*, 275: 40324 (2000).

Another strategy to incorporate unnatural amino acids into proteins in vivo is to modify synthetases that have proofreading mechanisms. These synthetases cannot discriminate and therefore activate amino acids that are structurally similar to the cognate natural amino acids. This error is corrected at a separate site, which deacylates the mischarged amino acid from the tRNA to maintain the fidelity of protein translation. If the proofreading activity of the synthetase is disabled, structural analogs that are misactivated may escape the editing function and be incorporated. This approach has been demonstrated recently with the valyl-tRNA synthetase (ValRS). See, V. Doring, H. D. Mootz, L. A. Nangle, T. L. Hendrickson, V. de Crecy-Lagard, P. Schimmel and P. Marliere, Science, 292:501 (2001). ValRS can misaminoacylate tRNAVal with Cys, Thr, or aminobutyrate (Abu); these non-cognate amino acids are subsequently hydrolyzed by the editing domain. After random mutagenesis of the Escherichia coli chromosome, a mutant Escherichia coli strain was selected that has a mutation in the editing site of ValRS. This edit-defective ValRS incorrectly charges tRNAVal with Cys. Because Abu sterically resembles Cys (—SH group of Cys is replaced with —CH3 in Abu), the mutant ValRS also incorporates Abu into proteins when this mutant Escherichia coli strain is grown in the presence of Abu. Mass spectrometric analysis shows that about 24% of valines are replaced by Abu at each valine position in the native protein.

Solid-phase synthesis and semisynthetic methods have also allowed for the synthesis of a number of proteins containing novel amino acids. For example, see the following publications and references cited within, which are as follows: Crick, F. H. C., Barrett, L. Brenner, S. Watts-Tobin, R. General nature of the genetic code for proteins. Nature, 192: 1227-1232 (1961); Hofmann, K., Bohn, H. Studies on polypeptides. XXXVI. The effect of pyrazole-imidazole replacements on the S-protein activating potency of an S-peptide fragment, J. Am Chem, 88(24):5914-5919 (1966); Kaiser, E. T. Synthetic approaches to biologically active peptides and proteins including enyzmes, Acc Chem Res, 22:47-54 (1989); Nakatsuka, T., Sasaki, T., Kaiser, E. T. Peptide segment coupling catalyzed by the semisynthetic enzyme thiosubtilisin, J Am Chem Soc, 109:3808-3810 (1987); Schnolzer, M., Kent, S B H. Constructing proteins by dovetailing unprotected synthetic peptides: backbone-engineered HIV protease, Science, 256(5054):221-225 (1992); Chaiken, I. M. Semisynthetic peptides and proteins, CRC Crit Rev Biochem, 11(3):255-301 (1981); Offord, R. E. Protein engineering by chemical means? Protein Eng., 1(3):151-157 (1987); and, Jackson, D. Y., Burnier, J., Quan, C., Stanley, M., Tom, J., Wells, J. A. A Designed Peptide Ligase for Total Synthesis of Ribonuclease A with Unnatural Catalytic Residues, Science, 266(5183): 243 (1994).

Chemical modification has been used to introduce a variety of unnatural side chains, including cofactors, spin labels and oligonucleotides into proteins in vitro. See, e.g., Corey, D. R., Schultz, P. G. Generation of a hybrid sequence-specific single-stranded deoxyribonuclease, Science, 238(4832): 1401-1403 (1987); Kaiser, E. T., Lawrence D. S., Rokita, S. E. The chemical modification of enzymatic specificity, Annu Rev Biochem, 54:565-595 (1985); Kaiser, E. T., Lawrence, D. S. Chemical mutation of enyzme active sites, Science, 226 (4674):505-511 (1984); Neet, K. E., Nanci A, Koshland, D. E. Properties of thiol-subtilisin, J. Biol. Chem, 243(24):6392-6401 (1968); Polgar, L. et M. L. Bender. A new enzyme containing a synthetically formed active site. Thiol-subtilisin. J. Am Chem Soc, 88:3153-3154 (1966); and, Pollack, S. J., Nakayama, G. Schultz, P. G. Introduction of nucleophiles and spectroscopic probes into antibody combining sites, Science, 242(4881): 1038-1040 (1988).

Alternatively, biosynthetic methods that employ chemically modified aminoacyl-tRNAs have been used to incorporate several biophysical probes into proteins synthesized in vitro. See the following publications and references cited within: Brunner, J. New Photolabeling and crosslinking methods, Annu. Rev Biochem, 62:483-514 (1993); and, Krieg, U. C., Walter, P., Hohnson, A. E. Photocrosslinking of the signal sequence of nascent preprolactin of the 54-kilodalton polypeptide of the signal recognition particle, Proc. Natl. Acad. Sci, 83(22):8604-8608 (1986).

Previously, it has been shown that unnatural amino acids can be site-specifically incorporated into proteins in vitro by the addition of chemically aminoacylated suppressor tRNAs to protein synthesis reactions programmed with a gene containing a desired amber nonsense mutation. Using these approaches, one can substitute a number of the common twenty amino acids with close structural homologues, e.g., fluorophenylalanine for phenylalanine, using strains auxotropic for a particular amino acid. See, e.g., Noren, C. J., Anthony-Cahill, Griffith, M. C., Schultz, P. G. A general method for site-specific incorporation of unnatural amino acids into proteins, Science, 244: 182-188 (1989); M. W. Nowak, et al., Science 268:43942 (1995); Bain, J. D., Glabe, C. G., Dix, T. A., Chamberlin, A. R., Diala, E. S. Biosynthetic site-specific Incorporation of a non-natural amino acid into a polypeptide, J. Am Chem Soc, 111:8013-8014 (1989); N. Budisa et al., FASEB J. 13:41-51 (1999); Ellman, J. A., Mendel, D., Anthony-Cahill, S., Noren, C. J., Schultz, P. G. Biosynthetic method for introducing unnatural amino acids site-specifically into proteins, Methods in Enz., vol. 202, 301-336 (1992); and, Mendel, D., Cornish, V. W. & Schultz, P. G. Site-Directed Mutagenesis with an Expanded Genetic Code, Annu Rev Biophys. Biomol Struct. 24, 435-62 (1995).

For example, a suppressor tRNA was prepared that recognized the stop codon UAG and was chemically aminoacylated with an unnatural amino acid. Conventional site-directed mutagenesis was used to introduce the stop codon TAG, at the site of interest in the protein gene. See, e.g., Sayers, J. R., Schmidt, W. Eckstein, F. 5'-3' Exonucleases in phosphorothioate-based olignoucleotide-directed mutagensis, Nucleic Acids Res, 16(3):791-802 (1988). When the acylated suppressor tRNA and the mutant gene were combined in an in vitro transcription/translation system, the unnatural amino acid was incorporated in response to the UAG codon which gave a protein containing that amino acid at the specified position. Experiments using [$^3$H]-Phe and experiments with α-hydroxy acids demonstrated that only the desired amino acid is incorporated at the position specified by the UAG codon and that this amino acid is not incorporated at any other site in the protein. See, e.g., Noren, et al, supra; Kobayashi et al., (2003) Nature Structural Biology 10(6):425-432; and, Ellman, J. A., Mendel, D., Schultz, P. G. Site-specific incorporation of novel backbone structures into proteins, Science, 255(5041):197-200 (1992).

Microinjection techniques have also been use incorporate unnatural amino acids into proteins. See, e.g., M. W. Nowak, P. C. Kearney, J. R. Sampson, M. E. Saks, C. G. Labarca, S. K. Silverman, W. G. Zhong, J. Thorson, J. N. Abelson, N. Davidson, P. G. Schultz, D. A. Dougherty and H. A. Lester, Science, 268:439 (1995); and, D. A. Dougherty, Curr. Opin. Chem. Biol., 4:645 (2000). A Xenopus oocyte was coinjected with two RNA species made in vitro: an mRNA encoding the target protein with a UAG stop codon at the amino acid position of interest and an amber suppressor tRNA aminoacylated with the desired unnatural amino acid. The translational machinery of the oocyte then inserts the unnatural amino acid at the position specified by UAG. This method has allowed in vivo structure-function studies of integral membrane proteins, which are generally not amenable to in vitro expression systems. Examples include the incorporation of a fluorescent amino acid into tachykinin neurokinin-2 receptor to measure distances by fluorescence resonance energy transfer, see, e.g., G. Turcatti, K. Nemeth, M. D. Edgerton, U. Meseth, F. Talabot, M. Peitsch, J. Knowles, H. Vogel and A. Chollet, *J. Biol. Chem.*, 271:19991 (1996); the incorporation of biotinylated amino acids to identify surface-exposed residues in ion channels, see, e.g., J. P. Gallivan, H. A. Lester and D. A. Dougherty, *Chem. Biol.*, 4:739 (1997); the use of caged tyrosine analogs to monitor conformational changes in an ion channel in real time, see, e.g., J. C. Miller, S. K. Silverman, P. M. England, D. A. Dougherty and H. A. Lester, Neuron, 20:619 (1998); and, the use of alpha hydroxy amino acids to change ion channel backbones for probing their gating mechanisms. See, e.g., P. M. England, Y. Zhang, D. A. Dougherty and H. A. Lester, Cell, 96:89 (1999); and, T. Lu, A. Y. Ting, J. Mainland, L. Y. Jan, P. G. Schultz and J. Yang, *Nat. Neurosci.*, 4:239 (2001).

The ability to incorporate unnatural amino acids directly into proteins in vivo offers the advantages of high yields of mutant proteins, technical ease, the potential to study the mutant proteins in cells or possibly in living organisms and the use of these mutant proteins in therapeutic treatments. The ability to include unnatural amino acids with various sizes, acidities, nucleophilicities, hydrophobicities, and other properties into proteins can greatly expand our ability to rationally and systematically manipulate the structures of proteins, both to probe protein function and create new proteins or organisms with novel properties. However, the process is difficult, because the complex nature of tRNA-synthetase interactions that are required to achieve a high degree of fidelity in protein translation.

In one attempt to site-specifically incorporate para-F-Phe, a yeast amber suppressor tRNAPheCUA/phenylalanyl-tRNA synthetase pair was used in a p-F-Phe resistant, Phe auxotrophic *Escherichia coli* strain. See, e.g., R. Furter, *Protein Sci.*, 7:419 (1998).

It may also be possible to obtain expression of BSP of the present invention using a cell-free (in-vitro) translational system. In these systems, which can include either mRNA as a template (in-vitro translation) or DNA as a template (combined in-vitro transcription and translation), the in vitro synthesis is directed by the ribosomes. Considerable effort has been applied to the development of cell-free protein expression systems. See, e.g., Kim, D. M. and J. R. Swartz, *Biotechnology and Bioengineering*, 74:309-316 (2001); Kim, D. M. and J. R. Swartz, *Biotechnology Letters*, 22, 1537-1542, (2000); Kim, D. M., and J. R. Swartz, *Biotechnology Progress*, 16, 385-390, (2000); Kim, D. M., and J. R. Swartz, *Biotechnology and Bioengineering*, 66, 180-188, (1999); and Patnaik, R. and J. R. Swartz, *Biotechniques* 24, 862-868, (1998); U.S. Pat. No. 6,337,191; U.S. Patent Publication No. 2002/0081660; WO 00/55353; WO 90/05785, which are incorporated by reference herein. Another approach that may be applied to the expression of BSPs comprising a non-naturally encoded amino acid includes the mRNA-peptide fusion technique. See, e.g., R. Roberts and J. Szostak, *Proc. Natl. Acad. Sci. (USA)* 94:12297-12302 (1997); A. Frankel, et al., *Chemistry & Biology* 10:1043-1050 (2003). In this approach, an mRNA template linked to puromycin is translated into peptide on the ribosome. If one or more tRNA molecules has been modified, non-natural amino acids can be incorporated into the peptide as well. After the last mRNA codon has been read, puromycin captures the C-terminus of the peptide. If the resulting mRNA-peptide conjugate is found to have interesting properties in an in vitro assay, its identity can be easily revealed from the mRNA sequence. In this way, one may screen libraries of BSPs comprising one or more non-naturally encoded amino acids to identify polypeptides having desired properties. More recently, in vitro ribosome translations with purified components have been reported that permit the synthesis of peptides substituted with non-naturally encoded amino acids. See, e.g., A. Forster et al., *Proc. Natl. Acad. Sci. (USA)* 100:6353 (2003).

IX. Macromolecular Polymers Coupled to BSP

Various modifications to the non-natural amino acid polypeptides described herein can be effected using the compositions, methods, techniques and strategies described herein. These modifications include the incorporation of further functionality onto the non-natural amino acid component of the polypeptide, including but not limited to, a label; a dye; a polymer; a water-soluble polymer; a derivative of polyethylene glycol; a photocrosslinker; a radionuclide; cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a water-soluble dendimer; a cyclodextrin; an inhibitory ribonucleic acid; a biomaterial; a nanoparticle; a spin label; a fluorophore, a metal-containing moiety; a radioactive moiety; a novel functional group; a group that covalently or noncovalently interacts with other molecules; a photocaged moiety; a photoisomerizable moiety; biotin; a derivative of biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; or any combination of the above, or any other desirable compound or substance. As an illustrative, non-limiting example of the compositions, methods, techniques and strategies described herein, the following description will focus on adding macromolecular polymers to the non-natural amino acid polypeptide with the understanding that the compositions, methods, techniques and strategies described thereto are also applicable (with appropriate modifications, if necessary and for which one of skill in the art could make with the disclosures herein) to adding other functionalities, including but not limited to those listed above.

A wide variety of macromolecular polymers and other molecules can be linked to BSPs of the present invention to modulate biological properties of the BSP, and/or provide new biological properties to the BSP molecule. These macromolecular polymers can be linked to BSP via a naturally encoded amino acid, via a non-naturally encoded amino acid, or any functional substituent of a natural or non-natural amino acid, or any substituent or functional group added to a natural or non-natural amino acid. The molecular weight of the polymer may be of a wide range, including but not limited to, between about 100 Da and about 100,000 Da or more.

The present invention provides substantially homogenous preparations of polymer:protein conjugates. "Substantially homogenous" as used herein means that polymer:protein conjugate molecules are observed to be greater than half of the total protein. The polymer:protein conjugate has biological activity and the present "substantially homogenous"

PEGylated BSP preparations provided herein are those which are homogenous enough to display the advantages of a homogenous preparation, e.g., ease in clinical application in predictability of lot to lot pharmacokinetics.

One may also choose to prepare a mixture of polymer: protein conjugate molecules, and the advantage provided herein is that one may select the proportion of mono-polymer: protein conjugate to include in the mixture. Thus, if desired, one may prepare a mixture of various proteins with various numbers of polymer moieties attached (i.e., di-, tri-, tetra-, etc.) and combine said conjugates with the mono-polymer: protein conjugate prepared using the methods of the present invention, and have a mixture with a predetermined proportion of mono-polymer:protein conjugates.

The polymer selected may be water soluble so that the protein to which it is attached does not precipitate in an aqueous environment, such as a physiological environment. The polymer may be branched or unbranched. Preferably, for therapeutic use of the end-product preparation, the polymer will be pharmaceutically acceptable.

The proportion of polyethylene glycol molecules to protein molecules will vary, as will their concentrations in the reaction mixture. In general, the optimum ratio (in terms of efficiency of reaction in that there is minimal excess unreacted protein or polymer) may be determined by the molecular weight of the polyethylene glycol selected and on the number of available reactive groups available. As relates to molecular weight, typically the higher the molecular weight of the polymer, the fewer number of polymer molecules which may be attached to the protein. Similarly, branching of the polymer should be taken into account when optimizing these parameters. Generally, the higher the molecular weight (or the more branches) the higher the polymer:protein ratio.

As used herein, and when contemplating PEG:BSP conjugates, the term "therapeutically effective amount" refers to an amount which gives the desired benefit to a patient. For example, the term "therapeutically effective amount" refers to an amount which gives a decrease in blood glucose that provides benefit to a patient if the BSP is GLP-1. For example, the term "therapeutically effective amount" refers to an amount which modulates viral level that provides benefit to a patient if the BSP is T-20. The amount will vary from one individual to another and will depend upon a number of factors, including the overall physical condition of the patient and the underlying cause of the condition to be treated (e.g. hyperglycemia if the BSP is GLP-1). The amount of BSP used for therapy gives an acceptable rate of change and maintains desired response at a beneficial level. A therapeutically effective amount of the present compositions may be readily ascertained by one skilled in the art using publicly available materials and procedures.

The water soluble polymer may be any structural form including but not limited to linear, forked or branched. Typically, the water soluble polymer is a poly(alkylene glycol), such as poly(ethylene glycol) (PEG), but other water soluble polymers can also be employed. By way of example, PEG is used to describe certain embodiments of this invention.

PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented as linked to the BSP by the formula:

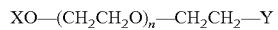

where n is 2 to 10,000 and X is H or a terminal modification, including but not limited to, a $C_{1-4}$ alkyl.

In some cases, a PEG used in the invention terminates on one end with hydroxy or methoxy, i.e., X is H or $CH_3$ ("methoxy PEG"). Alternatively, the PEG can terminate with a reactive group, thereby forming a bifunctional polymer. Typical reactive groups can include those reactive groups that are commonly used to react with the functional groups found in the 20 common amino acids (including but not limited to, maleimide groups, activated carbonates (including but not limited to, p-nitrophenyl ester), activated esters (including but not limited to, N-hydroxysuccinimide, p-nitrophenyl ester) and aldehydes) as well as functional groups that are inert to the 20 common amino acids but that react specifically with complementary functional groups present in non-naturally encoded amino acids (including but not limited to, azide groups, alkyne groups). It is noted that the other end of the PEG, which is shown in the above formula by Y, will attach either directly or indirectly to a BSP via a naturally-occurring or non-naturally encoded amino acid. For instance, Y may be an amide, carbamate or urea linkage to an amine group (including but not limited to, the epsilon amine of lysine or the N-terminus) of the polypeptide. Alternatively, Y may be a maleimide linkage to a thiol group (including but not limited to, the thiol group of cysteine). Alternatively, Y may be a linkage to a residue not commonly accessible via the 20 common amino acids. For example, an azide group on the PEG can be reacted with an alkyne group on the BSP to form a Huisgen [3+2] cycloaddition product. Alternatively, an alkyne group on the PEG can be reacted with an azide group present in a non-naturally encoded amino acid to form a similar product. In some embodiments, a strong nucleophile (including but not limited to, hydrazine, hydrazide, hydroxylamine, semicarbazide) can be reacted with an aldehyde or ketone group present in a non-naturally encoded amino acid to form a hydrazone, oxime or semicarbazone, as applicable, which in some cases can be further reduced by treatment with an appropriate reducing agent. Alternatively, the strong nucleophile can be incorporated into the BSP via a non-naturally encoded amino acid and used to react preferentially with a ketone or aldehyde group present in the water soluble polymer.

Any molecular mass for a PEG can be used as practically desired, including but not limited to, from about 100 Daltons (Da) to 100,000 Da or more as desired (including but not limited to, sometimes 0.1-50 kDa or 1040 kDa). Branched chain PEGs, including but not limited to, PEG molecules with each chain having a MW ranging from 1-100 kDa (including but not limited to, 1-50 kDa or 5-20 kDa) can also be used. A wide range of PEG molecules are described in, including but not limited to, the Shearwater Polymers, Inc. catalog, Nektar Therapeutics catalog, incorporated herein by reference.

Generally, at least one terminus of the PEG molecule is available for reaction with the non-naturally-encoded amino acid. For example, PEG derivatives bearing alkyne and azide moieties for reaction with amino acid side chains can be used to attach PEG to non-naturally encoded amino acids as described herein. If the non-naturally encoded amino acid comprises an azide, then the PEG will typically contain either an alkyne moiety to effect formation of the [3+2] cycloaddition product or an activated PEG species (i.e., ester, carbonate) containing a phosphine group to effect formation of the amide linkage. Alternatively, if the non-naturally encoded amino acid comprises an alkyne, then the PEG will typically contain an azide moiety to effect formation of the [3+2] Huisgen cycloaddition product. If the non-naturally encoded amino acid comprises a carbonyl group, the PEG will typically comprise a potent nucleophile (including but not limited to, a hydrazide, hydrazine, hydroxylamine, or semicarbazide functionality) in order to effect formation of corresponding hydrazone, oxime, and semicarbazone linkages, respectively. In other alternatives, a reverse of the orientation of the reactive groups described above can be used, i.e., an azide moiety in the non-naturally encoded amino acid can be reacted with a PEG derivative containing an alkyne.

In some embodiments, the BSP variant with a PEG derivative contains a chemical functionality that is reactive with the chemical functionality present on the side chain of the non-naturally encoded amino acid.

The invention provides in some embodiments azide- and acetylene-containing polymer derivatives comprising a water soluble polymer backbone having an average molecular weight from about 800 Da to about 100,000 Da. The polymer backbone of the water-soluble polymer can be poly(ethylene glycol). However, it should be understood that a wide variety of water soluble polymers including but not limited to poly(ethylene)glycol and other related polymers, including poly(dextran) and poly(propylene glycol), are also suitable for use in the practice of this invention and that the use of the term PEG or poly(ethylene glycol) is intended to encompass and include all such molecules. The term PEG includes, but is not limited to, poly(ethylene glycol) in any of its forms, including bifunctional PEG, multiarmed PEG, derivatized PEG, forked PEG, branched PEG, pendent PEG (i.e. PEG or related polymers having one or more functional groups pendent to the polymer backbone), or PEG with degradable linkages therein.

PEG is typically clear, colorless, odorless, soluble in water, stable to heat, inert to many chemical agents, does not hydrolyze or deteriorate, and is generally non-toxic. Poly(ethylene glycol) is considered to be biocompatible, which is to say that PEG is capable of coexistence with living tissues or organisms without causing harm. More specifically, PEG is substantially non-immunogenic, which is to say that PEG does not tend to produce an immune response in the body. When attached to a molecule having some desirable function in the body, such as a biologically active agent, the PEG tends to mask the agent and can reduce or eliminate any immune response so that an organism can tolerate the presence of the agent. PEG conjugates tend not to produce a substantial immune response or cause clotting or other undesirable effects. PEG having the formula —CH$_2$CH$_2$O—(CH$_2$CH$_2$O)$_n$—CH$_2$CH$_2$—, where n is from about 3 to about 4000, typically from about 20 to about 2000, is suitable for use in the present invention. PEG having a molecular weight of from about 800 Da to about 100,000 Da are in some embodiments of the present invention particularly useful as the polymer backbone.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, glycerol oligomers, pentaerythritol and sorbitol. The central branch moiety can also be derived from several amino acids, such as lysine. The branched poly(ethylene glycol) can be represented in general form as R(-PEG-OH)$_m$ in which R is derived from a core moiety, such as glycerol, glycerol oligomers, or pentaerythritol, and m represents the number of arms. Multi-armed PEG molecules, such as those described in U.S. Pat. Nos. 5,932,462 5,643,575; 5,229,490; 4,289,872; U.S. Pat. Appl. 2003/0143596; WO 96/21469; and WO 93/21259, each of which is incorporated by reference herein in its entirety, can also be used as the polymer backbone.

Branched PEG can also be in the form of a forked PEG represented by PEG(—YCHZ$_2$)$_n$, where Y is a linking group and Z is an activated terminal group linked to CH by a chain of atoms of defined length.

Yet another branched form, the pendant PEG, has reactive groups, such as carboxyl, along the PEG backbone rather than at the end of PEG chains.

In addition to these forms of PEG, the polymer can also be prepared with weak or degradable linkages in the backbone. For example, PEG can be prepared with ester linkages in the polymer backbone that are subject to hydrolysis. As shown below, this hydrolysis results in cleavage of the polymer into fragments of lower molecular weight:

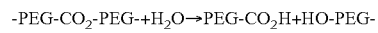

-PEG-CO$_2$-PEG-+H$_2$O→PEG-CO$_2$H+HO-PEG-

It is understood by those skilled in the art that the term poly(ethylene glycol) or PEG represents or includes all the forms known in the art including but not limited to those disclosed herein.

Many other polymers are also suitable for use in the present invention. In some embodiments, polymer backbones that are water-soluble, with from 2 to about 300 termini, are particularly useful in the invention. Examples of suitable polymers include, but are not limited to, other poly(alkylene glycols), such as poly(propylene glycol) ("PPG"), copolymers thereof (including but not limited to copolymers of ethylene glycol and propylene glycol), terpolymers thereof, mixtures thereof, and the like. Although the molecular weight of each chain of the polymer backbone can vary, it is typically in the range of from about 800 Da to about 100,000 Da, often from about 6,000 Da to about 80,000 Da.

Those of ordinary skill in the art will recognize that the foregoing list for substantially water soluble backbones is by no means exhaustive and is merely illustrative, and that all polymeric materials having the qualities described above are contemplated as being suitable for use in the present invention.

In some embodiments of the present invention the polymer derivatives are "multi-functional", meaning that the polymer backbone has at least two termini, and possibly as many as about 300 termini, functionalized or activated with a functional group. Multifunctional polymer derivatives include, but are not limited to, linear polymers having two termini, each terminus being bonded to a functional group which may be the same or different.

In one embodiment, the polymer derivative has the structure:

X-A-POLY-B-N=N=N wherein:

N=N=N is an azide moiety;

B is a linking moiety, which may be present or absent;

POLY is a water-soluble non-antigenic polymer;

A is a linking moiety, which may be present or absent and which may be the same as B or different; and X is a second functional group.

Examples of a linking moiety for A and B include, but are not limited to, a multiply-functionalized alkyl group containing up to 18, and more preferably between 1-10 carbon atoms. A heteroatom such as nitrogen, oxygen or sulfur may be included with the alkyl chain. The alkyl chain may also be branched at a heteroatom. Other examples of a linking moiety for A and B include, but are not limited to, a multiply functionalized aryl group, containing up to 10 and more preferably 5-6 carbon atoms. The aryl group may be substituted with one more carbon atoms, nitrogen, oxygen or sulfur atoms. Other examples of suitable linking groups include those linking groups described in U.S. Pat. Nos. 5,932,462; 5,643,575; and U.S. Pat. Appl. Publication 2003/0143596, each of which is incorporated by reference herein. Those of ordinary skill in the art will recognize that the foregoing list for linking moieties is by no means exhaustive and is merely illustrative, and that all linking moieties having the qualities described above are contemplated to be suitable for use in the present invention.

Examples of suitable functional groups for use as X include, but are not limited to, hydroxyl, protected hydroxyl, alkoxyl, active ester, such as N-hydroxysuccinimidyl esters and 1-benzotriazolyl esters, active carbonate, such as N-hydroxysuccinimidyl carbonates and 1-benzotriazolyl carbonates, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, tresylate, alkene, ketone, and azide. As is understood by those skilled in the art, the selected X moiety should be compatible with the azide group so that reaction with the azide group does not occur. The azide-containing polymer derivatives may be homobifunctional, meaning that the second functional group (i.e., X) is also an azide moiety, or heterobifunctional, meaning that the second functional group is a different functional group.

The term "protected" refers to the presence of a protecting group or moiety that prevents reaction of the chemically reactive functional group under certain reaction conditions. The protecting group will vary depending on the type of chemically reactive group being protected. For example, if the chemically reactive group is an amine or a hydrazide, the protecting group can be selected from the group of tert-butyloxycarbonyl (t-Boc) and 9-fluorenylmethoxycarbonyl (Fmoc). If the chemically reactive group is a thiol, the protecting group can be orthopyridyldisulfide. If the chemically reactive group is a carboxylic acid, such as butanoic or propionic acid, or a hydroxyl group, the protecting group can be benzyl or an alkyl group such as methyl, ethyl, or tert-butyl. Other protecting groups known in the art may also be used in the present invention.

Specific examples of terminal functional groups in the literature include, but are not limited to, N-succinimidyl carbonate (see e.g., U.S. Pat. Nos. 5,281,698, 5,468,478), amine (see, e.g., Buckmann et al. Makromol. Chem. 182:1379 (1981), Zalipsky et al. Eur. Polym. J. 19:1177 (1983)), hydrazide (See, e.g., Andresz et al. Makromol. Chem. 179: 301 (1978)), succinimidyl propionate and succinimidyl butanoate (see, e.g., Olson et al. in Poly(ethylene glycol) Chemistry & Biological Applications, pp 170-181, Harris & Zalipsky Eds., ACS, Washington, D.C., 1997; see also U.S. Pat. No. 5,672,662), succinimidyl succinate (See, e.g., Abuchowski et al. Cancer Biochem. Biophys. 7:175 (1984) and Joppich et al. Makrolol. Chem. 180:1381 (1979), succinimidyl ester (see, e.g., U.S. Pat. No. 4,670,417), benzotriazole carbonate (see, e.g., U.S. Pat. No. 5,650,234), glycidyl ether (see, e.g., Pitha et al. Eur. J. Biochem. 94:11 (1979), Elling et al., Biotech. Appl. Biochem. 13:354 (1991), oxycarbonylimidazole (see, e.g., Beauchamp, et al., Anal. Biochem. 131:25 (1983), Tondelli et al. J. Controlled Release 1:251 (1985)), p-nitrophenyl carbonate (see, e.g., Veronese, et al., Appl. Biochem. Biotech., 11: 141 (1985); and Sartore et al., Appl. Biochem. Biotech., 27:45 (1991)), aldehyde (see, e.g., Harris et al. J. Polym. Sci. Chem. Ed. 22:341 (1984), U.S. Pat. No. 5,824,784, U.S. Pat. No. 5,252,714), maleimide (see, e.g., Goodson et al. Biotechnology (NY) 8:343 (1990), Romani et al. in Chemistry of Peptides and Proteins 2:29 (1984)), and Kogan, Synthetic Comm. 22:2417 (1992)), orthopyridyl-disulfide (see, e.g., Woghiren, et al. Bioconj. Chem. 4:314(1993)), acrylol (see, e.g., Sawhney et al., Macromolecules, 26:581 (1993)), vinylsulfone (see, e.g., U.S. Pat. No. 5,900,461). All of the above references and patents are incorporated herein by reference.

In certain embodiments of the present invention, the polymer derivatives of the invention comprise a polymer backbone having the structure:

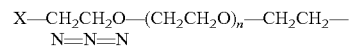

wherein:

X is a functional group as described above; and n is about 20 to about 4000.

In another embodiment, the polymer derivatives of the invention comprise a polymer backbone having the structure:

wherein:

W is an aliphatic or aromatic linker moiety comprising between 1-10 carbon atoms;

n is about 20 to about 4000; and

X is a functional group as described above. m is between 1 and 10.

The azide-containing PEG derivatives of the invention can be prepared by a variety of methods known in the art and/or disclosed herein. In one method, shown below, a water soluble polymer backbone having an average molecular weight from about 800 Da to about 100,000 Da, the polymer backbone having a first terminus bonded to a first functional group and a second terminus bonded to a suitable leaving group, is reacted with an azide anion (which may be paired with any of a number of suitable counter-ions, including sodium, potassium, tert-butylammonium and so forth). The leaving group undergoes a nucleophilic displacement and is replaced by the azide moiety, affording the desired azide-containing PEG polymer.

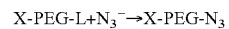

As shown, a suitable polymer backbone for use in the present invention has the formula X-PEG-L, wherein PEG is poly(ethylene glycol) and X is a functional group which does not react with azide groups and L is a suitable leaving group. Examples of suitable functional groups include, but are not limited to, hydroxyl, protected hydroxyl, acetal, alkenyl, amine, aminooxy, protected amine, protected hydrazide, protected thiol, carboxylic acid, protected carboxylic acid, maleimide, dithiopyridine, and vinylpyridine, and ketone.

Examples of suitable leaving groups include, but are not limited to, chloride, bromide, iodide, mesylate, tresylate, and tosylate.

In another method for preparation of the azide-containing polymer derivatives of the present invention, a linking agent bearing an azide functionality is contacted with a water soluble polymer backbone having an average molecular weight from about 800 Da to about 100,000 Da, wherein the linking agent bears a chemical functionality that will react selectively with a chemical functionality on the PEG polymer, to form an azide-containing polymer derivative product wherein the azide is separated from the polymer backbone by a linking group.

An exemplary reaction scheme is shown below:

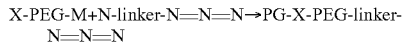

X-PEG-M+N-linker-N=N=N→PG-X-PEG-linker-N=N=N wherein:

PEG is poly(ethylene glycol) and X is a capping group such as alkoxy or a functional group as described above; and M is a functional group that is not reactive with the azide functionality but that will react efficiently and selectively with the N functional group.

Examples of suitable functional groups include, but are not limited to, M being a carboxylic acid, carbonate or active ester if N is an amine; M being a ketone if N is a hydrazide or aminooxy moiety; M being a leaving group if N is a nucleophile.

Purification of the crude product may be accomplished by known methods including, but are not limited to, precipitation of the product followed by chromatography, if necessary.

A more specific example is shown below in the case of PEG diamine, in which one of the amines is protected by a protecting group moiety such as tert-butyl-Boc and the resulting mono-protected PEG diamine is reacted with a linking moiety that bears the azide functionality:

BocHN-PEG-NH$_2$+HO$_2$C—(CH$_2$)$_3$—N=N=N

In this instance, the amine group can be coupled to the carboxylic acid group using a variety of activating agents such as thionyl chloride or carbodiimide reagents and N-hydroxysuccinimide or N-hydroxybenzotriazole to create an amide bond between the monoamine PEG derivative and the azide-bearing linker moiety. After successful formation of the amide bond, the resulting N-tert-butyl-Boc-protected azide-containing derivative can be used directly to modify bioactive molecules or it can be further elaborated to install other useful functional groups. For instance, the N-t-Boc group can be hydrolyzed by treatment with strong acid to generate an omega-amino-PEG-azide. The resulting amine can be used as a synthetic handle to install other useful functionality such as maleimide groups, activated disulfides, activated esters and so forth for the creation of valuable heterobifunctional reagents.

Heterobifunctional derivatives are particularly useful when it is desired to attach different molecules to each terminus of the polymer. For example, the omega-N-amino-N-azido PEG would allow the attachment of a molecule having an activated electrophilic group, such as an aldehyde, ketone, activated ester, activated carbonate and so forth, to one terminus of the PEG and a molecule having an acetylene group to the other terminus of the PEG.

In another embodiment of the invention, the polymer derivative has the structure:

X-A-POLY-B-C≡C—R wherein:

R can be either H or an alkyl, alkene, alkyoxy, or aryl or substituted aryl group;

B is a linking moiety, which may be present or absent;

POLY is a water-soluble non-antigenic polymer;

A is a linking moiety, which may be present or absent and which may be the same as B or different; and X is a second functional group.

Examples of a linking moiety for A and B include, but are not limited to, a multiply-functionalized alkyl group containing up to 18, and more preferably between 1-10 carbon atoms. A heteroatom such as nitrogen, oxygen or sulfur may be included with the alkyl chain. The alkyl chain may also be branched at a heteroatom. Other examples of a linking moiety for A and B include, but are not limited to, a multiply functionalized aryl group, containing up to 10 and more preferably 5-6 carbon atoms. The aryl group may be substituted with one more carbon atoms, nitrogen, oxygen, or sulfur atoms. Other examples of suitable linking groups include those linking groups described in U.S. Pat. Nos. 5,932,462 and 5,643,575 and U.S. Pat. Appl. Publication 2003/0143596, each of which is incorporated by reference herein. Those of ordinary skill in the art will recognize that the foregoing list for linking moieties is by no means exhaustive and is intended to be merely illustrative, and that a wide variety of linking moieties having the qualities described above are contemplated to be useful in the present invention.

Examples of suitable functional groups for use as X include hydroxyl, protected hydroxyl, alkoxyl, active ester, such as N-hydroxysuccinimidyl esters and 1-benzotriazolyl esters, active carbonate, such as N-hydroxysuccinimidyl carbonates and 1-benzotriazolyl carbonates, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, and tresylate, alkene, ketone, and acetylene. As would be understood, the selected X moiety should be compatible with the acetylene group so that reaction with the acetylene group does not occur. The acetylene-containing polymer derivatives may be homobifunctional, meaning that the second functional group (i.e., X) is also an acetylene moiety, or heterobifunctional, meaning that the second functional group is a different functional group.

In another embodiment of the present invention, the polymer derivatives comprise a polymer backbone having the structure:

X—CH$_2$CH$_2$O—(CH$_2$CH$_2$O)$_n$—CH$_2$CH$_2$—O—(CH$_2$)$_m$C≡CH wherein:

X is a functional group as described above;

n is about 20 to about 4000; and m is between 1 and 10.

Specific examples of each of the heterobifunctional PEG polymers are shown below.

The acetylene-containing PEG derivatives of the invention can be prepared using methods known to those skilled in the art and/or disclosed herein. In one method, a water soluble polymer backbone having an average molecular weight from about 800 Da to about 100,000 Da, the polymer backbone having a first terminus bonded to a first functional group and a second terminus bonded to a suitable nucleophilic group, is reacted with a compound that bears both an acetylene functionality and a leaving group that is suitable for reaction with the nucleophilic group on the PEG. When the PEG polymer bearing the nucleophilic moiety and the molecule bearing the leaving group are combined, the leaving group undergoes a nucleophilic displacement and is replaced by the nucleophilic moiety, affording the desired acetylene-containing polymer.

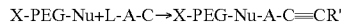

As shown, a preferred polymer backbone for use in the reaction has the formula X-PEG-Nu, wherein PEG is poly(ethylene glycol), Nu is a nucleophilic moiety and X is a functional group that does not react with Nu, L or the acetylene functionality.

Examples of Nu include, but are not limited to, amine, alkoxy, aryloxy, sulfhydryl, imino, carboxylate, hydrazide, aminoxy groups that would react primarily via a SN2-type mechanism. Additional examples of Nu groups include those functional groups that would react primarily via an nucleophilic addition reaction. Examples of L groups include chloride, bromide, iodide, mesylate, tresylate, and tosylate and other groups expected to undergo nucleophilic displacement as well as ketones, aldehydes, thioesters, olefins, alpha-beta unsaturated carbonyl groups, carbonates and other electrophilic groups expected to undergo addition by nucleophiles.

In another embodiment of the present invention, A is an aliphatic linker of between 1-10 carbon atoms or a substituted aryl ring of between 6-14 carbon atoms. X is a functional group which does not react with azide groups and L is a suitable leaving group In another method for preparation of the acetylene-containing polymer derivatives of the invention, a PEG polymer having an average molecular weight from about 800 Da to about 100,000 Da, bearing either a protected functional group or a capping agent at one terminus and a suitable leaving group at the other terminus is contacted by an acetylene anion.

An exemplary reaction scheme is shown below:

wherein:

PEG is poly(ethylene glycol) and X is a capping group such as alkoxy or a functional group as described above; and R' is either H, an alkyl, alkoxy, aryl or aryloxy group or a substituted alkyl, alkoxyl, aryl or aryloxy group.

In the example above, the leaving group L should be sufficiently reactive to undergo SN2-type displacement when contacted with a sufficient concentration of the acetylene anion. The reaction conditions required to accomplish SN2 displacement of leaving groups by acetylene anions are well known in the art.

Purification of the crude product can usually be accomplished by methods known in the art including, but are not limited to, precipitation of the product followed by chromatography, if necessary.

Water soluble polymers can be linked to BSPs of the invention. The water soluble polymers may be linked via a non-naturally encoded amino acid incorporated in the BSP or any functional group or substituent of a non-naturally encoded or naturally encoded amino acid, or any functional group or substituent added to a non-naturally encoded or naturally encoded amino acid. Alternatively, the water soluble polymers are linked to a BSP incorporating a non-naturally encoded amino acid via a naturally-occurring amino acid (including but not limited to, cysteine, lysine or the amine group of the N-terminal residue). In some cases, the BSPs of the invention comprise 1, 2, 3, 4, 5, 6, 7, 8, 9, 10 non-natural amino acids, wherein one or more non-naturally-encoded amino acid(s) are linked to water soluble polymer(s) (including but not limited to, PEG and/or oligosaccharides). In some cases, the BSPs of the invention further comprise 1, 2, 3, 4, 5, 6, 7, 8, 9, 10, or more naturally-encoded amino acid(s) linked to water soluble polymers. In some cases, the BSPs of the invention comprise one or more non-naturally encoded amino acid(s) linked to water soluble polymers and one or more naturally-occurring amino acids linked to water soluble polymers. In some embodiments, the water soluble polymers used in the present invention enhance the serum half-life of the BSP relative to the unconjugated form.

The number of water soluble polymers linked to a BSP (i.e., the extent of PEGylation or glycosylation) of the present invention can be adjusted to provide an altered (including but not limited to, increased or decreased) pharmacologic, pharmacokinetic or pharmacodynamic characteristic such as in vivo half-life. In some embodiments, the half-life of BSP is increased at least about 10, 20, 30, 40, 50, 60, 70, 80, 90 percent, 2-fold, 5-fold, 10-fold, 50-fold, or at least about 100-fold over an unmodified polypeptide.

PEG Derivatives Containing a Strong Nucleophilic Group (i.e., Hydrazide, Hydrazine, Hydroxylamine or Semicarbazide)

In one embodiment of the present invention, a BSP comprising a carbonyl-containing non-naturally encoded amino acid is modified with a PEG derivative that contains a terminal hydrazine, hydroxylamine, hydrazide or semicarbazide moiety that is linked directly to the PEG backbone.

In some embodiments, the hydroxylamine-terminal PEG derivative will have the structure:

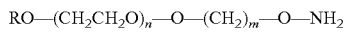

where R is a simple alkyl (methyl, ethyl, propyl, etc.), m is 2-10 and n is 100-1,000 (i.e., average molecular weight is between 5-40 kDa).

In some embodiments, the hydrazine- or hydrazide-containing PEG derivative will have the structure:

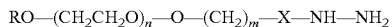

where R is a simple alkyl (methyl, ethyl, propyl, etc.), m is 2-10 and n is 100-1,000 and X is optionally a carbonyl group (C=O) that can be present or absent.

In some embodiments, the semicarbazide-containing PEG derivative will have the structure:

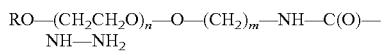

where R is a simple alkyl (methyl, ethyl, propyl, etc.), m is 2-10 and n is 100-1,000.

In another embodiment of the invention, a BSP comprising a carbonyl-containing amino acid is modified with a PEG derivative that contains a terminal hydroxylamine, hydrazide, hydrazine, or semicarbazide moiety that is linked to the PEG backbone by means of an amide linkage.

In some embodiments, the hydroxylamine-terminal PEG derivatives have the structure:

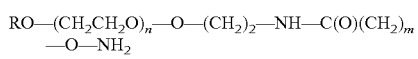

where R is a simple alkyl (methyl, ethyl, propyl, etc.), m is 2-10 and n is 100-1,000 (i.e., average molecular weight is between 5-40 kDa).

In some embodiments, the hydrazine- or hydrazide-containing PEG derivatives have the structure:

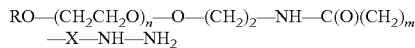

where R is a simple alkyl (methyl, ethyl, propyl, etc.), m is 2-10, n is 100-1,000 and X is optionally a carbonyl group (C=O) that can be present or absent.

In some embodiments, the semicarbazide-containing PEG derivatives have the structure:

where R is a simple alkyl (methyl, ethyl, propyl, etc.), m is 2-10 and n is 100-1,000.

In another embodiment of the invention, a BSP comprising a carbonyl-containing amino acid is modified with a branched PEG derivative that contains a terminal hydrazine, hydroxylamine, hydrazide or semicarbazide moiety, with each chain of the branched PEG having a MW ranging from 10-40 kDa and, more preferably, from 5-20 kDa.

In another embodiment of the invention, a BSP comprising a non-naturally encoded amino acid is modified with a PEG derivative having a branched structure. For instance, in some embodiments, the hydrazine- or hydrazide-terminal PEG derivative will have the following structure:

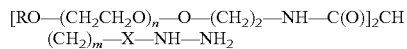

where R is a simple alkyl (methyl, ethyl, propyl, etc.), m is 2-10 and n is 100-1,000, and X is optionally a carbonyl group (C=O) that can be present or absent.

In some embodiments, the PEG derivatives containing a semicarbazide group will have the structure:

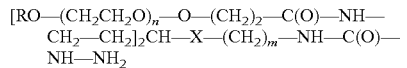

where R is a simple alkyl (methyl, ethyl, propyl, etc.), X is optionally NH, O, S, C(O) or not present, m is 2-10 and n is 100-1,000.

In some embodiments, the PEG derivatives containing a hydroxylamine group will have the structure:

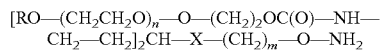

where R is a simple alkyl (methyl, ethyl, propyl, etc.), X is optionally NH, O, S, C(O) or not present, m is 2-10 and n is 100-1,000.

The degree and sites at which the water soluble polymer(s) are linked to the BSP can modulate the binding of the BSP to the BSP receptor or binding partner. In some embodiments, the linkages are arranged such that the BSP binds the BSP receptor with a $K_d$ of about 400 nM or lower, with a $K_d$ of 150 nM or lower, and in some cases with a $K_d$ of 100 nM or lower, as measured by an equilibrium binding assay.

Methods and chemistry for activation of polymers as well as for conjugation of peptides are described in the literature and are known in the art. Commonly used methods for activation of polymers include, but are not limited to, activation of functional groups with cyanogen bromide, periodate, glutaraldehyde, biepoxides, epichlorohydrin, divinylsulfone, carbodiimide, sulfonyl halides, trichlorotriazine, etc. (see, R. F. Taylor, (1991), PROTEIN IMMOBILISATION. FUNDAMENTAL AND APPLICATIONS, Marcel Dekker, N.Y.; S. S. Wong, (1992), CHEMISTRY OF PROTEIN CONJUGATION AND CROSSLINKING, CRC Press, Boca Raton; G. T. Hermanson et al., (1993), IMMOBILIZED AFFINITY LIGAND TECHNIQUES, Academic Press, N.Y.; Dunn, R. L., et al., Eds. POLYMERIC DRUGS AND DRUG DELIVERY SYSTEMS, ACS Symposium Series Vol. 469, American Chemical Society, Washington, D.C. 1991).

Several reviews and monographs on the functionalization and conjugation of PEG are available. See, for example, Harris, *Macromol. Chem. Phys.* C25: 325-373 (1985); Scouten, *Methods in Enzymology* 135: 30-65 (1987); Wong et al., *Enzyme Microb. Technol.* 14: 866-874 (1992); Delgado et al., *Critical Reviews in Therapeutic Drug Carrier Systems* 9: 249-304 (1992); Zalipsky, *Bioconjugate Chem.* 6: 150-165 (1995).

Methods for activation of polymers can also be found in WO 94/17039, U.S. Pat. No. 5,324,844, WO 94/18247, WO 94/04193, U.S. Pat. No. 5,219,564, U.S. Pat. No. 5,122,614, WO 90/13540, U.S. Pat. No. 5,281,698, and WO 93/15189, and for conjugation between activated polymers and enzymes including but not limited to Coagulation Factor VIII (WO 94/15625), hemoglobin (WO 94/09027), oxygen carrying molecule (U.S. Pat. No. 4,412,989), ribonuclease and superoxide dismutase (Veronese at al., *App. Biochem. Biotech.* 11: 141-52 (1985)). All references and patents cited are incorporated by reference herein.

PEGylation (i.e., addition of any water soluble polymer) of BSPs containing a non-naturally encoded amino acid, such as p-azido-L-phenylalanine, is carried out by any convenient method. For example, BSP is PEGylated with an alkyne-terminated mPEG derivative. Briefly, an excess of solid mPEG(5000)-O—CH$_2$—C≡CH is added, with stirring, to an aqueous solution of p-azido-L-Phe-containing BSP at room temperature. Typically, the aqueous solution is buffered with a buffer having a pK$_a$ near the pH at which the reaction is to be carried out (generally about pH 4-10). Examples of suitable buffers for PEGylation at pH 7.5, for instance, include, but are not limited to, HEPES, phosphate, borate, TRIS-HCl, EPPS, and TES. The pH is continuously monitored and adjusted if necessary. The reaction is typically allowed to continue for between about 1-48 hours.

The reaction products are subsequently subjected to hydrophobic interaction chromatography to separate the PEGylated BSP variants from free mPEG(5000)-O—CH$_2$—C—CH and any high-molecular weight complexes of the pegylated BSP which may form when unblocked PEG is activated at both ends of the molecule, thereby crosslinking BSP variant molecules. The conditions during hydrophobic interaction chromatography are such that free mPEG(5000)-O—CH$_2$—C≡CH flows through the column, while any crosslinked PEGylated BSP variant complexes elute after the desired forms, which contain one BSP variant molecule conjugated to one or more PEG groups. Suitable conditions vary depending on the relative sizes of the cross-linked complexes versus the desired conjugates and are readily determined by those skilled in the art. The eluent containing the desired conjugates is concentrated by ultrafiltration and desalted by diafiltration.

If necessary, the PEGylated BSP obtained from the hydrophobic chromatography can be purified further by one or more procedures known to those skilled in the art including, but are not limited to, affinity chromatography; anion- or cation-exchange chromatography (using, including but not limited to, DEAE SEPHAROSE); chromatography on silica; reverse phase HPLC; gel filtration (using, including but not limited to, SEPHADEX G-75); hydrophobic interaction chromatography; size-exclusion chromatography; metal-chelate chromatography; ultrafiltration/diafiltration; ethanol precipitation; ammonium sulfate precipitation; chromatofocusing; displacement chromatography; electrophoretic procedures (including but not limited to preparative isoelectric focusing), differential solubility (including but not limited to ammonium sulfate precipitation), or extraction. Apparent molecular weight may be estimated by GPC by comparison to globular protein standards (Preneta, A Z in PROTEIN PURIFICATION METHODS, A PRACTICAL APPROACH (Harris & Angal, Eds.) IRL Press 1989, 293-306). The purity of the BSP-PEG conjugate can be assessed by proteolytic degradation (including but not limited to, trypsin cleavage) followed by mass spectrometry analysis. Pepinsky R B., et al., *J. Pharmcol. & Exp. Ther.* 297(3):1059-66 (2001).

A water soluble polymer linked to an amino acid of a BSP of the invention can be further derivatized or substituted without limitation.

Azide-Containing PEG Derivatives

In another embodiment of the invention, a BSP is modified with a PEG derivative that contains an azide moiety that will react with an alkyne moiety present on the side chain of the non-naturally encoded amino acid. In general, the PEG derivatives will have an average molecular weight ranging from 1-100 kDa and, in some embodiments, from 10-40 kDa.

In some embodiments, the azide-terminal PEG derivative will have the structure:

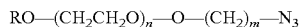

where R is a simple alkyl (methyl, ethyl, propyl, etc.), m is 2-10 and n is 100-1,000 (i.e., average molecular weight is between 540 kDa).

In another embodiment, the azide-terminal PEG derivative will have the structure:

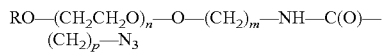

where R is a simple alkyl (methyl, ethyl, propyl, etc.), m is 2-10, p is 2-10 and n is 100-1,000 (i.e., average molecular weight is between 5-40 kDa).

In another embodiment of the invention, a BSP comprising a alkyne-containing amino acid is modified with a branched PEG derivative that contains a terminal azide moiety, with each chain of the branched PEG having a MW ranging from 10-40 kDa and, more preferably, from 5-20 kDa. For instance, in some embodiments, the azide-terminal PEG derivative will have the following structure:

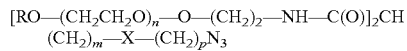

where R is a simple alkyl (methyl, ethyl, propyl, etc.), m is 2-10, p is 2-10, and n is 100-1,000, and X is optionally an O, N, S or carbonyl group (C=O), in each case that can be present or absent.

Alkyne-Containing PEG Derivatives

In another embodiment of the invention, a BSP is modified with a PEG derivative that contains an alkyne moiety that will react with an azide moiety present on the side chain of the non-naturally encoded amino acid.

In some embodiments, the alkyne-terminal PEG derivative will have the following structure:

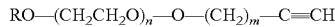

where R is a simple alkyl (methyl, ethyl, propyl, etc.), m is 2-10 and n is 100-1,000 (i.e., average molecular weight is between 5-40 kDa).

In another embodiment of the invention, a BSP comprising an alkyne-containing non-naturally encoded amino acid is modified with a PEG derivative that contains a terminal azide or terminal alkyne moiety that is linked to the PEG backbone by means of an amide linkage.

In some embodiments, the alkyne-terminal PEG derivative will have the following structure:

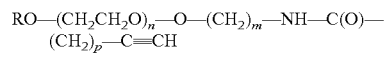

where R is a simple alkyl (methyl, ethyl, propyl, etc.), m is 2-10, p is 2-10 and n is 100-1,000.

In another embodiment of the invention, a BSP comprising an azide-containing amino acid is modified with a branched PEG derivative that contains a terminal alkyne moiety, with each chain of the branched PEG having a MW ranging from 10-40 kDa and, more preferably, from 5-20 kDa. For instance, in some embodiments, the alkyne-terminal PEG derivative will have the following structure:

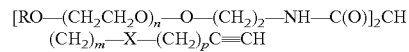

where R is a simple alkyl (methyl, ethyl, propyl, etc.), m is 2-10, p is 2-10, and n is 100-1,000, and X is optionally an O, N, S or carbonyl group (C=O), or not present.

Phosphine-Containing PEG Derivatives

In another embodiment of the invention, a BSP is modified with a PEG derivative that contains an activated functional group (including but not limited to, ester, carbonate) further comprising an aryl phosphine group that will react with an azide moiety present on the side chain of the non-naturally encoded amino acid. In general, the PEG derivatives will have an average molecular weight ranging from 1-100 kDa and, in some embodiments, from 1040 kDa.

In some embodiments, the PEG derivative will have the structure:

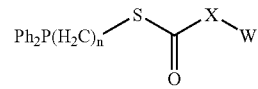

wherein n is 1-10; X can be O, N, S or not present, Ph is phenyl, and W is a water soluble polymer.

In some embodiments, the PEG derivative will have the structure:

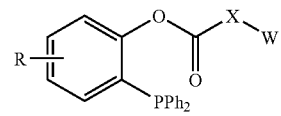

wherein X can be O, N, S or not present, Ph is phenyl, W is a water soluble polymer and R can be H, alkyl, aryl, substituted alkyl and substituted aryl groups. Exemplary R groups include but are not limited to —CH$_2$, —C(CH$_3$)$_3$, —OR', —NR'R", —SR', -halogen, —C(O)R', —CONR'R", —S(O)$_2$R', —S(O)$_2$NR'R", —CN and —NO$_2$. R', R", R'" and R"" each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, —$CF_3$ and —$CH_2CF_3$) and acyl (including but not limited to, —C(O)$CH_3$, —C(O)$CF_3$, —C(O)$CH_2OCH_3$, and the like).

Other PEG Derivatives and General PEGylation Techniques

Other exemplary PEG molecules that may be linked to BSPs, as well as PEGylation methods include those described in, e.g., U.S. Patent Publication No. 2004/0001838; 2002/0052009; 2003/0162949; 2004/0013637; 2003/0228274; 2003/0220447; 2003/0158333; 2003/0143596; 2003/0114647; 2003/0105275; 2003/0105224; 2003/0023023; 2002/0156047; 2002/0099133; 2002/0086939; 2002/0082345; 2002/0072573; 2002/0052430; 2002/0040076; 2002/0037949; 2002/0002250; 2001/0056171; 2001/0044526; 2001/0027217; 2001/0021763; U.S. Pat. Nos. 6,646,110; 5,824,778; 5,476,653; 5,219,564; 5,629,384; 5,736,625; 4,902,502; 5,281,698; 5,122,614; 5,473,034; 5,516,673; 5,382,657; 6,552,167; 6,610,281; 6,515,100; 6,461,603; 6,436,386; 6,214,966; 5,990,237; 5,900,461; 5,739,208; 5,672,662; 5,446,090; 5,808,096; 5,612,460; 5,324,844; 5,252,714; 6,420,339; 6,201,072; 6,451,346; 6,306,821; 5,559,213; 5,747,646; 5,834,594; 5,849,860; 5,980,948; 6,004,573; 6,129,912; WO 97/32607, EP 229,108, EP 402,378, WO 92/16555, WO 94/04193, WO 94/14758, WO 94/17039, WO 94/18247, WO 94/28024, WO 95/00162, WO 95/11924, WO95/13090, WO 95/33490, WO 96/00080, WO 97/18832, WO 98/41562, WO 98/48837, WO 99/32134, WO 99/32139, WO 99/32140, WO 96/40791, WO 98/32466, WO 95/06058, EP 439 508, WO 97/03106, WO 96/21469, WO 95/13312, EP 921 131, WO 98/05363, EP 809 996, WO 96/41813, WO 96/07670, EP 605 963, EP 510 356, EP 400 472, EP 183 503 and EP 154 316, which are incorporated by reference herein. Any of the PEG molecules described herein may be used in any form, including but not limited to, single chain, branched chain, multiarm chain, single functional, bi-functional, multi-functional, or any combination thereof.

Enhancing Affinity for Serum Albumin

Various molecules can also be fused to the BSPs of the invention to modulate the half-life of BSP in serum. In some embodiments, molecules are linked or fused to BSPs of the invention to enhance affinity for endogenous serum albumin in an animal.

For example, in some cases, a recombinant fusion of a BSP and an albumin binding sequence is made. Exemplary albumin binding sequences include, but are not limited to, the albumin binding domain from streptococcal protein G (see. e.g., Makrides et al., *J. Pharmacol. Exp. Ther.* 277:534-542 (1996) and Sjolander et al., *J, Immunol. Methods* 201:115-123 (1997)), or albumin-binding peptides such as those described in, e.g., Dennis, et al., *J. Biol. Chem.* 277:35035-35043 (2002).

In other embodiments, the BSPs of the present invention are acylated with fatty acids. In some cases, the fatty acids promote binding to serum albumin. See, e.g., Kurtzhals, et al., *Biochem. J.* 312:725-731 (1995).

In other embodiments, the BSPs of the invention are fused directly with serum albumin (including but not limited to, human serum albumin). Those of skill in the art will recognize that a wide variety of other molecules can also be linked to BSP in the present invention to modulate binding to serum albumin or other serum components.

X. Glycosylation of BSP

The invention includes BSPs incorporating one or more non-naturally encoded amino acids bearing saccharide residues. The saccharide residues may be either natural (including but not limited to, N-acetylglucosamine) or non-natural (including but not limited to, 3-fluorogalactose). The saccharides may be linked to the non-naturally encoded amino acids either by an N- or O-linked glycosidic linkage (including but not limited to, N-acetylgalactose-L-serine) or a non-natural linkage (including but not limited to, an oxime or the corresponding C- or S-linked glycoside).

The saccharide (including but not limited to, glycosyl) moieties can be added to BSPs either in vivo or in vitro. In some embodiments of the invention, a BSP comprising a carbonyl-containing non-naturally encoded amino acid is modified with a saccharide derivatized with an aminooxy group to generate the corresponding glycosylated polypeptide linked via an oxime linkage. Once attached to the non-naturally encoded amino acid, the saccharide may be further elaborated by treatment with glycosyltransferases and other enzymes to generate an oligosaccharide bound to the BSP. See, e.g., H. Liu, et al. *J. Am. Chem. Soc.* 125: 1702-1703 (2003).

In some embodiments of the invention, a BSP comprising a carbonyl-containing non-naturally encoded amino acid is modified directly with a glycan with defined structure prepared as an aminooxy derivative. One skilled in the art will recognize that other functionalities, including azide, alkyne, hydrazide, hydrazine, and semicarbazide, can be used to link the saccharide to the non-naturally encoded amino acid.

In some embodiments of the invention, a BSP comprising an azide or alkynyl-containing non-naturally encoded amino acid can then be modified by, including but not limited to, a Huisgen [3+2] cycloaddition reaction with, including but not limited to, alkynyl or azide derivatives, respectively. This method allows for proteins to be modified with extremely high selectivity.

XI. BSP Containing Dimers and Multimers

The present invention also provides for BSP combinations (including, but not limited to, GLP-1 and GLP-1 analogs, T-20 and T-20 analogs, PYY and PYY analogs) such as homodimers, heterodimers, homomultimers, or heteromultimers (i.e., trimers, tetramers, etc.) where a particular BSP containing one or more non-naturally encoded amino acids is bound to another BSP, analog, or variant thereof or any other polypeptide that is a non-GLP-1 (or non-T-20 or non-PYY) peptide or variant thereof, either directly to the polypeptide backbone or via a linker. Due to its increased molecular weight compared to monomers, the BSP (such as GLP-1, T-20, or PYY) dimer or multimer conjugates may exhibit new or desirable properties, including but not limited to different pharmacological, pharmacokinetic, pharmacodynamic, modulated therapeutic half-life, or modulated plasma half-life relative to the monomeric BSP. In some embodiments, the conjugates or fusions of the invention will modulate the interaction of the BSP with its receptor or binding partner. In other embodiments, the BSP conjugates, fusions, dimers or multimers of the present invention will act as a receptor antagonist, agonist, super agonist, or modulator.

In some embodiments, one or more of the BSPs present in a BSP containing dimer or multimer comprises a non-naturally encoded amino acid liked to a water soluble polymer that is present in the receptor binding region or region for binding to a binding partner. In some embodiments, the BSPs are linked directly, including but not limited to, via an Asn-Lys amide linkage or Cys-Cys disulfide linkage. In some embodiments, the linked BSP will comprise different non-naturally encoded amino acids to facilitate conjugation, fusion, dimerization, or multimerization including but not limited to, an alkyne in one non-naturally encoded amino acid of a first BSP and an azide in a second non-naturally encoded amino acid of a second BSP will be conjugated via a Huisgen [3+2] cycloaddition. Alternatively, a first BSP, and/or the linked BSP comprising a ketone-containing non-naturally encoded amino acid can be conjugated to a second BSP comprising a hydroxylamine-containing non-naturally encoded amino acid and the polypeptides are reacted via formation of the corresponding oxime.

Alternatively, the two BSPs are linked via a linker. Any hetero- or homo-bifunctional linker can be used to link the two BSPs, which can have the same or different primary sequence. In some cases, the linker used to tether the BSPs together can be a bifunctional PEG reagent. The linker may have a wide range of molecular weight or molecular length. Larger or smaller molecular weight linkers may be used to provide a desired spatial relationship or conformation between the BSP and the linked entity, or between the BSP and its binding partner, or between the linked entity and its binding partner, if any. Linkers having longer or shorter molecular length may also be used to provide a desired space or flexibility between the BSP and the linked entity, or between the BSP and its binding partner, or between the linked entity and its binding partner, if any. Similarly, a linker having a particular shape or conformation may be utilized to impart a particular shape or conformation to the BSP or the linked entity, either before or after the BSP reaches its target. This optimization of the spatial relationship between the BSP and the linked entity and the binding partner may provide new, modulated, or desired properties to the molecule.

In some embodiments, the invention provides water-soluble bifunctional linkers that have a dumbbell structure that includes: a) an azide, an alkyne, a hydrazine, a hydrazide, a hydroxylamine, or a carbonyl-containing moiety on at least a first end of a polymer backbone; and b) at least a second functional group on a second end of the polymer backbone. The second functional group can be the same or different as the first functional group. The second functional group, in some embodiments, is not reactive with the first functional group. The invention provides, in some embodiments, water-soluble compounds that comprise at least one arm of a branched molecular structure. For example, the branched molecular structure can be dendritic.

In some embodiments, the invention provides multimers comprising one or more GH supergene family member, such as BSP, formed by reactions with water soluble activated polymers that have the structure:

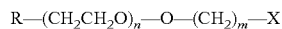
R—(CH$_2$CH$_2$O)$_n$—O—(CH$_2$)$_m$—X wherein n is from about 5 to 3,000, m is 2-10, X can be an azide, an alkyne, a hydrazine, a hydrazide, an aminooxy group, a hydroxylamine, a acetyl, or carbonyl-containing moiety, and R is a capping group, a functional group, or a leaving group that can be the same or different as X. R can be, for example, a functional group selected from the group consisting of hydroxyl, protected hydroxyl, alkoxyl, N-hydroxysuccinimidyl ester, 1-benzotriazolyl ester, N-hydroxysuccinimidyl carbonate, 1-benzotriazolyl carbonate, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, and tresylate, alkene, and ketone.

XII. Measurement of BSP Activity and Affinity of BSP for the BSP Receptor or Binding Partner BSP activity can be determined using standard in vitro or in vivo assays.

A number of assays may be used to monitor the activity of GLP-1 polypeptides of the invention. Peptide hormones such as GLP-1 activate specific G protein-coupled receptors, and thus GLP-1 polypeptides of the invention may be evaluated by assays detecting GLP-1 receptor dependent cAMP formation. Downstream intracellular cAMP production can be measured by a variety of methods, including but not limited to, colorimetric, luminescent, time-resolved fluorescence, or FP methods. Rat insulinoma-derived RIN-m5F cells possess endogenous GLP-1 receptor coupled to adenylate cyclase (Fehmann. et al., Mol Cell Endocrinol 85:C39-C44; Goke et al. Res Exp Med (Berl). 1989; 189(4):257-64) and may be used to measure cAMP after receptor activation. Similarly, hamster HIT-T15 cells (ATCC, Manassas, Va.) or rat BRIN-BD11 beta cells (Green et al. J Mol Endocrinol. 2003 December; 31(3):529-4) may be used.

Alternatively, cAMP production may be measured in cells transfected with recombinant hGLP-1 receptor (including, but not limited to CHO (Kim et al. 2003 Diabetes 52:751-59), BHK (baby hamster kidney; Knudsen et al. 2000 J. Med. Chem. 43:1664-1669), and CHL (Chinese hamster lung) cells) or primary cells such as pancreatic islet cells isolated from rats, mice or hamsters. The GLP-1 receptor can be prepared as described in Thorens, Proc. Natl. Acad. Sci. USA 1992, 89(18):8641-5 or U.S. Pat. Nos. 5,670,360 and 6,051,689, which is incorporated by reference herein. Forskolin (EMD Biosciences, San Diego, Calif.), an adenylate cyclase activator, and inhibitors of adenylate cyclase, PI3K, MAPK, or p38 may be used as assay controls. Agonist controls include GLP-1 (7-37) and exendin-4, a potent GLP-1 receptor agonist, and antagonist controls include the GLP-1 receptor antagonist Exendin (9-39) (available from Bachem AG). See, Goke et al., J Biol. Chem. 1993 September 15; 268(26): 19650-5. Dose response curves are plotted for each compound tested and EC$_{50}$ values are calculated. Alternatively, cAMP may be measured by other assays. Generally, these assays are well known in the art.

Insulin secretion is also a measure of the biological activity of GLP-1 polypeptides of the invention. In vitro studies of insulin secretion may be calculated in cells post incubation with a range of concentrations of GLP-1 polypeptide(s) and glucose via insulin RIA or ELISA. Green et al., supra evaluated insulinotropic effects of GLP-1 polypeptides in rat BRIN-BD11 beta cells. Rat pancreatic islets may alternatively be used in insulin secretion studies (Goke et al., J. Biol. Chem. 1993 268(26)19650-19655).

Alternatively, beta islet cell growth may be measured using reagents such as XTT or BrdU or CREB (cyclic AMP response element binding protein) transcription factor with the CRE reporter assay.

The affinity of the GLP-1 polypeptide comprising a non-natural amino acid for its receptor can be measured by using a BIAcore™ biosensor (Pharmacia). Cells or cell lines that modulate growth or bind GLP-1 (including but not limited to, cells containing active GLP-1 receptors such as human cells, or recombinant GLP-1 receptor producing cells) can be used to monitor GLP-1 receptor binding. For example, cells or cell lines that modulate growth or bind GLP-1 (including but not limited to, cells containing active GLP-1 receptors such as human cells, or recombinant GLP-1 receptor producing cells) can be used to monitor GLP-1 receptor binding.

Alternatively, binding can also be measured using cells transfected with recombinant hGLP-1 receptor (including, but not limited to CHO, BHK (baby hamster kidney), and CHL (Chinese hamster lung fibroblast) cells). See Kim et al. supra for binding studies in transfected CHO cells and Green et al. J Mol Endocrinol. 2003 December; 31(3):529-40 for studies in transfected CHL cells. The GLP-1 receptor can be prepared as described in Thorens, Proc. Natl. Acad. Sci. USA 1992, 89(18):8641-5 or U.S. Pat. Nos. 5,670,360 and 6,051,689, which is incorporated by reference herein.

Degradation of GLP-1 polypeptides of the invention by DPP IV or human plasma may be monitored by Liquid Chromatography/Mass Spectrometry (LC/MS) or by other methods. GLP-1 peptides of the invention may be incubated with either DPP IV or pooled human plasma for 0, 6, or 12 hours and reagents such as TFA added to end any enzymatic reactions prior to analysis. All references cited are incorporated by reference herein.

In vivo animal models as well as human clinical trials for testing GLP-1 activity include those described in, U.S. Patent Application Publication No. 20040082507A1; and 20030232754A1, which are incorporated by reference herein.

A number of assays may be used to monitor the activity of T-20 (DP-178) polypeptides of the invention. In vitro assays that test the DP-178 polypeptides' ability to inhibit syncytia formation or their ability to inhibit infection by cell-free virus may be used as described in U.S. Pat. No. 5,464,933, which is incorporated by reference herein. Parameters measured include the relative antiviral activity exhibited against a given strain of virus and/or the strain specific inhibitory activity of the peptide. A cell fusion assay may be utilized to test the peptides' ability to inhibit HIV-induced syncytia formation in vitro. Such an assay may comprise culturing uninfected CD-4+ cells (such as, but not limited to, Molt or CEM cells) in the presence of chronically HIV-infected cells and various concentrations of the peptide to be assayed. After incubation for an appropriate period, the culture is examined microscopically for the presence of multinucleated giant cells, which are indicative of cell fusion and syncytia formation.

A reverse transcriptase (RT) assay may be utilized to test the peptides' ability to inhibit infection of CD-4+ cells by cell-free HIV. Such an assay may comprise culturing an appropriate concentration (i.e., $TCID_{50}$) of virus and CD-4+ cells in the presence of the peptide to be tested. Culture conditions well known to those in the art are used. A range of peptide concentrations may be used, in addition to a control culture wherein no peptide has been added. After incubation for an appropriate period (e.g., 7 days) of culturing, a cell-free supernatant is prepared, using standard procedures, and tested for the presence of RT activity as a measure of successful infection. The RT activity may be tested using standard techniques such as those described by, for example, Goff et al. (Goff, S. et al., 1981, J. Virol. 38:239-248) and/or Willey et al. (Willey, R. et al., 1988, J. Virol. 62:139-147). These references are incorporated herein by reference in their entirety.

Other assays measuring antiviral activity are known to one skilled in the art. Modifications to these assays to test combination therapy with another antiviral agent are also known to one skilled in the art.

Standard methods which are well-known to those of skill in the art may be utilized for assaying non-retroviral activity. See, for example, Pringle et al. (Pringle, C. R. et al., 1985, J. Medical Virology 17:377-386) for a discussion of respiratory syncytial virus and parainfluenza virus activity assay techniques. Further, see, for example, "Zinsser Microbiology", 1988, Joklik, W. K. et al., eds., Appleton & Lange, Norwalk, Conn., 19th ed., for a general review of such techniques. These references are incorporated by reference herein in its entirety.

Preferred PYY agonists may have a potency in one of the assays described in WO 02/47712 and U.S. patent Publication No. 2002/0141985 (preferably food intake, gastric emptying, pancreatic secretion, or weight reduction assays) which is greater than the potency of NPY in that same assay.

Regardless of which methods are used to create the BSP analogs, the analogs are subject to assays for biological activity. In general, the test for biological activity should provide analysis for the desired result, such as increase or decrease in biological activity (as compared to non-altered BSP), different biological activity (as compared to non-altered BSP), receptor or binding partner affinity analysis, conformational or structural changes of the BSP itself or binding partner (as compared to the non-altered BSP), or serum half-life analysis.

The above compilation of references for assay methodologies is not exhaustive, and those skilled in the art will recognize other assays useful for testing for the desired end result.

XIII. Measurement of Potency, Functional in Vivo Half-Life, and Pharmacokinetic Parameters An important aspect of the invention is the prolonged biological half-life that is obtained by construction of the BSP with or without conjugation of the polypeptide to a water soluble polymer moiety. The rapid decrease of BSP serum concentrations has made it important to evaluate biological responses to treatment with conjugated and non-conjugated BSP and variants thereof. Preferably, the conjugated and non-conjugated BSP and variants thereof of the present invention have prolonged serum half-lives also after i.v. administration, making it possible to measure by, e.g. ELISA method or by a primary screening assay. Another example of an assay for the measurement of in vivo half-life of GLP-1 or variants thereof is described in U.S. Pat. No. 5,118,666; U.S. Patent Application Publication No. 20040082507A1; and 20030232754A1, which are incorporated by reference herein. Measurement of in vivo biological half-life is carried out as described herein.

The potency and functional in vivo half-life of a GLP-1 polypeptide comprising a non-naturally encoded amino acid can be determined according to the protocol described in U.S. Pat. No. 5,118,666; U.S. Patent Application Publication No. 20040082507A1 and 20030232754A1.

Pharmacokinetic parameters for a GLP-1 polypeptide comprising a non-naturally encoded amino acid can be evaluated in normal Sprague-Dawley male rats (N=5 animals per treatment group). Animals will receive either a single dose of 25 ug/rat iv or 50 ug/rat sc, and approximately 5-7 blood samples will be taken according to a pre-defined time course, generally covering about 6 hours for a GLP-1 polypeptide comprising a non-naturally encoded amino acid not conjugated to a water soluble polymer and about 4 days for a GLP-1 polypeptide comprising a non-naturally encoded amino acid and conjugated to a water soluble polymer. Pharmacokinetic data for GLP-1 is well-studied in several species and can be compared directly to the data obtained for GLP-1 comprising a non-naturally encoded amino acid.

Animal models that may be used for evaluating GLP-1 peptides of the invention include, but are not limited to: the fatty Zucker (fa/fa; ZDF) rat, the ob/ob mouse, and the db/db mouse. These models are produced by recessive inheritance of a single gene (Bray, G. A. 1977. Fed Proc. 36:148-153; Bray, G. A. and D. A. York. 1979. Physiol. Rev. 51:598-646; Kasiske, B. L. et al. 1992. Hypertension 19 Suppl. 1:1110-1115; Bray, G. A. 1992. Am. J. Clin. Nutr. 55 Suppl. 488S-494S). GLP-1 receptor knockout (GLP-1R−/−) mice may also be used in animal studies to show that the glucose lowering effects of GLP-1 molecules of the invention are dependent on a functional GLP-1 receptor. (U.S. Pat. No. 5,846,937, Scrocchi et al. 1996 Nat Med. 1996 November; 2(11): 1254-8, Scrocchi et al. Diabetes 1996 45:21A). The db/db mouse is a genetically obese and diabetic strain of mouse. The db/db mouse develops hyperglycemia and hyperinsulinemia concomitant with its development of obesity and thus serves as a model of obese type 2 diabetes (NIDDM). The db/db mice can purchased from, for example, The Jackson Laboratories (Bar Harbor, Me.). Young et al. Diabetes 1999 48:1026-1034 describe studies comparing unmodified GLP-1 with Exendin-4 in the fatty Zucker (fa/fa) rat, the ob/ob mouse, the db/db mouse and diabetic rhesus monkeys. The Zucker Diabetic Fatty fa/fa (ZDF) rats are insulin-resistant but normoglycemic from birth and they develop diabetes from about week 7 to week 10 of age. During the transitional period, the animals go through a state of impaired glucose tolerance. Although the animals are hyperinsulinemic before diabetes onset and during the early stages of diabetes, they later lose glucose-stimulated insulin secretion and finally become almost completely insulinopenic.

db/db or ob/ob mice will be dosed with GLP-1 peptides comprising a non-naturally encoded amino acid or exendin-4 as a comparator. Compounds will be administered at 0.1 µg per dose s.c., and levels of plasma glucose, glucagon, and blood insulin, weight loss, and anorectic effect will be compared between the two populations. The results will show superior activity with less frequent dosing and prolonged half-life of the GLP-1 peptides of the present invention compared to exendin-4. Studies in GLP-1 receptor knockout mice may be performed as described in Baggio et al. Diabetes (2004) 53:2492-2500.

Numerous methods exist to detect GLP-1 activity, as well as the activity of GLP-1 fusions and analogs. Assays such as those described in EP 619,322 to Gelfand, et al., and U.S. Pat. No. 5,120,712 may be used to test GLP-1 activity in vitro. U.S. Patent Publication U.S. 20040053370 A1, which is incorporated by reference herein, also describes GLP-1 analogs and fusion proteins and their effects on in vivo half-life of the peptides. Serum GLP-1 concentrations from in vivo studies may be measured by ELISA (Linco Research Co.).

DP-178's ability to inhibit HIV entry into cells can be assessed in vitro (e.g., in a syncytium assay, an infectivity assay) or in vivo (e.g. in an appropriate animal model or in humans). Safety, pharmokinetics, and antiviral activity of DP-178 administered intravenously to HIV-infected humans are described by Kilby, et al. Nature Medicine (1998) 4(11): 1302-1307. Similar studies may be performed with DP-178 molecules of the invention.

The procedures for determining the concentrations of peptide YY in blood serum, central nervous system (CNS) tissues or fluids, cerebral spinal fluid (CSF), or other tissues or fluids of a mammalian subject may be determined by immunologic assay for peptide YY. For example, radioimmunoassay (RIA), enzyme immunoassay (EIA), and antibody reagents for immunohistochemistry or immunofluorescence for peptide YY (Bachem AG; King of Prussia, Pa.) may be used. In vivo animal models as well as human clinical trials for testing PYY activity include those described in U.S. Patent Application Publication No. 20050002927.

The specific activity of BSPs in accordance with this invention can be determined by various assays known in the art. The biological activity of the BSP muteins, or fragments thereof, obtained and purified in accordance with this invention can be tested by methods described or referenced herein or known to those skilled in the art.

XIV. Administration and Pharmaceutical Compositions

The polypeptides or proteins of the invention (including but not limited to, BSP, synthetases, proteins comprising one or more unnatural amino acid, etc.) are optionally employed for therapeutic uses, including but not limited to, in combination with a suitable pharmaceutical carrier. Such compositions, for example, comprise a therapeutically effective amount of the compound, and a pharmaceutically acceptable carrier or excipient. Such a carrier or excipient includes, but is not limited to, saline, buffered saline, dextrose, water, glycerol, ethanol, and/or combinations thereof. The formulation is made to suit the mode of administration. In general, methods of administering proteins are well known in the art and can be applied to administration of the polypeptides of the invention.

Therapeutic compositions comprising one or more polypeptide of the invention are optionally tested in one or more appropriate in vitro and/or in vivo animal models of disease, to confirm efficacy, tissue metabolism, and to estimate dosages, according to methods well known in the art. In particular, dosages can be initially determined by activity, stability or other suitable measures of unnatural herein to natural amino acid homologues (including but not limited to, comparison of a BSP modified to include one or more unnatural amino acids to a natural amino acid BSP), i.e., in a relevant assay.

Administration is by any of the routes normally used for introducing a molecule into ultimate contact with blood or tissue cells. The unnatural amino acid polypeptides of the invention are administered in any suitable manner, optionally with one or more pharmaceutically acceptable carriers. Suitable methods of administering such polypeptides in the context of the present invention to a patient are available, and, although more than one route can be used to administer a particular composition, a particular route can often provide a more immediate and more effective action or reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention.

Polypeptide compositions can be administered by a number of routes including, but not limited to oral, intravenous, intraperitoneal, intramuscular, transdermal, subcutaneous, topical, sublingual, or rectal means. Compositions comprising non-natural amino acid polypeptides, modified or unmodified, can also be administered via liposomes. Such administration routes and appropriate formulations are generally known to those of skill in the art.

The BSP comprising a non-natural amino acid, alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations of BSP can be presented in unit-dose or multi-dose sealed containers, such as ampules and vials.

Parenteral administration and intravenous administration are preferred methods of administration. In particular, the routes of administration already in use for natural amino acid homologue therapeutics (including but not limited to, those typically used for GLP-1, DP-178, PYY, EPO, GH, G-CSF, GM-CSF, IFNs, interleukins, antibodies, and/or any other pharmaceutically delivered polypeptide or protein), along with formulations in current use, provide preferred routes of administration and formulation for the polypeptides of the invention.

The dose administered to a patient, in the context of the present invention, is sufficient to have a beneficial therapeutic response in the patient over time, or, including but not limited to, to inhibit infection by a pathogen, or other appropriate activity, depending on the application. The dose is determined by the efficacy of the particular vector, or formulation, and the activity, stability or serum half-life of the unnatural amino acid polypeptide employed and the condition of the patient, as well as the body weight or surface area of the patient to be treated. The size of the dose is also determined by the existence, nature, and extent of any adverse side-effects that accompany the administration of a particular vector, formulation, or the like in a particular patient.

In determining the effective amount of the vector or formulation to be administered in the treatment or prophylaxis of disease (including but not limited to, cancers, inherited diseases, diabetes, AIDS, or the like), the physician evaluates circulating plasma levels, formulation toxicities, progression of the disease, and/or where relevant, the production of anti-unnatural amino acid polypeptide antibodies.

The dose administered, for example, to a 70 kilogram patient, is typically in the range equivalent to dosages of currently-used therapeutic proteins, adjusted for the altered activity or serum half-life of the relevant composition. The vectors of this invention can supplement treatment conditions by any known conventional therapy, including antibody administration, vaccine administration, administration of cytotoxic agents, natural amino acid polypeptides, nucleic acids, nucleotide analogues, biologic response modifiers, and the like.

For administration, formulations of the present invention are administered at a rate determined by the LD-50 or ED-50 of the relevant formulation, and/or observation of any side-effects of the unnatural amino acids at various concentrations, including but not limited to, as applied to the mass and overall health of the patient. Administration can be accomplished via single or divided doses.

If a patient undergoing infusion of a formulation develops fevers, chills, or muscle aches, he/she receives the appropriate dose of aspirin, ibuprofen, acetaminophen or other pain/fever controlling drug. Patients who experience reactions to the infusion such as fever, muscle aches, and chills are premedicated 30 minutes prior to the future infusions with either aspirin, acetaminophen, or, including but not limited to, diphenhydramine. Meperidine is used for more severe chills and muscle aches that do not quickly respond to antipyretics and antihistamines. Cell infusion is slowed or discontinued depending upon the severity of the reaction.

Human BSPs of the invention can be administered directly to a mammalian subject. Administration is by any of the routes normally used for introducing BSP to a subject. The BSP compositions according to embodiments of the present invention include those suitable for oral, rectal, topical, inhalation (including but not limited to, via an aerosol), buccal (including but not limited to, sub-lingual), vaginal, parenteral (including but not limited to, subcutaneous, intramuscular, intradermal, intraarticular, intrapleural, intraperitoneal, inracerebral, intraarterial, or intravenous), topical (i.e., both skin and mucosal surfaces, including airway surfaces) and transdermal administration, although the most suitable route in any given case will depend on the nature and severity of the condition being treated. Administration can be either local or systemic. The formulations of compounds can be presented in unit-dose or multi-dose sealed containers, such as ampoules and vials. BSPs of the invention can be prepared in a mixture in a unit dosage injectable form (including but not limited to, solution, suspension, or emulsion) with a pharmaceutically acceptable carrier. BSPs of the invention can also be administered by continuous infusion (using, including but not limited to, minipumps such as osmotic pumps), single bolus or slow-release depot formulations.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. Solutions and suspensions can be prepared from sterile powders, granules, and tablets of the kind previously described.

The pharmaceutical compositions of the invention may comprise a pharmaceutically acceptable carrier. Pharmaceutically acceptable carriers are determined in part by the particular composition being administered, as well as by the particular method used to administer the composition. Accordingly, there is a wide variety of suitable formulations of pharmaceutical compositions (including optional pharmaceutically acceptable carriers, excipients, or stabilizers) of the present invention (see, e.g., *Remington's Pharmaceutical Sciences,* $17^{th}$ ed. 1985)).

Suitable carriers include buffers containing phosphate, borate, HEPES, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates, including glucose, mannose, or dextrins; chelating agents such as EDTA; divalent metal ions such as zinc, cobalt, or copper; sugar alcohols such as mannitol or sorbitol; salt-forming counter ions such as sodium; and/or nonionic surfactants such as Tween™, Pluronics™, or PEG.

BSPs of the invention, including those linked to water soluble polymers such as PEG can also be administered by or as part of sustained-release systems. Sustained-release compositions include, including but not limited to, semi-permeable polymer matrices in the form of shaped articles, including but not limited to, films, or microcapsules. Sustained-release matrices include from biocompatible materials such as poly(2-hydroxyethyl methacrylate) (Langer et al., *J. Biomed. Mater. Res.*, 15: 267-277 (1981); Langer, *Chem. Tech.*, 12: 98-105 (1982), ethylene vinyl acetate (Langer et al., supra) or poly-D-(-)-3-hydroxybutyric acid (EP 133,988), polylactides (polylactic acid) (U.S. Pat. No. 3,773,919; EP 58,481), polyglycolide (polymer of glycolic acid), polylactide co-glycolide (copolymers of lactic acid and glycolic acid) polyanhydrides, copolymers of L-glutamic acid and gamma-ethyl-L-glutamate (Sidman et al., *Biopolymers,* 22, 547-556 (1983), poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Sustained-release compositions also include a liposomally entrapped compound. Liposomes containing the compound are prepared by methods known per se: DE 3,218,121; Eppstein et al., *Proc. Natl. Acad. Sci. U.S.A.,* 82: 3688-3692 (1985); Hwang et al., *Proc. Natl. Acad. Sci. U.S.A.,* 77: 4030-4034 (1980); EP 52,322; EP 36,676; EP 88,046; EP 143,949; EP 142,641; Japanese Pat. Appln. 83-118008; U.S. Pat. Nos. 4,485,045 and 4,544,545; and EP 102,324. All references and patents cited are incorporated by reference herein.

Liposomally entrapped BSPs can be prepared by methods described in, e.g., DE 3,218,121; Eppstein et al., *Proc. Natl. Acad. Sci. U.S.A.,* 82: 3688-3692 (1985); Hwang et al., *Proc. Natl. Acad. Sci. U.S.A.,* 77: 4030-4034 (1980); EP 52,322; EP 36,676; EP 88,046; EP 143,949; EP 142,641; Japanese Pat. Appln. 83-118008; U.S. Pat. Nos. 4,485,045 and 4,544,545; and EP 102,324. Composition and size of liposomes are well known or able to be readily determined empirically by one skilled in the art. Some examples of liposomes as described in, e.g., Park J W, et al., *Proc. Natl. Acad. Sci. USA* 92:1327-1331 (1995); Lasic D and Papahadjopoulos D (eds): MEDICAL APPLICATIONS OF LIPOSOMES (1998); Drummond D C, et al., Liposomal drug delivery systems for cancer therapy, in Teicher B (ed): CANCER DRUG DISCOVERY AND DEVELOPMENT (2002); Park J W, et al., *Clin. Cancer Res.* 8:1172-1181 (2002); Nielsen U B, et al., *Biochim. Biophys. Acta* 1591(1-3):109-118 (2002); Mamot C, et al., *Cancer Res.* 63: 3154-3161 (2003). All references and patents cited are incorporated by reference herein.

The dose administered to a patient in the context of the present invention should be sufficient to cause a beneficial response in the subject over time. Generally, the total pharmaceutically effective amount of the BSP of the present invention administered parenterally per dose is in the range of about 0.01 µg/kg/day to about 100 µg/kg, or about 0.05 mg/kg to about 1 mg/kg, of patient body weight, although this is subject to therapeutic discretion. The frequency of dosing is also subject to therapeutic discretion, and may be more frequent or less frequent than the commercially available BSP products approved for use in humans. Generally, a PEGylated BSP of the invention can be administered by any of the routes of administration described above.

XV. Therapeutic Uses of BSPs of the Invention

The BSPs of the invention are useful for treating a wide range of disorders.

Administration of the BSP products of the present invention results in any of the activities demonstrated by other BSP preparations in humans. The pharmaceutical compositions containing the BSP products may be formulated at a strength effective for administration by various means to a human patient experiencing disorders that may be affected by BSP agonists or antagonists, either alone or as part of a condition or disease. Average quantities of the BSP product may vary and in particular should be based upon the recommendations and prescription of a qualified physician. The exact amount of BSP is a matter of preference subject to such factors as the exact type of condition being treated, the condition of the patient being treated, as well as the other ingredients in the composition. The invention also provides for administration of a therapeutically effective amount of another active agent. The amount to be given may be readily determined by one skilled in the art based upon therapy with BSP.

The polypeptides and fusion proteins of the present invention can be used to treat a wide variety of diseases and conditions. The GLP-1 polypeptides and fusion proteins of the present invention primarily exert their biological effects by acting at a receptor referred to as the "GLP-1 receptor." Subjects with diseases and/or conditions that respond favorably to GLP-1 receptor stimulation or to the administration of GLP-1 compounds can therefore be treated with the GLP-1 polypeptides and fusion proteins of the present invention. These subjects are said to "be in need of treatment with GLP-1 compounds" or "in need of GLP-1 receptor stimulation". Included are subjects with non-insulin dependent diabetes, insulin dependent diabetes, stroke (see WO 00/16797), myocardial infarction (see WO 98/08531), obesity (see WO 98/19698), catabolic changes after surgery (see U.S. Pat. No. 6,006,753), functional dyspepsia and irritable bowel syndrome (see WO 99/64060). Also included are subjects requiring prophylactic treatment with a GLP-1 compound, e.g., subjects at risk for developing non-insulin dependent diabetes (see WO 00/07617). Subjects with impaired glucose tolerance or impaired fasting glucose, subjects whose body weight is about 25% above normal body weight for the subject's height and body build, subjects with a partial pancreatectomy, subjects having one or more parents with non-insulin dependent diabetes, subjects who have had gestational diabetes and subjects who have had acute or chronic pancreatitis are at risk for developing non-insulin dependent diabetes.

The present invention comprises GLP-1 compounds that have improved biochemical and biophysical properties by virtue of being fused to an albumin protein, an albumin fragment, an albumin analog, a Fc protein, a Fc fragment, a Fc analog, a water soluble polymer, or a fatty acid. These heterologous proteins may be successfully expressed in host cells, retain signaling activities associated with activation of the GLP-1 receptor, and have prolonged half-lives.

Therapeutic uses of DP-178 include, but are not limited to, treating HIV-1 infection or inhibiting HIV-1 replication. DP-178 peptides of the invention preferably exhibit antiviral activity. As such, the peptides may be used as inhibitors of human and non-human viral and retroviral, especially HIV, transmission to uninfected cells. The human retroviruses whose transmission may be inhibited by the peptides of the invention include, but are not limited to all strains of HIV-1 and HIV-2 and the human T-lymphocyte viruses (HTLV-I and II). The non-human retroviruses whose transmission may be inhibited by the peptides of the invention include, but are not limited to bovine leukosis virus, feline sarcoma and leukemia viruses, simian immunodeficiency, sarcoma and leukemia viruses, and sheep progress pneumonia viruses. Non retroviral viruses whose transmission may be inhibited by the peptides of the invention include, but are not limited to human respiratory syncytial virus, canine distemper virus, Newcastle disease virus, human parainfluenza virus, and influenza viruses. The invention further encompasses the treatment of the above retroviral and non-retroviral viruses using the peptides in combination therapy with at least one other therapeutic, including but not limited to, an antiviral agent.

Therapeutic uses of PYY include, but are not limited to the treatment of obesity, diabetes, gastrointestinal conditions such as ulcers, irritable bowel disease and inflammatory bowel disease or any conditions involving the endocrine regulation of cell proliferation, nutrient transport, and intestinal water and electrolyte secretion. Therapeutic uses of PYY also include the treatment of metabolic conditions or disorders, particularly those which can be alleviated by reducing caloric availability, for example, eating disorders, insulin-resistance syndrome (Syndrome X), glucose intolerance, dyslipidemia, and cardiovascular disorders.

EXAMPLES

The following examples are offered to illustrate, but not to limit the claimed invention.

Example 1

This example describes a few of the many potential sets of criteria for the selection of preferred sites of incorporation of non-naturally encoded amino acids into GLP-1.

This example demonstrates how preferred sites within the GLP-1. polypeptide were selected for introduction of a non-naturally encoded amino acid. Sequence numbering used in this example is according to the amino acid sequence of GLP-1(7-37) shown in SEQ ID NO: 2. Position numbers cited are based positions 7-37 of the peptide unless otherwise indicated. For example, position 8 corresponds to the second amino acid in SEQ ID NO: 2. Those of skill in the art will appreciate that amino acid positions corresponding to positions in SEQ ID NO: 2, can be readily identified in SEQ ID NO: 1, 3, 21, or any other GLP-1 molecule.

Modeling of the potential alpha helical structure of GLP-1 was performed based on PDB ID 1JRJ from Neidigh, J. W., Fesinmeyer, R. M., Prickett, K. S., Andersen, N. H.: Exendin-4 and Glucagon-Like-Peptide-1: NMR Structural Comparisons in the Solution and Micelle-Associated States. *Biochemistry* 40 pp. 13188 (2001). The following criteria were used to evaluate each position of GLP-1 for the introduction of a non-naturally encoded amino acid: the residue (a) should not be affected by alanine scanning mutagenesis (See, Adelhorst et al. J. of Biol. Chem. 1994 269(9):6275-6278), (b) should be surface exposed and exhibit minimal van der Waals or hydrogen bonding interactions with surrounding residues based on modeling, (c) may either be variable or non-essential without affecting activity in GLP-1 variants, (d) would result in conservative substitutions upon substitution with a non-naturally encoded amino acid and (e) could be found in either highly flexible regions or structurally rigid regions. In addition, further calculations were performed on the GLP-1 molecule based on model structures, utilizing the Cx program (Pintar et al. (2002) *Bioinformatics,* 18, pp 980) to evaluate the extent of protrusion for each protein atom of the peptide. As a result, in some embodiments, the non-naturally encoded amino acid is substituted at, but not limited to, one or more of the following positions of GLP-1 (as in SEQ ID NO: 2, and the corresponding amino acids in other GLP-1 analogs): before position 7 (i.e., at the N-terminus), 19, 23, 26, 27, 28, 29, 30, or 33. In some embodiments, the GLP-1 polypeptides of the invention comprise one or more non-naturally occurring amino acids at one or more of the following positions providing an antagonist: 22, 18, 29, 25, 32, 21, 28, 17, 24, 31, and 20.

GLP-1 fusion proteins may comprise the Fc portion of an immunoglobulin. FIG. 1 is a diagram of a GLP-1 dimeric polypeptide comprising a GLP-1-Fc fusion protein. Two GLP-1 polypeptides are joined to human IgG1 Fc via linker sequence. The C-terminus of each GLP-1 polypeptide is fused to a linker sequence (Ala-Ala-Ala-Glu-Pro-Lys-Ser-Ser) which is fused to the Fc portion of IgG1. The GLP-1 polypeptides comprise a non-naturally encoded amino acid at position 1, 2 or 3 in which position 1=first amino acid of GLP-1 (SEQ ID NO: 2). Additional modifications to the GLP-1 comprise a substitution of Ala at positions 8-12, 16 or a deletion of Arg (in which position 1=first amino acid of GLP-1).

Figure 4:
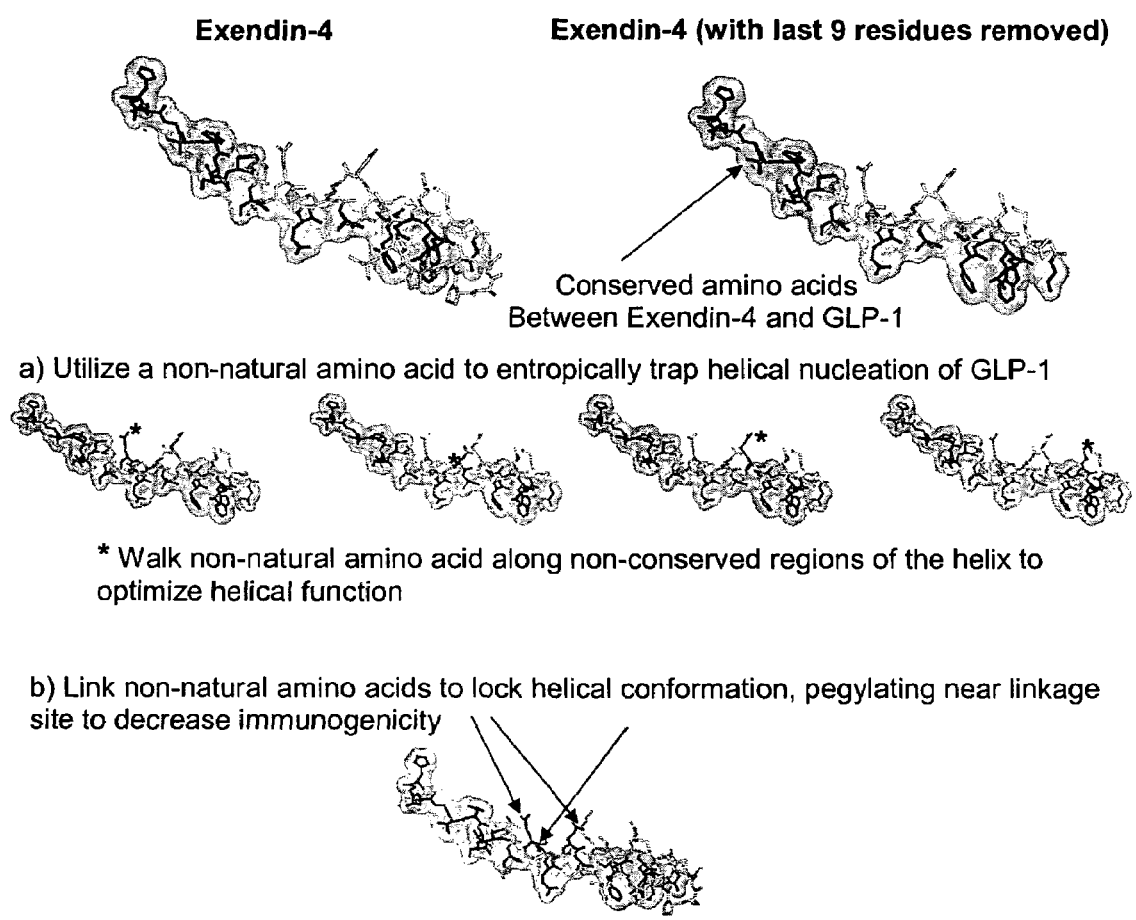
FIG. 4—A diagram of a strategy for the design of Exendin or GLP-1 analogs is shown.
Figure 5:
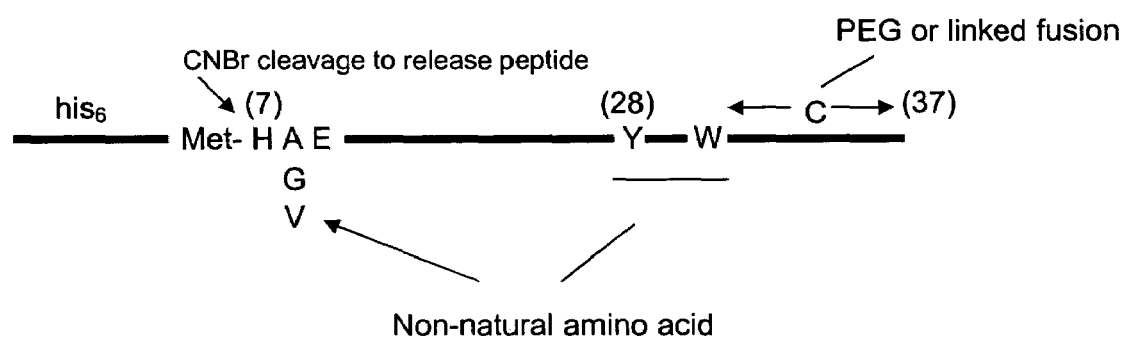
FIG. 5—A diagram of a strategy for the design of GLP-1 analogs having particular structural characteristics is shown.

FIG. 4 shows a diagram of a strategy for the design of Exendin or GLP-1 analogs. One strategy is to utilize a non-naturally encoded amino acid incorporated into GLP-1 to entropically trap helical nucleation of GLP-1. Substitutions with a non-natural amino acid include but are not limited to, residues along non-conserved regions of the alpha helix to optimize helical function. Another strategy is to link two or more non-natural amino acids present in GLP-1 to lock helical formation. Substitutions with a non-natural amino acid include but are not limited to, residues along non-conserved regions of the alpha helix. To modulate potential immunogenicity, the addition of poly(ethylene glycol) near the linkage site may be performed. FIG. 5-A diagram of a strategy for the design of GLP-1 analogs having particular structural characteristics is shown. Biosynthetic route: advantages—cost, homogeneity, flexibility in format for Cys conjugation. Critical observations: 1) Exendin-4 shares $1^{st}$ 10 amino acids with GLP-1, except A8G; 2) A8G substitution is DPPIV susceptible in GLP-1, not in exendin-4; and 3) Exendin-4 has helical structure based on aromatic stacking at positions Y28, W33 . . . not seen in GLP-1. Conclusion: Non-natural amino acid substitution to promote helical structure could both preserve stability and enhance potency . . . Y28 preferred site.

Residues were evaluated on their contribution to improve metabolic stability, stabilize the helical structure, decrease potential aggregation of the molecule, and modulate receptor binding affinity. A model of GLP-1 receptor-ligand interaction is detailed in Lopez de Maturana, R. et al. (2003) J. Biol. Chem. 278, 10195-10200.

In some embodiments, one or more non-naturally encoded amino acids are incorporated at any position in GLP-1, before the first amino acid (at the amino terminus), an addition at the carboxy terminus, or any combination thereof. In some embodiments, the GLP-1 polypeptide of the invention comprises one or more non-naturally encoded amino acids at positions: before the first amino acid at position 7 (i.e. at the N terminus), 7H, 8A, 9E, V16, 17S, 18S, 19Y, 20L, 21E, 22G, 23Q, 24A, 25A, 26K, 27E, 28F, 29I, 30A, 31W, 32L, 33V, 34K, 35G, 36R, 37G, an addition at position 38 (i.e. at the carboxyl terminus) or any combination thereof. In some embodiments, a GLP-1 polypeptide of the invention may comprise one or more non-naturally encoded amino acids at position: 18S, 19Y, 20L, 22G, 23Q, 25A, 26K, 27E, 30A, any of the amino acids W31 to G37, an addition at 38 (i.e. at the carboxyl terminus), or any combination thereof. In preferred embodiments, the GLP-1 polypeptide comprises a non-naturally encoded amino acid at position 19Y, 23Q, 26K, 27E, 30A, or 38 (i.e. at the carboxyl terminus). In some embodiments, the non-naturally encoded amino acid is linked to a water soluble polymer. In some embodiments the water soluble polymer is poly(ethylene glycol). In some embodiments, the non-naturally encoded amino acid is linked to the water soluble polymer with a linker. In some embodiments, the non-naturally encoded amino acid is linked to the water soluble polymer with a linker that is biodegradable. In some embodiments, the biodegradable linker can be used to form a prodrug comprising the BSP. In one example of this prodrug approach, the water soluble polymer blocks GLP-1 activity, and degradation of the linker releases active GLP-1. In some embodiments, the non-naturally encoded amino acid is linked to an acyl moiety or acyl chain. In some embodiments, the non-naturally encoded amino acid is linked to an acyl moiety or acyl chain by a linker. In some embodiments, the non-naturally encoded amino acid is linked to an acyl moiety or acyl chain by a poly(ethylene glycol) linker or a prodrug. In some embodiments, the non-naturally encoded amino acid is linked to serum albumin. In some embodiments, the non-naturally encoded amino acid is linked to serum albumin by a linker. In some embodiments, the linker is a poly(ethylene glycol) or a prodrug. In some embodiments, the linker is a dual cleavage prodrug in which step 1 is controlled release of a molecule such as albumin and step 2 is a second cleavage releasing the linker or a portion thereof.

Figure 6:
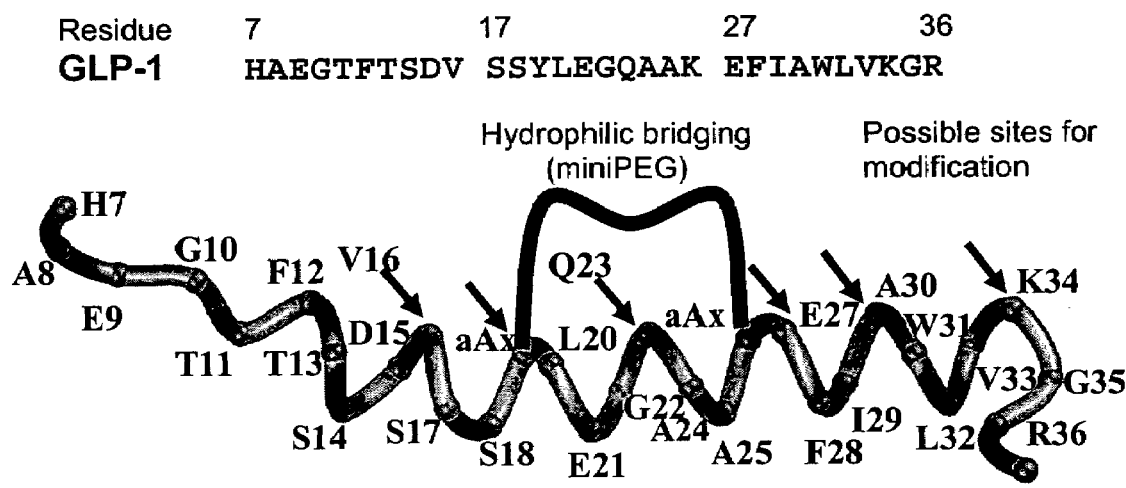
FIG. 6—A diagram of a strategy for the design of a GLP-1 polypeptide (SEQ ID NO: 1) with an intramolecular bridge is shown.
Figure 7:
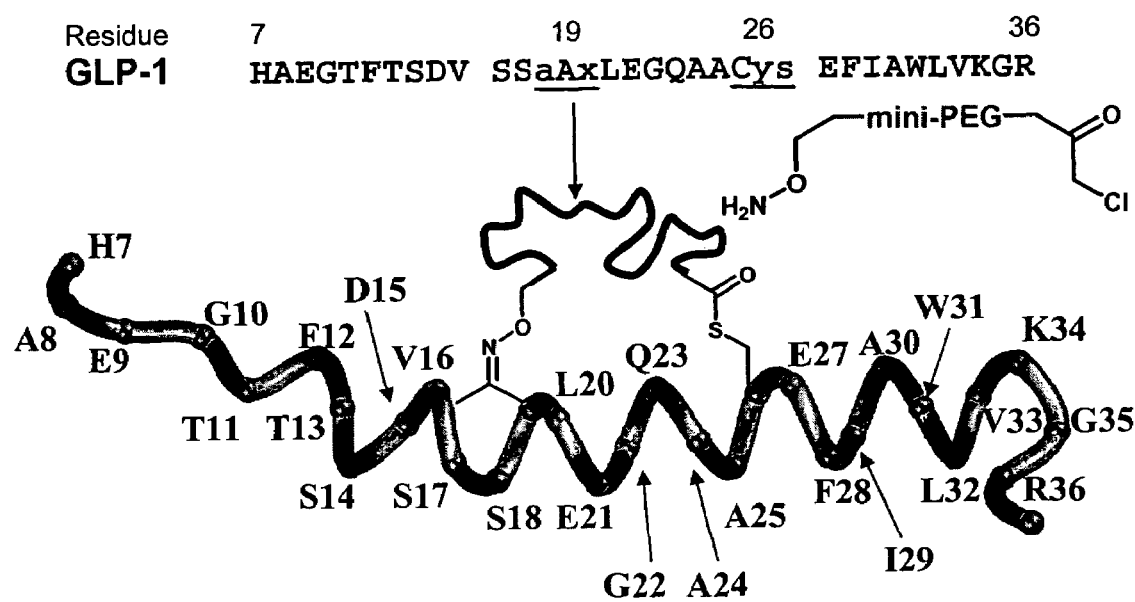
FIG. 7—A potential chemical strategy for intramolecular bridging in GLP-1 (SEQ ID NO: 1) is shown.

Another strategy for a GLP-1 polypeptide involves forming an intramolecular bridge between two non-naturally encoded amino acids present in the GLP-1 molecule. The bridge may be formed to enhance the alpha-helical structure of the molecule, reduce peptidase or protease digestion, increase the solubility, and/or improve the PK/PD profiles of the polypeptide. The GLP-1 molecule comprises one or more non-naturally encoded amino acids. One of the two bridged residues may be a non-naturally encoded amino acid or a naturally encoded amino acid. The two non-naturally encoded amino acids or non-naturally encoded amino acid and naturally encoded amino acid may be joined by a linker, polymer, or a biologically active molecule. The linkage between the two amino acids may be through a covalent bond between the two amino acids. A linker or polymer involved in bridging may be a bifunctional linker or a bifunctional polymer. In some embodiments, the non-natural amino acids are joined by a hydrophilic bridge (miniPEG). FIG. 6 shows one chemical strategy for intra-bridging is shown as FIG. 7. A non-naturally encoded amino acid in GLP-1 is linked to a naturally encoded amino acid present in the same polypeptide by a linker, polymer, or a biologically active molecule. The naturally encoded amino acid attached to the linker, polymer, or a biologically active molecule may be the result of an amino acid substitution.

In combination with any of the above strategies, the GLP-1 polypeptide may comprise one or more natural amino acid substitutions. In some embodiments, the GLP-1 polypeptide comprises one or more of the following substitutions: 8A to G; 16V to F or L; 22 G to E; 30 A to E; 34 K to R. In some embodiments, the GLP-1 polypeptide comprises one of the following substitutions: 8A to V or 8A to S. In some embodiments, the GLP-1 polypeptide comprises one or more substitutions with cysteine. In some embodiments, the GLP-1 polypeptide comprises one or more cysteine substitution at position 17, 18, 19, 20, 21, 22, 23, 24, 25, 26, 27, 28, 29, 30, 31, 32, 33, or any combination thereof. In some embodiments, the chemically reactive cysteine is conjugated to a water soluble polymer or acyl moiety. In some embodiments, the GLP-1 polypeptide comprises one or more hydrophilic amino acid substitution at a residue within the non-conserved face of the helix.

Example 2

This example details expression of BSP including a non-naturally encoded amino acid in *E. coli*. Isolation of GLP-1 and production of GLP-1 in host cells is described in, e.g., U.S. Pat. No. 5,118,666, which is incorporated by reference herein.

An introduced translation system that comprises an orthogonal tRNA (O-tRNA) and an orthogonal aminoacyl tRNA synthetase (O-RS) is used to express BSP containing a non-naturally encoded amino acid. The O-RS preferentially aminoacylates the O-tRNA with a non-naturally encoded amino acid. In turn the translation system inserts the non-naturally encoded amino acid into BSP, in response to an encoded selector codon.

TABLE 2

O-RS and O-tRNA sequences.

| | | |
|---|---|---|
| SEQ ID NO: 4 | *M. jannaschii* mtRNA$_{CUA}^{Tyr}$ | tRNA |
| SEQ ID NO: 5 | HLAD03; an optimized amber supressor tRNA | tRNA |
| SEQ ID NO: 6 | HL325A; an optimized AGGA frameshift supressor tRNA | tRNA |
| SEQ ID NO: 7 | Aminoacyl tRNA synthetase for the incorporation of p-azido-L-phenylalanine p-Az-PheRS(6) | RS |
| SEQ ID NO: 8 | Aminoacyl tRNA synthetase for the incorporation of p-benzoyl-L-phenylalanine p-BpaRS(1) | RS |
| SEQ ID NO: 9 | Aminoacyl tRNA synthetase for the incorporation of propargyl-phenylalanine Propargyl-PheRS | RS |
| SEQ ID NO: 10 | Aminoacyl tRNA synthetase for the incorporation of propargyl-phenylalanine Propargyl-PheRS | RS |
| SEQ ID NO: 11 | Aminoacyl tRNA synthetase for the incorporation of propargyl-phenylalanine Propargyl-PheRS | RS |
| SEQ ID NO: 12 | Aminoacyl tRNA synthetase for the incorporation of p-azido-phenylalanine p-Az-PheRS(1) | RS |
| SEQ ID NO: 13 | Aminoacyl tRNA synthetase for the incorporation of p-azido-phenylalanine p-Az-PheRS(3) | RS |
| SEQ ID NO: 14 | Aminoacyl tRNA synthetase for the incorporation of p-azido-phenylalanine p-Az-PheRS(4) | RS |
| SEQ ID NO: 15 | Aminoacyl tRNA synthetase for the incorporation of p-azido-phenylalanine p-Az-PheRS(2) | RS |
| SEQ ID NO: 16 | Aminoacyl tRNA synthetase for the incorporation of p-acetyl-phenylalanine (LW1) | RS |
| SEQ ID NO: 17 | Aminoacyl tRNA synthetase for the incorporation of p-acetyl-phenylalanine (LW5) | RS |
| SEQ ID NO: 18 | Aminoacyl tRNA synthetase for the incorporation of p-acetyl-phenylalanine (LW6) | RS |
| SEQ ID NO: 19 | Aminoacyl tRNA synthetase for the incorporation of p-azido-phenylalanine (AzPheRS-5) | RS |
| SEQ ID NO: 20 | Aminoacyl tRNA synthetase for the incorporation of p-azido-phenylalanine (AzPheRS-6) | RS | group of many potential sets of residues that may be joined by an intramolecular bridge. In some embodiments, the intramolecular bridge is formed between positions 16 and 19 or 20, or 16 and 23; 19 and 23 or 19 and 26; 20 and 27; 23 and 26 or 27, or 23 and 30; 27 and 30 or 31 or 27 and 33 or 34; 30 and 34. Residues 17-33 form the alpha-helix structure. A potential The transformation of *E. coli* with plasmids containing the modified BSP gene and the orthogonal aminoacyl tRNA synthetase/tRNA pair (specific for the desired non-naturally encoded amino acid) allows the site-specific incorporation of non-naturally encoded amino acid into the BSP. The transformed *E. coli*, grown at 37° C. in media containing between 0.01-100 mM of the particular non-naturally encoded amino acid, expresses modified BSP with high fidelity and efficiency. The His-tagged BSP containing a non-naturally encoded amino acid is produced by the *E. coli* host cells as inclusion bodies or aggregates. The aggregates are solubilized and affinity purified under denaturing conditions in 6M guanidine HCl. Refolding is performed by dialysis at 4° C. overnight in 50 mM TRIS-HCl, pH8.0, 40 μM CuSO$_4$, and 2% (w/v) Sarkosyl. The material is then dialyzed against 20 mM TRIS-HCl, pH 8.0, 100 mM NaCl, 2 mM CaCl$_2$, followed by removal of the His-tag. See Boissel et al., (1993) J. Biol. Chem. 268:15983-93. Methods for purification of BSP are well known in the art and are confirmed by SDS-PAGE, Western Blot analyses, or electrospray-ionization ion trap mass spectrometry and the like.

Figure 8:
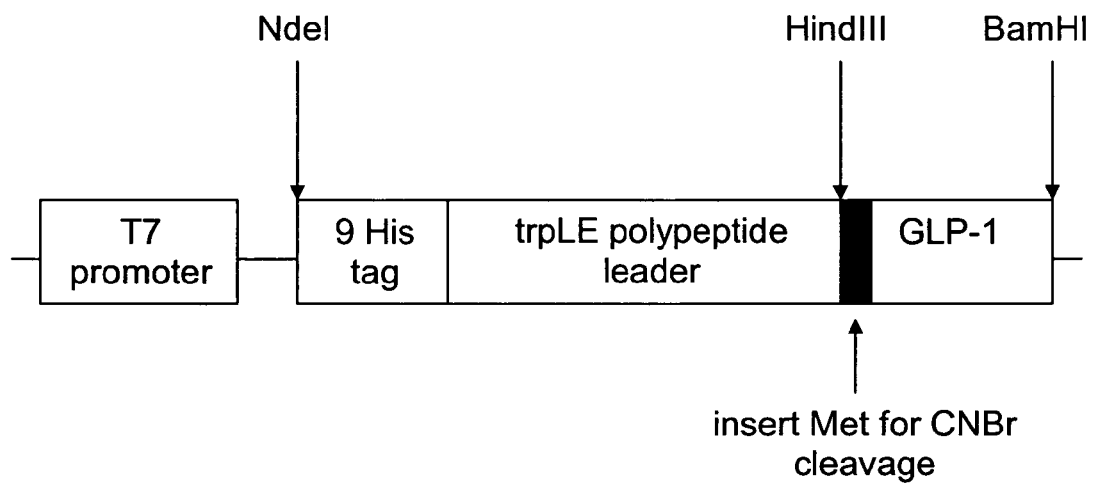
FIG. 8—A construct for GLP-1 expression is shown and the sequence of the trp LE polypeptide leader sequence (SEQ ID NO: 25) is shown.

FIG. 8 shows a construct for GLP-1 expression. Primer pairs were designed to obtain a GLP-1 insert with flanking BamHI and HindIII sites. The GLP-1 primers were annealed and ligated into an expression vector digested with BamHI-HindIII. The expression vector comprises the T7 promoter, an N-terminal His tag, and polynucleotide sequence encoding the TrpLE leader polypeptide sequence upstream of the GLP-1 insert. The TrpLE leader polypeptide sequence is shown in FIG. 8 and as SEQ ID NO: 25. The polynucleotide insert may or may not encode the amino acid methionine N terminal to the GLP-1 sequence. Constructs include, but are not limited to, GLP-1 polynucleotide sequence encoding a non-naturally encoded amino acid substitution at positions: Y19, Q23, K26, E27, or A30. The GLP-1 polypeptide may also comprise one or more natural amino acid substitution.

Example 3

This example details introduction of a carbonyl-containing amino acid and subsequent reaction with an aminooxy-containing PEG.

This Example demonstrates a method for the generation of a BSP that incorporates a ketone-containing non-naturally encoded amino acid that is subsequently reacted with an aminooxy-containing PEG of approximately 5,000 MW. For example, each of the residues identified according to the criteria of Example 1 for GLP-1 or Example 32 for T-20 is separately substituted with a non-naturally encoded amino acid having the following structure:

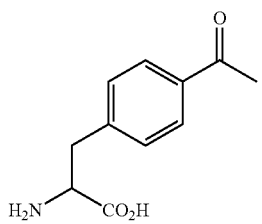

The sequences utilized for site-specific incorporation of p-acetyl-phenylalanine into GLP-1 are any of those described in Example 1 and SEQ ID NO: 4 (muttRNA, *M. jannaschii* mtRNA$_{CUA}^{Tyr}$), and 16, 17 or 18 (TyrRS LW1, 5, or 6) described in Example 2 above. The sequences utilized for site-specific incorporation of p-acetyl-phenylalanine into T-20 are any of those described in Example 32 and SEQ ID NO: 4 (muttRNA, *M. jannaschii* mtRNA$_{CUA}^{Tyr}$), and 16, 17 or 18 (TyrRS LW1, 5, or 6) described in Example 2 above.

Once modified, the BSP variant comprising the carbonyl-containing amino acid is reacted with an aminooxy-containing PEG derivative of the form:

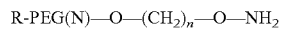

where R is methyl, n is 3 and N is approximately 5,000 MW. The purified BSP containing p-acetylphenylalanine dissolved at 10 mg/mL in 25 mM MES (Sigma Chemical, St. Louis, Mo.) pH 6.0, 25 mM Hepes (Sigma Chemical, St. Louis, Mo.) pH 7.0, or in 10 mM Sodium Acetate (Sigma Chemical, St. Louis, Mo.) pH 4.5, is reacted with a 10 to 100-fold excess of aminooxy-containing PEG, and then stirred for 10-16 hours at room temperature (Jencks, W. *J. Am. Chem. Soc.* 1959, 81, pp 475). The PEG-BSP is then diluted into appropriate buffer for immediate purification and analysis.

Example 4

Conjugation with a PEG consisting of a hydroxylamine group linked to the PEG via an amide linkage.

A PEG reagent having the following structure is coupled to a ketone-containing non-naturally encoded amino acid using the procedure described in Example 3:

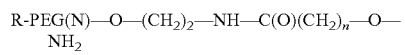

where R=methyl, n=4 and N is approximately 20,000 MW. The reaction, purification, and analysis conditions are as described in Example 3.

Example 5

This example details the introduction of two distinct non-naturally encoded amino acids into a BSP.

This example demonstrates a method for the generation of a GLP-1 polypeptide that incorporates non-naturally encoded amino acid comprising a ketone functionality at two positions among the residues identified according to Example 1, wherein X* represents a non-naturally encoded amino acid. The GLP-1 polypeptide is prepared as described in Examples 1 and 2, except that the selector codon is introduced at two distinct sites within the nucleic acid. This example demonstrates a method for the generation of a T-20 polypeptide that incorporates non-naturally encoded amino acid comprising a ketone functionality at two positions among the residues identified according to Example 32, wherein X* represents a non-naturally encoded amino acid. The T-20 polypeptide is prepared as described in Examples 32 and 33, except that the selector codon is introduced at two distinct sites within the nucleic acid.

Example 6

This example details conjugation of a BSP to a hydrazide-containing PEG and subsequent in situ reduction.

A GLP-1 polypeptide incorporating a carbonyl-containing amino acid is prepared according to the procedure described in Examples 2 and 3 or a T-20 polypeptide incorporating a carbonyl-containing amino acid is prepared according to the procedure described in Examples 32 and 33. Once modified, a hydrazide-containing PEG having the following structure is conjugated to the GLP-1 or T-20 polypeptide:

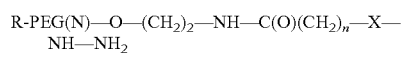

where R=methyl, n=2 and N=10,000 MW and X is a carbonyl (C═O) group. The purified GLP-1 containing p-acetylphenylalanine is dissolved at between 0.1-10 mg/mL in 25 mM MES (Sigma Chemical, St. Louis, Mo.) pH 6.0, 25 mM Hepes (Sigma Chemical, St. Louis, Mo.) pH 7.0, or in 10 mM Sodium Acetate (Sigma Chemical, St. Louis, Mo.) pH 4.5, is reacted with a 1 to 100-fold excess of hydrazide-containing PEG, and the corresponding hydrazone is reduced in situ by addition of stock 1M NaCNBH$_3$ (Sigma Chemical, St. Louis, Mo.), dissolved in H$_2$O, to a final concentration of 10-50 mM. Reactions are carried out in the dark at 4° C. to RT for 18-24 hours. Reactions are stopped by addition of 1 M Tris (Sigma Chemical, St. Louis, Mo.) at about pH 7.6 to a final Tris concentration of 50 mM or diluted into appropriate buffer for immediate purification.

Example 7

This example details introduction of an alkyne-containing amino acid into BSP and derivatization with mPEG-azide.

Any of the residues identified according to Example 1 (GLP-1) or Example 32 (T-20) are each substituted with the following non-naturally encoded amino acid:

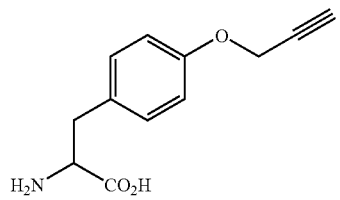

The sequences utilized for site-specific incorporation of p-propargyl-tyrosine into GLP-1 are SEQ ID NO: 2 (GLP-1), SEQ ID NO: 4 (muttRNA, *M. jannaschii* mtRNA$_{CUA}^{Tyr}$), and 9, 10 or 11 described in Example 2 above. The GLP-1 polypeptide containing the propargyl tyrosine is expressed in *E. coli* and purified using the conditions described in Example 3. The sequences utilized for site-specific incorporation of p-propargyl-tyrosine into T-20 are SEQ ID NO: 22 or 24, and SEQ ID NO: 4 (muttRNA, *M. jannaschii* mtRNA$_{CUA}^{Tyr}$), and 9, 10 or 11 described in Example 2 above. The T-20 polypeptide containing the propargyl tyrosine is expressed in *E. coli* and purified using the conditions described in Example 3.

The purified GLP-1 or T-20 containing propargyl-tyrosine dissolved at between 0.1-10 mg/mL in PB buffer (100 mM sodium phosphate, 0.15 M NaCl, pH=8) and a 10 to 1000-fold excess of an azide-containing PEG is added to the reaction mixture. A catalytic amount of CuSO$_4$ and Cu wire are then added to the reaction mixture. After the mixture is incubated (including but not limited to, about 4 hours at room temperature or 37° C., or overnight at 4° C.), H$_2$O is added and the mixture is filtered through a dialysis membrane. The sample can be analyzed for the addition, including but not limited to, by similar procedures described in Example 3.

In this Example, the PEG will have the following structure:

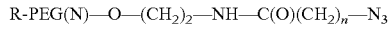

R-PEG(N)—O—(CH$_2$)$_2$—NH—C(O)(CH$_2$)$_n$—N$_3$ where R is methyl, n is 4 and N is 10,000 MW.

Example 8

This example details substitution of a large, hydrophobic amino acid in a BSP with propargyl tyrosine.

A Phe, Trp or Tyr residue present within GLP-1 or T-20 is substituted with the following non-naturally encoded amino acid as described in Example 7:

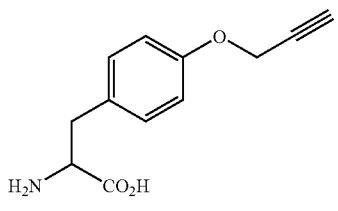

Once modified, a PEG is attached to the BSP variant comprising the alkyne-containing amino acid. The PEG will have the following structure:

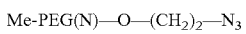

Me-PEG(N)—O—(CH$_2$)$_2$—N$_3$ and coupling procedures would follow those in Example 7. This will generate a BSP variant comprising a non-naturally encoded amino acid that is approximately isosteric with one of the naturally-occurring, large hydrophobic amino acids and which is modified with a PEG derivative at a distinct site within the polypeptide.

Example 9

This example details generation of a BSP homodimer, heterodimer, homomultimer, or heteromultimer separated by one or more PEG linkers.

The alkyne-containing BSP variant produced in Example 7 is reacted with a bifunctional PEG derivative of the form:

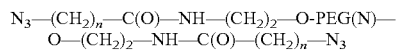

N$_3$—(CH$_2$)$_n$—C(O)—NH—(CH$_2$)$_2$—O-PEG(N)—
O—(CH$_2$)$_2$—NH—C(O)—(CH$_2$)$_n$—N$_3$ where n is 4 and the PEG has an average MW of approximately 5,000, to generate the corresponding BSP homodimer where the two BSP molecules are physically separated by PEG. In an analogous manner a BSP may be coupled to one or more other polypeptides to form heterodimers, homomultimers, or heteromultimers. Coupling, purification, and analyses will be performed as in Examples 7 and 3.

Example 10

This example details coupling of a saccharide moiety to BSP.

One residue of the following is substituted with the non-naturally encoded amino acid below: 19, 23, 26, 27, 28, 29, 30, or 33 (as in SEQ ID NO:1, 2, 3, 21, or the corresponding amino acids of other GLP-1 polypeptides), as described in Example 3. Alternatively, one residue of T-20 is substituted with the non-naturally encoded amino acid below, as described in Example 3.

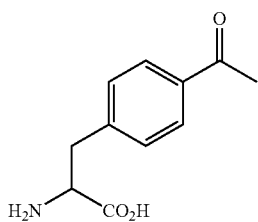

Once modified, the BSP variant comprising the carbonyl-containing amino acid is reacted with a β-linked aminooxy analogue of N-acetylglucosamine (GlcNAc). The BSP variant (10 mg/mL) and the aminooxy saccharide (21 mM) are mixed in aqueous 100 mM sodium acetate buffer (pH 5.5) and incubated at 37° C. for 7 to 26 hours. A second saccharide is coupled to the first enzymatically by incubating the saccharide-conjugated BSP (5 mg/mL) with UDP-galactose (16 mM) and β-1,4-galacytosyltransferase (0.4 units/mL) in 150 mM HEPES buffer (pH 7.4) for 48 hours at ambient temperature (Schanbacher et al. *J. Biol. Chem.* 1970, 245, 5057-5061).

Example 11

This example details generation of a PEGylated BSP antagonist.

One of the following residues of GLP-1, 19, 23, 26, 27, 28, 29, 30, or 33, is substituted with the following non-naturally encoded amino acid as described in Example 3.

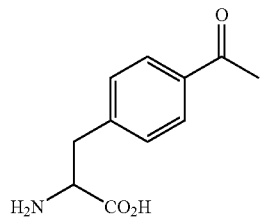

Once modified, the BSP comprising the carbonyl-containing amino acid will be reacted with an aminooxy-containing PEG derivative of the form:

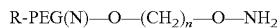

R-PEG(N)—O—(CH$_2$)$_n$—O—NH$_2$ where R is methyl, n is 4 and N is 20,000 MW to generate a BSP antagonist comprising a non-naturally encoded amino acid that is modified with a PEG derivative at a single site within the polypeptide. Coupling, purification, and analyses are performed as in Example 3.

Example 12

Generation of a BSP Homodimer, Heterodimer, Homomultimer, or Heteromultimer in which the BSP Molecules are Linked Directly A GLP-1 variant comprising the alkyne-containing amino acid can be directly coupled to another GLP-1 variant comprising the azido-containing amino acid, each of which comprise non-naturally encoded amino acid substitutions at the sites described in, but not limited to, Example 1. In an analogous manner a GLP-1 polypeptide may be coupled to one or more other polypeptides to form heterodimers, homomultimers, or heteromultimers. Coupling, purification, and analyses are performed as in Examples 3, 6, and 7.

A T-20 variant comprising the alkyne-containing amino acid can be directly coupled to another T-20 variant comprising the azido-containing amino acid, each of which comprise non-naturally encoded amino acid substitutions at the sites described in, but not limited to, Example 32. In an analogous manner a T-20 polypeptide may be coupled to one or more other polypeptides to form heterodimers, homomultimers, or heteromultimers. Coupling, purification, and analyses are performed as in Examples 3, 6, and 7.

Example 13

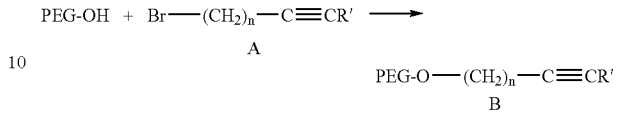

PEG-OH + Br—(CH$_2$)$_n$—C≡CR' ⟶
A
PEG-O—(CH$_2$)$_n$—C≡CR'
B

The polyalkylene glycol (P—OH) is reacted with the alkyl halide (A) to form the ether (B). In these compounds, n is an integer from one to nine and R' can be a straight- or branched-chain, saturated or unsaturated C1, to C20 alkyl or heteroalkyl group. R' can also be a C3 to C7 saturated or unsaturated cyclic alkyl or cyclic heteroalkyl, a substituted or unsubstituted aryl or heteroaryl group, or a substituted or unsubstituted alkaryl (the alkyl is a C1 to C20 saturated or unsaturated alkyl) or heteroalkaryl group. Typically, PEG-OH is polyethylene glycol (PEG) or monomethoxy polyethylene glycol (mPEG) having a molecular weight of 800 to 40,000 Daltons (Da).

Example 14

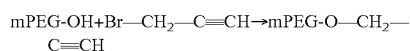

mPEG-OH+Br—CH$_2$—C≡CH→mPEG-O—CH$_2$—C≡CH mPEG-OH with a molecular weight of 20,000 Da (mPEG-OH 20 kDa; 2.0 g, 0.1 mmol, Sunbio) was treated with NaH (12 mg, 0.5 mmol) in THF (35 mL). A solution of propargyl bromide, dissolved as an 80% weight solution in xylene (0.56 mL, 5 mmol, 50 equiv., Aldrich), and a catalytic amount of KI were then added to the solution and the resulting mixture was heated to reflux for 2 hours. Water (1 mL) was then added and the solvent was removed under vacuum. To the residue was added CH$_2$Cl$_2$ (25 mL) and the organic layer was separated, dried over anhydrous Na$_2$SO$_4$, and the volume was reduced to approximately 2 mL. This CH$_2$Cl$_2$ solution was added to diethyl ether (150 mL) drop-wise. The resulting precipitate was collected, washed with several portions of cold diethyl ether, and dried to afford propargyl-O-PEG.

Example 15

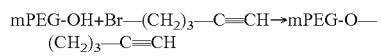

mPEG-OH+Br—(CH$_2$)$_3$—C≡CH→mPEG-O—(CH$_2$)$_3$—C≡CH

The mPEG-OH with a molecular weight of 20,000 Da (mPEG-OH 20 kDa; 2.0 g, 0.1 mmol, Sunbio) was treated with NaH (12 mg, 0.5 mmol) in THF (35 mL). Fifty equivalents of 5-bromo-1-pentyne (0.53 mL, 5 mmol, Aldrich) and a catalytic amount of KI were then added to the mixture. The resulting mixture was heated to reflux for 16 hours. Water (1 mL) was then added and the solvent was removed under vacuum. To the residue was added CH$_2$Cl$_2$ (25 mL) and the organic layer was separated, dried over anhydrous Na$_2$SO$_4$, and the volume was reduced to approximately 2 mL. This CH$_2$Cl$_2$ solution was added to diethyl ether (150 mL) drop-wise. The resulting precipitate was collected, washed with several portions of cold diethyl ether, and dried to afford the corresponding alkyne. 5-chloro-1-pentyne may be used in a similar reaction.

Example 16

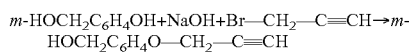

(1)

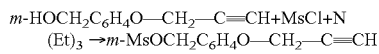

(2)

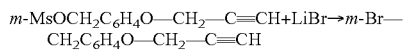

(3)

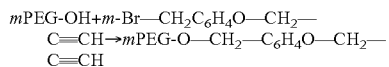

(4)

To a solution of 3-hydroxybenzylalcohol (2.4 g, 20 mmol) in THF (50 mL) and water (2.5 mL) was first added powdered sodium hydroxide (1.5 g, 37.5 mmol) and then a solution of propargyl bromide, dissolved as an 80% weight solution in xylene (3.36 mL, 30 mmol). The reaction mixture was heated at reflux for 6 hours. To the mixture was added 10% citric acid (2.5 mL) and the solvent was removed under vacuum. The residue was extracted with ethyl acetate (3×15 mL) and the combined organic layers were washed with saturated NaCl solution (10 mL), dried over $MgSO_4$ and concentrated to give the 3-propargyloxybenzyl alcohol.

Methanesulfonyl chloride (2.5 g, 15.7 mmol) and triethylamine (2.8 mL, 20 mmol) were added to a solution of compound 3 (2.0 g, 11.0 mmol) in $CH_2Cl_2$ at 0° C. and the reaction was placed in the refrigerator for 16 hours. A usual work-up afforded the mesylate as a pale yellow oil. This oil (2.4 g, 9.2 mmol) was dissolved in THF (20 mL) and LiBr (2.0 g, 23.0 mmol) was added. The reaction mixture was heated to reflux for 1 hour and was then cooled to room temperature. To the mixture was added water (2.5 mL) and the solvent was removed under vacuum. The residue was extracted with ethyl acetate (3×15 mL) and the combined organic layers were washed with saturated NaCl solution (10 mL), dried over anhydrous $Na_2SO_4$, and concentrated to give the desired bromide.

mPEG-OH 20 kDa (1.0 g, 0.05 mmol, Sunbio) was dissolved in THF (20 mL) and the solution was cooled in an ice bath. NaH (6 mg, 0.25 mmol) was added with vigorous stirring over a period of several minutes followed by addition of the bromide obtained from above (2.55 g, 11.4 mmol) and a catalytic amount of KI. The cooling bath was removed and the resulting mixture was heated to reflux for 12 hours. Water (1.0 mL) was added to the mixture and the solvent was removed under vacuum. To the residue was added $CH_2Cl_2$ (25 mL) and the organic layer was separated, dried over anhydrous $Na_2SO_4$, and the volume was reduced to approximately 2 mL. Drop-wise addition to an ether solution (150 mL) resulted in a white precipitate, which was collected to yield the PEG derivative.

Example 17

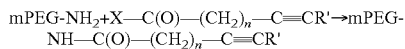

The terminal alkyne-containing poly(ethylene glycol) polymers can also be obtained by coupling a poly(ethylene glycol) polymer containing a terminal functional group to a reactive molecule containing the alkyne functionality as shown above. n is between 1 and 10. R' can be H or a small alkyl group from C1 to C4.

Example 18

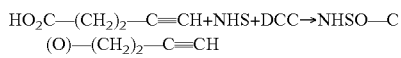

(1)

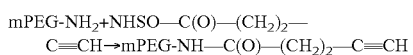

(2)

4-pentynoic acid (2.943 g, 3.0 mmol) was dissolved in $CH_2Cl_2$ (25 mL). N-hydroxysuccinimide (3.80 g, 3.3 mmol) and DCC (4.66 g, 3.0 mmol) were added and the solution was stirred overnight at room temperature. The resulting crude NHS ester 7 was used in the following reaction without further purification.

mPEG-$NH_2$ with a molecular weight of 5,000 Da (mPEG-$NH_2$, 1 g, Sunbio) was dissolved in THF (50 mL) and the mixture was cooled to 4° C. NHS ester 7 (400 mg, 0.4 mmol) was added portion-wise with vigorous stirring. The mixture was allowed to stir for 3 hours removed under vacuum. To the residue was added $CH_2Cl_2$ (50 mL) and the organic layer was separated, dried over anhydrous $Na_2SO_4$, and the volume was reduced to approximately 2 mL. This $CH_2Cl_2$ solution was added to ether (150 mL) drop-wise. The resulting precipitate was collected and dried in vacuo.

Example 19

This Example represents the preparation of the methane sulfonyl ester of poly(ethylene glycol), which can also be referred to as the methanesulfonate or mesylate of poly(ethylene glycol). The corresponding tosylate and the halides can be prepared by similar procedures.

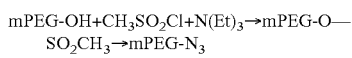

The mPEG-OH (MW=3,400, 25 g, 10 mmol) in 150 mL of toluene was azeotropically distilled for 2 hours under nitrogen and the solution was cooled to room temperature. 40 mL of dry $CH_2Cl_2$ and 2.1 mL of dry triethylamine (15 mmol) were added to the solution. The solution was cooled in an ice bath and 1.2 mL of distilled methanesulfonyl chloride (15 mmol) was added dropwise. The solution was stirred at room temperature under nitrogen overnight, and the reaction was quenched by adding 2 mL of absolute ethanol. The mixture was evaporated under vacuum to remove solvents, primarily those other than toluene, filtered, concentrated again under vacuum, and then precipitated into 100 mL of diethyl ether. The filtrate was washed with several portions of cold diethyl ether and dried in vacuo to afford the mesylate.

The mesylate (20 g, 8 mmol) was dissolved in 75 ml of THF and the solution was cooled to 4° C. To the cooled solution was added sodium azide (1.56 g, 24 mmol). The reaction was heated to reflux under nitrogen for 2 hours. The solvents were then evaporated and the residue diluted with $CH_2Cl_2$ (50 mL). The organic fraction was washed with NaCl solution and dried over anhydrous $MgSO_4$. The volume was reduced to 20 ml and the product was precipitated by addition to 150 ml of cold dry ether.

Example 20

  (1)

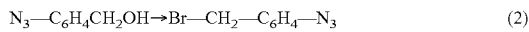  (2)

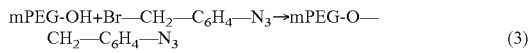  (3)

4-azidobenzyl alcohol can be produced using the method described in U.S. Pat. No. 5,998,595, which is incorporated by reference herein. Methanesulfonyl chloride (2.5 g, 15.7 mmol) and triethylamine (2.8 mL, 20 mmol) were added to a solution of 4-azidobenzyl alcohol (1.75 g, 11.0 mmol) in $CH_2Cl_2$ at 0° C. and the reaction was placed in the refrigerator for 16 hours. A usual work-up afforded the mesylate as a pale yellow oil. This oil (9.2 mmol) was dissolved in THF (20 mL) and LiBr (2.0 g, 23.0 mmol) was added. The reaction mixture was heated to reflux for 1 hour and was then cooled to room temperature. To the mixture was added water (2.5 mL) and the solvent was removed under vacuum. The residue was extracted with ethyl acetate (3×15 mL) and the combined organic layers were washed with saturated NaCl solution (10 mL), dried over anhydrous $Na_2SO_4$, and concentrated to give the desired bromide.

mPEG-OH 20 kDa (2.0 g, 0.1 mmol, Sunbio) was treated with NaH (12 mg, 0.5 mmol) in THF (35 mL) and the bromide (3.32 g, 15 mmol) was added to the mixture along with a catalytic amount of KI. The resulting mixture was heated to reflux for 12 hours. Water (1.0 mL) was added to the mixture and the solvent was removed under vacuum. To the residue was added $CH_2Cl_2$ (25 mL) and the organic layer was separated, dried over anhydrous $Na_2SO_4$, and the volume was reduced to approximately 2 mL. Dropwise addition to an ether solution (150 mL) resulted in a precipitate, which was collected to yield mPEG-O—$CH_2$—$C_6H_4$—$N_3$.

Example 21

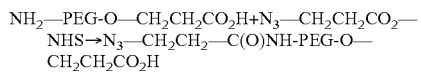

$NH_2$—PEG-O—$CH_2CH_2CO_2H$ (MW 3,400 Da, 2.0 g) was dissolved in a saturated aqueous solution of $NaHCO_3$ (10 mL) and the solution was cooled to 0° C. 3-azido-1-N-hydroxysuccinimido propionate (5 equiv.) was added with vigorous stirring. After 3 hours, 20 mL of $H_2O$ was added and the mixture was stirred for an additional 45 minutes at room temperature. The pH was adjusted to 3 with 0.5 N $H_2SO_4$ and NaCl was added to a concentration of approximately 15 wt %. The reaction mixture was extracted with $CH_2Cl_2$ (100 mL×3), dried over $Na_2SO_4$ and concentrated. After precipitation with cold diethyl ether, the product was collected by filtration and dried under vacuum to yield the omega-carboxy-azide PEG derivative.

Example 22

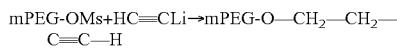

To a solution of lithium acetylide (4 equiv.), prepared as known in the art and cooled to −78° C. in THF, is added dropwise a solution of mPEG-OMs dissolved in THF with vigorous stirring. After 3 hours, the reaction is permitted to warm to room temperature and quenched with the addition of 1 mL of butanol. 20 mL of $H_2O$ is then added and the mixture was stirred for an additional 45 minutes at room temperature. The pH was adjusted to 3 with 0.5 N $H_2SO_4$ and NaCl was added to a concentration of approximately 15 wt %. The reaction mixture was extracted with $CH_2Cl_2$ (100 mL×3), dried over $Na_2SO_4$ and concentrated. After precipitation with cold diethyl ether, the product was collected by filtration and dried under vacuum to yield the 1-(but-3-ynyloxy)-methoxy-polyethylene glycol (mPEG).

Example 23

The azide- and acetylene-containing amino acids were incorporated site-selectively into proteins using the methods described in L. Wang, et al., (2001), Science 292:498-500, J. W. Chin et al., Science 301:964-7 (2003)), J. W. Chin et al., (2002), Journal of the American Chemical Society 124:9026-9027; J. W. Chin, & P. G. Schultz, (2002), Chem Bio Chem 3(11):1135-1137; J. W. Chin, et al., (2002), PNAS United States of America 99:11020-11024: and, L. Wang, & P. G. Schultz, (2002), Chem. Comm. 1:1-11. Once the amino acids were incorporated, the cycloaddition reaction was carried out with 0.01 mM protein in phosphate buffer (PB), pH 8, in the presence of 2 mM PEG derivative, 1 mM $CuSO_4$, and ~1 mg Cu-wire for 4 hours at 37° C.

Example 24

This example describes methods to measure in vitro and in vivo activity of GLP-1 comprising a non-naturally encoded amino acid and PEGylated GLP-1.

A number of assays may be used to monitor the activity of GLP-1 polypeptides of the invention. Peptide hormones such as GLP-1 activate specific G protein-coupled receptors, and thus GLP-1 polypeptides of the invention may be evaluated by assays detecting GLP-1 receptor dependent cAMP formation. Downstream intracellular cAMP production can be measured by a variety of methods, including but not limited to, colorimetric, luminescent, time-resolved fluorescence, or FP methods. Rat insulinoma-derived RIN-m5F cells possess endogenous GLP-1 receptor coupled to adenylate cyclase (Fehmann. et al., Mol Cell Endocrinol 85:C39-C44; Goke et al. Res Exp Med (Berl). 1989; 189(4):257-64) and may be used to measure cAMP after receptor activation. Similarly, hamster HIT-T15 cells (ATCC, Manassas, Va.) or rat BRIN-BD11 beta cells (Green et al. J Mol Endocrinol. 2003 December; 31(3):529-4) may be used.

Alternatively, cAMP production may be measured in cells transfected with recombinant hGLP-1 receptor including, but not limited to CHO (Kim et al. 2003 Diabetes 52:751-59), BHK (baby hamster kidney; Knudsen et al. 2000 J. Med. Chem. 43:1664-1669), and CHL (Chinese hamster lung) cells or primary cells such as pancreatic islet cells isolated from rats, mice or hamsters. The GLP-1 receptor can be prepared as described in Thorens, Proc. Natl. Acad. Sci. USA 1992, 89(18):8641-5 or U.S. Pat. Nos. 5,670,360 and 6,051,689, which is incorporated by reference herein. Forskolin (EMD Biosciences, San Diego, Calif.), an adenylate cyclase activator, and inhibitors of adenylate cyclase, P13K, MAPK, or p38 may be used as assay controls. Agonist controls include GLP-1(7-37) and exendin-4, a potent GLP-1 receptor agonist, and antagonist controls include the GLP-1 receptor antagonist Exendin (9-39) (available from Bachem AG). Dose response curves are plotted for each compound tested and $EC_{50}$ values are calculated. Alternatively, cAMP may be measured by other assays. Generally, these assays are well known in the art.

Insulin secretion is also a measure of the biological activity of GLP-1 polypeptides of the invention. In vitro studies of insulin secretion may be calculated in cells post incubation with a range of concentrations of GLP-1 polypeptide(s) and glucose via insulin RIA or ELISA. Green et al., supra evaluated insulinotropic effects of GLP-1 polypeptides in rat BRIN-BD11 beta cells. Rat pancreatic islets may alternatively be used in insulin secretion studies (Goke et al., J. Biol. Chem. 1993 268(26)19650-19655).

Alternatively, beta islet cell growth may be measured using reagents such as XTT or BrdU. In vitro assays measuring CREB (cyclic AMP response element binding protein) transcription factor with the CRE reporter assay may also be performed.

The affinity of the GLP-1 polypeptide comprising a non-natural amino acid for its receptor can be measured by using a BIAcore™ biosensor (Pharmacia). Cells or cell lines that modulate growth or bind GLP-1 (including but not limited to, cells containing active GLP-1 receptors such as human cells, or recombinant GLP-1 receptor producing cells) can be used to monitor GLP-1 receptor binding. For example, cells or cell lines that modulate growth or bind GLP-1 (including but not limited to, cells containing active GLP-1 receptors such as human cells, or recombinant GLP-1 receptor producing cells) can be used to monitor GLP-1 receptor binding.

Alternatively, binding can also be measured using cells transfected with recombinant hGLP-1 receptor (including, but not limited to, CHO, BHK (baby hamster kidney), and CHL (Chinese hamster lung fibroblast) cells). See Kim et al. supra for binding studies in transfected CHO cells and Green et al. J Mol Endocrinol. 2003 December; 31(3):529-40 for studies in transfected CHL cells. The GLP-1 receptor can be prepared as described in Thorens, Proc. Natl. Acad. Sci. USA 1992, 89(18):8641-5 or U.S. Pat. Nos. 5,670,360 and 6,051, 689, which is incorporated by reference herein.

Degradation of GLP-1 polypeptides of the invention by DPP IV or human plasma may be monitored by Liquid Chromatography/Mass Spectrometry (LC/MS) or by other methods. GLP-1 peptides of the invention may be incubated with either DPP IV or pooled human plasma for 0, 6, or 12 hours and reagents such as TFA added to end any enzymatic reactions prior to analysis. All references cited are incorporated by reference herein.

Cell Binding Assays

Cells ($3 \times 10^6$) are incubated in duplicate in PBS/1% BSA (100 μL) in the absence or presence of various concentrations (volume: 10 μl) of unlabeled GLP-1, GLP-1 or GLP-1 analog and in the presence of 125I-GLP-1 (approx. 100,000 cpm or 1 ng) at 0° C. for 90 minutes (total volume: 120 μl). Cells are then resuspended and layered over 200 μl ice cold FCS in a 350 μl plastic centrifuge tube and centrifuged (1000 g; 1 minute). The pellet is collected by cutting off the end of the tube and pellet and supernatant counted separately in a gamma counter (Packard).

Specific binding (cpm) is determined as total binding in the absence of a competitor (mean of duplicates) minus binding (cpm) in the presence of 100-fold excess of unlabeled GLP-1 (non-specific binding). The non-specific binding is measured for each of the cell types used. Experiments are run on separate days using the same preparation of $^{125}$I-GLP-1 and should display internal consistency. $^{125}$I-GLP-1 demonstrates binding to the cells. The binding is inhibited in a dose dependent manner by unlabeled natural GLP-1 or GLP-1, but not by the negative control. The ability of GLP-1 to compete for the binding of natural $^{125}$I-GLP-1, similar to natural GLP-1, suggests that the receptors recognize both forms equally well.

In Vivo Studies of PEGylated GLP-1

PEG-GLP-1, unmodified GLP-1 and buffer solution are administered to mice or rats. The results will show superior activity and prolonged half-life of the PEGylated GLP-1 of the present invention compared to unmodified GLP-1 which is indicated by significantly decreased blood glucose.

In vivo animal models for testing GLP-1 activity include those described in, U.S. Patent Application Publication No. 20040082507A1; and 20030232754A1, which are incorporated by reference herein.

Measurement of the In Vivo Half-Life of Conjugated and Non-Conjugated GLP-1 and Variants Thereof.

Male Sprague Dawley rats (about 7 weeks old) are used. On the day of administration, the weight of each animal is measured. 100 μg per kg body weight of the non-conjugated and conjugated GLP-1 samples are each injected intravenously into the tail vein of three rats. At 1 minute, 30 minutes, 1, 2, 4, 6, and 24 hours after the injection, 500 μL of blood is withdrawn from each rat while under $CO_2$-anesthesia. The blood samples are stored at room temperature for no more than 1.5 hours followed by isolation of serum by centrifugation (4° C., 18000×g for 5 minutes). The serum samples are stored at −80° C. until the day of analysis. The amount of active GLP-1 in the serum samples is quantified by the GLP-1 in vitro activity assay after thawing the samples on ice.

Animal Models

Animal models that may be used for evaluating GLP-1 peptides of the invention include, but are not limited to: the fatty Zucker (fa/fa; ZDF) rat, the ob/ob mouse, and the db/db mouse. These models are produced by recessive inheritance of a single gene (Bray, G. A. 1977. Fed Proc. 36:148-153; Bray, G. A. and D. A. York. 1979. Physiol. Rev. 51:598-646; Kasiske, B. L. et al. 1992. Hypertension 19 Suppl. 1:1110-1115; Bray, G. A. 1992. Am. J. Clin. Nutr. 55 Suppl. 488S-494S). GLP-1 receptor knockout (GLP-1R−/−) mice may also be used in animal studies to show that the glucose lowering effects of GLP-1 molecules of the invention are dependent on a functional GLP-1 receptor. (U.S. Pat. No. 5,846, 937, Scrocchi et al. 1996 Nat Med. 1996 November; 2(11): 1254-8, Scrocchi et al. Diabetes 1996 45:21A) and compared to wild-type mice to determine glucose tolerance. Young et al. Diabetes 1999 48:1026-1034 describe studies comparing unmodified GLP-1 with Exendin-4 in the fatty Zucker (fa/fa) rat, the ob/ob mouse, the db/db mouse and diabetic rhesus monkeys.

The db/db mouse is a genetically obese and diabetic strain of mouse. The db/db mouse develops hyperglycemia and hyperinsulinemia concomitant with its development of obesity and thus serves as a model of obese type 2 diabetes (NIDDM). Key phenotypic characteristics of these mice are that they are obese, hyperglycemic, hyperinsulinemic, and insulin resistant. The db/db mice may purchased from The Jackson Laboratories (Bar Harbor, Me.). The Zucker Diabetic Fatty fa/fa (ZDF) rats are insulin-resistant but normoglycemic from birth and they develop diabetes from about week 7 to week 10 of age. During the transitional period, the animals go through a state of impaired glucose tolerance. Although the animals are hyperinsulinemic before diabetes onset and during the early stages of diabetes, they later lose glucose-stimulated insulin secretion and finally become almost completely insulinopenic. Key phenotypic characteristics of these rats are that they are obese, hyperlipemic, hyperinsulinemic, insulin resistant, and hypercholesterolemic.

db/db or ob/ob mice will be dosed with GLP-1 peptides comprising a non-naturally encoded amino acid, or unmodified GLP-1 as a control or exendin-4 as a comparator. Compounds will be administered at 0.1 μg per dose s.c., and levels of plasma glucose, glucagon, and blood insulin, weight loss, and anorectic effect will be compared between the two populations. The results will show superior activity and prolonged half-life of the GLP-1 peptides of the present invention compared to exendin-4.

Zucker fatty rats will be dosed in acute and chronic studies with GLP-1 peptides comprising a non-naturally encoded amino acid, or unmodified GLP-1 as a control, or exendin-4 as a comparator. In the acute studies, the duration of effects on glucose and insulin levels will be measured. In the chronic studies, these rats will be monitored for lowered food intake, body weight and HbA1 c levels. The results will show superior activity with less frequent dosing and prolonged half-life of the GLP-1 peptides of the present invention compared to exendin-4.

Example 31

Human Clinical Trial of the Safety and/or Efficacy of PEGylated GLP-1 Comprising a Non-Naturally Encoded Amino Acid.

Objective To compare the safety and pharmacokinetics of subcutaneously administered PEGylated recombinant human GLP-1 comprising a non-naturally encoded amino acid with exendin-4.

Patients Eighteen healthy volunteers ranging between 20-40 years of age and weighing between 60-90 kg are enrolled in the study. The subjects will have no clinically significant abnormal laboratory values for hematology or serum chemistry, and a negative urine toxicology screen, HIV screen, and hepatitis B surface antigen. They should not have any evidence of the following: hypertension; a history of any primary hematologic disease; history of significant hepatic, renal, cardiovascular, gastrointestinal, genitourinary, metabolic, neurologic disease; a history of anemia or seizure disorder; a known sensitivity to bacterial or mammalian-derived products, PEG, or human serum albumin; habitual and heavy consumer to beverages containing caffeine; participation in any other clinical trial or had blood transfused or donated within 30 days of study entry; had exposure to GLP-1 within three months of study entry; had an illness within seven days of study entry; and have significant abnormalities on the pre-study physical examination or the clinical laboratory evaluations within 14 days of study entry. All subjects are evaluable for safety and all blood collections for pharmacokinetic analysis are collected as scheduled. All studies are performed with institutional ethics committee approval and patient consent.

Study Design This will be a Phase I, single-center, open-label, randomized, two-period crossover study in healthy male volunteers. Eighteen subjects are randomly assigned to one of two treatment sequence groups (nine subjects/group). GLP-1 is administered over two separate dosing periods as a bolus s.c. injection in the upper thigh using equivalent doses of the PEGylated GLP-1 comprising a non-naturally encoded amino acid and exendin-4. The dose and frequency of administration of exendin-4 is as instructed in the package label. Additional dosing, dosing frequency, or other parameter as desired, using the commercially available products may be added to the study by including additional groups of subjects. Each dosing period is separated by a 14-day washout period. Subjects are confined to the study center at least 12 hours prior to and 72 hours following dosing for each of the two dosing periods, but not between dosing periods. Additional groups of subjects may be added if there are to be additional dosing, frequency, or other parameter, to be tested for the PEGylated GLP-1 as well. Multiple formulations of GLP-1 that are approved for human use may be used in this study. The experimental formulation of GLP-1 is the PEGylated GLP-1 comprising a non-naturally encoded amino acid.

Blood Sampling Serial blood is drawn by direct vein puncture before and after administration of GLP-1. Venous blood samples (5 mL) for determination of serum GLP-1 concentrations are obtained at about 30, 20, and 10 minutes prior to dosing (3 baseline samples) and at approximately the following times after dosing: 30 minutes and at 1, 2, 5, 8, 12, 15, 18, 24, 30, 36, 48, 60 and 72 hours. Each serum sample is divided into two aliquots. All serum samples are stored at −20° C. Serum samples are shipped on dry ice. Fasting clinical laboratory tests (hematology, serum chemistry, and urinalysis) are performed immediately prior to the initial dose on day 1, the morning of day 4, immediately prior to dosing on day 16, and the morning of day 19.

Bioanalytical Methods An ELISA kit procedure (Linco Research Co.), is used for the determination of serum GLP-1 concentrations.

Safety Determinations Vital signs are recorded immediately prior to each dosing (Days 1 and 16), and at 6, 24, 48, and 72 hours after each dosing. Safety determinations are based on the incidence and type of adverse events and the changes in clinical laboratory tests from baseline. In addition, changes from pre-study in vital sign measurements, including blood pressure, and physical examination results are evaluated.

Data Analysis Post-dose serum concentration values are corrected for pre-dose baseline GLP-1 concentrations by subtracting from each of the post-dose values the mean baseline GLP-1 concentration determined from averaging the GLP-1 levels from the three samples collected at 30, 20, and 10 minutes before dosing. Pre-dose serum GLP-1 concentrations are not included in the calculation of the mean value if they are below the quantification level of the assay. Pharmacokinetic parameters are determined from serum concentration data corrected for baseline GLP-1 concentrations. Pharmacokinetic parameters are calculated by model independent methods on a Digital Equipment Corporation VAX 8600 computer system using the latest version of the BIOAVL software. The following pharmacokinetics parameters are determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule; and terminal elimination half-life ($t_{1/2}$), computed from the elimination rate constant. The elimination rate constant is estimated by linear regression of consecutive date points in the terminal linear region of the log-linear concentration-time plot. The mean, standard deviation (SD), and coefficient of variation (CV) of the pharmacokinetic parameters are calculated for each treatment. The ratio of the parameter means (preserved formulation/non-preserved formulation) is calculated.

Safety Results The incidence of adverse events is equally distributed across the treatment groups. There are no clinically significant changes from baseline or pre-study clinical laboratory tests or blood pressures, and no notable changes from pre-study in physical examination results and vital sign measurements. The safety profiles for the two treatment groups should appear similar.

Pharmacokinetic Results Mean serum GLP-1 concentration-time profiles (uncorrected for baseline GLP-1 levels) in all 18 subjects after receiving a single dose of one or more of available GLP-1 are compared to the PEGylated GLP-1 comprising a non-naturally encoded amino acid at each time point measured. All subjects should have pre-dose baseline GLP-1 concentrations within the normal physiologic range. Pharmacokinetic parameters are determined from serum data corrected for pre-dose mean baseline GLP-1 concentrations and the $C_{max}$ and $t_{max}$ are determined. The mean $t_{max}$ for the GLP-1 is significantly shorter than the $t_{max}$ for the PEGylated GLP-1 comprising the non-naturally encoded amino acid. Terminal half-life values are significantly shorter for the GLP-1 compared with the terminal half-life for the PEGylated GLP-1 comprising a non-naturally encoded amino acid.

Although the present study is conducted in healthy male subjects, similar absorption characteristics and safety profiles would be anticipated in other patient populations; such as male or female patients with cancer or chronic renal failure, pediatric renal failure patients, patients in autologous predeposit programs, or patients scheduled for elective surgery.

In conclusion, subcutaneously administered single doses of PEGylated GLP-1 comprising non-naturally encoded amino acid will be safe and well tolerated by healthy male subjects. Based on a comparative incidence of adverse events, clinical laboratory values, vital signs, and physical examination results, the safety profiles of GLP-1 and PEGylated GLP-1 comprising non-naturally encoded amino acid will be equivalent. The PEGylated GLP-1 comprising non-naturally encoded amino acid potentially provides large clinical utility to patients and health care providers.

Example 32

This example describes a few of the many potential sets of criteria for the selection of preferred sites of incorporation of non-naturally encoded amino acids into T-20.

This example demonstrates how preferred sites within the T-20 polypeptide were selected for introduction of a non-naturally encoded amino acid. Sequence numbering used in this example is according to the amino acid sequence of T-20 (SEQ ID NO: 22) and TEX (SEQ ID NO: 24). TEX is an N-terminal extended polypeptide of T-20. Position numbers cited are based positions 638-673 of the T-20 peptide and 630-673 of the TEX peptide, unless otherwise indicated. For example, position 639 corresponds to the second amino acid in SEQ ID NO: 22. Those of skill in the art will appreciate that amino acid positions corresponding to positions in SEQ ID NO: 22, can be readily identified in SEQ ID NO: 24, or any other T-20 molecule.

Modeling of the potential alpha helical structure of T-20 was performed based on PDB 1DLB from W. Shu, J. Liu, H. Ji, L. Rading, S. Jiang, M. Lu, Helical Interactions in the HIV-1 gp41 Core Reveal Structural Basis for the Inhibitory Activity of gp41 Peptides (Biochemistry 39:1634 (2000). The following criteria were used to evaluate each position of T-20 for the introduction of a non-naturally encoded amino acid: the residue (a) should not be affected by alanine scanning mutagenesis, (b) should be surface exposed and exhibit minimal van der Waals or hydrogen bonding interactions with surrounding residues based on modeling, (c) may either be variable or non-essential without affecting activity in T-20 variants, (d) would result in conservative substitutions upon substitution with a non-naturally encoded amino acid and (e) could be found in either highly flexible regions or structurally rigid regions. In addition, further calculations were performed on the T-20 molecule, utilizing the Cx program (Pintar et al. (2002) *Bioinformatics,* 18, pp 980) to evaluate the extent of protrusion for each protein atom from the peptide.

In some embodiments, one or more non-naturally encoded amino acids are incorporated at any position in T-20 (including TEX), before the first amino acid, an addition at the carboxy terminus, or any combination thereof. In some embodiments, one or more non-naturally encoded amino acids are incorporated at any position in T-20 (including TEX), including but not limited to, the residues as follows: W631, D632, I635, N636, N637, Y638, T639, S640, L641, L645, N651, or any combination thereof.

Example 33

Cloning Strategy to Produce Biosynthetically T-20 and TEX

Figure 9:
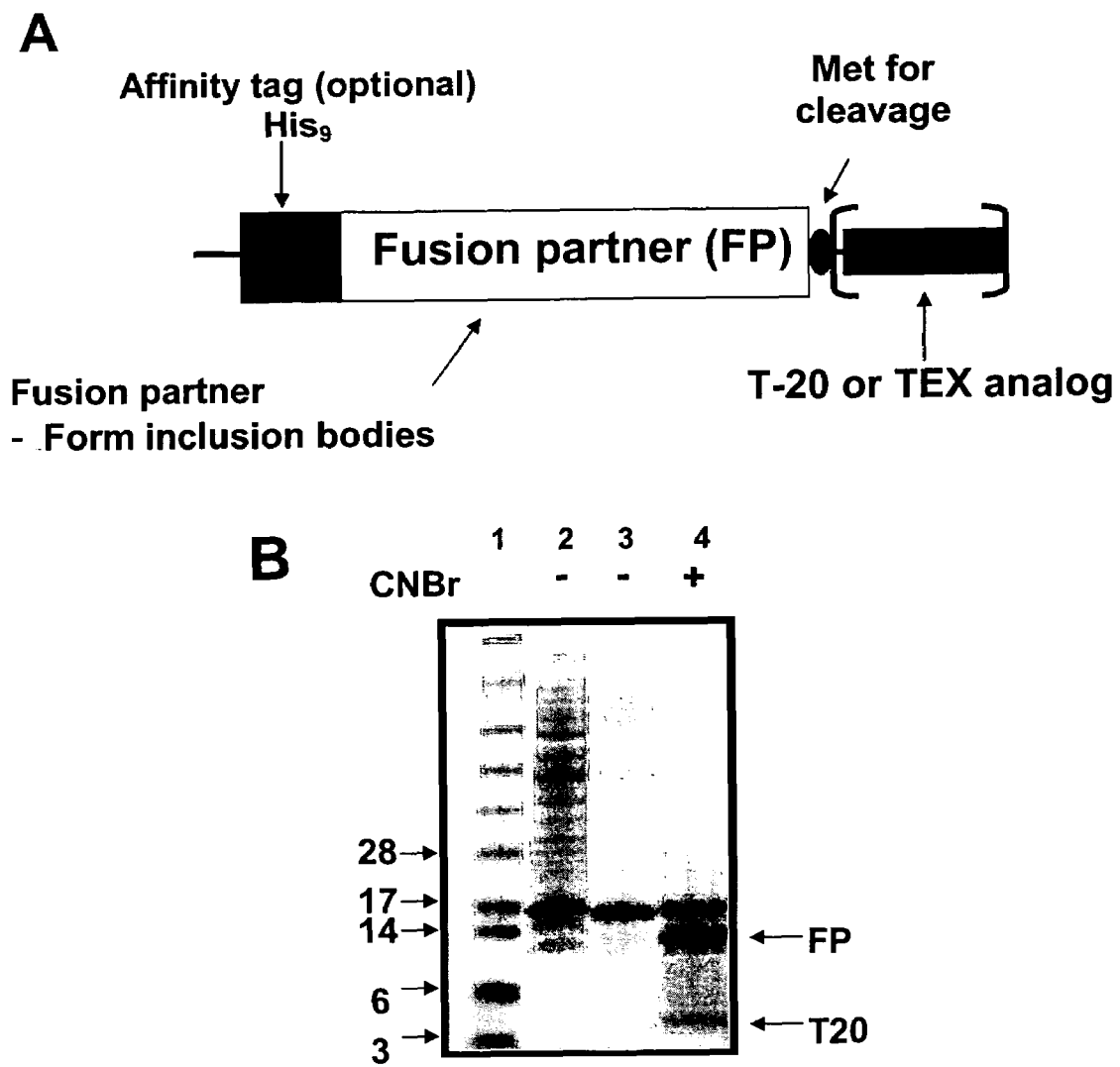
FIG. 9—Constructs for incorporation of a non-naturally encoded amino acid into T-20 and TEX are shown (FIG. 9, Panel A).

FIG. 9A shows a schematic of constructs that were designed to incorporate a non-naturally encoded amino acid into T-20 polypeptide and into a polypeptide of T-20 extended at the N terminus (TEX). HIV proviral DNA was used to amplify the sequence encoding T-20 and TEX, including a methionine at the N terminus of the peptide product. Primers used to amplify T-20 sequence from HIV proviral DNA were F-T20 5'AAG CTT TGG ATG TAC ACA AGT TTA ATA CAC TCC3' (SEQ ID NO: 26) and R-T20 5'GCG GAT CCC ATT AAA ACC AAT TCC ACA AAC TTG C3' (SEQ ID NO: 27). Primers used to amplify TEX sequence from HIV proviral DNA were F-EXT20 5'CG AAG CTT TGG ATG GAG TGG GAT AGA GAA ATT AAC AAT TAC ACA AGT TTA ATA CAC TCC3' (SEQ ID NO: 28) and R-T20 (SEQ ID NO: 27). F-T20 AND F-EXT20 contained a HindIII restriction site, and R-T20 contained a BamHI site for cloning.

T-20 and TEX sequences were cloned in frame into an expression vector containing a TrpLE fusion partner (FP) and a nine histidine tag at the N terminus of the fusion partner.

FIG. 10 shows a comparison of the wild-type T-20 and TEX sequences. The extended version of the peptide T-20 (TEX) was generated using the primers indicated above to amplify the corresponding DNA region of the gp41 heptad repeat 2 (HR2). TEX is 8 amino acids longer than T-20 at the N-terminus, providing a polypeptide that is 44 amino acids in length. TEX corresponds to amino acids 630 to 673 of the $HIV_{NL4-3}$ transmembrane protein (TM). T-20 corresponds to amino acids 638 to 673 of the $HIV_{NL4-3}$ transmembrane protein (TM).

Purification of Biosynthefically Produced T20 and TEX Peptide Analogues

The resulting fusion peptides were biosynthetically produced in bacteria. Orthogonal tRNA and its specific orthogonal aminoacyl tRNA synthetase were expressed to perform suppression of the T-20 or TEX constructs. To avoid protein degradation in the bacterial cytoplasm, expression occurred by directing the fusion peptide into inclusion bodies (IB). The IBs containing the fusion peptides were resuspended in Inclusion Body Resuspension Buffer (IBRB; 50 mM Tris, pH 7.5, 200 mM NaCl, 2 mM EDTA) containing 100 ug/ml lysozyme and 10 ug/ml DNase. After six rounds of sonication of the resuspension, the samples were centrifuged to spin down the pellets. The IB pellets were washed four times to eliminate residual contaminants by sonication with Inclusion Body wash buffer (50 mM Tris, pH 7.5, 30 mM NaCl, 1 mM EDTA) with 1% Triton X-100 and centrifugation between washes. Then the IB pellets were washed twice by sonication with Inclusion Body wash buffer (50 mM Tris, pH 7.5, 100 mM NaCl, 1 mM EDTA) and centrifugation between washes. The pellets were solubilized in Guanidinium Binding Buffer, pH 7.8 (6M Guanidine HCl, 20 mM NaPO4, pH 7.8, 500 nM NaCl) and bound to equilibrated ProBond resin for His-tag purification of the fusion peptides. The resin was washed twice with Guanidinium Binding Buffer, pH 7.8; twice with Guanidinium Wash Buffer, pH 6.0 (6M Guanidine HCl, 20 mM NaPO4, pH 6.0, 500 nM NaCl); and twice with Guanidinium Wash Buffer, pH 5.3 (6M Guanidine HCl, 20 mM NaPO4, pH 5.3, 500 nM NaCl). The His-tag bound fusion peptides were eluted with Guanidinium Elution Buffer, pH 4.0 (6M Guanidine HCl, 200 mM Acetic Acid, 20 mM NaPO4, pH 4, 500 nM NaCl).

Prior to sample lyophilization, a buffer exchange with Guanidinium Elution Buffer with 10% formic acid was performed using a PD-10 desalting column. After lyophilization, the samples were then resuspended in 70% formic acid for overnight cyanogen bromide (CNBr) cleavage. Since CNBr specifically cleaves C-terminal to methionine, cleavage with CNBr allows T-20 or TEX to be separated from its fusion partner and further purified to obtain pure peptides for testing in anti-viral activity assays. Lane 4 of FIG. 9, Panel B shows the cleavage products of CNBr treatment. T-20 and the fusion partner (FP) are indicated with arrows. The other lanes were loaded as follows: lane 1—marker, lane 2—before induction, lane 3—after induction.

After cleavage with CNBr, the samples were lyophilized and resuspended in 8M urea and separated through preparative HPLC. The samples were run on a C8 prep HPLC column to purify away residual CNBr. The product was lyophilized and then resuspended in Guanidinium Binding Buffer, pH 7.8. The solubilized product was bound to equilibrated Pro-Bond Resin, and the flow through was collected. The samples were then run on a C8 prep HPLC column to purify the T-20 or TEX, and lyophilized. The purified peptides were then resuspended in the following buffer: 22.5 mg/ml mannitol, 2.39 mg/ml sodium carbonate, pH 9.

Mutations to Modify T20 and TEX

A selector codon was introduced into polynucleotides encoding both T-20 and TEX analogue peptides to incorporate a non-naturally encoded amino acid at designated conserved positions. The location of each selector codon was chosen based on the published crystal structure of the 6-helix bundle formation during HIV fusion. The selector codons were introduced by QuickChange mutagenesis according to manufacturer's instructions (Stratagene) and were confirmed by the sequencing of each individual mutant.

Five different constructs of T-20 were generated with a selector codon encoding a substitution with a non-naturally encoded amino acid. FIG. 10 shows a map of the five residues of T-20 encoded by codons that were substituted with an amber codon: Threonine designated as T20 639; Serine T20 640; Leucine T20 641; Leucine T20 645; and Asparagine T20 651.

Figure 12:
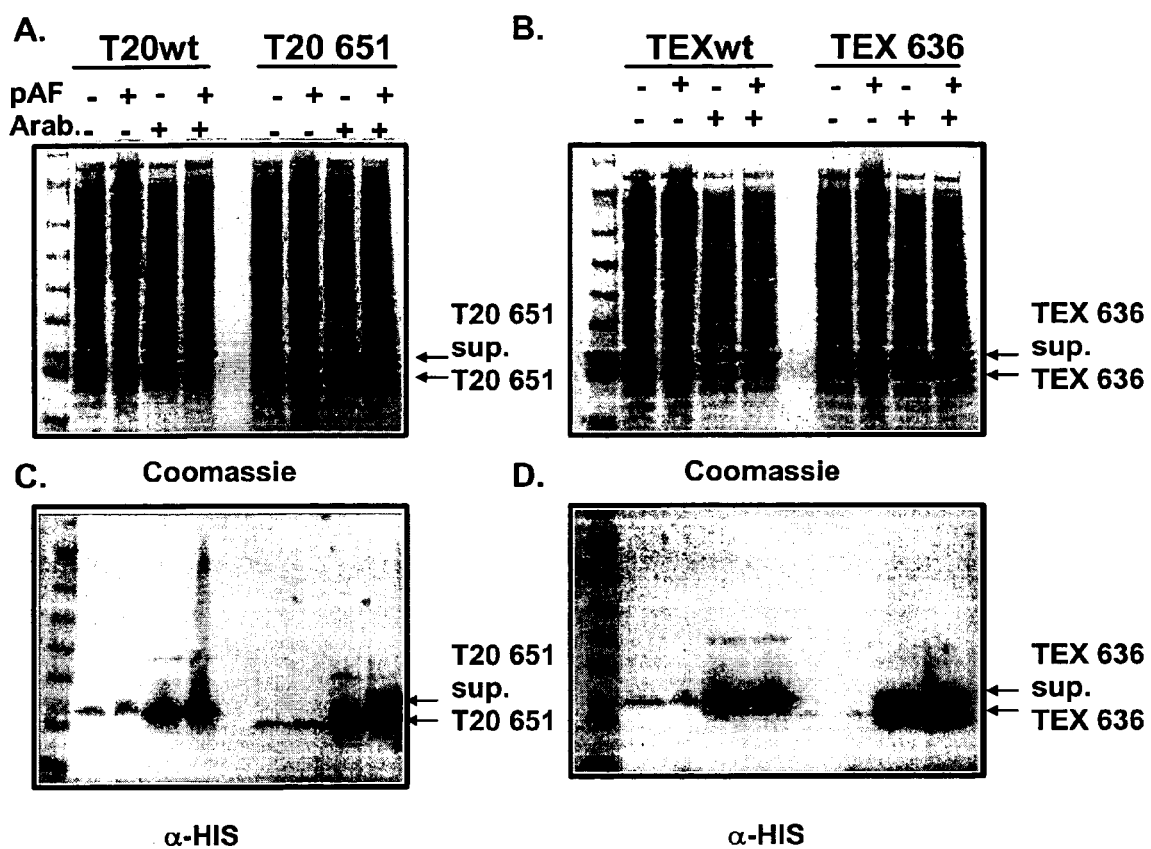
FIG. 12—Coomassie stained polyacrylamide gels of T20 651 suppression (FIG. 12, Panel A) and TEX 636 suppression (FIG. 12, Panel B) are shown. Westerns (anti-His) of the samples shown in Panel A and B are shown in FIG. 12, Panels C and D.

Eleven different constructs of TEX were generated with a selector codon encoding a substitution with a non-naturally encoded amino acid. FIG. 10 also shows a map of the eleven residues of TEX encoded by codons that were substituted with an amber codon: Tryptophan designated as TEX 631; Aspartic acid designated as TEX 632; Isoleucine designated as TEX 635; Asparagine designated as TEX 636; Asparagine designated as TEX 637, Tyrosine designated as TEX 638; Threonine designated as TEX 639; Serine designated as TEX 640; Leucine designated as TEX 641; Leucine designated as TEX 645; and Asparagine designated as TEX 651. FIG. 12 shows suppression occurred in both T20 651 (Panel A) and TEX 636 (Panel B). sup. is the abbreviation for suppressed. FIG. 12, Panels C and D show Western blots of the samples run in FIG. 12, Panels A and B. Panel E shows the residues substituted with p-acetyl-phenylalanine with asterisks in T-20 (T-20-Mut651) and in TEX (TEX-Mut636).

Example 34

This example describes methods to measure biological activity of T-20 comprising a non-naturally encoded amino acid.

In Vitro Fusion Assay to Test T20 and TEX Antiviral Activity

Figure 11:
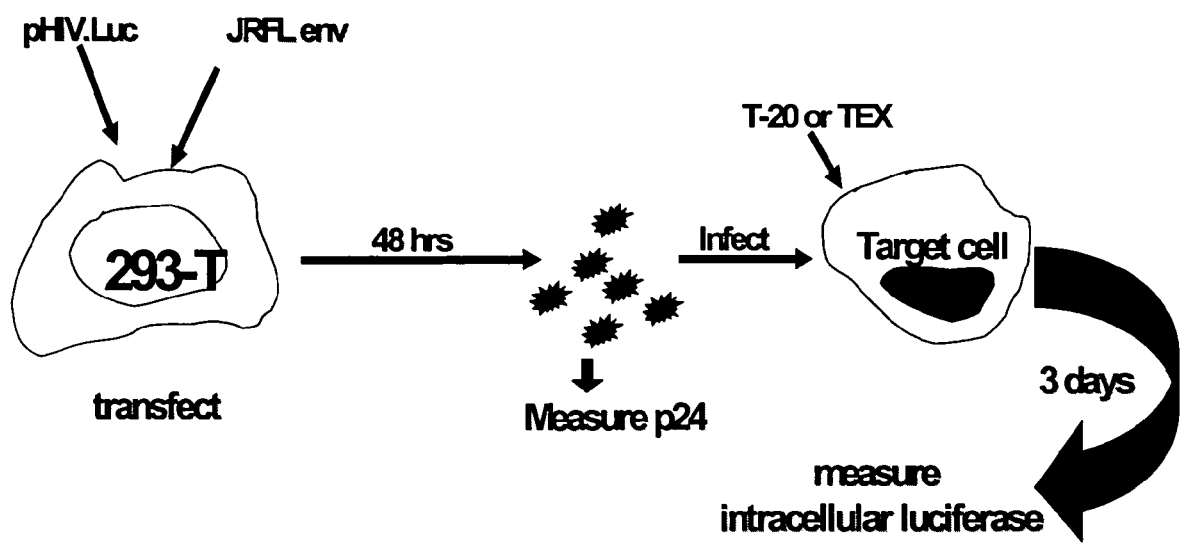
FIG. 11—An in vitro fusion assay to test T-20 and TEX antiviral activity is shown.

To evaluate T20 or TEX antiviral activity, a fusion assay is used based on single-cycle infectivity. A schematic representation of the assay is shown in FIG. 11. Briefly, 293-T cells are cotransfected with two plasmids: one plasmid that expresses only an HIV envelope gene (JRFL or JC2 env), and a second plasmid expressing a modified HIV proviral DNA that carries the luciferase gene in place of HIV Nef gene and does not express its endogenous envelope gene (pHIV.Luc). Such pseudotyped env HIV-Luc virus is able to infect target cells only by one round of infection. HIV is produced 48 hours postransfection and is collected in the supernatant of transfected cells. Quantitation of the virus is made by measuring p24$^{gag}$ by ELISA. Once the HIV concentration is determined, human target cells expressing human CD4 receptor and either one of the two human coreceptors CCR5 or CXCR4 are infected at different MOI in the presence or absence of T20, TEX and their corresponding mutants. The cells are lysed three days post infection, and loaded with substrate to determine luciferase activity measured by an illuminometer. This assay is quantitative and the inhibition level of HIV fusion of different peptides is evaluated.

Alternatively, a number of other assays including but not limited to, other assays measuring antiviral activity, including but not limited to, assays measuring viral entry or viral fusion, known to one skilled in the art may be used to monitor the activity of T-20 or TEX polypeptides of the invention. Modifications to these assays to test combination therapy with another antiviral agent are also known to one skilled in the art.

Also, standard methods which are well-known to those of skill in the art may be utilized for assaying non-retroviral activity. See, for example, Pringle et al. (Pringle, C. R. et al., 1985, J. Medical Virology 17:377-386) for a discussion of respiratory syncytial virus and parainfluenza virus activity assay techniques. Further, see, for example, "Zinsser Microbiology", 1988, Joklik, W. K. et al., eds., Appleton & Lange, Norwalk, Conn., 19th ed., for a general review of such techniques. These references are incorporated by reference herein in its entirety.

Animal studies may be performed with T-20 polypeptides of the invention. Such studies include, but are not limited to, toxicity studies.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference herein in their entirety for all purposes.

TABLE 3

| SEQ ID # | Notes |
| --- | --- |
| 1 | amino acid sequence of GLP-1 (7-36) |
| 2 | amino acid sequence of GLP-1 (7-37) |
| 3 | amino acid sequence of Exendin-4 |
| 21 | amino acid sequence of Exendin-3 |

TABLE 3-continued

| SEQ ID # | Notes |
|---|---|
| 22 | amino acid sequence of T-20 (DP-178) |
| 23 | amino acid sequence of Peptide YY (3-36) |
| 24 | amino acid sequence of TEX |
| 25 | amino acid sequence of TrpLE |
| 26 | Primer sequence of F-T20 |
| 27 | Primer sequence of R-T20 |
| 28 | Primer sequence of F-EXT20 |

Additional and Alternate Embodiments of the Invention

1. A polypeptide comprising the formula:
(LT)-P-T',
wherein (LT) is selected from the group consisting of: a localization peptide (L), a tag or linker (T), a localization peptide (L) and tag or linker (T) in any order, methionine, and absent;
P comprises a BSP sequence; and
T' comprises a tag or linker, or is absent,
wherein L, T, P, or T' comprises one or more non-naturally encoded amino acids.

2. The polypeptide of claim 1 wherein L is selected from a group consisting of a TrpLE sequence, a prokaryotic secretion signal sequence, an eukaryotic secretion signal sequence, an eukaryotic secretion signal sequence 5'-optimized for bacterial expression, a bacterial secretion signal sequence, a yeast secretion signal sequence, an insect secretion signal sequence, a mammalian secretion signal sequence, a novel secretion signal sequence, a unique secretion signal sequence, a pectate lyase secretion signal sequence, an Omp A secretion signal sequence, and a phage secretion signal sequence.

3. The polypeptide of claim 1, wherein T or T' is a tag or linker selected from a group consisting of a polypeptide, a polymer, an affinity tag, an antigen, a detection tag, an imaging tag, a member of a multiple-member binding complex, and a radio-isotope tag.

4 The polypeptide of claim 3, wherein T or T' is an affinity tag selected from a group consisting of poly-His tag, biotin, avidin, protein A, protein G, and an antigen.

5. The polypeptide of claim 3, wherein T or T' is a detection tag selected from a group consisting of poly-His tag, biotin, avidin, protein A, protein G, and an antigen.

6. The polypeptide of claim 3, wherein T or T' is an antigen selected from a group consisting of an immunoglobulin epitope.

7. The polypeptide of claim 3, wherein T or T' is an imaging tag selected from a group consisting of a metal, a radionuclide, and a magnetic molecule.

8. The polypeptide of claim 3, wherein T or T' is a member of a multiple-member binding complex tag selected from a group consisting of streptavidin, avidin, biotin, protein A, and protein G.

9. The polypeptide of claim 1, wherein the non-naturally encoded amino acid has a functional group determined to cleave a peptide bond under selected conditions selected from a group consisting of a photo-activated functional group, a pH activated functional group, a temperature activated functional group, a functional group that requires a catalyst, a functional group that is recognized by a protease, an enzyme, or another chemical functional group.

10. The polypeptide of claim 9, wherein the selected conditions are selected from a group consisting of exposure to photon energy, increased temperature, decreased temperature, increased pH, decreased pH, exposure to sub-atomic particles, addition of a catalyst, incubation with an enzyme, and contact with another chemical functional group.

11. The polypeptide of claim 1, wherein the BSP is GLP-1.

12. The polypeptide of claim 1, wherein the BSP is T-20.

13. A polypeptide comprising a formula:

F-(LT)-P-T'-F', wherein F comprises a polypeptide sequence, or is absent;
(LT) is selected from the group consisting of: a localization peptide (L), a tag or linker (T), a localization peptide (L) and tag or linker (T) in any order, methionine, and absent;
P comprises a desired polypeptide sequence having up to 100 amino acids and is different from F or F';
T' comprises a tag or linker, or is absent,
F' comprises a polypeptide sequence, or is absent,
wherein F, L, T, P, T', or F' comprises one or more non-naturally encoded amino acids.

14. The polypeptide of claim 13, wherein T or T' is a tag or linker selected from a group consisting of a polypeptide, a polymer, an affinity tag, an antigen, a detection tag, an imaging tag, a member of a multiple-member binding complex, and a radio-isotope tag.

15. The polypeptide of claim 14, wherein T or T' is an affinity tag selected from a group consisting of poly-His tag, biotin, avidin, protein A, protein G, an antigen.

16. The polypeptide of claim 13, wherein F or F' is a polypeptide fused to P.

17. The polypeptide of claim 16, wherein F or F' is selected from a group consisting of Fc, albumin, and albumin binding protein.

18. The polypeptide of claim 13, wherein F comprises one or more non-naturally encoded amino acids.

19. The polypeptide of claim 13, wherein F' comprises one or more non-naturally encoded amino acids.

20. The polypeptide of claim 13, wherein P further comprises a BSP comprising one or more non-naturally encoded amino acids.

21. The polypeptide of claim 20, wherein the non-naturally encoded amino acid in the BSP has a functional group determined to cleave a peptide bond under selected conditions selected from a group consisting of a photo-activated functional group, a pH activated functional group, a temperature activated functional group, a functional group that requires a catalyst, a functional group that is recognized by a protease, an enzyme, or another chemical functional group.

22. The polypeptide of claim 21, wherein the selected conditions are selected from a group consisting of exposure to photon energy, increased temperature, decreased temperature, increased pH, decreased pH, exposure to sub-atomic particles, addition of a catalyst, incubation with an enzyme, and contact with another chemical functional group.

22. The polypeptide of claim 20, wherein BSP is GLP-1.

23. The polypeptide of claim 20, wherein BSP is T-20.

24. A nucleic acid molecule comprising:
a promoter sequence operably linked to a polypeptide coding sequence, wherein said polypeptide coding sequence has the formula (WX)-Z, wherein (WX) is selected from the group consisting of: a nucleotide sequence encoding a localization peptide (W), a nucleotide sequence encoding a tag or linker (X), a nucleotide sequence encoding a localization peptide (W) and a nucleotide sequence encoding a tag or linker (X) in any order, and absent; and Z comprises a nucleotide sequence encoding a desired BSP, wherein the nucleotide sequence encoding W, X, or Z comprises a selector codon.

25. The nucleic acid molecule of claim 24, wherein the promoter is selected from a group consisting of a prokaryofic promoter, a eukaryotic promoter, a bacterial promoter, a yeast promoter, an insect promoter, a mammalian promoter, a unique promoter, and an inducible promoter.

26. The nucleic acid molecule of claim 24, wherein W encodes a TrpLE sequence, a prokaryotic secretion signal sequence, a eukaryotic secretion signal sequence, an eukaryotic secretion signal sequence 5'-optimized for bacterial expression, a bacterial secretion signal sequence, a yeast secretion signal sequence, an insect secretion signal sequence, a mammalian secretion signal sequence, a novel secretion signal sequence, a unique secretion signal sequence, a pectate lyase secretion signal sequence, an Omp A secretion signal sequence, and a phage signal sequence.

27. The nucleic acid molecule of claim 24, wherein X encodes a tag selected from a group consisting of an affinity tag, an antigen, a detection tag, an imaging tag, a member of a multiple-member binding complex, and a radio-isotope tag.

28. The nucleic acid molecule of claim 24 wherein said selector codon is selected from a group consisting of an amber codon, an opal codon, an ochre codon, a four base codon, and a unique codon.

29. The nucleic acid molecule of claim 24, further comprising—Y' operably linked to Z, wherein Y' comprises a nucleotide sequence encoding a tag, wherein said nucleotide sequence encoding said tag optionally comprises a selector codon.

30. The nucleic acid molecule of claim 29 wherein Y' encodes a tag selected from a group consisting of an affinity tag, an antigen, a detection tag, an imaging tag, a member of a multiple-member binding complex, and a radio-isotope tag.

31. An expression vector comprising the nucleic acid molecule of claim 24 or 29.

32. A host cell comprising the expression vector of claim 31.

33. The host cell of claim 32 wherein said host cell is selected from a group consisting of prokaryotic, eukaryotic, insect, yeast, bacterial, mammalian or plant cells.

34. A method comprising:
a) producing in a recombinant host cell a polypeptide comprising the formula:

(LT)-P-T', wherein (LT) is selected from the group consisting of: a localization peptide (L), a tag or linker (T), a localization peptide (L) and tag or linker (T) in any order, methionine, and absent;

P comprises a BSP sequence; and

T' comprises a tag or linker, or is absent, wherein L, T, P, or T' comprises one or more non-naturally encoded amino acids having a functional group determined to cleave one or more peptide bonds under selected conditions;

b) reacting the polypeptide under the selected conditions for a period of time sufficient to at least partially cleave one or more peptide bonds; and c) recovering peptides comprising P from the reaction products.

35. The method of claim 34, wherein the recovered peptides comprising P of step c) comprises a desired functional group at an N terminus or a C terminus.

36. The method of claim 35 wherein the desired functional group at the N terminus is selected from a group consisting of a photo-activated functional group, a pH activated functional group, a temperature activated functional group, a functional group that requires a catalyst, a functional group that is recognized by a protease, an enzyme, or another chemical functional group.

37. The method of claim 35 wherein the desired functional group at the C terminus is selected from a group consisting of a photo-activated functional group, a pH activated functional group, a temperature activated functional group, a functional group that requires a catalyst, a functional group that is recognized by a protease, an enzyme, or another chemical functional group.

38. The method of claim 34 wherein said selected conditions are selected from a group consisting of exposure to photon energy, increased temperature, decreased temperature, increased pH, decreased pH, exposure to sub-atomic particles, addition of a catalyst, incubation with an enzyme, and contact with another chemical functional group.

39. A BSP comprising one or more non-naturally encoded amino acids.

40. The BSP of claim 39, wherein the BSP comprises one or more post-translational modifications.

41. The BSP of claim 39, wherein the polypeptide is linked to a linker, polymer, or biologically active molecule.

42. The BSP of claim 41, wherein the polypeptide is linked to a water soluble polymer.

43. The BSP of claim 39, wherein the polypeptide is linked to a bifunctional polymer, bifunctional linker, or at least one additional BSP.

44. The BSP of claim 43, wherein the bifunctional linker or polymer is linked to a second polypeptide.

45. The BSP of claim 44, wherein the second polypeptide is a BSP.

46. The BSP of claim 42, wherein the water soluble polymer comprises a poly(ethylene glycol) moiety.

47. The BSP of claim 42, wherein said water soluble polymer is linked to a non-naturally encoded amino acid present in said BSP.

48. The BSP of claim 39, wherein the non-naturally encoded amino acid is substituted at a position selected from the group consisting of residues before the first amino acid at position 7 (i.e. at the N terminus), 7H, 8A, 9E, V16, 17S, 18S, 19Y, 20L, 21E, 22G, 23Q, 24A, 25A, 26K, 27E, 28F, 29I, 30A, 31W, 32L, 33V, 34K, 35G, 36R, 37G, an addition at position 38 (i.e. at the carboxyl terminus), and any combination thereof from SEQ ID NO: 2 (GLP-1).

49. The BSP of claim 39, wherein the non-naturally encoded amino acid is substituted at a position selected from the group consisting of residues W631, D632, I635, N636, N637, Y638, T639, S640, L641, L645, N651, and any combination thereof from SEQ ID NO: 22 or 24 (T-20).

50. The BSP of claim 1, 20, 24, or 34, wherein the BSP comprises one or more amino acid substitution, addition or deletion that modulates affinity of the BSP for its receptor or a binding partner.

51. The BSP of claim 1, 20, 24, or 34, wherein the BSP comprises one or more amino acid substitution, addition or deletion that increases the stability or solubility of the BSP.

52. The BSP of claim 1, 20, 24, or 34, wherein the BSP comprises one or more amino acid substitution, addition or deletion that increases the expression of the BSP in a recombinant host cell or synthesized in vitro.

53. The BSP of claim 1, 20, 24, or 34, wherein the BSP comprises one or more amino acid substitution, addition or deletion that increases protease resistance of the BSP.
54. The BSP of claim 1, 20, 24, or 34, wherein the non-naturally encoded amino acid is reactive toward a linker, polymer, or biologically active molecule that is otherwise unreactive toward any of the 20 common amino acids in the polypeptide.
55. The BSP of claim 1, 20, 24, or 34, wherein the non-naturally encoded amino acid comprises a carbonyl group, an aminooxy group, a hydrazine group, a hydrazide group, a semicarbazide group, an azide group, or an alkyne group.
56. The BSP of claim 55, wherein the non-naturally encoded amino acid comprises a carbonyl group.
57. The BSP of claim 56, wherein the non-naturally encoded amino acid has the structure:

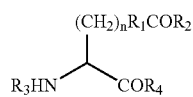

wherein n is 0-10; $R_1$ is an alkyl, aryl, substituted alkyl, or substituted aryl; R2 is H, an alkyl, aryl, substituted alkyl, and substituted aryl; and R3 is H, an amino acid, a polypeptide, or an amino terminus modification group, and R4 is H, an amino acid, a polypeptide, or a carboxy terminus modification group.
58. The BSP of claim 55, wherein the non-naturally encoded amino acid comprises an aminooxy group.
59. The BSP of claim 55, wherein the non-naturally encoded amino acid comprises a hydrazide group.
60. The BSP of claim 55, wherein the non-naturally encoded amino acid comprises a hydrazine group.
61. The BSP of claim 55, wherein the non-naturally encoded amino acid residue comprises a semicarbazide group.
62. The BSP of claim 55, wherein the non-naturally encoded amino acid residue comprises an azide group.
63. The BSP of claim 62, wherein the non-naturally encoded amino acid has the structure:

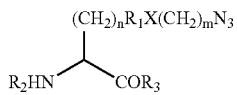

wherein n is 0-10; R1 is an alkyl, aryl, substituted alkyl, substituted aryl or not present; X is O, N, S or not present; m is 0-10; R2 is H, an amino acid, a polypeptide, or an amino terminus modification group, and R3 is H, an amino acid, a polypeptide, or a carboxy terminus modification group.
64. The BSP of claim 55, wherein the non-naturally encoded amino acid comprises an alkyne group.
65. The BSP of claim 64, wherein the non-naturally encoded amino acid has the structure:

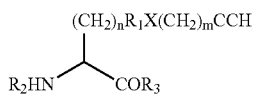

wherein n is 0-10; R1 is an alkyl, aryl, substituted alkyl, or substituted aryl; X is O, N, S or not present; m is 0-10, R2 is H, an amino acid, a polypeptide, or an amino terminus modification group, and R3 is H, an amino acid, a polypeptide, or a carboxy terminus modification group.
66. The BSP of claim 42, wherein the water soluble polymer has a molecular weight of between about 0.1 kDa and about 100 kDa.
67. The BSP of claim 66, wherein the water soluble polymer has a molecular weight of between about 0.1 kDa and about 50 kDa.
68. The BSP of claim 42, which is made by reacting a BSP comprising a carbonyl-containing amino acid with a water soluble polymer comprising an aminooxy, hydrazine, hydrazide or semicarbazide group.
69. The BSP of claim 68, wherein the aminooxy, hydrazine, hydrazide or semicarbazide group is linked to the water soluble polymer through an amide linkage.
70. The BSP of claim 42, which is made by reacting a water soluble polymer comprising a carbonyl group with a polypeptide comprising a non-naturally encoded amino acid that comprises an aminooxy, a hydrazine, a hydrazide or a semicarbazide group.
71. The BSP of claim 42, which is made by reacting a BSP comprising an alkyne-containing amino acid with a water soluble polymer comprising an azide moiety.
72. The BSP of claim 42, which is made by reacting a BSP comprising an azide-containing amino acid with a water soluble polymer comprising an alkyne moiety.
73. The BSP of claim 55, wherein the azide or alkyne group is linked to a water soluble polymer through an amide linkage.
74. The BSP of claim 42, wherein the water soluble polymer is a branched or multiarmed polymer.
75. The BSP of claim 74, wherein each branch of the water soluble polymer has a molecular weight of between about 1 kDa and about 100 kDa.
76. The BSP of claim 39, wherein the polypeptide is an antagonist.
77. The BSP of claim 76, wherein the polypeptide comprises one or more post-translational modification, linker, polymer, or biologically active molecule.
78. The BSP of claim 77, wherein the polymer comprises a moiety selected from a group consisting of a water soluble polymer and poly(ethylene glycol).
79. The BSP of claim 39, wherein the non-naturally encoded amino acid comprises a saccharide moiety.
80. The BSP of claim 41, wherein the linker, polymer, or biologically active molecule is linked to the polypeptide via a saccharide moiety.
81. An isolated nucleic acid comprising a polynucleotide that hybridizes under stringent conditions to polynucleotide sequences that encode SEQ ID NO: 1, 2, 3, 21, 22, 23, or 24, wherein the polynucleotide comprises at least one selector codon.
82. The isolated nucleic acid of claim 81, wherein the selector codon is selected from the group consisting of an amber codon, ochre codon, opal codon, a unique codon, a rare codon, and a four-base codon.
83. A method of making the BSP of claim 41, the method comprising contacting an isolated BSP comprising a non-naturally encoded amino acid with a linker, polymer, or biologically active molecule comprising a moiety that reacts with the non-naturally encoded amino acid.
84. The method of claim 83, wherein the polymer comprises a moiety selected from a group consisting of a water soluble polymer and poly(ethylene glycol).
85. The method of claim 83, wherein the non-naturally encoded amino acid comprises a carbonyl group, an aminooxy group, a hydrazide group, a hydrazine group, a semicarbazide group, an azide group, or an alkyne group.

86. The method of claim 83, wherein the non-naturally encoded amino acid comprises a carbonyl moiety and the linker, polymer, or biologically active molecule comprises an aminooxy, a hydrazine, a hydrazide or a semicarbazide moiety.

87. The method of claim 86, wherein the aminooxy, hydrazine, hydrazide or semicarbazide moiety is linked to the linker, polymer, or biologically active molecule through an amide linkage.

88. The method of claim 83, wherein the non-naturally encoded amino acid comprises an alkyne moiety and the linker, polymer, or biologically active molecule comprises an azide moiety.

89. The method of claim 83, wherein the non-naturally encoded amino acid comprises an azide moiety and the linker, polymer, or biologically active molecule comprises an alkyne moiety.

90. The method of claim 85, wherein the azide or alkyne moiety is linked to a linker, polymer, or biologically active molecule through an amide linkage.

91. The method of claim 84, wherein the poly(ethylene glycol) moiety has an average molecular weight of between about 0.1 kDa and about 100 kDa.

92. The method of claim 84, wherein the poly(ethylene glycol) moiety is a branched or multiarmed polymer.

93. A composition comprising the BSP of claim 39 and a pharmaceutically acceptable carrier.

94. The composition of claim 93, wherein the non-naturally encoded amino acid is linked to a water soluble polymer.

95. A method of treating a patient having a disorder modulated by the BSP comprising administering to the patient a therapeutically-effective amount of the composition of claim 93.

96. A cell comprising the nucleic acid of claim 81.

97. The cell of claim 96, wherein the cell comprises an orthogonal tRNA synthetase or an orthogonal tRNA.

98. A method of making a BSP comprising a non-naturally encoded amino acid, the method comprising, culturing cells comprising a polynucleotide or polynucleotides encoding a BSP comprising a selector codon, an orthogonal RNA synthetase and an orthogonal tRNA under conditions to permit expression of the BSP comprising a non-naturally encoded amino acid; and purifying the BSP.

99. A method of modulating serum half-life or circulation time of a BSP, the method comprising substituting one or more non-naturally encoded amino acids for any one or more naturally occurring amino acids in the BSP.

100. A BSP encoded by a polynucleotide, wherein said polynucleotide comprises a selector codon, and wherein said polypeptide comprises at least one non-naturally encoded amino acid.

101. The BSP of claim 100, wherein the non-naturally encoded amino acid is linked to a linker, polymer, water soluble polymer, or biologically active molecule.

102. The BSP of claim 101, wherein the water soluble polymer comprises a poly(ethylene glycol) moiety.

103. The BSP of claim 100, wherein the non-naturally encoded amino acid comprises a carbonyl group, an aminooxy group, a hydrazide group, a hydrazine group, a semicarbazide group, an azide group, or an alkyne group.

104. The BSP of claim 101, wherein the poly(ethylene glycol) moiety has a molecular weight of between about 0.1 kDa and about 100 kDa.

105. The BSP of claim 101, wherein the poly(ethylene glycol) moiety is a branched or multiarmed polymer.

106. The BSP of claim 104, wherein the poly(ethylene glycol) moiety has a molecular weight of between about 1 kDa and about 100 kDa.

107. A composition comprising the BSP of claim 100 and a pharmaceutically acceptable carrier.

108. A BSP comprising a water soluble polymer linked by a covalent bond to the BSP at a single amino acid.

109. The BSP of claim 107, wherein the water soluble polymer comprises a poly(ethylene glycol) moiety.

110. The BSP of claim 107, wherein the amino acid covalently linked to the water soluble polymer is a non-naturally encoded amino acid.

111. The BSP of claim 48 wherein said non-naturally encoded amino acid is linked to a poly(ethylene glycol) molecule.

112. The BSP of claim 49 wherein said non-naturally encoded amino acid is linked to a poly(ethylene glycol) molecule.

113. A BSP comprising at least one linker, polymer, or biologically active molecule, wherein said linker, polymer, or biologically active molecule is attached to the polypeptide through a functional group of a non-naturally encoded amino acid ribosomally incorporated into the polypeptide.

114. The BSP of claim 112, wherein said BSP is monoPEGylated.

115. A BSP comprising a linker, polymer or biologically active molecule that is attached to one or more non-naturally encoded amino acids wherein said non-naturally encoded amino acid is ribosomally incorporated into the polypeptide at pre-selected sites.

116. The BSP of claim 114, wherein the BSP comprises one said linker, polymer, or biologically active molecule.

117. The BSP of claim 1, 20, 24, or 34, wherein the BSP comprises one or more amino acid substitution, addition, or deletion that modulates immunogenicity of the BSP.

118. The BSP of claim 1, 20, 24, or 34, wherein the BSP comprises one or more amino acid substitution, addition, or deletion that modulates serum half-life or circulation time of the BSP.

119. A method of modulating immunogenicity of a BSP, the method comprising substituting one or more non-naturally encoded amino acids for any one or more naturally occurring amino acids in the BSP.

120. A BSP wherein the polypeptide is selected from the group consisting of SEQ ID NO: 1, 2, 3, 21, 22, 23, 24, and fragments thereof.

What is claimed is:

1. A method for making a biosynthetic polypeptide (BSP) less than 100 amino acids in length comprising two or more non-naturally encoded amino acids wherein said BSP is a (glucagon like polypeptide 1 (GLP-1) comprising;
expressing an mRNA encoding said GLP-1 peptide in a translation system, wherein said mRNA comprises two or more selector codons, and said translation system further comprises an orthogonal aminoacyl tRNA synthetase (O-RS) and an orthogonal tRNA (O-tRNA) wherein said O-RS preferentially aminoacylates said O-tRNA with said non-naturally encoded amino acids, and said O-tRNA recognizes the two or more selector codons on the mRNA and wherein at least two of the non-naturally encoded amino acids are linked together.

2. The method of claim 1, wherein the BSP further comprises at least one poly(ethylene glycol) moiety.

3. The method of claim 1, wherein the non-naturally encoded amino acids in the BSP are substituted at a position selected from the group consisting of residues at, H7, A8, E9, V16, S17, S18, Y19, L20, E21, G22, Q23, A24, A25, K26, E27, F28, I29, A30, W31, L32, V33, K34, G35, R36, G37, and any combination thereof wherein position 7-37 of GLP-1 correspond to position 1-31 of SEQ ID NO: 2.

4. The method of claim 1, wherein one or more of the non-naturally encoded amino acids in the BSP has a functional group determined to cleave a peptide bond under selected conditions selected from a group consisting of a photo-activated functional group, a pH activated functional group, a temperature activated functional group, a functional group that requires a catalyst, a functional group that is recognized by a protease, and a functional group that is recognized by an enzyme.

5. The method of claim 4, wherein the selected conditions of the BSP are selected from a group consisting of exposure to photon energy, increased temperature, decreased temperature, increased pH, decreased pH, exposure to sub-atomic particles, addition of a catalyst, incubation with an enzyme, and contact with another chemical functional group.

6. The method of claim 2, wherein the BSP comprising a poly(ethylene glycol) moiety has a molecular weight of between about 0.1 kDa and about 100 kDa.

7. The method of claim 2, wherein the BSP comprising a poly(ethylene glycol) moiety is a branched or multiarmed polymer.

8. The method of claim 7, wherein the BSP comprising a poly(ethylene glycol) moiety has a molecular weight of between about 1 kDa and about 100 kDa.

9. The method of claim 1, wherein the BSP comprising a polyalkylene glycol has a molecular weight of between about 0.1 kDa and about 50 kDa.

10. The method of claim 1, wherein the BSP further comprises at least one polyalkylene glycol polymer.

11. The method of claim 3, wherein the non-naturally encoded amino acids in the BSP further comprises an addition at a position selected from the group consisting of a position before the amino acid residue at position 7, and an addition at position 38, and any combination thereof wherein position 7-37 of GLP-1 correspond to position 1-31 of SEQ ID NO: 2.

* * * * *

UNITED STATES PATENT AND TRADEMARK OFFICE
CERTIFICATE OF CORRECTION

PATENT NO. : 7,638,299 B2  Page 1 of 1
APPLICATION NO. : 11/187687
DATED : December 29, 2009
INVENTOR(S) : Cho et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 452 days.

Signed and Sealed this

Twenty-first Day of December, 2010

David J. Kappos
*Director of the United States Patent and Trademark Office*

SEQUENCE LISTING

<160> NUMBER OF SEQ ID NOS: 28

<210> SEQ ID NO 1
<211> LENGTH: 30

```
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 2
<211> LENGTH: 31
<212> TYPE: PRT
<213> ORGANISM: Homo sapiens

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 3
<211> LENGTH: 39
<212> TYPE: PRT
<213> ORGANISM: Homo sapiens

<400> SEQUENCE: 3

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 4
<211> LENGTH: 77
<212> TYPE: DNA
<213> ORGANISM: Methanococcus jannaschii

<400> SEQUENCE: 4
ccggcggtag ttcagcaggg cagaacggcg gactctaaat ccgcatggcg ctggttcaaa    60
tccggcccgc cggacca                                                   77

<210> SEQ ID NO 5
<211> LENGTH: 88
<212> TYPE: DNA
<213> ORGANISM: Halobacterium sp. NRC-1

<400> SEQUENCE: 5
cccagggtag ccaagctcgg ccaacggcga cggactctaa atccgttctc gtaggagttc    60
gagggttcga atcccttccc tgggacca                                       88

<210> SEQ ID NO 6
<211> LENGTH: 89
<212> TYPE: DNA
<213> ORGANISM: Halobacterium sp. NRC-1

<400> SEQUENCE: 6
gcgagggtag ccaagctcgg ccaacggcga cggacttcct aatccgttct cgtaggagtt    60
cgagggttcg aatccctccc ctcgcacca                                      89
```

```
<210> SEQ ID NO 7
<211> LENGTH: 306
<212> TYPE: PRT
<213> ORGANISM: Methanococcus jannaschii

<400> SEQUENCE: 7

Met Asp Glu Phe Glu Met Ile Lys Arg Asn Thr Ser Glu Ile Ile Ser
 1               5                  10                  15

Glu Glu Glu Leu Arg Glu Val Leu Lys Lys Asp Glu Lys Ser Ala Gly
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Thr Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Thr Tyr Tyr
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 8
<211> LENGTH: 306
<212> TYPE: PRT
<213> ORGANISM: Methanococcus jannaschii

<400> SEQUENCE: 8

Met Asp Glu Phe Glu Met Ile Lys Arg Asn Thr Ser Glu Ile Ile Ser
 1               5                  10                  15

Glu Glu Glu Leu Arg Glu Val Leu Lys Lys Asp Glu Lys Ser Ala Gly
```

```
                        20                  25                  30
Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Thr Ser His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 9
<211> LENGTH: 305
<212> TYPE: PRT
<213> ORGANISM: Methanococcus jannaschii

<400> SEQUENCE: 9

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80
```

```
Glu Ile Arg Lys Ile Gly Asp Tyr Asn Lys Lys Val Phe Glu Ala Met
                85                  90                  95
Gly Leu Lys Ala Lys Tyr Val Tyr Gly Ser Pro Phe Gln Leu Asp Lys
            100                 105                 110
Asp Tyr Thr Leu Asn Val Tyr Arg Leu Ala Leu Lys Thr Thr Leu Lys
        115                 120                 125
Arg Ala Arg Arg Ser Met Glu Leu Ile Ala Arg Glu Asp Glu Asn Pro
    130                 135                 140
Lys Val Ala Glu Val Ile Tyr Pro Ile Met Gln Val Asn Ala Ile Tyr
145                 150                 155                 160
Leu Ala Val Asp Val Ala Val Gly Gly Met Glu Gln Arg Lys Ile His
                165                 170                 175
Met Leu Ala Arg Glu Leu Leu Pro Lys Lys Val Val Cys Ile His Asn
            180                 185                 190
Pro Val Leu Thr Gly Leu Asp Gly Glu Gly Lys Met Ser Ser Ser Lys
        195                 200                 205
Gly Asn Phe Ile Ala Val Asp Asp Ser Pro Glu Glu Ile Arg Ala Lys
    210                 215                 220
Ile Lys Lys Ala Tyr Cys Pro Ala Gly Val Val Glu Gly Asn Pro Ile
225                 230                 235                 240
Met Glu Ile Ala Lys Tyr Phe Leu Glu Tyr Pro Leu Thr Ile Lys Arg
                245                 250                 255
Pro Glu Lys Phe Gly Gly Asp Leu Thr Val Asn Ser Tyr Glu Glu Leu
            260                 265                 270
Glu Ser Leu Phe Lys Asn Lys Glu Leu His Pro Met Asp Leu Lys Asn
        275                 280                 285
Ala Val Ala Glu Glu Leu Ile Lys Ile Leu Glu Pro Ile Arg Lys Arg
    290                 295                 300
Leu
305

<210> SEQ ID NO 10
<211> LENGTH: 305
<212> TYPE: PRT
<213> ORGANISM: Methanococcus jannaschii

<400> SEQUENCE: 10

Met Asp Glu Phe Glu Met Ile Lys Arg Asn Thr Ser Glu Ile Ile Ser
1               5                   10                  15
Glu Glu Glu Leu Arg Glu Val Leu Lys Lys Asp Glu Lys Ser Ala Ala
                20                  25                  30
Ile Gly Phe Glu Pro Ser Gly Lys Ile His Leu Gly His Tyr Leu Gln
            35                  40                  45
Ile Lys Lys Met Ile Asp Leu Gln Asn Ala Gly Phe Asp Ile Ile Ile
        50                  55                  60
Leu Leu Ala Asp Leu His Ala Tyr Leu Asn Gln Lys Gly Glu Leu Asp
65                  70                  75                  80
Glu Ile Arg Lys Ile Gly Asp Tyr Asn Lys Lys Val Phe Glu Ala Met
                85                  90                  95
Gly Leu Lys Ala Lys Tyr Val Tyr Gly Ser Pro Phe Gln Leu Asp Lys
            100                 105                 110
Asp Tyr Thr Leu Asn Val Tyr Arg Leu Ala Leu Lys Thr Thr Leu Lys
        115                 120                 125
Arg Ala Arg Arg Ser Met Glu Leu Ile Ala Arg Glu Asp Glu Asn Pro
    130                 135                 140
```

```
Lys Val Ala Glu Val Ile Tyr Pro Ile Met Gln Val Asn Ile Pro Tyr
145                 150                 155                 160

Leu Pro Val Asp Val Ala Val Gly Gly Met Glu Gln Arg Lys Ile His
                165                 170                 175

Met Leu Ala Arg Glu Leu Leu Pro Lys Lys Val Val Cys Ile His Asn
                180                 185                 190

Pro Val Leu Thr Gly Leu Asp Gly Glu Gly Lys Met Ser Ser Ser Lys
                195                 200                 205

Gly Asn Phe Ile Ala Val Asp Asp Ser Pro Glu Glu Ile Arg Ala Lys
                210                 215                 220

Ile Lys Lys Ala Tyr Cys Pro Ala Gly Val Val Glu Gly Asn Pro Ile
225                 230                 235                 240

Met Glu Ile Ala Lys Tyr Phe Leu Glu Tyr Pro Leu Thr Ile Lys Arg
                245                 250                 255

Pro Glu Lys Phe Gly Gly Asp Leu Thr Val Asn Ser Tyr Glu Glu Leu
                260                 265                 270

Glu Ser Leu Phe Lys Asn Lys Glu Leu His Pro Met Asp Leu Lys Asn
                275                 280                 285

Ala Val Ala Glu Glu Leu Ile Lys Ile Leu Glu Pro Ile Arg Lys Arg
                290                 295                 300

Leu
305

<210> SEQ ID NO 11
<211> LENGTH: 305
<212> TYPE: PRT
<213> ORGANISM: Methanococcus jannaschii

<400> SEQUENCE: 11

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
                20                  25                  30

Ile Gly Phe Glu Pro Ser Gly Lys Ile His Leu Gly His Tyr Leu Gln
                35                  40                  45

Ile Lys Lys Met Ile Asp Leu Gln Asn Ala Gly Phe Asp Ile Ile Ile
50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Lys Phe Gln Leu Asp Lys
                100                 105                 110

Asp Tyr Thr Leu Asn Val Tyr Arg Leu Ala Leu Lys Thr Thr Leu Lys
                115                 120                 125

Arg Ala Arg Arg Ser Met Glu Leu Ile Ala Arg Glu Asp Glu Asn Pro
                130                 135                 140

Lys Val Ala Glu Val Ile Tyr Pro Ile Met Gln Val Asn Ala Ile Tyr
145                 150                 155                 160

Leu Ala Val Asp Val Ala Val Gly Gly Met Glu Gln Arg Lys Ile His
                165                 170                 175

Met Leu Ala Arg Glu Leu Leu Pro Lys Lys Val Val Cys Ile His Asn
                180                 185                 190

Pro Val Leu Thr Gly Leu Asp Gly Glu Gly Lys Met Ser Ser Ser Lys
```

```
                195                 200                 205
Gly Asn Phe Ile Ala Val Asp Asp Ser Pro Glu Glu Ile Arg Ala Lys
    210                 215                 220

Ile Lys Lys Ala Tyr Cys Pro Ala Gly Val Val Glu Gly Asn Pro Ile
225                 230                 235                 240

Met Glu Ile Ala Lys Tyr Phe Leu Glu Tyr Pro Leu Thr Ile Lys Arg
                245                 250                 255

Pro Glu Lys Phe Gly Gly Asp Leu Thr Val Asn Ser Tyr Glu Leu
                260                 265                 270

Glu Ser Leu Phe Lys Asn Lys Glu Leu His Pro Met Asp Leu Lys Asn
            275                 280                 285

Ala Val Ala Glu Glu Leu Ile Lys Ile Leu Glu Pro Ile Arg Lys Arg
        290                 295                 300

Leu
305

<210> SEQ ID NO 12
<211> LENGTH: 306
<212> TYPE: PRT
<213> ORGANISM: Methanococcus jannaschii

<400> SEQUENCE: 12

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Asn Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Leu His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255
```

```
Arg Pro Glu Lys Phe Gly Gly Asp Leu Thr Val Asn Ser Tyr Glu Glu
        260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
        290                 295                 300

Arg Leu
305

<210> SEQ ID NO 13
<211> LENGTH: 306
<212> TYPE: PRT
<213> ORGANISM: Methanococcus jannaschii

<400> SEQUENCE: 13

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Leu His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```

<210> SEQ ID NO 14
<211> LENGTH: 306
<212> TYPE: PRT
<213> ORGANISM: Methanococcus jannaschii

<400> SEQUENCE: 14

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Thr Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Val His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 15
<211> LENGTH: 306
<212> TYPE: PRT
<213> ORGANISM: Methanococcus jannaschii

<400> SEQUENCE: 15

Met Asp Glu Phe Glu Met Ile Lys Arg Asn Thr Ser Glu Ile Ile Ser
1               5                   10                  15

-continued

Glu Glu Glu Leu Arg Glu Val Leu Lys Lys Asp Glu Lys Ser Ala Thr
            20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
 50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Pro Ser His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
            195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
            275                 280                 285

Asn Ala Val Ala Glu Glu Leu Ile Lys Ile Leu Glu Pro Ile Arg Lys
            290                 295                 300

Arg Leu
305

<210> SEQ ID NO 16
<211> LENGTH: 306
<212> TYPE: PRT
<213> ORGANISM: Methanococcus jannaschii

<400> SEQUENCE: 16

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
 50                  55                  60

Leu Leu Ala Asp Leu His Ala Tyr Leu Asn Gln Lys Gly Glu Leu Asp

```
              65                  70                  75                  80
Glu Ile Arg Lys Ile Gly Asp Tyr Asn Lys Lys Val Phe Glu Ala Met
                85                  90                  95
Gly Leu Lys Ala Lys Tyr Val Tyr Gly Ser Glu Phe Gln Leu Asp Lys
                100                 105                 110
Asp Tyr Thr Leu Asn Val Tyr Arg Leu Ala Leu Lys Thr Thr Leu Lys
                115                 120                 125
Arg Ala Arg Arg Ser Met Glu Leu Ile Ala Arg Glu Asp Glu Asn Pro
            130                 135                 140
Lys Val Ala Glu Val Ile Tyr Pro Ile Met Gln Val Asn Gly Cys His
145                 150                 155                 160
Tyr Arg Gly Val Asp Val Ala Val Gly Gly Met Glu Gln Arg Lys Ile
                165                 170                 175
His Met Leu Ala Arg Glu Leu Leu Pro Lys Lys Val Val Cys Ile His
                180                 185                 190
Asn Pro Val Leu Thr Gly Leu Asp Gly Glu Gly Lys Met Ser Ser Ser
                195                 200                 205
Lys Gly Asn Phe Ile Ala Val Asp Asp Ser Pro Glu Glu Ile Arg Ala
            210                 215                 220
Lys Ile Lys Lys Ala Tyr Cys Pro Ala Gly Val Val Glu Gly Asn Pro
225                 230                 235                 240
Ile Met Glu Ile Ala Lys Tyr Phe Leu Glu Tyr Pro Leu Thr Ile Lys
                245                 250                 255
Arg Pro Glu Lys Phe Gly Gly Asp Leu Thr Val Asn Ser Tyr Glu Glu
            260                 265                 270
Leu Glu Ser Leu Phe Lys Asn Lys Glu Leu His Pro Met Asp Leu Lys
            275                 280                 285
Asn Ala Val Ala Glu Glu Leu Ile Lys Ile Leu Glu Pro Ile Arg Lys
        290                 295                 300
Arg Leu
305

<210> SEQ ID NO 17
<211> LENGTH: 306
<212> TYPE: PRT
<213> ORGANISM: Methanococcus jannaschii

<400> SEQUENCE: 17

Met Asp Glu Phe Glu Met Ile Lys Arg Asn Thr Ser Glu Ile Ile Ser
1               5                   10                  15
Glu Glu Glu Leu Arg Glu Val Leu Lys Lys Asp Glu Lys Ser Ala Leu
                20                  25                  30
Ile Gly Phe Glu Pro Ser Gly Lys Ile His Leu Gly His Tyr Leu Gln
            35                  40                  45
Ile Lys Lys Met Ile Asp Leu Gln Asn Ala Gly Phe Asp Ile Ile Ile
        50                  55                  60
Leu Leu Ala Asp Leu His Ala Tyr Leu Asn Gln Lys Gly Glu Leu Asp
65                  70                  75                  80
Glu Ile Arg Lys Ile Gly Asp Tyr Asn Lys Lys Val Phe Glu Ala Met
                85                  90                  95
Gly Leu Lys Ala Lys Tyr Val Tyr Gly Ser Glu Phe Gln Leu Asp Lys
                100                 105                 110
Asp Tyr Thr Leu Asn Val Tyr Arg Leu Ala Leu Lys Thr Thr Leu Lys
                115                 120                 125
```

```
Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Thr His
145                 150                 155                 160

Tyr Arg Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
290                 295                 300

Arg Leu
305

<210> SEQ ID NO 18
<211> LENGTH: 306
<212> TYPE: PRT
<213> ORGANISM: Methanococcus jannaschii

<400> SEQUENCE: 18

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
        50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Gly His
145                 150                 155                 160

Tyr Leu Gly Val Asp Val Ile Val Gly Gly Met Glu Gln Arg Lys Ile
                165                 170                 175

His Met Leu Ala Arg Glu Leu Leu Pro Lys Lys Val Val Cys Ile His
            180                 185                 190
```

```
Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```

<210> SEQ ID NO 19
<211> LENGTH: 306
<212> TYPE: PRT
<213> ORGANISM: Methanococcus jannaschii

<400> SEQUENCE: 19

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
        50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Arg Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Val Ile His
145                 150                 155                 160

Tyr Asp Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
```

```
                        245                 250                 255
Arg Pro Glu Lys Phe Gly Gly Asp Leu Thr Val Asn Ser Tyr Glu Glu
                260                 265                 270
Leu Glu Ser Leu Phe Lys Asn Lys Glu Leu His Pro Met Asp Leu Lys
            275                 280                 285
Asn Ala Val Ala Glu Glu Leu Ile Lys Ile Leu Glu Pro Ile Arg Lys
        290                 295                 300
Arg Leu
305

<210> SEQ ID NO 20
<211> LENGTH: 306
<212> TYPE: PRT
<213> ORGANISM: Methanococcus jannaschii

<400> SEQUENCE: 20

Met Asp Glu Phe Glu Met Ile Lys Arg Asn Thr Ser Glu Ile Ile Ser
1               5                   10                  15
Glu Glu Glu Leu Arg Glu Val Leu Lys Lys Asp Glu Lys Ser Ala Gly
            20                  25                  30
Ile Gly Phe Glu Pro Ser Gly Lys Ile His Leu Gly His Tyr Leu Gln
        35                  40                  45
Ile Lys Lys Met Ile Asp Leu Gln Asn Ala Gly Phe Asp Ile Ile Ile
    50                  55                  60
Leu Leu Ala Asp Leu His Ala Tyr Leu Asn Gln Lys Gly Glu Leu Asp
65                  70                  75                  80
Glu Ile Arg Lys Ile Gly Asp Tyr Asn Lys Lys Val Phe Glu Ala Met
                85                  90                  95
Gly Leu Lys Ala Lys Tyr Val Tyr Gly Ser Thr Phe Gln Leu Asp Lys
            100                 105                 110
Asp Tyr Thr Leu Asn Val Tyr Arg Leu Ala Leu Lys Thr Thr Leu Lys
        115                 120                 125
Arg Ala Arg Arg Ser Met Glu Leu Ile Ala Arg Glu Asp Glu Asn Pro
    130                 135                 140
Lys Val Ala Glu Val Ile Tyr Pro Ile Met Gln Val Asn Thr Tyr Tyr
145                 150                 155                 160
Tyr Leu Gly Val Asp Val Ala Val Gly Gly Met Glu Gln Arg Lys Ile
                165                 170                 175
His Met Leu Ala Arg Glu Leu Leu Pro Lys Lys Val Val Cys Ile His
            180                 185                 190
Asn Pro Val Leu Thr Gly Leu Asp Gly Glu Gly Lys Met Ser Ser Ser
        195                 200                 205
Lys Gly Asn Phe Ile Ala Val Asp Asp Ser Pro Glu Glu Ile Arg Ala
    210                 215                 220
Lys Ile Lys Lys Ala Tyr Cys Pro Ala Gly Val Val Glu Gly Asn Pro
225                 230                 235                 240
Ile Met Glu Ile Ala Lys Tyr Phe Leu Glu Tyr Pro Leu Thr Ile Lys
                245                 250                 255
Arg Pro Glu Lys Phe Gly Gly Asp Leu Thr Val Asn Ser Tyr Glu Glu
            260                 265                 270
Leu Glu Ser Leu Phe Lys Asn Lys Glu Leu His Pro Met Asp Leu Lys
        275                 280                 285
Asn Ala Val Ala Glu Glu Leu Ile Lys Ile Leu Glu Pro Ile Arg Lys
    290                 295                 300
```

Arg Leu
305

<210> SEQ ID NO 21
<211> LENGTH: 39
<212> TYPE: PRT
<213> ORGANISM: Homo sapiens

<400> SEQUENCE: 21

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 22
<211> LENGTH: 36
<212> TYPE: PRT
<213> ORGANISM: Human immunodeficiency virus

<400> SEQUENCE: 22

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 23
<211> LENGTH: 34
<212> TYPE: PRT
<213> ORGANISM: Homo sapiens

<400> SEQUENCE: 23

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 24
<211> LENGTH: 44
<212> TYPE: PRT
<213> ORGANISM: Human immunodeficiency virus

<400> SEQUENCE: 24

Glu Trp Asp Arg Glu Ile Asn Asn Tyr Thr Ser Leu Ile His Ser Leu
1               5                   10                  15

Ile Glu Glu Ser Gln Asn Gln Gln Glu Lys Asn Glu Gln Glu Leu Leu
            20                  25                  30

Glu Leu Asp Lys Trp Ala Ser Leu Trp Asn Trp Phe
        35                  40

<210> SEQ ID NO 25
<211> LENGTH: 107
<212> TYPE: PRT
<213> ORGANISM: Escherichia coli

<400> SEQUENCE: 25

Lys Ala Ile Phe Val Leu Lys Gly Ser Leu Asp Arg Asp Leu Asp Ser

```
                1               5                    10                   15
              Arg Ile Glu Leu Glu Leu Arg Thr Asp His Lys Glu Leu Ser Glu His
                             20                   25                  30

Leu Leu Leu Val Asp Leu Ala Arg Asn Asp Leu Ala Arg Ile Ala Thr
                             35                   40                  45

Pro Gly Ser Arg Tyr Val Ala Asp Leu Thr Lys Val Asp Arg Tyr Ser
                        50                   55                  60

Tyr Val Leu His Leu Val Ser Arg Val Val Gly Glu Leu Arg His Asp
              65                   70                  75                  80

Leu Asp Ala Leu His Ala Tyr Arg Ala Ala Leu Asn Leu Gly Thr Leu
                                  85                  90                  95

Ser Gly Ala Pro Lys Val Arg Ala Lys Leu Trp
                             100                 105

<210> SEQ ID NO 26
<211> LENGTH: 33
<212> TYPE: DNA
<213> ORGANISM: Artificial Sequence
<220> FEATURE:
<223> OTHER INFORMATION: Synthetic construct

<400> SEQUENCE: 26
aagctttgga tgtacacaag tttaatacac tcc                                    33

<210> SEQ ID NO 27
<211> LENGTH: 34
<212> TYPE: DNA
<213> ORGANISM: Artificial Sequence
<220> FEATURE:
<223> OTHER INFORMATION: Synthetic construct

<400> SEQUENCE: 27
gcggatccca ttaaaaccaa ttccacaaac ttgc                                   34

<210> SEQ ID NO 28
<211> LENGTH: 59
<212> TYPE: DNA
<213> ORGANISM: Artificial Sequence
<220> FEATURE:
<223> OTHER INFORMATION: Synthetic construct

<400> SEQUENCE: 28
cgaagctttg gatggagtgg gatagagaaa ttaacaatta cacaagttta atacactcc        59
```